US007405295B2

(12) United States Patent
Currie et al.

(10) Patent No.: US 7,405,295 B2
(45) Date of Patent: Jul. 29, 2008

(54) CERTAIN IMIDAZO[1,2-A]PYRAZIN-8-YLAMINES AND METHOD OF INHIBITION OF BRUTON'S TYROSINE KINASE BY SUCH COMPOUNDS

(75) Inventors: Kevin S. Currie, North Branford, CT (US); Robert W. DeSimone, Durham, CT (US); Scott A. Mitchell, East Haven, CT (US); Douglas A. Pippin, Branford, CT (US); James W. Darrow, Wallingford, CT (US); Xiaobing Qian, Guilford, CT (US); Mark Velleca, New Haven, CT (US); Dapeng Qian, Guilford, CT (US)

(73) Assignee: CGI Pharmaceuticals, Inc., Branford, CT (US)

( * ) Notice: Subject to any disclaimer, the term of this patent is extended or adjusted under 35 U.S.C. 154(b) by 208 days.

(21) Appl. No.: 10/861,791

(22) Filed: Jun. 4, 2004

(65) Prior Publication Data
US 2005/0090499 A1 Apr. 28, 2005

Related U.S. Application Data

(60) Provisional application No. 60/519,311, filed on Nov. 11, 2003, provisional application No. 60/475,634, filed on Jun. 4, 2003.

(51) Int. Cl.
*C07D 417/00* (2006.01)
*C07D 413/00* (2006.01)
*C07D 471/00* (2006.01)
*C07D 487/00* (2006.01)
*C07D 491/00* (2006.01)
*C07D 497/00* (2006.01)

(52) U.S. Cl. .................. 544/61; 544/117; 544/119; 544/350

(58) Field of Classification Search .................. 544/61, 544/117, 119, 350
See application file for complete search history.

(56) References Cited

U.S. PATENT DOCUMENTS

| 5,028,605 | A | * | 7/1991 | Sablayrolles et al. ..... 514/228.5 |
| 5,593,997 | A | | 1/1997 | Dow et al. |
| 5,658,857 | A | | 8/1997 | Andree et al. |
| 5,738,576 | A | | 4/1998 | Ohno et al. |
| 5,783,576 | A | | 7/1998 | Roos et al. |
| 6,919,340 | B2 | * | 7/2005 | Currie et al. ................. 514/249 |
| 6,919,341 | B2 | | 7/2005 | Paruch et al. |
| 2003/0212073 | A1 | | 11/2003 | Currie et al. |
| 2004/0063715 | A1 | | 4/2004 | Paruch et al. |
| 2004/0067951 | A1 | | 4/2004 | DeSimone et al. |
| 2004/0072835 | A1 | | 4/2004 | Paruch et al. |
| 2004/0102455 | A1 | * | 5/2004 | Burns et al. ............ 514/255.05 |
| 2004/0220189 | A1 | | 11/2004 | Sun et al. |
| 2005/0009832 | A1 | | 1/2005 | Sun et al. |
| 2005/0054648 | A1 | | 3/2005 | Mitchell et al. |
| 2005/0054649 | A1 | | 3/2005 | Currie et al. |
| 2005/0085484 | A1 | | 4/2005 | Mitchell et al. |
| 2005/0101604 | A1 | | 5/2005 | Currie et al. |
| 2005/0288295 | A1 | | 12/2005 | Currie et al. |

FOREIGN PATENT DOCUMENTS

DE 0 43 37 609 5/1995
EP 0 480 713 4/1992

(Continued)

OTHER PUBLICATIONS

Al-Dabbagh and Smith, "Species differences in oxidative drug metabolism: some basic considerations." Archives of toxicology. Supplement. Archiv fur Toxikologie. supplement, vol. 7, pp. 219-231 (1984).*

(Continued)

*Primary Examiner*—Zachary C Tucker
(74) *Attorney, Agent, or Firm*—Millen, White, Zelano & Branigan, P.C.

(57) ABSTRACT

Compounds of Formula I-a

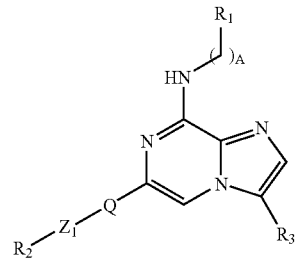

(Formula I-a)

and all pharmaceutically-acceptable forms thereof, are described herein.

The variables $R_1$, $R_2$, $R_3$, $Z_1$, Q, and A shown in Formula I-a are defined herein.

Pharmaceutical compositions containing one or more compounds of Formula I-a, or a pharmaceutically acceptable form of such compounds, and one or more pharmaceutically acceptable carriers, excipients, or diluents are provided herein.

Methods of treating patients suffering from certain diseases responsive to inhibition of tyrosine kinase activity are also given. In certain embodiments the diseases are responsive to inhibition of Btk activity and/or B-cell proliferation. Such methods comprise administering to such patients an amount of a compound of Formula I-a effective to reduce signs or symptoms of the disease. These diseases include cancer, an autoimmune and/or inflammatory disease, or an acute inflammatory reaction. Thus methods of treatment include administering a sufficient amount of a compound or salt as provided herein to decrease the symptoms or slow the progression of these diseases.

59 Claims, No Drawings

FOREIGN PATENT DOCUMENTS

| WO | WO 88/04298 | 6/1988 |
|---|---|---|
| WO | WO 95/12594 | 5/1995 |
| WO | WO 96/04298 | 2/1996 |
| WO | WO 96/34866 | 11/1996 |
| WO | WO 99/28322 | 6/1999 |
| WO | WO 01/27119 | 4/2001 |
| WO | WO 02/10170 | 2/2002 |
| WO | WO 02/30428 | 4/2002 |
| WO | WO 02/060492 | 8/2002 |
| WO | WO 02/066481 | 8/2002 |
| WO | WO 02/076985 | 10/2002 |
| WO | WO 03/070732 | 8/2003 |
| WO | WO 03/089434 | 10/2003 |
| WO | WO 2004/022562 | 3/2004 |
| WO | WO 2004/026310 | 4/2004 |
| WO | WO 2004/026877 | 4/2004 |
| WO | WO 2004/072080 | 8/2004 |
| WO | WO 2004/072081 | 8/2004 |
| WO | WO 2005/005429 | 1/2005 |
| WO | WO 2005/014599 | 2/2005 |
| WO | WO 2005/019220 | 3/2005 |
| WO | WO 2005/047290 | 5/2005 |

OTHER PUBLICATIONS

Hans Bundgaard, Design of Prodrugs, p. 1. © 1985 Elsevier Science Publishers.*

Richard B. Silverman, The Organic Chemistry of Drug Design and Drug Action, pp. 352-400. © 1992 Academic Press, Inc.*

Vippagunta et al, "Crystalline Solids" Advanced Drug Delivery Reviews, vol. 48, pp. 3-26 (2001).*

Gavezzotti, "Are Crystal Structures Predictable?" Accounts of Chemical Research, vol. 27, pp. 309-314 (1994).*

Vassilev and Uckun "Therapeutic Potential of Inhibiting Bruton's Tyrosine Kinase, (BTK)" Current Pharmaceutical Design, vol. 10, pp. 1757-1766 (2004).*

Ding et al. (2002) "A Combinatorial Scaffold Approach toward Kinase-Directed Heterocycle Libraries," J. Am. Chem. Soc., 124(8): 1594-1596.

Hanks (Apr. 1, 1994) "Hanks Classification: Protein Kinase Classification, provided by Steven K. Harks," pp. 1-4, from http://pkr.sdsc.edu/html/pk_classification/pk_catalytic/pk_hanks_class.html.

Jeffrey et al. (1998) "Phosphodiesterase III and V Inhibitors on Pulmonary Artery from Pulmonary Hypertensive Rats: Differences Between Early and Established Pulmonary Hypertension," J. Cardiovascular Pharmacology, 32:213-219.

Lumma Jr. et al. (1983) "Piperazinylimidazo[1,2-a]pyrazines with Selective Affinity for in Vitro alpha-Adrenergic Receptor Subtypes," J. Med. Chem., 26:357-363.

"Protein Kinases in Disease," references produced from a Sep. 24, 1997, search of the On-line Meddelian Inheritance in Man (OMIM) database, pp. 1-11, from http://bioinformatics.weizmann.ac.il/Kinases/pkr/pk$_{13}$ medicine.html.

Stenberg et al. (2000) "KinMutBase, a database of human disease-causing protein kinase mutations," Nucleic Acids Research, 28(1):369-371.

Vitse et al. (1999) "New Imidazo[1,2-a]pyrazine Derivatives with Brochodilatory and Cyclic Nucleotide Phosphodiesterase Inhibitory Activities," Bioorganic & Medicinal Chemistry, 7: 1059-1065.

Restriction Requirement dated Oct. 20, 2004, for U.S. Appl. No. 10/419,682, filed Apr. 21, 2003.

Office Action dated Apr, 3, 2006, for U.S. Appl. No. 10/776,002, filed Feb. 10, 2004.

Office Action dated May 24, 2006, for U.S. Appl. No. 10/776,631, filed Feb. 10, 2004.

Ding et al. (2002) "A Combinatorial Scaffold Approach toward Kinase-Directed Heterocycle Libraries," J. Am. Chem. Soc., 124(8): 1594-1596.

Hanks (Apr. 1, 1994) "Hanks Classification: Protein Kinase Classification, provided by Steven K. Hanks," pp. 1-4, from http://pkr.sdsc.edu/html/pk_classification/pk_catalytic/pk_hanks_class.html.

Jeffrey et al. (1998) "Phosphodiesterase III and V Inhibitors on Pulmonary Artery from Pulmonary Hypertensive Rats: Differences Between Early and Established Pulmonary Hypertension," J. Cardiovascular Pharmacology, 32:213-219.

Lumma Jr. et al. (1983) "Piperazinylimidazo[1,2-a]pyrazines with Selective Affinity for in Vitro alpha-Adrenergic Receptor Subtypes," J. Med. Chem., 26:357-363.

"Protein Kinases in Disease," references produced from a Sep. 24, 1997, search of the On-line Meddelian http:/bioinformatics.weizmann.ac.il/Kinases/pkr/pk_medicine.html.

Stenberg et al, (2000) "KinMutBase, a database of human disease-causing protein kinase mutations," Nucleic Acids Research, 28(1):369-371.

Vitse et al. (1999) "New Imidazo[1,2-a]pyrazine Derivatives with Brochodilatory and Cyclic Nucleotide Phosphodiesterase Inhibitory Activities," Bioorganic & Medicinal Chemistry, 7: 1059-1065.

Restriction Requirement dated Oct. 20, 2004, for U.S. Appl. No. 10/419,682, filed Apr. 21, 2003.

International Search Report dated Oct. 22, 2003, for Application No. PCT/US03/12222, International filing date Apr. 21, 2003.

Written Opinion dated Dec. 5, 2003, for Application No. PCT/US03/12222, International filing date Apr. 21, 2003.

Second Written Opinion dated Apr. 13, 2004, for Application No. PCT/US03/12222, International Filing date Apr. 21, 2003.

International Preliminary Examination Report dated Aug. 3, 2004, for Application No. PCT/US03/12222, International filing date Apr. 21, 2003.

International Search Report dated Feb. 9, 2004, for Application No. PCT/US03/28329, International filing date Sep. 9, 2003.

Written Opinion dated Jul. 6, 2004, for Application No. PCT/US03/28329, International filing date Sep. 9, 2003.

International Preliminary Examination Report dated Oct. 27, 2004, for Application No. PCT/US03/28329, International filing date Sep. 9, 2003.

International Search Report and Written Opinion dated Jul. 7, 2004, for Application No. PCT/US2004/003922, International filing date Feb. 10, 2004.

International Search Report and Written Opinion dated Jul. 7, 2004, for Application No. PCT/US2004/003923, International filing date Feb. 10, 2004.

International Search Report and Written Opinion dated Dec. 8, 2004, for Application No. PCT/US2004/021150, International filing date Jun. 30, 2004.

Tsukada, S., et al., *Deficient expression of a B cell cytoplasmic kinase in human X-linked agammaglobulinemia*. Cell, 1993. 72: p. 279-290.

Vetrie, D., et al., *The gene involved in X-linked agammaglobulinemia is a member of the src family of protein kinases*. Nature, 1993. 361: p. 226-233.

Steinberg, B.J., et al., *Ability of the xid gene to prevent autoimmunity in (NZB xNZW)F1 mice during the course of their natural history, after polyclonal stimulation, or following immunization with DNA*. J Clin Invest, 1982. 70(3): p. 587-97.

Smith, H.R., T.M. Chused, and A.D. Steinberg, *The Effect of the X-linked Immune Deficiency Gene (xid) upon the Y Chromosome-Related Disease of BXSB Mice*. The Journal of Immunology, 1983. 131: p. 1257-1262.

Steinberg, E.B., et al., *Studies of Congenic MRL-Ipr/Ipr.xid Mice*. The Journal of Immunology, 1983. 131(2789-2795).

Fieser, T.M., et al., *Abrogation of Murine Lupus by the xid Gene is Associated with Reduced Responsiveness of B Cells to T-Cell-Helper Signals*. Cellular Immunology, 1984. 87: p. 708-713.

Steinberg, A.D., et al., *Systemic Lupus Erythematosus: Insights from Animal Models*. Annals of Internal Medicine, 1984. 100: p. 714-727.

Reeves, J.P. and A.D. Steinberg, *Effect of the xid Gene on Graft-versus-Host-Induced Autoantibody Production in Nonautoimmune Mice*. Clinical Immunology and Imunopathology, 1985. 36: p. 320-329.

Jansson, L. and R. Holmdahl, *Genes on the X chromosome affect development of collagen-induced arthritis in mice*. Clin Exp Immunol, 1993. 94: p. 459-465.

Zhao, Y.X., et al., *Mice with the xid B cell defect are less susceptible to developing Staphyococcus aureus-induced arthritis*. J Immunol., 1995. 155(4): p. 2067-76.

Farrar, J.E., J. Rohrer, and M.E. Conley, *Neutropenia in X-linked agammaglobulinemia.* Clin Immunol Immunopathol, 1996. 81(3): p. 271-6.

Hata, D., et al., *Involvement of Bruton's tyrosine kinase in FcepsilonRI-dependent mast cell degranulation and cytokine production.* J Exp Med, 1998. 187(8): p. 1235-47.

Svensson, L., et al., *B cell-deficient mice do not develop type II collagen-induced arthritis (CIA).* Clin Exp Immunol, 1998. 111: p. 521-526.

Mukhopadhyay, S., et al., *Macrophage effector functions controlled by Bruton's tyrosine kinase are more crucial than the cytokine balance of T cell responses for microfilarial clearance.* J Immunol, 2002. 168(6): p. 2914-21.

Whyburn, L.R., et al. *Reduced dosage of Bruton's tyrosine kinase uncouples B cell hyperresponsiveness from autoimmunity in lyn-l- mice.* J Immunol, 2003. 171(4): p. 1850-8.

Feldhahn, N., et al., *Deficiency of Bruton's tyrosine kinase in B cell precursor leukemia cells.* Proc Natl Acad Sci U S A., 2005. 102(37): p. 13266-71. Epub Sep. 2, 2005.

Feldhahn, N., et al., *Mimicry of a constitutively active pre-B cell receptor in acute lymphoblastic leukemia cells.* J Exp Med., 2005. 201(11): p. 1837-52.

Irish, J.M., et al., *Altered B-cell receptor signaling kinetics distinguish human follicular lymphoma B cells from tumor-infiltrating nonmalignant B cells.* Blood., 2006. 108(9): p. 3135-42. Epub Jul. 11, 2006.

* cited by examiner

CERTAIN IMIDAZO[1,2-A]PYRAZIN-8-YLAMINES AND METHOD OF INHIBITION OF BRUTON'S TYROSINE KINASE BY SUCH COMPOUNDS

CROSS-REFERENCE TO RELATED APPLICATIONS

This application claims priority to US provisional application 60/475,634 filed Jun. 4, 2003, and U.S. provisional application 60/519,311 filed Nov. 11, 2003, which are hereby incorporated by reference in their entirety.

FIELD OF INVENTION

Certain imidazo[1,2-a]pyrazin-8-ylamine and related compounds, which when appropriately substituted are inhibitors of tyrosine kinase activity, including Bruton's tyrosine kinase (Btk) activity, are provided herein. Certain compounds provided herein are highly active and/or specific inhibitors of Btk activity. Pharmaceutical compositions comprising such compounds, and methods of using certain imidazo[1,2-a] pyrazin-8-ylamine and related compounds to treat a variety of diseases responsive to inhibition of Btk activity and/or inhibition of B-cell proliferation, are also disclosed. Additionally, methods for using such compounds as probes for the detection and/or localization of Btk in biological samples are given.

BACKGROUND

Protein kinases, the largest family of human enzymes, encompass well over 500 proteins. Kinases play critical roles in signaling pathways controlling fundamental cellular processes such as proliferation, differentiation, and death (apoptosis). Abnormal kinase activity has been implicated in a wide range of diseases, including multiple cancers and autoimmune and inflammatory diseases. The multifaceted role of kinases in key cell signaling pathways provides a significant opportunity to identify novel drugs targeting kinases and signaling pathways. Diseases mediated by receptor kinase activity include, but are not limited to, diseases characterized in part by abnormal levels of cell proliferation (i.e. tumor growth), programmed cell death (apoptosis), cell migration and invasion, and angiogenesis associated with tumor growth.

Because kinases are key regulators they are ideal drug design targets. Inhibitors of kinases are among the most important classes of pharmaceutical compounds known. Highly specific, cell-permeable inhibitors of one or more individual kinases are useful for the treatment of various kinase-implicated diseases. Kinase inhibiting compounds are additionally useful for the systematic investigation of the cellular function of one or more kinases, and thus, provide valuable tools for the identification of various kinases of therapeutic interest.

Bruton's Tyrosine Kinase (Btk) is a member of the Tec family of tyrosine kinases, and is a critical regulator of early B-cell development as well as mature B-cell activation, signaling and survival.

B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause disregulated B-cell proliferation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, comprised T-cell-independent immune responses and marked attenuation of the sustained calcium sign upon BCR stimulation.

Evidence for the role of Btk in autoimmune and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice are also resistant to developing collagen-induced arthritis and are less susceptible to Staphylococcus-induced arthritis.

A large body of evidence supports the role of B-cells and the humoral immune system in the pathogenesis of autoimmune and/or inflammatory diseases. Protein-based therapeutics (such as Rituxan) developed to deplete B-cells, represent an important approach to the treatment of a number of autoimmune and/or inflammatory diseases. Because of Btk's role in B-cell activation, inhibitors of Btk are useful as inhibitors of B-cell mediated pathogenic activity (such as autoantibody production).

Btk is also expressed in mast cells and monocytes and has been shown to be important for the function of these cells. For example, Btk deficiency in mice is associated with impaired IgE-mediated mast cell activation (marked diminution of TNFα and other inflammatory cytokine release), and greatly reduced TNFα production by activated monocytes.

Thus, inhibition of Btk activity is useful for the treatment of autoimmune and/or inflammatory diseases such as: SLE, rheumatoid arthritis, multiple vasculitides, idiopathic thrombocytopenic purpura (ITP), myasthenia gravis, and asthma. In addition, Btk has been reported to play a role in apoptosis, thus inhibition of Btk activity is useful for the treatment of B-cell lymphoma and leukemia.

Agents capable of inhibiting Btk kinase activity, are highly desirable for the treatment of a variety of diseases, including cancer, an autoimmune and/or inflammatory disease, or an acute inflammatory reaction. Specific, cell-penetrating, small molecule, non-peptide antagonists of Btk are of particular value for such therapies. Such compounds are also useful for the systematic investigation of the cellular function of Btk, and thus, are valuable research tools for the identification of cell signalling proteins of therapeutic interest.

The present invention fulfills this need, and provides further related advantages.

SUMMARY

Inhibitors of kinase activity, which may generally be described as imidazo[1,2-a]pyrazin-8-ylamines and related compounds, are disclosed herein. Certain compounds provided herein are highly active and/or specific inhibitors of Btk (Bruton's tyrosine kinase) activity.

One embodiment provides a compound of Formula I-a

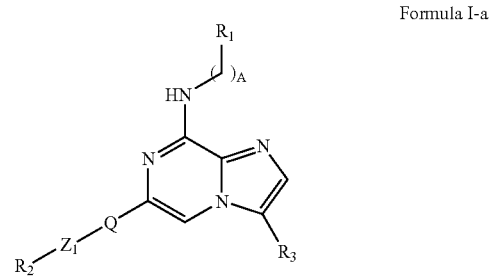

Formula I-a or a pharmaceutically acceptable form thereof

Within Formula I-a:

A is 0 or 1.

$R_1$ is phenyl or heteroaryl, each of which is optionally substituted with one of (i) oxo, —CHO, —COOH, —CONH$_2$, or —CONHOH, (ii) $C_2$-$C_6$ alkenyl, $C_2$-$C_6$ alkynyl, $C_1$-$C_6$hydroxyalkyl, $C_1$-$C_6$hydroxyalkoxy, (mono- or di-$C_1$-$C_6$alkylamino)$C_1$-$C_6$alkoxy, ($C_1$-$C_6$alkoxy)($C_1$-$C_6$alkylamino)$C_0$-$C_6$alkyl, ($C_1$-$C_6$alkoxy)($C_1$-$C_6$alkoxy)$C_1$-$C_6$alkoxy, heterocycloalkyl, aryl, or heteroaryl, (iii) —$C_1$-$C_6$alkyl(C=O)O$R_{10}$, —$C_0$-$C_6$alkyl(C=O)N$R_{10}R_{11}$, —$C_1$-$C_6$alkylN$R_{10}$(SO$_2$)$R_{11}$, —$C_0$-$C_6$alkylN$R_{10}$(C=O)$R_{11}$, —$C_0$-$C_6$alkyl(SO$_2$)$R_{10}$, or —$C_0$-$C_6$alkylN$R_{10}$(C=O)N$R_{11}R_{12}$ where $R_{10}$, $R_{11}$, and $R_{12}$ are independently hydrogen, hydroxy, $C_1$-$C_6$alkyl, $C_1$-$C_6$alkoxy, $C_3$-$C_{10}$-cycloalkyl, or heterocycloalkyl, or (iv) -L-G, where L is $C_1$-$C_2$alkyl, $C_0$-$C_2$alkoxy, —(C=O)—, or —(C$_1$-$C_2$alkyl)(C=O)—, and G is heterocycloalkyl, $C_3$-$C_7$cycloalkyl, aryl, or heteroaryl.

Each of which (ii), (iii), and (iv) is substituted with 0 to 3 substituents independently chosen from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl.

And, $R_1$ is substituted with 0 or 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono- and di-$C_1$-$C_6$ alkylamino)$C_0$-$C_6$ alkyl, and $C_1$-$C_6$alkoxycarbonyl.

$R_2$ is $C_1$-$C_7$ alkyl, ($C_1$-$C_6$alkoxy)$C_0$-$C_6$alkoxy, (heterocycloalkyl)$C_0$-$C_2$alkyl, ($C_3$-$C_7$cycloalkyl)$C_0$-$C_2$alkyl, or $R_2$ is (phenyl)$C_0$-$C_2$alkyl, (phenoxy)$C_0$-$C_2$alkyl, or (heteroaryl)$C_0$-$C_2$alkyl, each of which is substituted with 0 to 3 substituents independently chosen from hydroxy, nitro, cyano, amino, halogen, —SO$_2$NH$_2$, oxo, —COOH, $C_1$-$C_6$ alkyl, $C_2$-$C_6$alkenyl, $C_2$-$C_6$alkynyl, $C_1$-$C_6$ alkoxy, $C_2$-$C_6$alkanoyl, $C_1$-$C_6$hydroxyalkyl, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$alkyl, mono- and di-$C_1$-$C_6$alkylamino, mono- and di-$C_1$-$C_6$alkylcarboxamide, $C_1$-$C_6$alkoxycarbonyl, phenyl, and heteroaryl, and —(C=O)$R_{13}$ wherein $R_{13}$ is $C_1$-$C_6$alkyl, ($C_3$-$C_7$cycloalkyl)$C_0$-$C_2$alkyl, $C_1$-$C_3$haloalkyl, heterocycloalkyl, phenyl, or heteroaryl.

$Z_1$ is

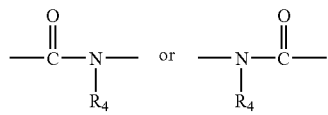

wherein $R_4$ is hydrogen, or $R_4$ is $C_1$-$C_6$alkyl, $C_3$-$C_7$cycloalkyl, heterocycloalkyl, phenyl, or heteroaryl, each of which is substituted with 0 or 1 or more substituents independently chosen from hydroxy, nitro, cyano, amino, halogen, oxo, $C_1$-$C_6$ alkyl, $C_2$-$C_6$alkenyl, $C_2$-$C_6$alkynyl, $C_1$-$C_6$ alkoxy, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$ alkyl, mono- and di-$C_1$-$C_6$ alkylamino, and —C(O)$R_{14}$ wherein $R_{14}$ is $C_1$-$C_6$ alkyl, $C_1$-$C_3$haloalkyl, or phenyl.

Q is phenyl or pyridyl.

$R_3$ is hydrogen, $C_1$-$C_7$ alkyl, or halogen, or $R_3$ is heterocycloalkyl, $C_3$-$C_7$cycloalkyl, or heteroaryl, each of which is substituted with from 0 to 3 substituents independently chosen from hydroxy, nitro, cyano, amino, halogen, —SO$_2$NH$_2$, oxo, $C_1$-$C_6$ alkyl, $C_2$-$C_6$alkenyl, $C_2$-$C_6$alkynyl, $C_1$-$C_6$ alkoxy, $C_1$-$C_3$haloalkyl, $C_1$-$C_3$haloalkoxy, $C_1$-$C_6$ alkylthio, ($C_1$-$C_6$-alkoxy)$C_1$-$C_6$ alkoxy, mono- and di-$C_1$-$C_6$alkylamino, amino$C_1$-$C_6$ alkyl, and —C(O)$R_{14}$.

In certain embodiments compounds of Formula I-a, which exhibit an IC$_{50}$ of 1 micromolar or less, 100 nanomolar or less, or 10 nanomolar or less in standard biochemical assay for Btk activity, such as the biochemical assay described in Example 6, are provided herein. Preferred compounds described herein are highly active inhibitors of B-cell proliferation. For example certain compounds described herein exhibit an IC$_{50}$ value less than or equal to 10 micromolar, or an IC$_{50}$ value less than or equal to 1 micromolar, or an IC$_{50}$ value less than or equal to 500 nM in the tritiated thymidine incorporation assay for B-cell proliferation described in Example 8. Preferred compounds described herein are specific inhibitors of B-cell proliferation, exhibiting an IC$_{50}$ value that is at least 3-fold, preferably 5-fold, and more preferably 10-fold greater for T-cell proliferation than the IC$_{50}$ for B-cell proliferation. The IC$_{50}$ for T-cell proliferation may be determined via a standard assay for T-cell proliferation such as the thymidine incorporation assay of Example 9.

A method for determining the presence of Btk in a sample, comprising contacting the sample with a compound or form thereof of Formula I-a under conditions that permit detection of Btk activity, detecting a level of Btk activity in the sample, and therefrom determining the presence or absence of Btk in the sample, is also provided herein.

Pharmaceutical compositions, comprising one or more compounds of Formula I-a, or any pharmaceutically acceptable form thereof, together with at least one pharmaceutically acceptable carrier or excipient, are provided herein.

Other embodiments pertain to packaged pharmaceutical compositions which comprise a pharmaceutical composition, comprising one or more compounds of Formula I-a or any pharmaceutically acceptable form thereof, together with at least one pharmaceutically acceptable carrier or excipient in a container and with instructions for using the pharmaceutical composition to treat a patient. Preferably the instructions are for using the pharmaceutical composition to treat a patient suffering from a disease responsive to inhibition of Btk activity.

Still other embodiments pertain to a method of inhibiting Btk kinase. In certain embodiments the method comprises contacting a cell or cells expressing Btk, either in vivo or in vitro, with a compound of Formula I-a or form thereof in an amount sufficient to detectably inhibit Btk activity in vitro.

Inhibiting Btk activity can effectively inhibit B-cell proliferation. Small molecule (less than 600 amu) Btk inhibitors that are orally bioavailable, such as certain compounds and forms of Formula I-a, are particularly desirable for this purpose. Thus a method of inhibiting B-cell proliferation, by contacting cells expressing Btk, either in vivo or in vitro with a compound having a molecular weight less than 600 amu in an amount sufficient to detectably inhibit the activity of Btk in vitro is provided herein. In certain embodiments the compound will be a heterocyclic compound, such as a heterocyclic compound having a bicyclic heterocyclic group. In certain embodiments the compound is a compound of Formula I-a.

A method of treating a mammal suffering from at least one disease responsive to inhibition of Btk activity, by administering to the mammal an effective amount of a compound that is a highly active Btk inhibitor in an in vitro assay of Btk activity is included herein. Preferably the compound is also a specific inhibitor of B-cell proliferation, exhibiting an $IC_{50}$ value that is at least 3-fold, preferably 5-fold, and more preferably 10-fold greater for T-cell proliferation than the $IC_{50}$ value for B-cell proliferation.

Methods for treating a patient having a disease responsive to inhibition of Btk activity and/or responsive to inhibition of B-cell proliferation, are provided herein. Such methods comprise administering to the patient an effective amount of a compound or form thereof of Formula I-a. The patient may be a mammal. Preferably the patient is a human patient, however methods of treating non-human patients are included herein. For example in some embodiments the patient is a companion animal, such as a cat or dog, or the patient is a livestock animal, such as a horse, cow, or pig. Particularly included herein are methods in which the disease responsive to Btk inhibition is cancer, an autoimmune and/or inflammatory disease, or an acute inflammatory reaction.

Methods of treatment include administering a compound of Formula I-a as a single active agent or administering a compound of Formula I-a in combination with one or more other active agents.

DETAILED DESCRIPTION

Certain terms to be used herein are provided prior to setting forth the invention in detail. Compounds of the present invention are described using standard nomenclature. Unless defined otherwise, all technical and scientific terms used herein have the same meaning as is commonly understood by one of skill in the art to which this invention belongs.

Chemical Description and Terminology

Formula I-a includes all subformulae thereof. For example Formula I-a includes compounds of Formulas 1 to 9.

Certain compounds are described herein using a general formula that includes variables, e.g. $R_1$, $R_2$, $R_3$, Q, $Z_1$, and A. Unless otherwise specified, each variable within such a formula is defined independently of other variables. When any variable occurs more than one time in Formula I-a, its definition on each occurrence is independent of its definition at every other occurrence.

In accordance with the usual meaning of "a" and "the" in patents, reference to "a" kinase or "the" kinase is inclusive of one or more kinases. Unless otherwise specified the term "compounds" includes all pharmaceutically acceptable forms of the disclosed structures.

In certain situations, the compounds of Formula I-a may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, the single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Where a compound exists in various tautomeric forms, the invention is not limited to any one of the specific tautomers, but rather includes all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

The term "substituted", as used herein, means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

Suitable groups that may be present on a "substituted" position include, but are not limited to, e.g., halogen; cyano; hydroxyl; nitro; azido; alkanoyl (such as a $C_2$-$C_6$ alkanoyl group such as acyl or the like); carboxamido; alkyl groups (typically having 1 to about 8 carbon atoms, or 1 to about 6 carbon atoms); cycloalkyl groups, alkenyl and alkynyl groups (including groups having one or more unsaturated linkages and from 2 to about 8, or 2 to about 6 carbon atoms); alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O, or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen or amino.

A dash ("-") that is not between two letters or symbols is used to indicate a point of attachment for a substituent. For example, —CHO is attached through carbon of the carbonyl (C=O) group.

As used herein, "alkyl" includes both branched and straight chain saturated aliphatic hydrocarbon groups, having the specified number of carbon atoms, generally from 1 to about 12 carbon atoms. The term $C_1$-$C_7$alkyl as used herein indicates an alkyl group having from 1 to 7 carbon atoms. When $C_0$-$C_n$alkyl is used herein in conjunction with another group, for example, (heterocycloalkyl)$C_0$-$C_2$alkyl, the indicated group, in this case heterocycloalkyl, is either directly bound by a single covalent bond ($C_0$), or attached by an alkyl chain having the specified number of carbon atoms, in this case from 1 to 2 carbon atoms. Examples of alkyl include, but are not limited to, methyl, ethyl, n-propyl, isopropyl, n-butyl, 3-methylbutyl, t-butyl, n-pentyl, and sec-pentyl. Alkyl groups described herein typically have from 1 to about 12 carbons atoms. Preferred alkyl groups are lower alkyl groups, those alkyl groups having from 1 to about 8 carbon atoms, from 1 to about 6 carbon atoms, or from 1 to about 4 carbons atoms e.g. $C_1$-$C_8$, $C_1$-$C_6$, and $C_1$-$C_4$alkyl groups.

"Alkenyl" as used herein, indicates a straight or branched hydrocarbon chain comprising one or more unsaturated carbon-carbon bonds, which may occur in any stable point along the chain. Alkenyl groups described herein typically have from 2 to about 12 carbons atoms. Preferred alkenyl groups are lower alkenyl groups, those alkenyl groups having from 2 to about 8 carbon atoms, e.g. $C_2$-$C_8$, $C_2$-$C_6$, and $C_2$-$C_4$ alkenyl groups. Examples of alkenyl groups include ethenyl, propenyl, and butenyl groups.

"Alkynyl" as used herein, indicates a straight or branched hydrocarbon chain comprising one or more triple carbon-carbon bonds that may occur in any stable point along the chain, such as ethynyl and propynyl. Alkynyl groups described herein typically have from 2 to about 12 carbons atoms. Preferred alkynyl groups are lower alkynyl groups; those alkynyl groups having from 2 to about 8 carbon atoms, e.g. $C_2$-$C_8$, $C_2$-$C_6$, and $C_2$-$C_4$ alkynyl groups.

"Alkoxy" indicates an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

In the term "(Alkoxy)alkyl" alkoxy and alkyl are as defined above and the point of attachment is on the alkyl group. For example ($C_1$-$C_6$alkoxy)$C_1$-$C_6$alkyl indicates an alkoxy group having from 1 to about 6 carbon atom attached through its oxygen atom to an alkyl group having from 1 to about 6 carbon atoms and further attached to the core molecule through a carbon atom in the $C_1$-$C_6$alkyl portion.

In the term "(Alkoxy)alkoxy" alkoxy is as defined above and the point of attachment is on the oxygen of the second listed alkoxy group. For example ($C_1$-$C_6$alkoxy)$C_1$-$C_4$alkoxy indicates an alkoxy group have from 1 to about 6 carbon atom attached through its oxygen atom to an second alkoxy group, this one having, for example, from 1 to about 4 carbon atoms, and further attached to the core molecule through an oxygen bridge. Similarly the term "(alkoxy)(alkoxy)alkoxy" refers to two such alkoxy groups attached to a third alkoxy, which is further attached to the core molecule through an oxygen bridge.

"Alkanoyl" indicates an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

As used herein, "alkylthio" means alkyl-S—, where the alkyl group is an alkyl group as defined above having the defined number of carbon atoms. An exemplary alkylthio group is methylthio.

As used herein the term "alkoxycarbonyl" indicates an alkoxy group, as defined above, having the indicated number of carbon atoms, attached through a keto (—(C=O)—) bridge. The alkoxy moiety of the alkoxycarbonyl group has the indicated number of carbon atoms. The carbon of the keto bridge is not included in this number. $C_3$alkoxycarbonyl indicates for example, groups of the formula $CH_3(CH_2)_2$—O—(C=O)—or $(CH_3)_2(CH)$—O—(C=O)—.

As used herein "aminoalkyl" is an alkyl group as defined herein, having the indicated number of carbon atoms, and substituted with at least one amino substituent (—$NH_2$). When indicated, aminoalkyl groups, like other groups described herein, may be additionally substituted.

As used herein, the term "mono- and/or di-alkylamino" indicates secondary or tertiary alkylamino groups, wherein the alkyl groups are as defined above and have the indicated number of carbon atoms. The point of attachment of the alkylamino group is on the nitrogen. The alkyl groups are independently chosen. Examples of mono- and/or di-alkylamino groups include ethylamino, dimethylamino, and methyl-propyl-amino. "Mono- and/or di-alkylaminoalkyl" groups are mono- and/or di-alkylamino groups attached through an alkyl linker having the specified number of carbon atoms, for example a di-methylaminoethyl group. Tertiary amino substituents may by designated by nomenclature of the form N—R—N—R', indicating that the groups R and R' are both attached to a single nitrogen atom.

As used herein, the term "mono- and/or di-(alkylamino)alkyl" indicates a mono- and/or di-alkylamino group as defined attached through an alkyl linker having the specified number of carbon atoms. Similarly "mono- and/or di-(alkylamino)alkoxy" indicates a mono- and/or di-alkylamino group as defined attached through an alkoxy linker having the specified number of carbon atoms.

As used herein the term "mono- and/or di-alkylcarboxamide" refers to groups of formula (alkyl$_1$)—NH—(C=O)— and (alkyl$_1$)(alkyl$_2$)—N—(C=O)—in which the alkyl$_1$ and alkyl$_2$ groups are independently chosen alkyl groups as defined above having the indicated number of carbon atoms. "Carboxamide" is a group of the formula —(C=O)$NH_2$.

As used herein, the term "aryl" indicates aromatic groups containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Where indicated, aryl groups may be substituted. Such substitution may include fusion to a 5 to 7-membered saturated cyclic group that optionally contains 1 or 2 heteroatoms independently chosen from N, 0, and S, to form, for example, a 3,4-methylenedioxy-phenyl group. Aryl groups include, for example, phenyl, naphthyl, including 1-naphthyl and 2-naphthyl, and bi-phenyl.

"Cycloalkyl" as used herein, indicates a monocyclic or multicyclic saturated hydrocarbon ring group, having the specified number of carbon atoms, usually from 3 to about 10 ring carbon atoms. Monocyclic cycloalkyl groups typically have from 3 to about 8 carbon ring atoms or from 3 to about 7 carbon ring atoms. Multicyclic cycloalkyl groups may have 2 or 3 fused cycloalkyl rings or contain bridged or caged cycloalkyl groups. Cycloalkyl substituents may be pendant to the substituted nitrogen or carbon atom, or where a substituted carbon atom may have two substituents a cycloalkyl group may be attached as a spiro group. Examples of cycloalkyl groups include cyclopropyl, cyclobutyl, cyclopentyl, or cyclohexyl as well as bridged or caged saturated ring groups such as norbornane or adamantane.

As used herein "(cycloalkyl)$C_0$-$C_2$alkyl indicates a cycloalkyl groups as defined above either directly attached via a single covalent bond or attached through an ethylene (—$CH_2CH_2$—) or methylene (—$CH_2$—) linker.

As used herein "haloalkyl" indicates both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and pentafluoroethyl.

"Haloalkoxy" indicates a haloalkyl group as defined above attached through an oxygen bridge.

"Halo" or "halogen" as used herein refers to fluoro, chloro, bromo, and/or iodo.

As used herein, "heteroaryl" indicates a stable 5- to 7-membered monocyclic aromatic ring which contains from 1 to 4, or preferably from 1 to 2, heteroatoms chosen from N, O, and S, with remaining ring atoms being carbon, or a stable bicyclic or tricyclic system containing at least one 5 to 7 membered aromatic ring which contains from 1 to 4, or preferably from 1 to 2, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, and isoxazolyl.

The term "heterocycloalkyl" indicates a saturated monocyclic group containing from 1 to about 3 heteroatoms chosen from N, O, and S, with remaining ring atoms being carbon, or a saturated bicyclic ring system having at least one N, O, or S ring atom with remaining atoms being carbon. Monocyclic heterocycloalkyl groups have from 4 to about 8 ring atoms, and more typically have from 5 to 7 ring atoms. Bicyclic heterocycloalkyl groups typically have from about five to about 12 ring atoms. Preferred heterocycloalkyl groups include monocyclic heterocycloalkyl groups that contain from 5 to 7 ring atoms and 1 or 2 heteroatoms independently chosen from N, O, and S. Examples of heterocycloalkyl groups include morpholinyl, piperazinyl, piperidinyl, and pyrrolidinyl groups.

In the term "(heterocycloalkyl)alkyl" the groups heterocycloalkyl and alkyl are as defined above and the point of attachment to the core structure is on the alkyl group.

As used herein "hydroxyalkyl" is an alkyl group as defined herein, having the indicated number of carbon atoms, and substituted with at least one hydroxyl substituent (—OH). When indicated, hydroxyalkyl groups, like other groups described herein, may be additionally substituted. Similarly the term "hydroxyalkoxy" indicates an alkoxy group as defined herein, having the indicated number of carbon atoms, and substituted with at least one hydroxyl substituent (—OH).

"Pharmaceutically acceptable forms" of the compounds recited herein include pharmaceutically acceptable salts, hydrates, solvates, crystal forms, polymorphs, chelates, non-covalent complexes, esters, clathrates, prodrugs, and mixtures of such compounds. Pharmaceutically acceptable salts are a preferred pharmaceutically acceptable form.

"Pharmaceutically acceptable salts" include derivatives of the disclosed compounds wherein the parent compound is modified by making non-toxic acid or base salts thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences*, 17th ed., Mack Publishing Company, Easton, Pa., p. 1418 (1985).

The term "prodrugs" includes any compounds that become compounds of Formula I-a when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of Formula I-a.

The term "active agent" is used to indicate a compound, including any pharmaceutically form thereof, or natural product, which has biological activity. Preferably an "active agent" is a compound having pharmaceutical utility. For example an active agent may be a compound of Formula I-a, or an anti-cancer or anti-inflammatory therapeutic, which is not a compound of Formula I-a.

The term "effective amount" of a compound of this invention means an amount effective, when administered to a human or non-human patient, to provide a therapeutic benefit such as amelioration of symptoms, slowing of disease progression, or prevention of disease e.g., an effective amount may be an amount sufficient to decrease the symptoms of a disease responsive to Btk inhibition, and preferably is an amount sufficient to reduce cancer symptoms, the symptoms of an autoimmune and/or inflammatory disease, or the symptoms of an acute inflammatory reaction. In some embodiments an effective amount of a compound described herein is an amount sufficient to decrease the number of detectable cancerous cells in an organism, detectably slow or stop the growth of a cancerous tumor, or more preferably an amount sufficient to shrink a cancerous tumor. In certain circumstances a patient suffering from cancer may not present symptoms of being affected. Thus, a therapeutically effective amount of a compound is also an amount sufficient to prevent a significant increase or significantly reduce the detectable level of cancerous cells or cancer markers in the patient's blood, serum, or tissues. In methods described herein for treating autoimmune and/or inflammatory diseases or acute inflammatory reactions, an effective amount may also be an amount sufficient, when administered to a patient, to detectably slow progression of the disease, or prevent the patient to whom the compound is given from presenting symptoms of the autoimmune and/or inflammatory disease, or acute inflammatory response. In certain methods described herein for treating autoimmune and/or inflammatory diseases or acute inflammatory reactions, an effective amount may also be an amount sufficient to produce a detectable decrease in the amount of a marker protein or cell type in the patient's blood or serum. For example, in some embodiments an effective amount is an amount of a compound described herein sufficient to significantly decrease the number of B-cells. In another example, in some embodiments an effective amount is an amount of a compound described herein sufficient to decrease the level of anti-acetylcholine receptor antibody in a patient's blood with the disease myasthenia gravis,.

The term "inhibition" indicates a significant decrease in the baseline activity of a biological activity or process. "Inhibition of Btk activity" refers to a decrease in Btk activity as a direct or indirect response to the presence of a compound of Formula I-a, relative to the activity of Btk in the absence of the compound. The decrease in activity may be due to the direct interaction of the compound with Btk, or due to the interaction of the compound with one or more other factors that in turn affect Btk activity. For example, the presence of the compound may decrease Btk activity by directly binding to the Btk, by causing (directly or indirectly) another factor to decrease Btk activity, or by (directly or indirectly) decreasing the amount of Btk present in the cell or organism.

Inhibition of Btk activity also refers to observable inhibition of Btk activity in a standard biochemical assay for Btk activity, such as the ATP hydrolysis assay of Example 6. Preferred inhibitors of Btk activity have an $IC_{50}$ value less than or equal to 1 micromolar, more preferably less than or equal to less than 100 nanomolar, and still more preferably less than or equal to 10 nanomolar.

Without wishing to be bound to any particular theory it is believed that the inhibition of Btk activity causes an inhibition of B-cell proliferation. "Inhibition of B-cell proliferation" refers to inhibition of proliferation of abnormal B-cells, such as cancerous B-cells, e.g. lymphoma B-cells and/or inhibition of normal, non-diseased B-cells. The term "inhibition of B-cell proliferation" indicates any significant decrease in the number of B-cells, either in vitro or in vivo. Thus in vitro an inhibition of B-cell proliferation would be any significant decrease in the number of B-cells in an in vitro sample contacted with a compound of Formula I-a as compared to a matched sample not contacted with a compound of Formula I-a.

Inhibition of B-cell proliferation also refers to observable inhibition of B-cell proliferation in a standard thymidine incorporation assay for B-cell proliferation, such as the assay of Example 8. Preferred inhibitors of B-cell proliferation have an $IC_{50}$ value less than or equal to 10 micromolar, more preferably less than or equal to less than 1 micromolar, and still more preferably less than or equal to 500 nanomolar.

By "significant" is meant any detectable change that is statistically significant in a standard parametric test of statistical significance such as Student's T-test, where $p<0.05$.

A "disease responsive to Btk inhibition" is a disease in which inhibiting Btk kinase provides a therapeutic benefit such as an amelioration of symptoms, decrease in disease progression, prevention or delay of disease onset, or inhibition of aberrant activity of certain cell-types (monocytes, B-cells, and mast cells).

IMIDAZO[1,2-a]PYRAZINE COMPOUNDS

In addition to compounds of Formula I-a (above), compounds of Formula 1

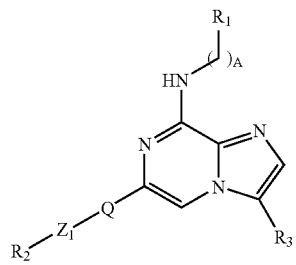

(Formula 1)

and the pharmaceutically acceptable form thereof, are also disclosed.

Within Formula 1:

A is 0 or 1.

$R_1$ is phenyl or heteroaryl, each of which is substituted with one of (i) oxo, —CHO, —COOH, —CONH$_2$, or —CONHOH, (ii) $C_2$-$C_6$ alkenyl, $C_2$-$C_6$ alkynyl, $C_1$-$C_6$hydroxyalkyl, $C_1$-$C_6$hydroxyalkoxy, (mono- or di-$C_1$-$C_6$alkylamino)$C_1$-$C_6$alkoxy, ($C_1$-$C_6$alkoxy)($C_1$-$C_6$alkylamino)$C_0$-$C_6$alkyl, ($C_1$-$C_6$alkoxy)($C_1$-$C_6$alkoxy)$C_1$-$C_6$alkoxy, heterocycloalkyl, aryl, or heteroaryl, (iii) —$C_1$-$C_6$alkyl(C=O)O$R_{10}$, —$C_0$-$C_6$alkyl(C=O)N$R_{10}R_{11}$, —$C_1$-$C_6$alkylN$R_{10}$(SO$_2$)$R_{11}$, —$C_0$-$C_6$alkylN$R_{10}$(C=O)$R_{11}$, —$C_0$-$C_6$alkyl(SO$_2$)$R_{10}$, or —$C_o$-$C_6$alkylN$R_{10}$(C=O)N$R_{11}R_{12}$ where $R_{10}$, $R_{11}$, and $R_{12}$ are independently hydrogen, hydroxy, $C_1$-$C_6$alkyl, $C_1$-$C_6$alkoxy, $C_3$-$C_{10}$cycloalkyl, or heterocycloalkyl, or (iv) -L-G, where L is $C_1$-$C_2$alkyl, $C_0$-$C_2$alkoxy, —(C=O)—, or —($C_1$-$C_2$alkyl)(C=O)—, and G is heterocycloalkyl, $C_3$-$C_7$cycloalkyl, aryl, or heteroaryl.

Each of which (ii), (iii), and (iv) is substituted with 0 to 3 substituents independently chosen from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl.

And, $R_1$ is substituted with 0 or 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono- and di-$C_1$-$C_6$ alkylamino)$C_0$-$C_6$ alkyl, and $C_1$-$C_6$alkoxycarbonyl.

$R_2$ is $C_1$-$C_7$ alkyl, ($C_1$-$C_6$alkoxy)$C_0$-$C_6$alkoxy, (heterocycloalkyl)$C_0$-$C_2$alkyl, ($C_3$-$C_7$cycloalkyl)$C_0$-$C_2$alkyl, or $R_2$ is (phenyl)$C_0$-$C_2$alkyl, (phenoxy)$C_0$-$C_2$alkyl, or (heteroaryl) $C_0$-$C_2$alkyl, each of which is substituted with 0 to 3 substituents independently chosen from hydroxy, nitro, cyano, amino, halogen, —SO$_2$NH$_2$, oxo, —COOH, $C_1$-$C_6$ alkyl, $C_2$-$C_6$alkenyl, $C_2$-$C_6$alkynyl, $C_1$-$C_6$ alkoxy, $C_2$-$C_6$alkanoyl, $C_1$-$C_6$hydroxyalkyl, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$alkyl, mono- and di-$C_1$-$C_6$alkylamino, mono- and di-$C_1$-$C_6$alkylcarboxamide, $C_1$-$C_6$alkoxycarbonyl, phenyl, heteroaryl, and —(C=O)$R_{13}$ wherein $R_{13}$ is $C_1$-$C_6$alkyl, ($C_3$-$C_7$cycloalkyl)$C_0$-$C_2$alkyl, $C_1$-$C_3$haloalkyl, heterocycloalkyl, phenyl, or heteroaryl.

Z, is

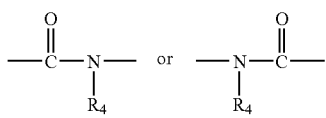

wherein $R_4$ is hydrogen, or $R_4$ is $C_1$-$C_6$alkyl, $C_3$-$C_7$cycloalkyl, heterocycloalkyl, phenyl, or heteroaryl, each of which is substituted with 0 or 1 or more substituents independently chosen from hydroxy, nitro, cyano, amino, halogen, oxo, $C_1$-$C_6$ alkyl, $C_2$-$C_6$alkenyl, $C_2$-$C_6$alkynyl, $C_1$-$C_6$ alkoxy, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$ alkyl, mono- and di-$C_1$-$C_6$ alkylamino, and —C(O)$R_{14}$ wherein $R_{14}$ is $C_1$-$C_6$ alkyl, $C_1$-$C_3$haloalkyl, or phenyl.

Q is phenyl or pyridyl.

$R_3$ is hydrogen, halogen, or $C_1$-$C_7$ alkyl, or $R_3$ is heterocycloalkyl, $C_3$-$C_7$cycloalkyl, or heteroaryl, each of which is substituted with from 0 to 3 substituents independently chosen from hydroxy, nitro, cyano, amino, halogen, —SO$_2$NH$_2$, oxo, $C_1$-$C_6$ alkyl, $C_2$-$C_6$alkenyl, $C_2$-$C_6$alkynyl, $C_1$-$C_6$ alkoxy, $C_1$-$C_3$halooalkyl, $C_1$-$C_3$haloalkoxy, $C_1$-$C_6$ alkylthio, ($C_1$-$C_6$-alkoxy)$C_1$-$C_6$ alkoxy, mono- and di-$C_1$-$C_6$alkylamino, amino$C_1$-$C_6$ alkyl, and —C(O)$R_{14}$.

The Variable A

Also included herein are compounds of Formula 1 wherein A is 0 and compounds of Formula 1 wherein A is 1.

The Variable $R_1$

Further provided herein are compounds of Formula 1 and pharmaceutically acceptable forms thereof, wherein the variable $R_1$ satisfies one or more of the following conditions set forth in A. to O.

A. $R_1$ is phenyl or pyridyl, each of which is substituted with one of (i) oxo, —CHO, —COOH, —CONH$_2$, or —CONHOH, (ii) $C_2$-$C_6$ alkenyl, $C_2$-$C_6$ alkynyl, $C_1$-$C_6$hydroxyalkyl, $C_1$-$C_6$hydroxyalkoxy, (mono- or di-$C_1$-$C_6$alkylamino)$C_1$-$C_6$alkoxy, ($C_1$-$C_6$alkoxy)($C_1$-$C_6$alkylamino)$C_0$-$C_6$alkyl, ($C_1$-$C_6$alkoxy)($C_1$-$C_6$alkoxy)$C_1$-$C_6$alkoxy, heterocycloalkyl, aryl, or heteroaryl, (iii) —$C_1$-$C_6$alkyl(C=O)O$R_{10}$, —$C_0$-$C_6$alkyl(C=O)N$R_{10}R_{11}$, —$C_1$-$C_6$alkylN$R_{10}$(SO$_2$)$R_{11}$, —$C_0$-$C_6$alkylN$R_{10}$(C=O)$R_{11}$, —$C_0$-$C_6$alkyl(SO$_2$)$R_{10}$, or —$C_0$-$C_6$alkylN$R_{10}$(C=O)N$R_{11}R_{12}$, where $R_{10}$, $R_{11}$, and $R_{12}$ are independently hydrogen, hydroxy, $C_1$-$C_6$alkyl, $C_1$-$C_6$alkoxy, $C_3$-$C_{10}$cycloalkyl, or heterocycloalkyl, or (iv) -L-G, where L is $C_1$-$C_2$alkyl, $C_0$-$C_2$alkoxy, —(C=O)—, or —($C_1$-$C_2$alkyl)(C=O)—, and G is heterocycloalkyl, $C_3$-$C_7$cycloalkyl, aryl, or heteroaryl.

Each of which (ii), (iii), and (iv) is substituted with 0 to 3 substituents independently chosen from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl.

And, $R_1$ is substituted with 0 or 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono- and di-$C_1$-$C_6$ alkylamino)$C_0$-$C_6$ alkyl, and $C_1$-$C_6$alkoxycarbonyl.

B. $R_1$ is phenyl or pyridyl, each of which is substituted with one of oxo, —CHO, —COOH, —CONH$_2$, or —CONHOH, and $R_1$ is substituted with 0 or 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono- and di-$C_1$-$C_6$ alkylamino)$C_0$-$C_6$ alkyl, and $C_1$-$C_6$alkoxycarbonyl.

C. $R_1$ is phenyl or pyridyl, each of which is substituted with one of oxo, —CHO, —COOH, —CONH$_2$, or —CONHOH, and $R_1$ is substituted with from 0 to 3 substituents independently chosen from hydroxy, cyano, halogen, $C_1$-$C_4$alkyl, $C_2$-$C_4$alkanoyl, $C_1$-$C_2$haloalkyl, $C_1$-$C_2$haloalkoxy, $C_1$-$C_4$alkoxy, and mono- and di-$C_1$-$C_4$alkylamino.

D. $R_1$ is phenyl or pyridyl, each of which is substituted with one of oxo, —CHO, —COOH, —CONH$_2$, or —CONHOH, and $R_1$ is substituted with from 0 to 3 substituents independently chosen from hydroxy, cyano, halogen, $C_1$-$C_2$alkyl, and $C_1$-$C_2$alkoxy.

E. $R_1$ is phenyl or pyridyl, each of which is substituted with one of (ii) $C_2$-$C_6$ alkenyl, $C_2$-$C_6$ alkynyl, $C_1$-$C_6$hydroxyalkyl, $C_1$-$C_6$hydroxyalkoxy, (mono- or di-$C_1$-$C_6$alkylamino)$C_1$-$C_6$alkoxy, ($C_1$-$C_6$alkoxy)($C_1$-$C_6$alkylamino)$C_0$-$C_6$alkyl, ($C_1$-$C_6$alkoxy)($C_1$-$C_6$alkoxy)$C_1$-$C_6$alkoxy, heterocycloalkyl, aryl, or heteroaryl.

Each of which (ii) is substituted with 0 to 3 substituents independently chosen from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl.

And, $R_1$ is substituted with 0 or 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono- and di-$C_1$-$C_6$ alkylamino)$C_0$-$C_6$ alkyl, and $C_1$-$C_6$alkoxycarbonyl.

F. $R_1$ is phenyl or pyridyl, each of which is substituted with one of $C_1$-$C_6$hydroxyalkyl, $C_1$-$C_6$hydroxyalkoxy, (mono- or di-$C_1$-$C_6$alkylamino)$C_1$-$C_6$alkoxy, ($C_1$-$C_6$alkoxy)($C_1$-$C_6$alkylamino)$C_0$-$C_6$alkyl, or ($C_1$-$C_6$alkoxy)($C_1$-$C_6$alkoxy)$C_1$-$C_6$alkoxy, each of which is substituted with 0 to 3 substituents independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono- and di-$C_1$-$C_4$alkylamino, and mono- and di-$C_1$-$C_4$alkylcarboxamide.

And, $R_1$ is substituted with from 0 to 3 substituents independently chosen from hydroxy, cyano, halogen, $C_1$-$C_4$alkyl, $C_2$-$C_4$alkanoyl, $C_1$-$C_2$haloalkyl, $C_1$-$C_2$haloalkoxy, $C_1$-$C_4$alkoxy, and mono- and di-$C_1$-$C_4$alkylamino.

G. $R_1$ is phenyl or pyridyl, each of which is substituted with one of $C_1$-$C_6$hydroxyalkyl, $C_1$-$C_6$hydroxyalkoxy, (mono- or di-$C_1$-$C_6$alkylamino)$C_1$-$C_6$alkoxy, ($C_1$-$C_6$alkoxy)($C_1$-$C_6$alkylamino)$C_0$-$C_6$alkyl, or ($C_1$-$C_6$alkoxy)($C_1$-$C_6$alkoxy)$C_1$-$C_6$alkoxy.

And, $R_1$ is substituted with from 0 to 3 substituents independently chosen from hydroxy, cyano, halogen, $C_1$-$C_2$alkyl, and $C_1$-$C_2$alkoxy.

H. $R_1$ is phenyl or pyridyl, each of which is substituted with one of pyrrolidinyl, morpholinyl, thiomorpholinyl, piperazinyl, piperidinyl, [1,4]diazepanyl, phenyl, imidazolyl, or 5,6-dihydro-8H-[1,2,4]triazolo[4,3-a]pyrazine, each of which is substituted with 0 to 3 substituents independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono- and di-$C_1$-$C_4$alkylamino, and mono- and di-$C_1$-$C_4$alkylcarboxamide.

And, $R_1$ is substituted with from 0 to 3 substituents independently chosen from hydroxy, cyano, halogen, $C_1$-$C_4$alkyl, $C_2$-$C_4$alkanoyl, $C_1$-$C_2$haloalkyl, $C_1$-$C_2$haloalkoxy, $C_1$-$C_4$alkoxy, and mono- and di-$C_1$-$C_4$alkylamino.

I. $R_1$ is phenyl or pyridyl, each of which is substituted with one of pyrrolidinyl, morpholinyl, thiomorpholinyl, piperazinyl, piperidinyl, [1,4]diazepanyl, phenyl, imidazolyl, or 5,6-dihydro-8H-[1,2,4]triazolo[4,3-a]pyrazine, each of which is substituted with 0 to 3 substituents independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono- and di-$C_1$-$C_4$alkylamino, and mono- and di-$C_1$-$C_4$alkylcarboxamide.

And, $R_1$ is substituted with from 0 to 3 substituents independently chosen from hydroxy, cyano, halogen, $C_1$-$C_2$alkyl, and $C_1$-$C_2$alkoxy.

J. $R_1$ is phenyl or pyridyl, each of which is substituted with one of (iii) —$C_1$-$C_6$alkyl(C=O)O$R_{10}$, —$C_0$-$C_6$alkyl(C=O)N$R_{10}R_{11}$, —$C_1$-$C_6$alkylN$R_{10}$(SO$_2$)$R_{11}$, —$C_0$-$C_6$alkylN$R_{10}$(C=O)$R_{11}$, —$C_0$-$C_6$alkyl(SO$_2$)$R_{10}$, or —$C_0$-$C_6$alkylN$R_{10}$(C=O)N$R_{11}R_{12}$ where $R_{10}$, $R_{11}$, and $R_{12}$ are independently hydrogen, hydroxy, $C_1$-$C_6$alkyl, $C_1$-$C_6$alkoxy, $C_3$-$C_7$cycloalkyl, or heterocycloalkyl, Each of which (iii) is substituted with 0 to 3 substituents independently chosen from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl.

And, $R_1$ is substituted with 0 or 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono- and di-$C_1$-$C_6$ alkylamino)$C_0$-$C_6$ alkyl, and $C_1$-$C_6$alkoxycarbonyl.

K. $R_1$ is phenyl or pyridyl, each of which is substituted with one of —$C_1$-$C_4$alkyl(C=O)O$R_{10}$, —$C_0$-$C_4$alkyl(C=O)N$R_{10}R_{11}$, —$C_1$-$C_4$alkylN$R_{10}$(SO$_2$)$R_{11}$, —$C_0$-$C_4$alkylN$R_{10}$(C=O)$R_{11}$, —$C_0$-$C_4$alkyl(SO$_2$)$R_{10}$, or —$C_0$-$C_4$alkylN$R_{10}$(C=O)N$R_{11}R_{12}$ where $R_{10}$, $R_{11}$, and $R_{12}$ are independently hydrogen, hydroxy, $C_1$-$C_6$alkyl, $C_1$-$C_6$alkoxy, $C_3$-$C_{10}$cycloalkyl, pyrrolidinyl, morpholinyl, thiomorpholinyl, piperazinyl, piperidinyl, or [1,4]diazepanyl, each of which is substituted with 0 to 3 substituents independently chosen from halogen, hydroxy, amino, oxo, —COOH, —CONH$_2$, $C_1$-$C_4$alkoxy, $C_2$-$C_4$alkanoyl, $C_1$-$C_4$alkoxycarbonyl, mono- and di-$C_1$-$C_4$alkylamino, and mono- and di-$C_1$-$C_4$alkylcarboxamide.

And, $R_1$ is substituted with from 0 to 3 substituents independently chosen from hydroxy, cyano, halogen, $C_1$-$C_2$alkyl, and $C_1$-$C_2$alkoxy.

L. $R_1$ is phenyl or pyridyl, each of which is substituted with one of (iv) -L-G, where L is $C_1$-$C_2$alkyl, $C_0$-$C_2$alkoxy, —(C=O)—, or —($C_1$-$C_2$alkyl)(C=O)—, and G is heterocycloalkyl, $C_3$-$C_7$cycloalkyl, aryl, or heteroaryl, each of which (iv) is substituted with 0 to 3 substituents independently chosen from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl.

And, $R_1$ is substituted with 0 or 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono- and di-$C_1$-$C_6$ alkylamino)$C_0$-$C_6$ alkyl, and $C_1$-$C_6$alkoxycarbonyl.

M. $R_1$ is phenyl or pyridyl, each of which is substituted with one of -L-G, where L is $C_1$-$C_2$alkyl, $C_0$-$C_2$alkoxy, —(C=O)—, or —($C_1$-$C_2$alkyl)(C=O)—, and G is pyrrolidinyl, morpholinyl, thiomorpholinyl, piperazinyl, piperidinyl, [1,4]diazepanyl, phenyl, imidazolyl, or 5,6-dihydro-8H-[1,2,4]triazolo[4,3-a]pyrazine, each of which is substituted with 0 to 3 substituents independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono- and di-$C_1$-$C_4$alkylamino, and mono- and di-$C_1$-$C_4$alkylcarboxamide.

And, $R_1$ is substituted with from 0 to 3 substituents independently chosen from hydroxy, cyano, halogen, $C_1$-$C_4$alkyl, $C_2$-$C_4$alkanoyl, $C_1$-$C_2$haloalkyl, $C_1$-$C_2$haloalkoxy, and mono- and di-$C_1$-$C_4$alkylamino.

N. $R_1$ is phenyl or pyridyl, each of which is substituted with one of -L-G, where L is $C_1$-$C_2$alkyl, $C_0$-$C_2$alkoxy, —(C=O)—, or —($C_1$-$C_2$alkyl)(C=O)—, and G is pyrrolidinyl, morpholinyl, thiomorpholinyl, piperazinyl, piperidinyl, [1,4]diazepanyl, phenyl, imidazolyl, or 5,6-dihydro-8H-[1,2,4]triazolo[4,3-a]pyrazine, each of which is substituted with 0 to 3 substituents independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono- and di-$C_1$-$C_4$alkylamino, and mono- and di-$C_1$-$C_4$alkylcarboxamide.

And, $R_1$ is substituted with from 0 to 3 substituents independently chosen from hydroxy, cyano, halogen, $C_1$-$C_2$alkyl, and $C_1$-$C_2$alkoxy.

O. L is phenyl or pyridyl, each of which is substituted with one of —CH$_2$—, —(C=O)—, or —(CH$_2$)(C=O)—, and G is pyrrolidinyl, morpholinyl, thiomorpholinyl, piperazinyl, piperidinyl, or [1,4]diazepanyl, each of which is substituted with 0 to 3 substituents independently chosen from halogen, hydroxy, oxo, —COOH, —CONH$_2$, $C_1$-$C_2$alkyl, $C_1$-$C_2$alkoxy, $C_2$-$C_2$alkanoyl, $C_1$-$C_2$alkoxycarbonyl, mono- and di-$C_1$-$C_2$alkylamino, and mono- and di-$C_1$-$C_2$alkylcarboxamide.

And, $R_1$ is substituted with from 0 to 3 substituents independently chosen from hydroxy, halogen, $C_1$-$C_2$alkyl, and $C_1$-$C_2$alkoxy.

Also disclosed herein are compounds and pharmaceutically acceptable forms of Formula 2:

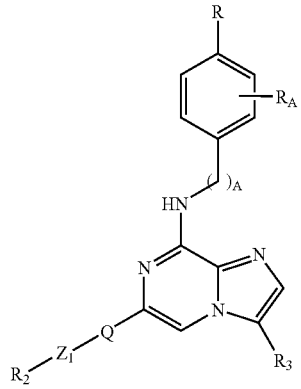

Formula 2

Within Formula 2

A, $R_2$, $Z_1$, Q, and $R_3$ carry any of the definitions set forth herein for these variables. For example $R_2$ may have the definition set forth for this variable in Formula I-a, $R_2$ may have the definition set forth for this variable in Formula 1, $R_2$ may have any of the values set forth for this variable in the claims, or in the subsection titled "the $R_2$ variable."

R is (i) oxo, —CHO, —COOH, —CONH$_2$, or —CONHOH, (ii) $C_2$-$C_6$ alkenyl, $C_2$-$C_6$ alkynyl, $C_1$-$C_6$hydroxyalkyl, $C_1$-$C_6$hydroxyalkoxy, (mono- or di-$C_1$-$C_6$alkylamino)$C_1$-$C_6$alkoxy, ($C_1$-$C_6$alkoxy)($C_1$-$C_6$alkylamino)$C_0$-$C_6$alkyl, ($C_1$-$C_6$alkoxy)($C_1$-$C_6$alkoxy)$C_1$-$C_6$alkoxy, heterocycloalkyl, aryl, or heteroaryl, (iii) —$C_1$-$C_6$alkyl(C=O)O$R_{10}$, —$C_0$-$C_6$alkyl(C=O)N$R_{10}R_{11}$, —$C_1$-$C_6$alkylN$R_{10}$(SO$_2$)$R_{11}$, —$C_0$-$C_6$alkylN$R_{10}$(C=O)$R_{11}$, —$C_0$-$C_6$alkyl(SO$_2$)$R_{10}$, or —$C_0$-$C_6$alkylN$R_{10}$(C=O)N$R_{11}R_{12}$ where $R_{10}$, $R_{11}$, and $R_{12}$ are independently hydrogen, hydroxy, $C_1$-$C_6$alkyl, $C_1$-$C_6$alkoxy, $C_3$-$C_{10}$cycloalkyl, or heterocycloalkyl, or (iv) -L-G, where L is $C_1$-$C_2$alkyl, $C_0$-$C_2$alkoxy, —(C=O)—, or —($C_1$-$C_2$alkyl)(C=O)—, and G is heterocycloalkyl, $C_3$-$C_7$cycloalkyl, aryl, or heteroaryl, Each of which (ii), (iii), and (iv) is substituted with 0 to 3 substituents independently chosen from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl.

$R_A$ is 0 or 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_2$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono- and di-$C_1$-$C_6$ alkylamino)$C_0$-$C_6$ alkyl, and $C_1$-$C_6$alkoxycarbonyl.

Another embodiment includes compounds and pharmaceutically acceptable forms in which $R_1$ is a phenyl substituted at the para position by R, and substituted at any other position by $R_A$ i.e. the invention provides compounds and pharmaceutically acceptable forms of Formula 3

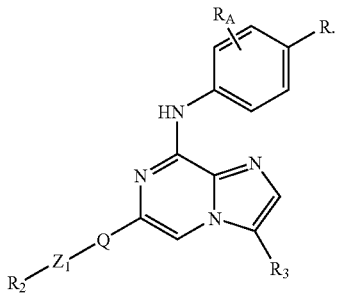

Formula 3

Within Formula 3

$R_2$, $Z_1$, Q, and $R_3$ carry any of the definitions set forth herein for these variables and R and $R_A$ carry the definitions set forth for these variables for Formula 2.

The $R_2$ Variable

Further provided herein are compounds of Formula 1 and pharmaceutically acceptable forms thereof, wherein the variable $R_2$ satisfies one or more of the following conditions.

A. $R_2$ is (phenyl)$C_0$-$C_2$alkyl, (phenoxy)$C_0$-$C_2$alkyl, or (pyridyl)$C_0$-$C_2$alkyl, each of which is substituted with 0 to 3 substituents independently chosen from hydroxy, nitro, cyano, amino, halogen, —SO$_2$NH$_2$, oxo, —COOH, $C_1$-$C_6$ alkyl, $C_2$-$C_6$alkenyl, $C_2$-$C_6$alkynyl, $C_1$-$C_6$ alkoxy, $C_2$-$C_6$alkanoyl, $C_1$-$C_6$hydroxyalkyl, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$alkyl, mono- and di-$C_1$-$C_6$ alkylamino, mono- and di-$C_1$-$C_6$alkylcarboxamide, $C_1$-$C_6$alkoxycarbonyl, phenyl, heteroaryl, and —C=O)$R_{13}$ wherein $R_{13}$ is $C_1$-$C_6$alkyl, ($C_3$-$C_7$cycloalkyl)$C_0$-$C_2$alkyl, $C_1$-$C_3$haloalkyl, heterocycloalkyl, phenyl, or heteroaryl.

B. $R_2$ is (phenyl)$C_0$-$C_2$alkyl, (phenoxy)$C_0$-$C_2$alkyl, or (pyridyl)$C_0$-$C_2$alkyl, each of which is substituted with 0 to 3 substituents independently chosen from hydroxy, cyano, amino, halogen, —SO$_2$NH$_2$, oxo, —COOH, $C_1$-$C_4$ alkyl, $C_1$-$C_4$ alkoxy, $C_2$-$C_4$alkanoyl, $C_1$-$C_4$hydroxyalkyl, $C_1$-$C_2$haloalkyl, $C_1$-$C_2$haloalkoxy, mono- and di-$C_1$-$C_6$alkylamino, mono- and di-$C_1$-$C_6$alkylcarboxamide, $C_1$-$C_4$alkoxycarbonyl, phenyl, and imidazolyl.

The $Z_1$ Variable

Within certain embodiments $Z_1$ is

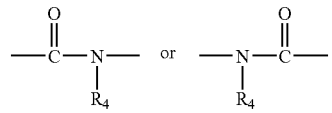

wherein $R_4$ is hydrogen, $C_1$-$C_6$alkyl, or $C_3$-$C_7$cycloalkyl. In some of these embodiments $R_4$ is hydrogen or methyl.

The Q Variable

Additional embodiments, pertain to compounds and pharmaceutically acceptable forms of Formula 4 and Formula 5

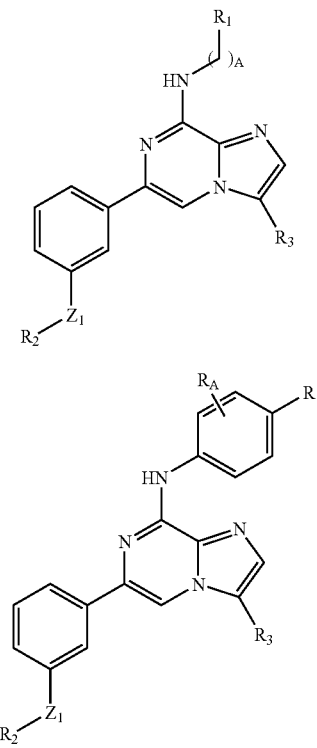

Formula 4

Formula 5

Within Formula 4 and 5:

A, R, $R_4$, $R_1$, $R_2$, $Z_1$, and $R_3$ carry any of the definitions set forth herein for these variables.

In certain embodiments of Formula 5, R is (i) oxo, —CHO, —COOH, —CONH$_2$, or —CONHOH, (ii) $C_2$-$C_6$ alkenyl, $C_2$-$C_6$ alkynyl, $C_1$-$C_6$hydroxyalkyl, $C_1$-$C_6$hydroxyalkoxy, (mono- or di-$C_1$-$C_6$alkylamino)$C_1$-$C_6$alkoxy, ($C_1$-$C_6$alkoxy)($C_1$-$C_6$alkylamino)$C_0$-$C_6$alkyl, ($C_1$-$C_6$alkoxy)($C_1$-$C_6$alkoxy)$C_1$-$C_6$alkoxy, heterocycloalkyl, aryl, or heteroaryl, (iii) —$C_1$-$C_6$alkyl(C=O)OR$_{10}$, —$C_0$-$C_6$alkyl(C=O)NR$_{10}$R$_{11}$, —$C_1$-$C_6$alkylNR$_{10}$(SO$_2$)R$_1$, —$C_0$-$C_6$alkylNR$_{10}$(C=O)R$_{11}$, —$C_0$-$C_6$alkyl(SO$_2$)R$_{10}$, or —$C_o$-$C_6$alkylNR$_0$(C=O)NR$_{11}$R$_{12}$ where $R_{10}$, $R_{11}$, and $R_{12}$ are independently hydrogen, hydroxy, $C_1$-$C_6$alkyl, $C_1$-$C_6$alkoxy, $C_3$-$C_{10}$cycloalkyl, or heterocycloalkyl, or (iv) -L-G, where L is $C_1$-$C_2$alkyl, $C_0$-$C_2$alkoxy, —(C=O)—, or —(C$_1$-$C_2$alkyl)(C=O)—, and G is heterocycloalkyl, $C_3$-$C_7$cycloalkyl, aryl, or heteroaryl.

Each of which (ii), (iii), and (iv) is substituted with 0 to 3 substituents independently chosen from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl.

$R_4$ is 0 or 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono- and di-$C_1$-$C_6$ alkylamino)$C_0$-$C_6$ alkyl, and $C_1$-$C_6$alkoxycarbonyl.

The $R_3$ Variable $R_3$ is hydrogen or methyl in certain compounds of the invention and pharmaceutically acceptable forms described herein.

Additional embodiments of the invention pertain to compounds of Formula 6

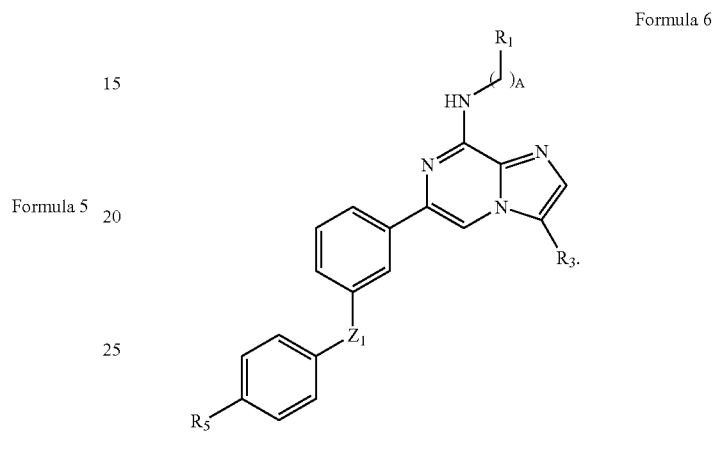

Formula 6 and the pharmaceutically acceptable forms thereof.

Within Formula 6

$Z_1$, $R_3$ and A variables carry any of the definitions set forth herein for these variables.

$R_1$ is phenyl or heteroaryl, each of which is optionally substituted with one of (i) oxo, —CHO, —COOH, —CONH$_2$, or —CONHOH, (ii) $C_2$-$C_6$ alkenyl, $C_2$-$C_6$ alkynyl, $C_1$-$C_6$hydroxyalkyl, $C_1$-$C_6$hydroxyalkoxy, (mono- or di-$C_1$-$C_6$alkylamino) $C_1$-$C_6$alkoxy, ($C_1$-$C_6$alkoxy)($C_1$-$C_6$alkylamino)$C_0$-$C_6$alkyl, ($C_1$-$C_6$alkoxy)($C_1$-$C_6$alkoxy)$C_1$-$C_6$alkoxy, heterocycloalkyl, aryl, or heteroaryl, (iii) —$C_1$-$C_6$alkyl(C=O)OR$_{10}$, —$C_0$-$C_6$alkyl(C=O)NR$_{10}$R$_{11}$, —$C_1$-$C_6$alkylNR$_{10}$(SO$_2$)R$_{11}$, —$C_0$-$C_6$alkylNR$_{10}$(C=O)R$_{11}$, —$C_0$-$C_6$alkyl(SO$_2$)R$_{10}$, or —$C_o$-$C_6$alkylNR$_{10}$(C=O)NR$_{11}$R$_{12}$ where $R_{10}$, $R_{11}$, and $R_{12}$ are independently hydrogen, hydroxy, $C_1$-$C_6$alkyl, $C_1$-$C_6$alkoxy, $C_3$-$C_{10}$cycloalkyl, or heterocycloalkyl, or (iv) -L-G, where L is $C_1$-$C_2$alkyl, $C_0$-$C_2$alkoxy, —(C=O)—, or —(C$_1$-$C_2$alkyl)(C=O)—, and G is heterocycloalkyl, $C_3$-$C_7$cycloalkyl, aryl, or heteroaryl.

Each of which (ii), (iii), and (iv) is substituted with 0 to 3 substituents independently chosen from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl.

And, $R_1$ is substituted with 0 or 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono- and di-$C_1$-$C_6$ alkylamino)$C_0$-$C_6$ alkyl, and $C_1$-$C_6$alkoxycarbonyl.

$R_5$ is isopropyl or t-butyl.

Other embodiments pertain to compounds and forms thereof of Formula 7 to Formula 9

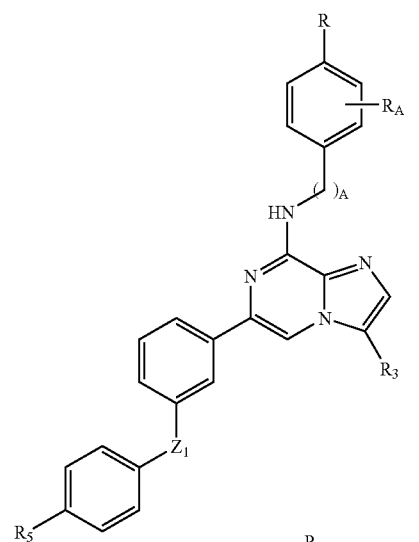

Formula 7

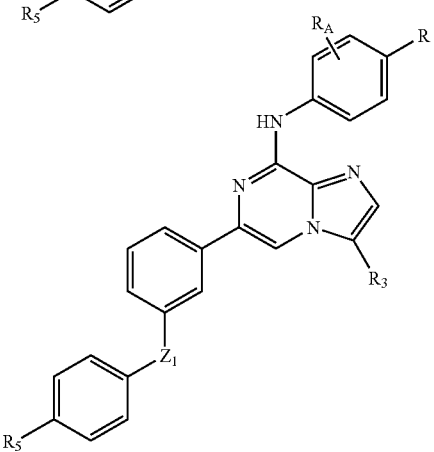

Formula 8

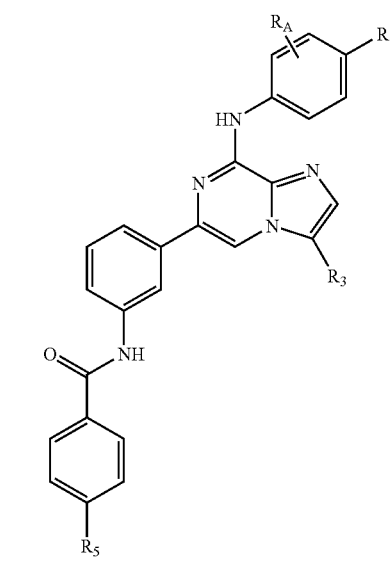

Formula 9

Within Formula 7 to Formula 9:

R is (i) oxo, —CHO, —COOH, —CONH$_2$, or —CONHOH, (ii) $C_2$-$C_6$ alkenyl, $C_2$-$C_6$ alkynyl, $C_1$-$C_6$hydroxyalkyl, $C_1$-$C_6$hydroxyalkoxy, (mono- or di-$C_1$-$C_6$alkylamino)$C_1$-$C_6$alkoxy, ($C_1$-$C_6$alkoxy) ($C_1$-$C_6$alkylamino)$C_0$-$C_6$alkyl, ($C_1$-$C_6$alkoxy)($C_1$-$C_6$alkoxy)$C_1$-$C_6$alkoxy, heterocycloalkyl, aryl, or heteroaryl, (iii) —$C_1$-$C_6$alkyl(C=O)OR$_{10}$, —$C_0$-$C_6$alkyl(C=O)NR$_{10}$R$_{11}$, —$C_1$-$C_6$alkylNR$_{10}$(SO$_2$)R$_{11}$, —$C_0$-$C_6$alkylNR$_{10}$(C=O)R$_{11}$, —$C_0$-$C_6$alkyl(SO$_2$)R$_{10}$, or —$C_o$-$C_6$alkylNR$_{10}$(C=O)NR$_{11}$R$_{12}$ where R$_{10}$, R$_{11}$, and R$_{12}$ are independently hydrogen, hydroxy, $C_1$-$C_6$alkyl, $C_1$-$C_6$alkoxy, $C_3$-$C_{10}$cycloalkyl, or heterocycloalkyl, or (iv) -L-G, where L is $C_1$-$C_2$alkyl, $C_0$-$C_2$alkoxy, —(C=O)—, or —($C_1$-$C_2$alkyl)(C=O)—, and G is heterocycloalkyl, $C_3$-$C_7$cycloalkyl, aryl, or heteroaryl.

Each of which (ii), (iii), and (iv) is substituted with 0 to 3 substituents independently chosen from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl.

$R_A$ is 0 or 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono- and di-$C_1$-$C_6$ alkylamino)$C_0$-$C_6$ alkyl, and $C_1$-$C_6$alkoxycarbonyl.

$R_5$ is isopropyl or t-butyl.

A, $Z_1$, and $R_3$ may carry any of the definitions set forth above for these variables. It certain embodiments it is preferred that $R_3$ is hydrogen or methyl.

PARMACEUTICAL PREPARATIONS

Compounds, salts, and any other pharmaceutically acceptable forms of the invention can be administered as the neat chemical, but are preferably administered as a pharmaceutical composition or formulation. Accordingly, the invention provides pharmaceutical formulations comprising a compound or pharmaceutically acceptable form of Formula I-a, together with one or more pharmaceutically acceptable carriers, excipients, adjuvants, diluents, or other ingredients.

Pharmaceutical carriers must be of sufficiently high purity and sufficiently low toxicity to render them suitable for administration to the animal being treated. The carrier can be inert or it can possess pharmaceutical benefits. The amount of carrier employed in conjunction with the compound is sufficient to provide a practical quantity of material for administration per unit dose of the compound.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound of the present invention.

Effective concentrations of one or more of the compounds of the invention including pharmaceutically acceptable salts, esters or other derivatives thereof are mixed with a suitable pharmaceutical carrier, excipients, adjuvant, or vehicle. In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as salts of the compounds or prodrugs of the compounds may also be used in formulating effective pharmaceutical compositions.

Upon mixing or addition of the compound(s) of the invention, the resulting mixture may be a solution, suspension, emulsion or the like. The form of the resulting mixture depends upon a number of factors, including the intended mode of administration and the solubility of the compound in the chosen carrier or vehicle. The effective concentration sufficient for ameliorating the symptoms of the disease treated and may be empirically determined.

Compounds of provided herein may be administered orally, topically, parenterally, intravenously, by intramuscular injection, by inhalation or spray, sublingually, transdermally, via buccal administration, rectally, as an ophthalmic solution, or by other means, in dosage unit formulations.

Dosage formulations suitable for oral use, include, for example, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. Oral formulations contain between 0.1 and 99% of a compound of the invention and usually at least about 5% (weight %) of a compound of the present invention. Some embodiments contain from about 25% to about 50% or from 5% to 75% of a compound of invention.

Orally administered compositions also include liquid solutions, emulsions, suspensions, powders, granules, elixirs, tinctures, syrups, and the like. The pharmaceutically acceptable carriers suitable for preparation of such compositions are well known in the art. Oral formulations may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such formulations may also contain a demulcent.

Orally Administered Liquids Formulations

Compounds of the invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

Suspensions

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Emulsions

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible Powders

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets and Capsules

Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Injectable and Parenteral Formulations

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid are useful in the preparation of injectables.

Compounds of the invention may be administered parenterally in a sterile medium. Parenteral administration includes subcutaneous injections, intravenous, intramuscular, intrathecal injection or infusion techniques. The compound or compounds of the invention, depending on the vehicle and concentration used, can either be suspended or dissolved in the vehicle. Advantageously, adjuvants such as local anesthetics, preservatives and buffering agents can be dissolved in the vehicle. In many compositions for parenteral administration the carrier comprises at least about 90% by weight of the total composition. Preferred carriers for parenteral administration include propylene glycol, ethyl oleate, pyrrolidone, ethanol, and sesame oil.

Suppositories

Compounds of the invention may also be administered in the form of suppositories for rectal administration of the drug. These compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Topical Formulations

Compounds of the invention may be formulated for local or topical application, such as for topical application to the skin and mucous membranes, such as in the eye, in the form of gels, creams, and lotions and for application to the eye. Topical compositions of the present invention may be in any form including, for example, solutions, creams, ointments, gels, lotions, milks, cleansers, moisturizers, sprays, skin patches, and the like.

Such solutions may be formulated as 0.01%-10% isotonic solutions, pH about 5-7, with appropriate salts. Compounds of the invention may also be formulated for transdermal administration as a transdermal patch.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Emollients, such as stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, isobutane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydro furan; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, filmed silica, carboxyvinyl polymer, sodium carboxymethyl cellulose, and ethylene glycol monostearate.

Compounds of the invention may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other Formulations

Other compositions useful for attaining systemic delivery of the subject compounds include sublingual, buccal and nasal dosage forms. Such compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Additional Components

The compositions of the present invention may also optionally comprise an activity enhancer. The activity enhancer can be chosen from a wide variety of molecules that function in different ways to enhance therapeutic effects of compounds of the invention. Particular classes of activity enhancers include skin penetration enhancers and absorption enhancers.

Pharmaceutical compositions of the invention may also contain additional active agents can be chosen from a wide variety of molecules, which can function in different ways to enhance the therapeutic effects of a compound of the invention. These optional other active agents, when present, are typically employed in the compositions of the invention at a level ranging from about 0.01% to about 15%. Some embodiments contain from about 0.1% to about 10% by weight of the composition. Other embodiments contain from about 0.5% to about 5% by weight of the composition.

Packaged Formulations

The invention includes packaged pharmaceutical formulations. Such packaged formulations include a pharmaceutical composition containing one or more compounds, salts, or other pharmaceutically acceptable forms thereof, of the invention in a container and instructions for using the composition to treat a mammal (typically a human patient). Preferably the instructions are for using the pharmaceutical composition to treat a patient suffering from a disease responsive to inhibition of Btk activity and/or inhibition of B-cell proliferation. The invention includes providing prescribing information; for example, to a patient or health care provider, or as a label in a packaged pharmaceutical formulation. Prescribing information may include for example efficacy, dosage and administration, contraindication and adverse reaction information pertaining to the pharmaceutical formulation.

In all of the foregoing the compounds of the invention can be administered alone, as mixtures, or in combination with other active agents.

METHODS OF TREATMENT

Imidazo[1,2-a]pyrazines active as kinase inhibitors, in particular Btk inhibitors are described herein. These inhibitors are useful for treating diseases responsive to kinase inhibition, including diseases responsive to Btk inhibition and/or inhibition of B-cell proliferation, in mammals. Without wishing to be bound to any particular theory, it is believed that the interaction of the compounds of Formula I-a with Btk results in the inhibition of Btk activity and thus in the pharmaceutical utility of these compounds. Other kinases that may be affected in addition to Btk include, but are not limited to, other tyrosine kinases and serine/threonine kinases.

Accordingly, the invention includes a method of treating a mammal, preferably a human, having a disease responsive to inhibition of Btk activity, comprising administrating to the mammal having such a disease, an effective amount of a compound of Formula I-a.

To the extent that Btk is implicated in any of the following, alleviation of the disease, disease symptoms, preventative, and prophylactic treatment is within the scope of this invention. In addition, as noted above, the compounds of Formula I-a may also inhibit other kinases, such that alleviation of disease, disease symptoms, preventative, and prophylactic treatment of conditions associated with these kinases is also within the scope of this invention.

Methods of treatment also include inhibiting Btk activity and/or inhibiting B-cell proliferation, by inhibiting ATP binding or hydrolysis by Btk or by some other mechanism, in vivo, in a patient suffering from a disease responsive to inhibition of Btk activity, by administering an effective concentration of a compound of Formula I-a to inhibit Btk activity in vitro. An effective concentration may be ascertained experimentally, for example by assaying blood concentration of the compound, or theoretically, by calculating bioavailability.

Diseases Responsive to Kinase Inhibition

Certain compounds described herein are useful for treating a patient suffering from a disease responsive to kinase inhibition.

Protein kinases, the largest family of human enzymes, are now considered to be the largest druggable target class. Encompassing well over 500 proteins (2% of the human genome), kinases play critical roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

Diseases Responsive to Btk Inhibition

The invention includes a method of treating a patient having cancer, an autoimmune and/or inflammatory disease, or an acute inflammatory reaction, by administering an effective amount of a compound of Formula I-a.

In a preferred embodiment, the condition responsive to inhibition of Btk activity and/or B-cell proliferation is cancer, an autoimmune and/or inflammatory disease, or an acute inflammatory reaction.

Preferably, the conditions, diseases that can be affected using compounds and compositions according to the invention include, but are not limited to:

autoimmune and/or inflammatory diseases, including but not limited to psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, myasthenia gravis, and the like, acute inflammatory reactions, including but not limited to skin sunburn, inflammatory pelvic disease, inflammatory bowel disease, urethritis, uvitis, sinusitis, pneumonitis, encephalitis, meningitis, myocarditis, nephritis, osteomyelitis, myositis, hepatitis, gastritis, enteritis, dermatitis, gingivitis, appendicitis, pancreatitis, and cholocystitis, and cancer, including but not limited to, B-cell lymphoma, lymphoma (including Hodgkin's and non-Hodgkins lymphoma), hairy cell leukemia, multiple myeloma, chronic and acute myelogenous leukemia, and chronic and acute lymphocytic leukemia.

Btk is a known inhibitor of apoptosis in lymphoma B-cells. Defective apoptosis contributes to the pathogenesis and drug resistance of human leukemias and lymphomas. Thus, a method of promoting or inducing apoptosis in cells expressing Btk comprising contacting the cell with an agent that inhibits Btk activity is also provided herein.

Combination Therapy

The invention provides methods of treatment in which a compound of the invention is the only active agent given to a patient and also includes methods of treatment in which a compound of Formula I-a is given to a patient in combination with one or more additional active agent. Thus in one embodiment the invention provides a method of treating cancer, an autoimmune and/or inflammatory disease, or an acute inflammatory reaction, which comprises administering to a mammal in need thereof an effective amount of a compound of Formula I-a together with a second active agent, which is useful for treating an cancer, an autoimmune and/or inflammatory disease, or an acute inflammatory reaction. For example the second agent may be an anti-inflammatory agent. Treatment with the second active agent may be prior to, concomitant with, or following treatment with a compound of Formula I-a. In certain embodiments a compound of Formula I-a is combined with another active agent in a single dosage form. Suitable antitumor therapeutics that may be used in combination with a compound of Formula I-a include, but are not limited to chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

Btk inhibitors are useful as chemosensitizing agents, and, thus, are useful in combination with other chemotherapeutic drugs, in particular, drugs that induce apoptosis.

A method for increasing sensitivity of cancer cells to chemotherapy, comprising administering to a patient undergoing chemotherapy a chemotherapeutic agent together with a Btk inhibitor in an amount sufficient to increase the sensitivity of cancer cells to the chemotherapeutic agent is also provided herein.

Examples of other chemotherapeutic drugs that can be used in combination with Btk inhibitors include topoisomerase I inhibitors (camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Included herein are methods of treatment in which a compound of Formula I-a in administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, and prednisone.

In additional embodiments the anti-inflammatory agent is therapeutic agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as methotrexate, leflunomide, cyclosporine, tacrolimus, azathioprine, or mycophenolate mofetil.

Dosage Levels

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most autoimmune and/or inflammatory, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

EXAMPLES

Example 1

EXEMPLARY SYNTHESIS OF CERTAIN IMIDAZO[1,2-A]PYRAZIN-8-YLAMINES

Step 1. 6,8-dibromoimidazo[1,2-a]pyrazine (3)

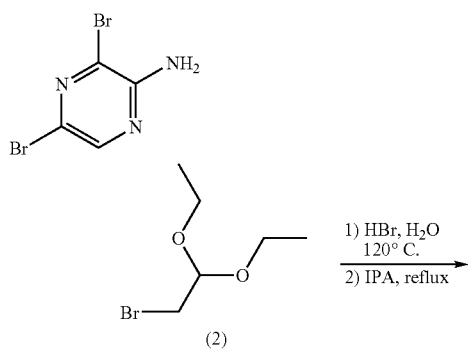

A mixture of bromoacetaldehyde diethyl acetal (51 grams (g)), 48% hydrobromic acid (HBr) (11 milliliters (mL)), and water (11 mL) is heated at 120° C. for 1 hour (hr). The solution is cooled, poured into a mixture of sodium bicarbonate (NaHCO$_3$) (60 g) and isopropyl alcohol (IPA) (200 mL), and stirred for 0.5 hr. The mixture is filtered, and the filtrate is treated with 3,5-dibromo-2-aminopyrazine (1) (33 g) and heated under reflux for 16 hr. The suspension is cooled in ice, treated with 48% HBr (3 mL) and diethyl ether (60 mL) and filtered to afford (3) as the hydrobromide salt.

Step 2. (6-Bromo-imidazo[1,2-a]pyrazin-8-yl)-phenyl-amine (4)

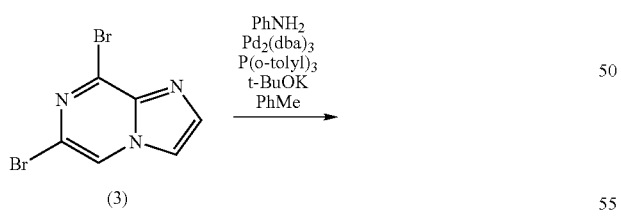

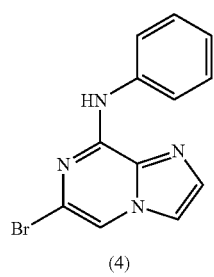

Tri-o-tolylphosphine (1.1 g) is added to a suspension of tris(dibenzylideneacetone)dipalladium (1.65 g) in degassed toluene (50 mL) and the mixture is stirred at room temperature for 15 minutes (min). 6,8-Dibromo-imidazo[1,2-a]pyrazine (5.0 g) is then added and the mixture is stirred at room temperature for 15 minutes more. Aniline (1.52 g) is added followed by potassium t-butoxide (2.84 g) and the mixture is stirred at room temperature for 72 hr. Water (150 mL) is added and the mixture is extracted with ethyl acetate (3×150 mL), the extracts are washed with water (1×100 mL) and brine (1×100 mL), dried over MgSO$_4$, and evaporated in vacuo to afford a gum. Trituration with diethyl ether affords (6-bromo-imidazo[1,2-a]pyrazin-8-yl)-phenyl-amine (4) as a brown solid.

Step 3-[6-(3-Amino-phenyl)-imidazo[1,2-a]pyrazin-8-yl]-phenyl-amine (5)

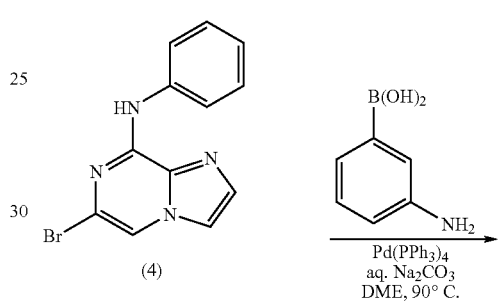

A mixture of (6-bromo-imidazo[1,2-a]pyrazin-8-yl)-phenyl-amine (4) (1.9 g), 3-aminophenylboronic acid hemisulfate (1.35 g), tetrakis(triphenylphosphine) palladium (380 mg), 1M aqueous sodium carbonate (20 mL), and 1,2-dimethoxyethane (40 mL) is heated at 90° for 16 hr. The mixture is cooled to room temperature, treated with water (50 mL) and extracted with ethyl acetate (3×80 mL). The extracts are washed with water (1×50 mL) and brine (1×50 mL), dried over MgSO$_4$, and evaporated in vacuo to afford a gum which is purified by flash chromatography over silica gel, eluting with ethyl acetate, to afford [6-(3-amino-phenyl)-imidazo[1,2-a]pyrazin-8-yl]-phenyl-amine (5) as a light brown solid.

Step 4. 4-tert-Butyl-N-[3-(8-phenylamino-imidazo[1,2-a]pyrazin-6-yl)-phenyl]-benzamide (6)

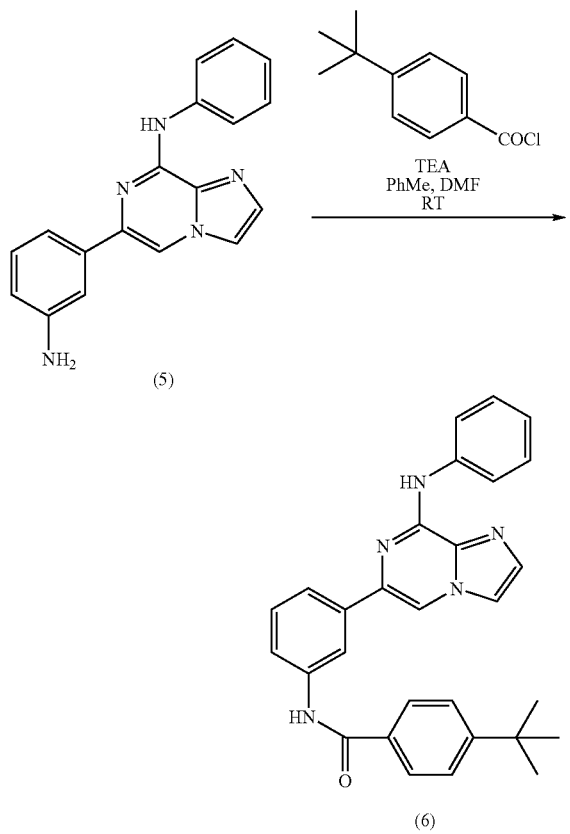

A solution of [6-(3-amino-phenyl)-imidazo[1,2-a]pyrazin-8-yl]-phenyl-amine (5) (50 mg), 4-tert-butyl-benzoyl chloride (0.83 mL of a 0.2M solution in toluene), and triethylamine (0.034 mL) in toluene (1 mL) and N,N,-dimethylformamide (1 mL) is stirred at room temperature for 16 hr. The mixture is purified by preparative thin layer chromatography over silica gel, eluting with diethyl ether/dichloromethane (1:1) to afford 4-tert-butyl-N-[3-(8-phenylamino-imidazo[1,2-a]pyrazin-6-yl)-phenyl]-benzamide (6) as a cream foam.

Example 2

SYNTHESIS OF N-(4-TERT-BUTYL-PHENYL)-3-{8-[4-(MORPHOLIN-4-CARBONYL)-PHENYLAMINO]-IMIDAZO[1,2-A]PYRAZIN-6-YL}-BENZAMIDE

Step. 1. 4-(6-Bromo-imidazo[1,2-a]pyrazin-8-ylamino)-benzoic Acid (7)

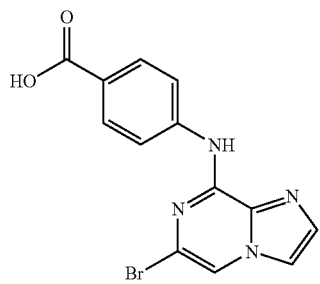

A mixture of 4-(6-Bromo-imidazo[1,2-a]pyrazin-8-ylamino)-benzoic acid ethyl ester (30 mmol), 1N aqueous sodium hydroxide (50 mL), and ethanol (80 mL) is heated at reflux for 1.5 hr. The mixture is cooled and the ethanol removed in vacuo. The residue is diluted with iN sodium hydroxide (30 mL) and washed with ethyl acetate (2×100 mL). The aqueous layer is brought to pH 6 with 3N HCl, and the mixture filtered to give 4-(6-Bromo-imidazo[1,2-a]pyrazin-8-ylamino)-benzoic acid (7) as a light orange solid.

Step 2. [4-(6-Bromo-imidazo[1,2-a]pyrazin-8-ylamino)-phenyl]-morpholin-4-yl-methanone (8)

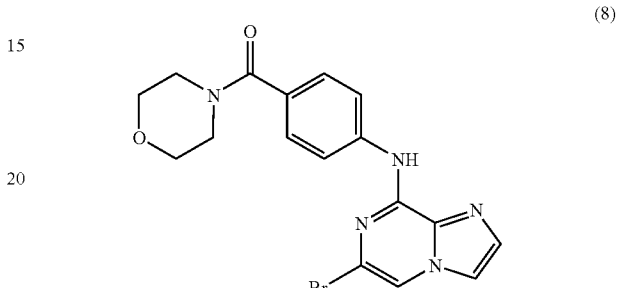

A mixture of 4-(6-Bromo-imidazo[1,2-a]pyrazin-8-ylamino)-benzoic acid (7) (0.16 mmol), benzotriazol-1-yloxy-tris(dimethylamino)-phosphonium hexafluorophosphate (0.16 mmol), and N'N-diisopropylethylamine (0.48 mmol) is stirred at room temperature for 20 min. under $N_2$. Morpholine (0.48 mmol) is added and the mixture is stirred at room temperature for 16 hr. Water (10 mL) is added and the mixture extracted with ethyl acetate (2×70 mL). The extracts are subsequently washed with water (2×30 mL) and brine (1×30 mL), dried over sodium sulfate, and concentrated in vacuo. The residue is triturated with diethyl ether to give [4-(6-Bromo-imidazo[1,2-a]pyrazin-8-ylamino)-phenyl]-morpholin-4-yl-methanone (8) as a cream solid.

Step 3. 3-{8-[4-(Morpholine-4-carbonyl)-phenylamino]-imidazo[1,2-a]pyrazin-6-yl}-benzoic acid (9)

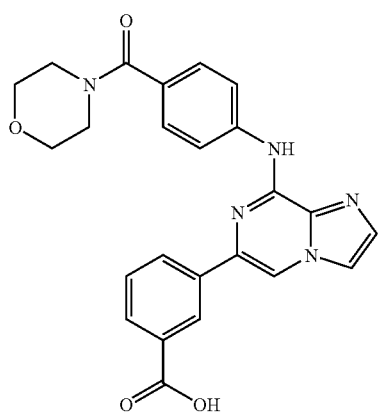

The bromide (8) (2,46 mmol) is dissolved in 10 mL DME (ethylene glycol, dimethyl ether) in a sealable pressure vessel and $N_2$ is bubbled through for 10 min. Tetrakis(triphenylphosphine)palladium (0.24 mmol) is added and $N_2$ is bubbled through the reaction for another 10 minutes. 3-Carboxyphenyl boronic acid (3.1 mmol) and 1N $Na_2CO_3$ solution (10 mL) are then added, the vessel sealed, and the reaction heated to 95° C. for 16 hrs. with vigorous stirring. After cooling to room temperature, the reaction is acidified to pH 3 with 1N HCl and extracted with ethyl acetate (3×25 mL). The pooled ethyl acetate layers are washed with brine, dried over sodium sulfate, and the solvent removed in vacuo. The resulting solid is then dissolved in a minimal volume of $CH_2Cl_2$ and precipitated out as a whitish-tan solid by slow addition of ethyl acetate (5 mL) followed by hexanes (30 mL) to yield 3-{8-[4-(Morpholine-4-carbonyl)-phenylamino]-imidazo[1,2-a]pyrazin-6-yl}-benzoic acid (9).

Step 4. N-(4-tert-Butyl-phenyl)-3-{8-[4-(morpholine-4-carbonyl)-phenylamino]-imidazo[1,2-a]pyrazin-6-yl}-benzamide (10)

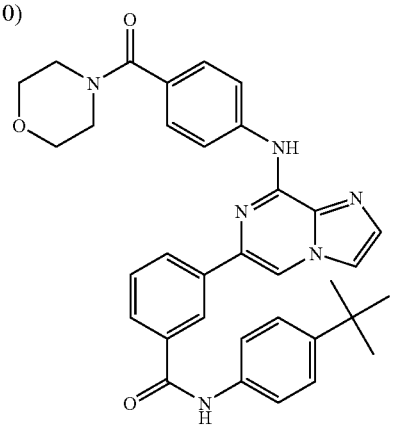

(10)

A mixture of 3-{8-[4-(Morpholine-4-carbonyl)-phenylamino]-imidazo[1,2-a]pyrazin-6-yl}-benzoic acid (9) (0.23 mmol), benzotriazol-1-yloxy-tris(dimethylamino)-phosphonium hexafluorophosphate reagent (0.23 mmol) and N,N'-diisopropylethylamine (0.77 mmol) is stirred under $N_2$ for 15 min. in 1 mL DMF. 4-tert-Butyl-phenylamine (0.37 mmol) is added and the reaction stirred at rt for 8 hrs. The reaction is partitioned between ethyl acetate (15 mL) and water (15 mL) and the ethyl acetate layer washed with water (2×15 mL) and brine (1×15 mL). The organic layer is dried over sodium sulfate and the solvent removed in vacuo. The resulting crude oil is dissolved in 1 ml $CH_2Cl_2$ and clean yellow solid is precipitated by slow addition of diethyl ether, yielding the final product, (10) N-(4-tert-Butyl-phenyl)-3-{8-[4-(morpholine-4-carbonyl)-phenylamino]-imidazo[1,2-a]pyrazin-6-yl}-benzamide.

Example 3

SYNTHESIS OF N-(3-{8-[4-(4-ACETYL-PIPERAZIN-1-YL)-PHENYLAMINO]-IMIDAZO[1,2-A]PYRAZIN-6-YL}-PHENYL)-4-TERT-BUTYL-BENZAMIDE

Step 1. 4-(4-Nitro-phenyl)-piperazine-1-carboxylic Acid Tert-Butyl Ester

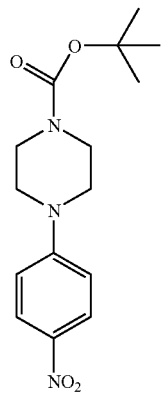

(11)

A mixture of 1-fluoro-4-nitrobenzene (20.4 mmol), piperazine-1-carboxylic acid tert-butyl ester (20.4 mmol), potassium carbonate (40.8 mmol), and N'N-dimethylformamide (80 mL) is heated at 60° C. for 3 hrs. The mixture is cooled to room temperature, treated with water (100 mL), extracted with ethyl acetate (3×80 mL). The extracts are washed with water (3×60 mL) and brine (1×75 ml), dried over magnesium sulfate, and concentrated in vacuo to give 4-(4-nitro-phenyl)-piperazine-1-carboxylic acid tert-butyl ester (11) as a yellow solid.

Step 2. 4-(4-Amino-phenyl)-piperazine-1-carboxylic acid tert-butyl ester

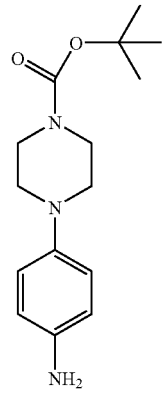

(12)

A mixture of 4-(4-nitro-phenyl)-piperazine-1-carboxylic acid tert-butyl ester (11) (18.9 mmol), 10% palladium-on-carbon (600 mg), ethanol (100 mL), and ethyl acetate (100 mL) is hydrogenated at room temperature and 40 psi for 2 hrs. The mixture is filtered through celite, washing with ethyl acetate (2×100 mL), and concentrated in vacuo to give 4-(4-amino-phenyl)-piperazine-1-carboxylic acid tert-butyl ester (12) as a brown oil.

Step 3. 4-[4-(6-bromo-imidazo[1,2-a]pyrazin-8-ylamino)-phenyl]-piperazine-1-carboxylic acid tert-butyl ester

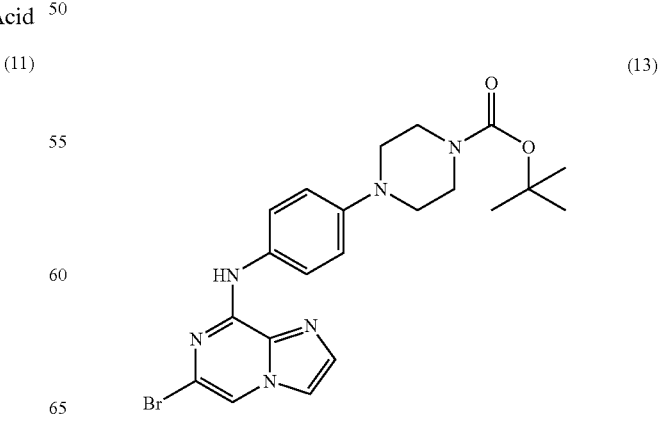

(13)

A mixture of 6,8-dibromoimidazo[1,2-a]pyrazine (12.5 mmol), 4-(4-amino-phenyl)-piperazine-1-carboxylic acid tert-butyl ester (12) (13.1 mmol), potassium carbonate (25 mmol), acetonitrile (50 mL) and N,N-dimethylacetamide (20 mL) is heated at 65° C. for 16 hrs. The mixture is cooled to room temperature, treated water (100 mL), and extracted with ethyl acetate (3×80 mL). The extracts are washed with water (3×60 mL) and brine (1×60 mL), dried over magnesium sulfate, and concentrated in vacuo. The residue is chromatographed over silica gel, eluting with ethyl acetate, to give 4-[4-(6-bromo-imidazo[1,2-a]pyrazin-8-ylamino)-phenyl]-piperazine-1-carboxylic acid tert-butyl ester (13) as a light brown foam.

Step 4. 4-{4-[6-(3-amino-phenyl)-imidazo[1,2-a]pyrazin-8-ylamino]-phenyl}-piperazine-1-carboxylic acid tert-butyl ester (14)

(14)

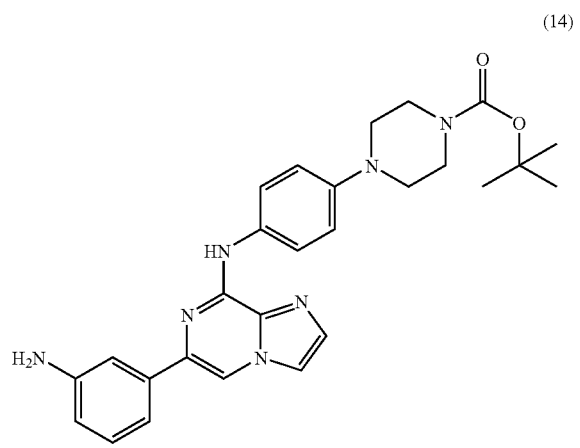

A mixture of 4-(6-bromoimidazo[1,2-a]pyrazin-8-ylamino)benzoic acid ethyl ester (13) (4,33 mmol), 3-aminophenylboronic acid hemisulfate (5,63 mmol), tetrakis(triphenylphosphine)palladium (0.2 mmol), 1N aqueous sodium carbonate solution (13 mL), and dimethoxyethane (70 mL) is heated at 95° C. for 2 days. The mixture is allowed to cool, treated with water (100 mL), and extracted with ethyl acetate (3×80 mL). The extracts are washed with water (2×75 mL) and brine (1×75 mL), dried over magnesium sulfate, and evaporated in vacuo. The residue is chromatographed over silica gel, eluting with ethyl acetate, to give 4-{4-[6-(3-amino-phenyl)-imidazo[1,2-a]pyrazin-8-ylamino]-phenyl}-piperazine-1-carboxylic acid tert-butyl ester (14) as a cream solid.

Step 5. 4-(4-{6-[3-(4-tert-Butyl-benzoylamino)-phenyl]-imidazo[1,2-a]pyrazin-8-ylamino}-phenyl)-piperazine-1-carboxylic acid tert-butyl ester (15)

(15)

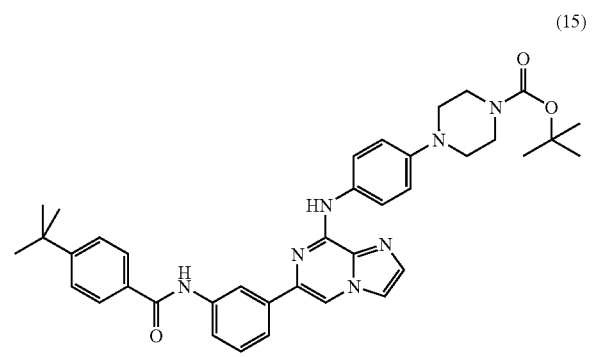

An ice-cold solution of 4-{4-[6-(3-Amino-phenyl)-imidazo[1,2-a]pyrazin-8-ylamino]-phenyl}-piperazine-1-carboxylic acid tert-butyl ester (14) (2.35 mmol), triethylamine (3.53 mmol), and tetrahydrofuran (20 mL) is treated dropwise with a solution of 4-t-butylbenzoyl chloride (2.35 mmol) in tetrahydrofuran (10 mL). The mixture is stirred at room temperature for 1 hr. Water (50 mL) is added and the mixture extracted with ethyl acetate (3×70 mL). The extracts are washed with water (2×50 mL) and brine (1×50 mL), dried over magnesium sulfate, and evaporated in vacuo. The residue is triturated with diethyl ether to give 4-(4-{6-[3-(4-tert-butyl-benzoylamino)-phenyl]-imidazo[1,2-a]pyrazin-8-ylamino}-phenyl)-piperazine-1-carboxylic acid tert-butyl ester (15) as a cream solid.

Step 6. 4-tert-Butyl-N-{3-[8-(4-piperazin-1-yl-phenylamino)-imidazo[1,2-a]pyrazin-6-yl]-phenyl}-benzamide (16)

(16)

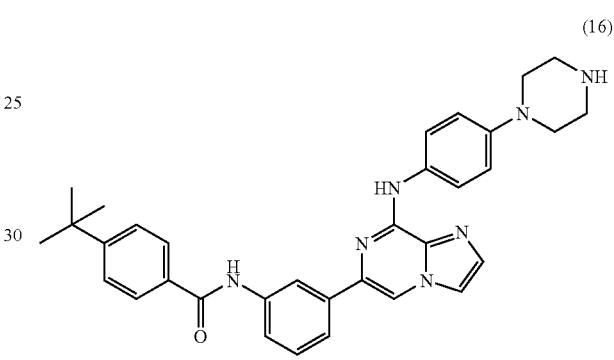

A mixture of 4-(4-{6-[3-(4-tert-butyl-benzoylamino)-phenyl]-imidazo[1,2-a]pyrazin-8-ylamino}-phenyl)-piperazine-1-carboxylic acid tert-butyl ester (15) (2.0 mmol), 1M HCl in diethyl ether (20 mL), and dioxane (60 mL) is stirred at room temperature for 16 hr. Water (100 mL) is added and the pH brought to 11 with 1N NaOH. The mixture is extracted with ethyl acetate (3×80 mL), the extracts washed with water (2×70 mL) and brine (1×70 mL), dried over magnesium sulfate, and concentrated in vacuo. The residue is slurried with diethyl ether and filtered to give 4-tert-butyl-N-{3-[8-(4-piperazin-1-yl-phenylamino)-imidazo[1,2-a]pyrazin-6-yl]-phenyl}-benzamide (16) as a cream solid.

Step 7. N-(3-{8-[4-(4-Acetyl-piperazin-1-yl)-phenylamino]-imidazo[1,2-a]pyrazin-6-yl}-phenyl)-4-tert-butyl-benzamide (17)

(17)

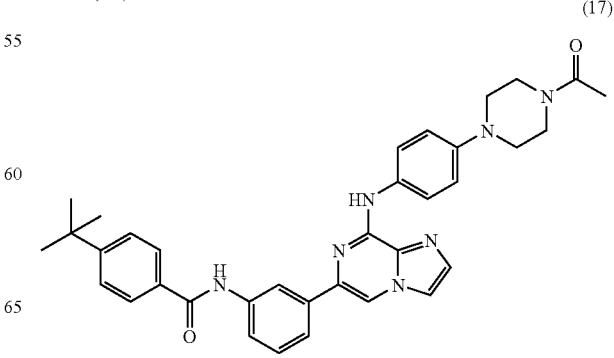

A mixture of 4-tert-butyl-N-{3-[8-(4-piperazin-1-yl-phenylamino)-imidazo[1,2-a]pyrazin-6-yl]-phenyl}-benzamide (16) (0.55 mmol), triethylamine (1.1 mmol), acetic anhydride (0.60 mmol), and dichloromethane (10 mL) is stirred at room temperature for 1 hr. Water (30 mL) is added, the mixture extracted with dichloromethane (2×50 mL), the extracts washed with water (2×30 mL) and brine (1×30 mL), dried over magnesium sulfate, and concentrated in vacuo. The residue is triturated with diethyl ether and ethyl acetate to give N-(3-{8-[4-(4-Acetyl-piperazin-1-yl)-phenylamino]-imidazo[1,2-a]pyrazin-6-yl}-phenyl)-4-tert-butyl-benzamide (17) as a cream solid.

Example 4

SYNTHESIS OF 4-TERT-BUTYL-N-(3-{8-[4-(MORPHOLINE-4-CARBONYL)-PHENYLAMINO]-IMIDAZO[1,2-A]PYRAZIN-6-YL}-PHENYL)-BENZAMIDE

Step 1. 4-(6-Bromo-imidazo[1,2-a]pyrazin-8-ylamino)-benzoic Acid Ethyl Ester (18)

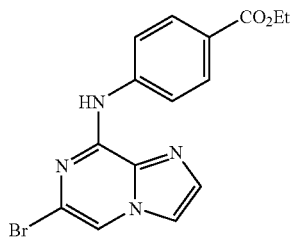

(18)

A mixture of 6,8-dibromoimidazo[1,2-a]pyrazine (0.18 mol), 4-aminobenzoic acid ethyl ester (2) (0.18 mol), and N,N-dimethylacetamide (30 mL) is heated at 160° C. for 30 min. The mixture is cooled to room temperature, treated with ethyl acetate (150 mL), stirred, and filtered to afford an orange/brown solid. This solid is slurried with ethyl acetate and saturated sodium bicarbonate solution to give 4-(6-bromoimidazo[1,2-a]pyrazin-8-ylamino)benzoic acid ethyl ester (18) freebase.

Step 2. 4-[6-(3-Amino-phenyl)-imidazo[1,2-a]pyrazin-8-ylamino]-benzoic Acid Ethyl Ester (19)

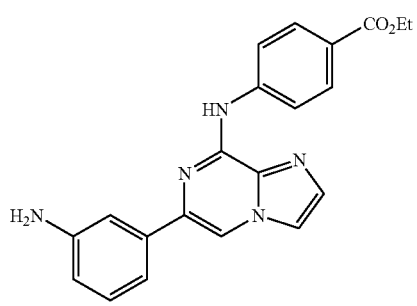

(19)

A mixture of 4-(6-bromoimidazo[1,2-a]pyrazin-8-ylamino)benzoic acid ethyl ester (18) (55.3 mmol), 3-aminophenylboronic acid hemisulfate (72 mmol), tetrakis(triphenylphosphine)palladium (2.8 mmol), 1N aqueous sodium carbonate solution (166 mmol), and dimethoxyethane (200 mL) is heated at reflux for 4 days. The mixture is allowed to cool, treated with water (200 mL), and extracted with ethyl acetate (4×100 mL). The extracts are washed with water (2×150 mL) and brine (1×100 mL), dried over magnesium sulfate, and evaporated in vacuo. The residue is triturated with dichloromethane and diethyl ether to give 4-[6-(3-aminophenyl)imidazo[1,2-a]pyrazin-8-ylamino]benzoic acid ethyl ester (19) as a yellow solid.

Step 3. 4-{6-[3-(4-tert-Butyl-benzoylamino)-phenyl]-imidazo[1,2-a]pyrazin-8-ylamino}-benzoic acid ethyl ester (20)

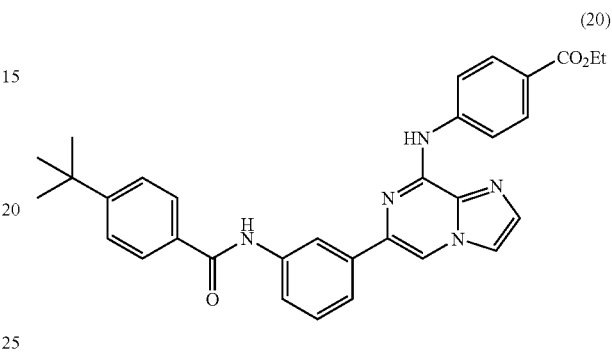

(20)

An ice-cold solution of 4-[6-(3-aminophenyl)imidazo[1,2-a]pyrazin-8-ylamino]benzoic acid ethyl ester (19) (44.2 mmol), triethylamine (66.4 mmol), and tetrahydrofuran (140 mL) is treated dropwise with a solution of 4-t-butylbenzoyl chloride (44.2 mmol) in tetrahydrofuran (60 mL) and the mixture is stirred at room temperature for 1 hr. Water (100 mL) is added and the mixture extracted with ethyl acetate (3×100 mL), the extracts are washed with water (2×100 mL) and brine (1×100 mL), dried over magnesium sulfate and evaporated in vacuo. The residue is triturated with dichloromethane to give 4-{6-[3-(4-tert-butyl-benzoylamino)phenyl]imidazo[1,2-a]pyrazin-8-ylamino}benzoic acid ethyl ester (20) as a pale orange solid.

Step 4. 4-{6-[3-(4-tert-Butyl-benzoylamino)-phenyl]-imidazo[1,2-a]pyrazin-8-ylamino}-benzoic acid (21)

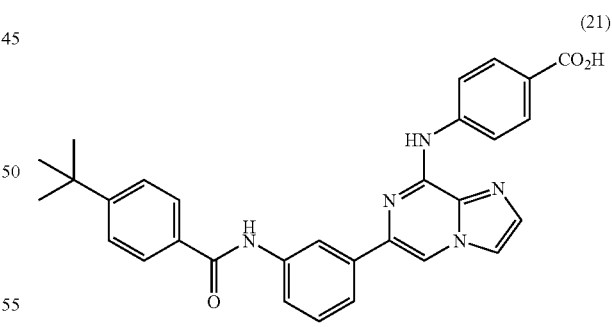

(21)

A mixture of 4-{6-[3-(4-tert-butyl-benzoylamino)phenyl]imidazo[1,2-a]pyrazin-8-ylamino}benzoic acid ethyl ester (20) (30 mmol), 1N aqueous sodium hydroxide (50 mL), and ethanol (80 mL) is heated at reflux for 1.5 hrs. The mixture is cooled and the ethanol removed in vacuo. The residue is diluted with 1N sodium hydroxide (30 mL) and washed with ethyl acetate (2×100 mL). The aqueous layer is brought to pH 6 with 3 N HCl, and the mixture is filtered to give 4-{6-[3-(4-tert-butyl-benzoylamino)phenyl]imidazo[1,2-a]pyrazin-8-ylamino}benzoic acid (21) as a cream solid.

Step 5. 4-tert-Butyl-N-(3-{8-[4-(morpholine-4-carbonyl)-phenylamino]-imidazo[1,2-a]pyrazin-6-yl}-phenyl)-benzamide (22)

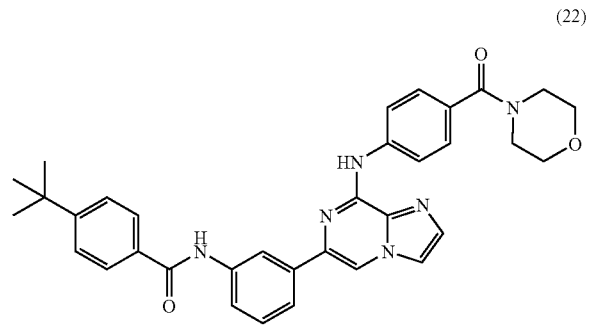
(22)

A mixture of 4-{6-[3-(4-tert-butyl-benzoylamino)phenyl]imidazo[1,2-a]pyrazin-8-ylamino}benzoic acid (21) (0.16 mmol), benzotriazol-1-yloxy-tris(dimethylamino)-phosphonium hexafluorophosphate (0.16 mmol), and N'N-diisopropylethylamine (0.48 mmol) is stirred at room temperature for 20 min. Morpholine (0.48 mmol) is added and the mixture is stirred at room temperature or 16 hrs. Water (10 mL) is added and the mixture extracted with ethyl acetate (2×70 mL), the extracts are washed with water (2×30 mL) and brine (1×30 mL), dried over magnesium sulfate, and concentrated in vacuo. The residue is triturated with diethyl ether to give 4-tert-B\butyl-N-(3-{8-[4-(morpholine-4-carbonyl)-phenylamino]imidazo[1,2-a]pyrazin-6-yl}-phenyl)benzamide (22) as a cream solid.

Example 5

ADDITIONAL IMIDAZO[1,2-a]PYRAZIN-8-YLAMINES

The following compounds are synthesized via the procedure set forth in Examples 1 to 4. In some instances changes in starting materials and reaction conditions that will be readily apparent to those skilled in the art of organic synthesis may be required.

LC-MS data reported in this example is obtained as follows:

LC conditions: RP-HPLC is performed on an AGILENT 1100 Binary HPLC system. The column is a Restek Ultra IBD 5 μm 1.0×30 mm (Cat. #: 9175331). The Mobile Phase contains component A, 0.2% Formic Acid/Water), and component B, Acetonitrile. The following Gradient is used:

| Time (min.) | % B | Flow Rate (μl/min) |
|---|---|---|
| 0 | 10 | 500 |
| 1.8 | 60 | 500 |
| 2.0 | 95 | 500 |
| 2.2 | 95 | 500 |
| 2.4 | 10 | 500 |

MS conditions: Electrospray MS is performed on a MICROMASS LCT equipped with a LockSpray source for accurate mass measurements. Spectra are acquired in positive ion mode from 100-1000 Da at an acquisition rate of 1 spectrum/0.9 s with a 0.1 s interscan delay. The instrument is tuned for a resolution of 5000 (FWHM). Every 5$^{th}$ scan is taken from the reference position of the Lockspray source. Leucine enkephalin (556.2771 [M+H]$^+$) is used as the reference, or lock mass.

TABLE I

| Cmp. # | Structure | Name and Molecular Formula | MW | MS m/z (M$^+$ 1) |
|---|---|---|---|---|
| 23 | 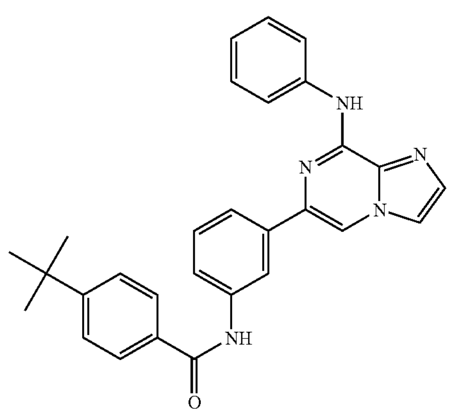 | 4-tert-Butyl-N-[3-(8-phenylamino-imidazo[1,2-a]pyrazin-6-yl)-phenyl]-benzamide MF = C$_{29}$H$_{27}$N$_5$O | 461.22 | 462.21 |

TABLE I-continued

| Cmp. # | Structure | Name and Molecular Formula | MW | MS m/z (M+ 1) |
|---|---|---|---|---|
| 24 | 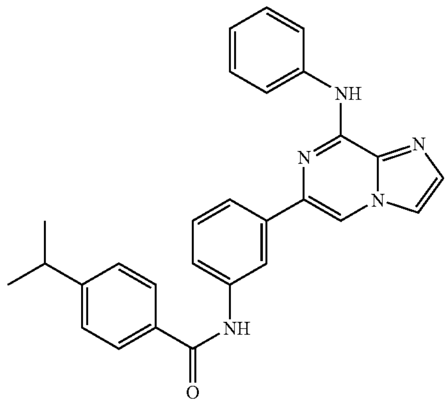 | 4-Isopropyl-N-[3-(8-phenylamino-imidazo[1,2-a]pyrazin-6-yl)-phenyl]-benzamide MF = $C_{28}H_{25}N_5O$ | 447.21 | 448.21 |
| 25 | 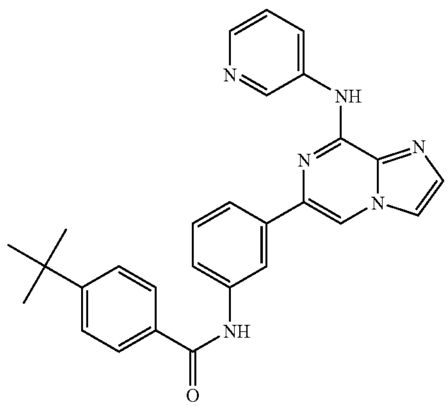 | 4-tert-Butyl-N-{3-[8-(pyridin-3-ylamino)-imidazo[1,2-a]pyrazin-6-yl]-phenyl}-benzamide MF = $C_{28}H_{26}N_6O$ | 462.21 | 463.07 |
| 26 | 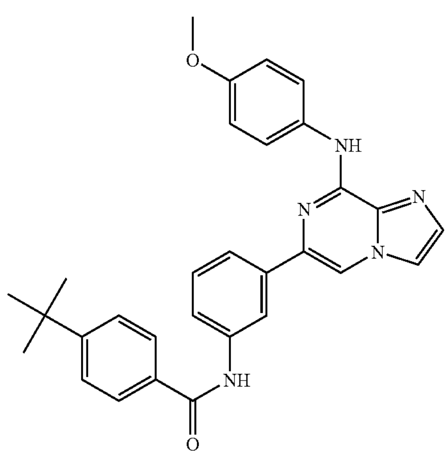 | 4-tert-Butyl-N-{3-[8-(4-methoxy-phenylamino)-imidazo[1,2-a]pyrazin-6-yl]-phenyl}-benzamide MF = $C_{30}H_{29}N_5O_2$ | 491.23 | 492.10 |

TABLE I-continued

| Cmp. # | Structure | Name and Molecular Formula | MW | MS m/z (M+1) |
|---|---|---|---|---|
| 27 | 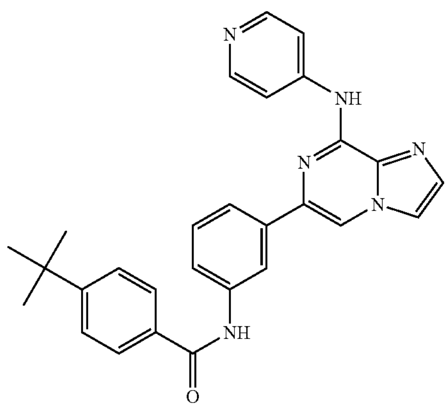 | 4-tert-Butyl-N-{3-[8-(pyridin-4-ylamino)-imidazo[1,2-a]pyrazin-6-yl]-phenyl}-benzamide<br>MF = C₂₈H₂₆N₆O | 462.22 | 463.19 |
| 28 | 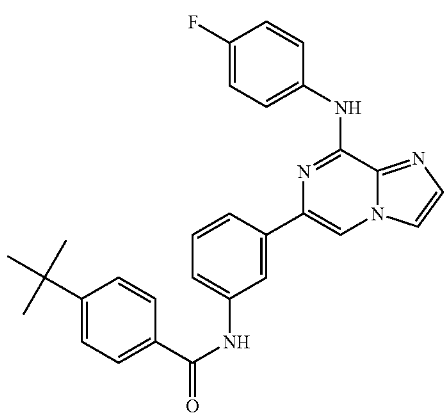 | 4-tert-Butyl-N-{3-[8-(4-fluoro-phenylamino)-imidazo[1,2-a]pyrazin-6-yl]-phenyl}-benzamide<br>MF = C₂₉H₂₆FN₅O | 479.21 | 480.10 |
| 29 | 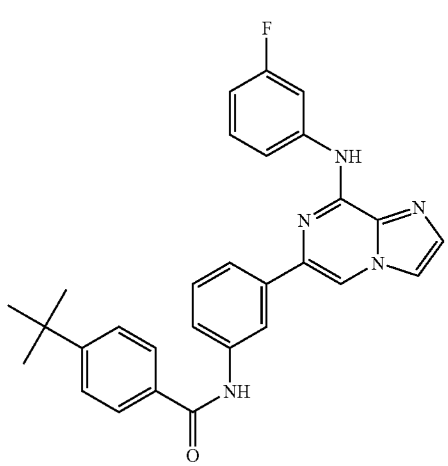 | 4-tert-Butyl-N-{3-[8-(3-fluoro-phenylamino)-imidazo[1,2-a]pyrazin-6-yl]-phenyl}-benzamide<br>MF = C₂₉H₂₆FN₅O | 479.21 | 480.10 |

TABLE I-continued

| Cmp. # | Structure | Name and Molecular Formula | MW | MS m/z (M+ 1) |
|---|---|---|---|---|
| 30 | 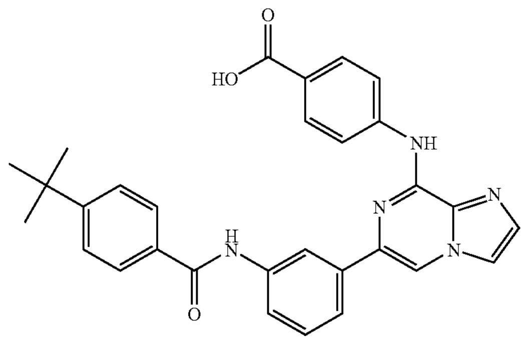 | 4-{6-[3-(4-tert-Butyl-benzoylamino)-phenyl]-imidazo[1,2-a]pyrazin-8-ylamino}-benzoic acid MF = $C_{30}H_{27}N_5O_3$ | 505.21 | 506.08 |
| 31 | 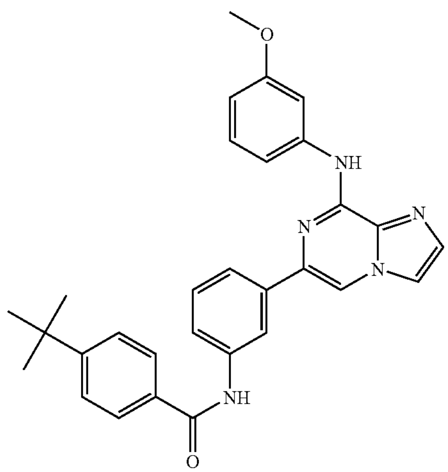 | 4-tert-Butyl-N-{3-[8-(3-methoxy-phenylamino)-imidazo[1,2-a]pyrazin-6-yl]-phenyl}-benzamide MF = $C_{30}H_{29}N_5O_2$ | 491.23 | 492.08 |
| 32 | 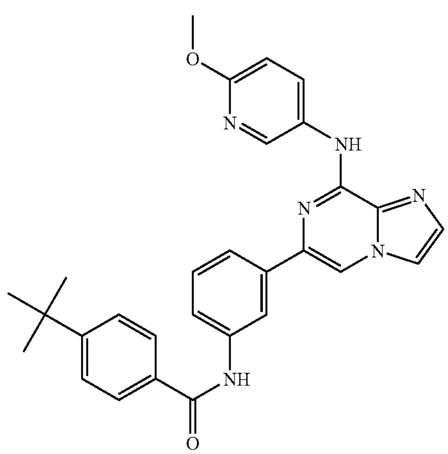 | 4-tert-Butyl-N-{3-[8-(6-methoxy-pyridin-3-ylamino)-imidazo[1,2-a]pyrazin-6-yl]-phenyl}-benzamide MF = $C_{29}H_{28}N_6O_2$ | 492.22 | 493.08 |
| 33 | 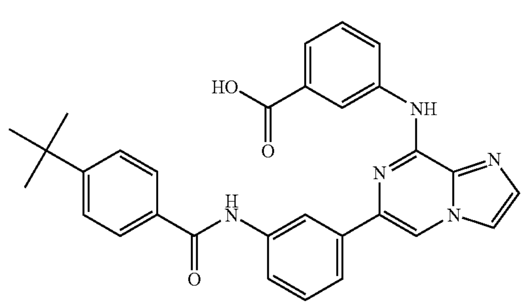 | 3-{6-[3-(4-tert-Butyl-benzoylamino)-phenyl]-imidazo[1,2-a]pyrazin-8-ylamino}-benzoic acid MF = $C_{30}H_{27}N_5O_3$ | 505.21 | 506.25 |

TABLE I-continued

| Cmp. # | Structure | Name and Molecular Formula | MW | MS m/z (M+ 1) |
|---|---|---|---|---|
| 34 | 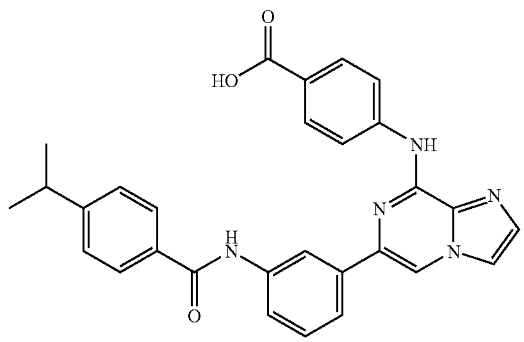 | 4-{6-[3-(4-Isopropyl-benzoylamino)-phenyl]-imidazo[1,2-a]pyrazin-8-ylamino}-benzoic acid<br>MF = $C_{29}H_{25}N_5O_3$ | 491.19 | 492.19 |
| 35 | 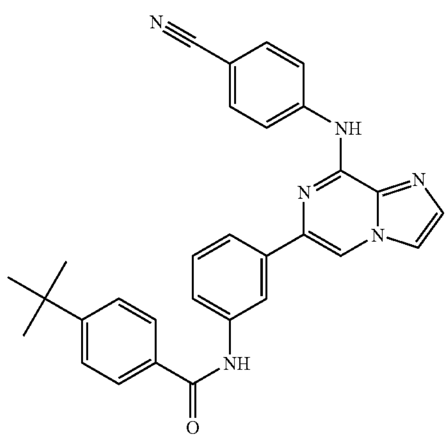 | 4-tert-Butyl-N-{3-[8-(4-cyano-phenylamino)-imidazo[1,2-a]pyrazin-6-yl]-phenyl}-benzamide<br>MF = $C_{30}H_{26}N_6O$ | 486.22 | 487.28 |
| 36 | 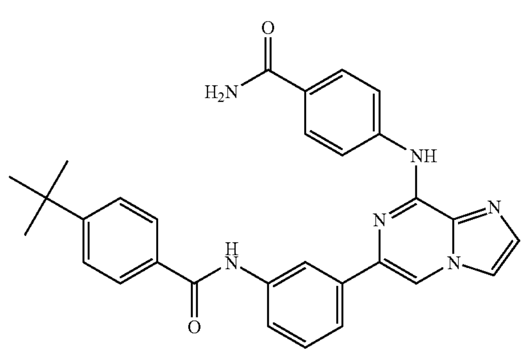 | 4-{6-[3-(4-tert-Butyl-benzoylamino)-phenyl]-imidazo[1,2-a]pyrazin-8-ylamino}-benzamide<br>MF = $C_{30}H_{28}N_6O_2$ | 504.22 | 505.21 |

TABLE II

| Cmp. # | STRUCTURE | NAME | MW | MS m/z (M+1) |
|---|---|---|---|---|
| 37 | 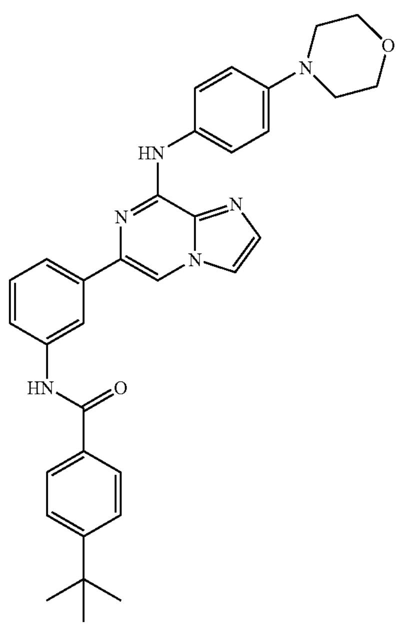 | 4-tert-Butyl-N-{3-[8-(4-morpholin-4-yl-phenylamino)-imidazo[1,2-a]pyrazin-6-yl]-phenyl}-benzamide C33H34N6O2 | 546.27 | 547.11 |
| 38 | 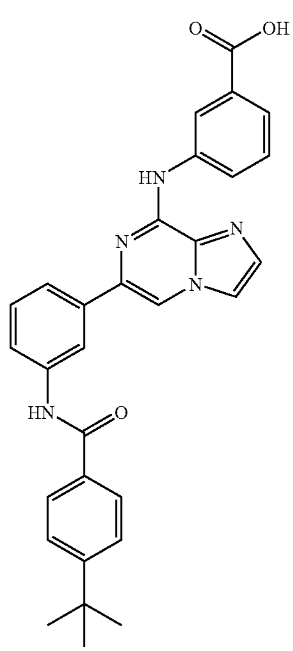 | 3-{6-[3-(4-tert-Butyl-benzoylamino)-phenyl]-imidazo[1,2-a]pyrazin-8-ylamino}-benzoic acid C30H27N5O3 | 505.21 | 506.25 |

TABLE II-continued
| Cmp. # | STRUCTURE | NAME | MW | MS m/z (M+1) |
|---|---|---|---|---|
| 39 | 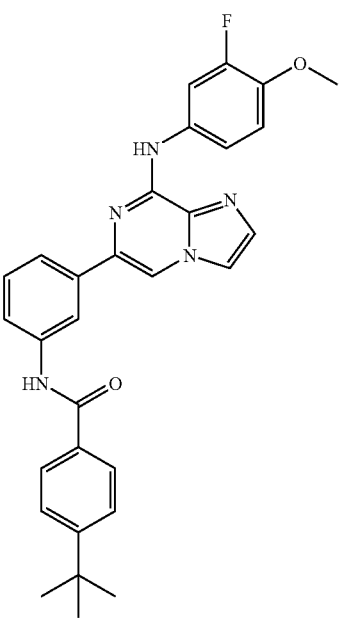 | 4-tert-Butyl-N-{3-[8-(3-fluoro-4-methoxy-phenylamino)-imidazo[1,2-a]pyrazin-6-yl]-phenyl}-benzamide C30H28FN5O2 | 509.22 | 510.26 |
| 40 | 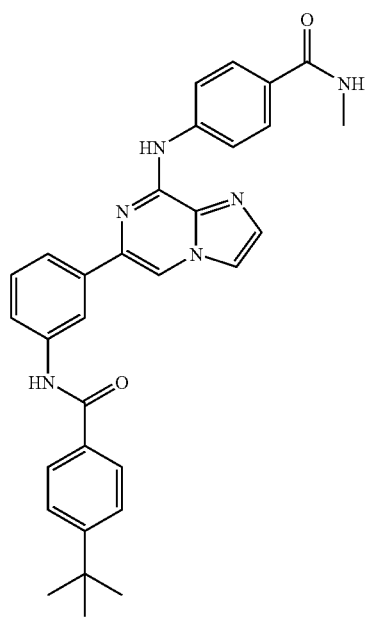 | 4-{6-[3-(4-tert-Butyl-benzoylamino)-phenyl]-imidazo[1,2-a]pyrazin-8-ylamino}-benzoic N-Methyl amide C31H30N6O2 | 518.24 | 519.21 |

TABLE II-continued

| Cmp. # | STRUCTURE | NAME | MW | MS m/z (M+1) |
|---|---|---|---|---|
| 41 | 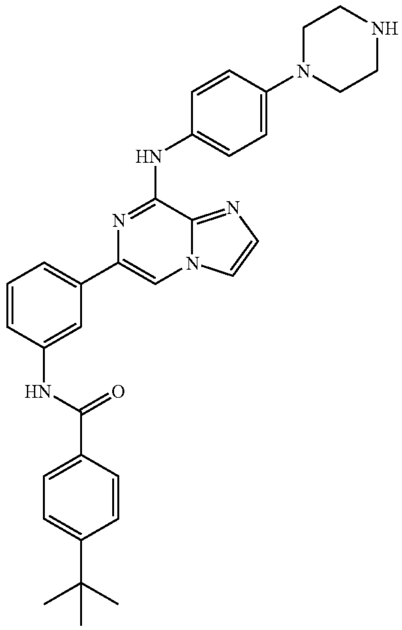 | 4-tert-Butyl-N-{3-[8-(4-piperazin-1-yl-phenylamino)-imidazo[1,2-a]pyrazin-6-yl]-phenyl}-benzamide<br>C33H35N7O | 545.29 | 546.19 |
| 42 | 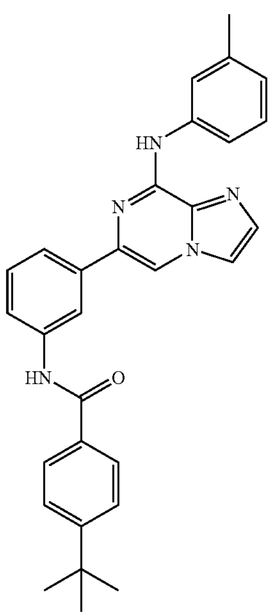 | 4-tert-Butyl-N-[3-(8-m-tolylamino-imidazo[1,2-a]pyrazin-6-yl)-phenyl]-benzamide<br>C30H29N5O | 475.23 | 476.22 |

TABLE II-continued

| Cmp. # | STRUCTURE | NAME | MW | MS m/z (M$^{+1}$) |
|---|---|---|---|---|
| 43 | 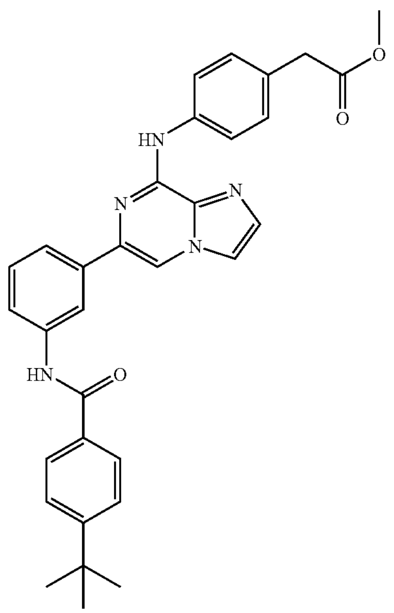 | (4-{6-[3-(4-tert-Butyl-benzoylamino)-phenyl]-imidazo[1,2-a]pyrazin-8-ylamino}-phenyl)-acetic acid methyl ester C32H31N5O3 | 533.24 | 534.22 |
| 44 | 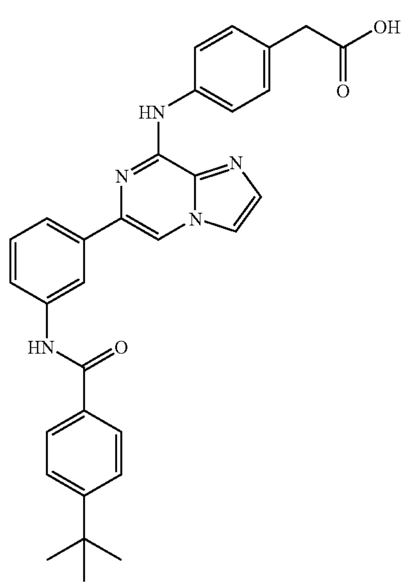 | (4-{6-[3-(4-tert-Butyl-benzoylamino)-phenyl]-imidazo[1,2-a]pyrazin-8-ylamino}-phenyl)-acetic acid C31H29N5O3 | 519.22 | 520.22 |

TABLE II-continued

| Cmp. # | STRUCTURE | NAME | MW | MS m/z (M+1) |
|---|---|---|---|---|
| 45 | 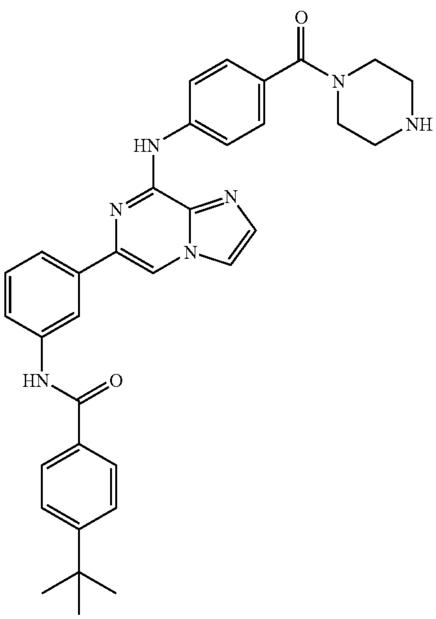 | 4-tert-Butyl-N-(3-{8-[4-(piperazine-1-carbonyl)-phenylamino]-imidazo[1,2-a]pyrazin-6-yl}-phenyl)-benzamide C34H35N7O2 | 573.28 | 574.85 |
| 46 | 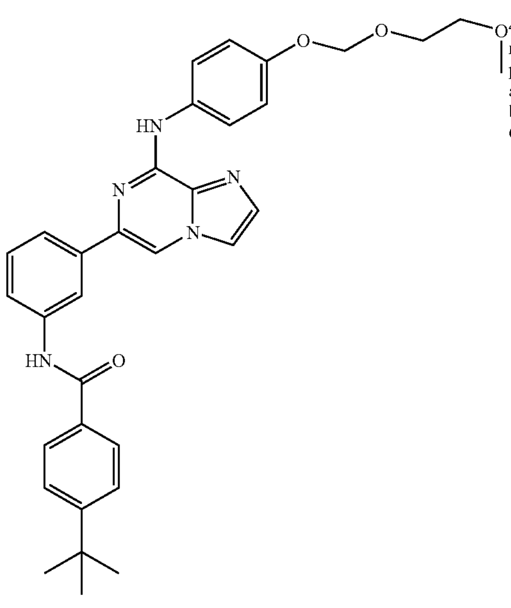 | 4-tert-Butyl-N-(3-{8-[4-(2-methoxy-ethoxymethoxy)-phenylamino]-imidazo[1,2-a]pyrazin-6-yl}-phenyl)-benzamide C33H35N5O4 | 565.26 | 566.25 |

TABLE II-continued
| Cmp. # | STRUCTURE | NAME | MW | MS m/z (M$^{+1}$) |
|---|---|---|---|---|
| 47 | 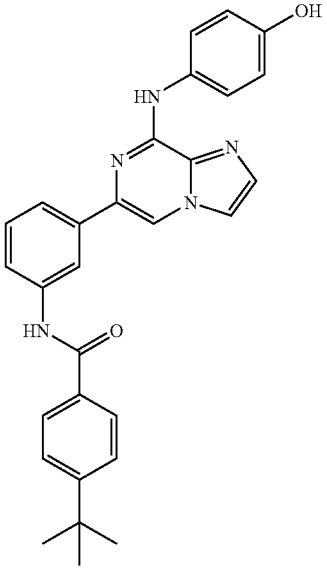 | 4-tert-Butyl-N-{3-[8-(4-hydroxy-phenylamino)-imidazo[1,2-a]pyrazin-6-yl]-phenyl}-benzamide C29H27N5O2 | 477.22 | 478.22 |
| 48 | 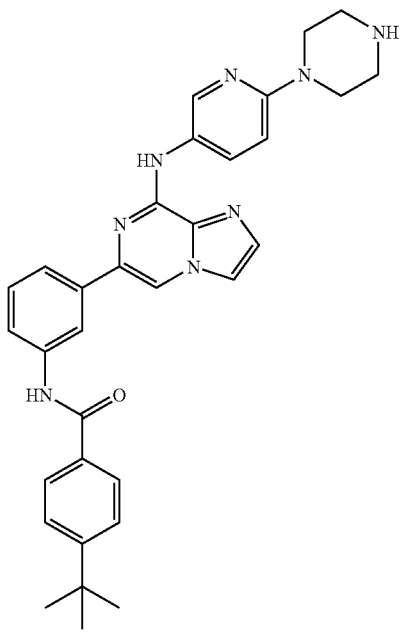 | 4-tert-Butyl-N-{3-[8-(6-piperazin-1-yl-pyridin-3-ylamino)-imidazo[1,2-a]pyrazin-6-yl]-phenyl}-benzamide C32H34N8O | 546.28 | 547.24 |

TABLE II-continued

| Cmp. # | STRUCTURE | NAME | MW | MS m/z (M+1) |
|---|---|---|---|---|
| 49 | 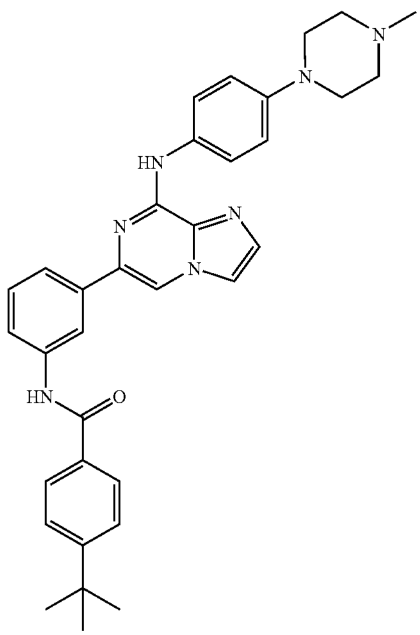 | 4-tert-Butyl-N-(3-{8-[4-(4-methyl-piperazin-1-yl)-phenylamino]-imidazo[1,2-a]pyrazin-6-yl}-phenyl)-benzamide<br>C34H37N7O | 559.31 | 560.26 |
| 50 | 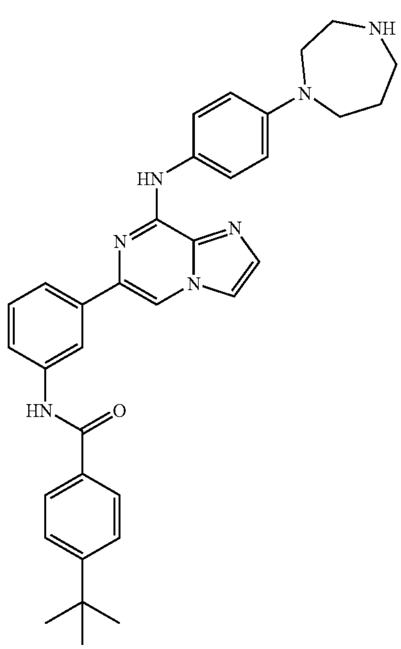 | 4-tert-Butyl-N-{3-[8-(4-[1,4]diazepan-1-yl-phenylamino)-imidazo[1,2-a]pyrazin-6-yl]-phenyl}-benzamide<br>C34H37N7O | 559.31 | 561.17 |

TABLE II-continued
| Cmp. # | STRUCTURE | NAME | MW | MS m/z (M+1) |
|---|---|---|---|---|
| 51 | 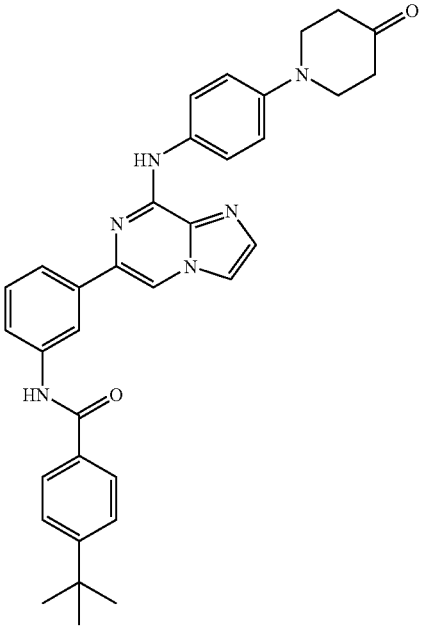 | 4-tert-Butyl-N-(3-{8-[4-(4-oxo-piperidin-1-yl)-phenylamino]-imidazo[1,2-a]pyrazin-6-yl}-phenyl)-benzamide C34H34N6O2 | 558.27 | 559.22 |
| 52 | 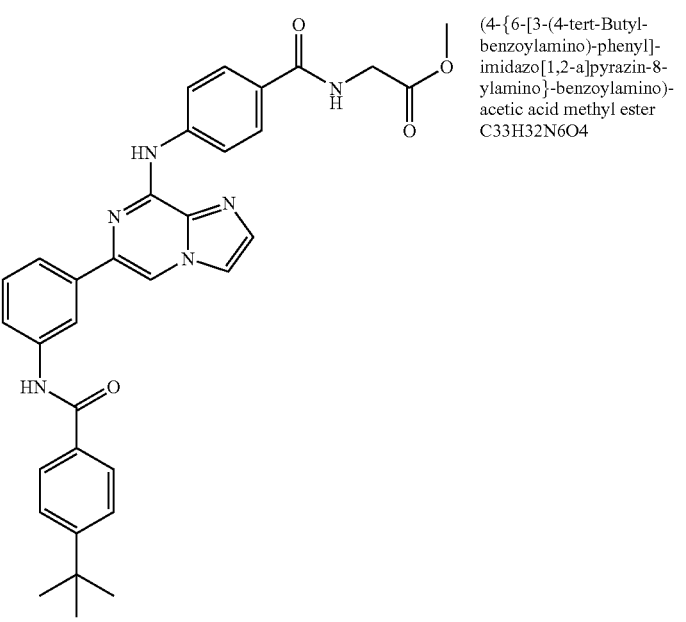 | (4-{6-[3-(4-tert-Butyl-benzoylamino)-phenyl]-imidazo[1,2-a]pyrazin-8-ylamino}-benzoylamino)-acetic acid methyl ester C33H32N6O4 | 576.24 | 577.29 |

TABLE II-continued

| Cmp. # | STRUCTURE | NAME | MW | MS m/z (M+1) |
|---|---|---|---|---|
| 53 | 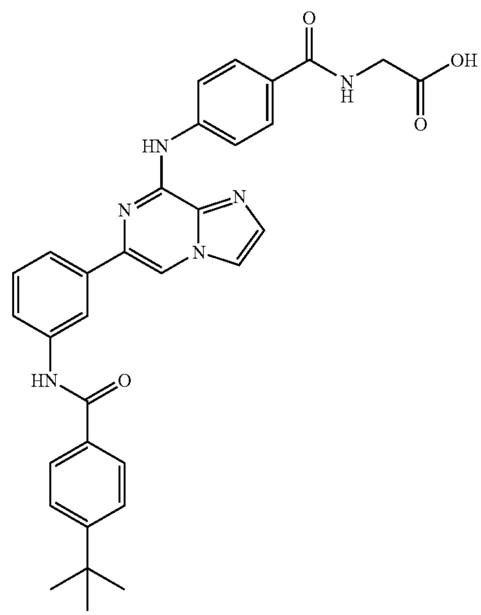 | (4-{6-[3-(4-tert-Butyl-benzoylamino)-phenyl]-imidazo[1,2-a]pyrazin-8-ylamino}-benzoylamino)-acetic acid C32H30N6O4 | 562.23 | 563.26 |
| 54 | 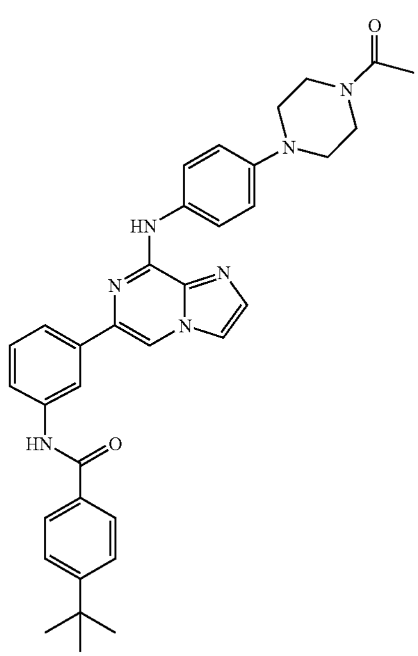 | N-(3-{8-[4-(4-Acetyl-piperazin-1-yl)-phenylamino]-imidazo[1,2-a]pyrazin-6-yl}-phenyl)-4-tert-butyl-benzamide C35H37N7O2 | 587.3 | 588.31 |

TABLE II-continued

| Cmp. # | STRUCTURE | NAME | MW | MS m/z (M+1) |
|---|---|---|---|---|
| 55 | 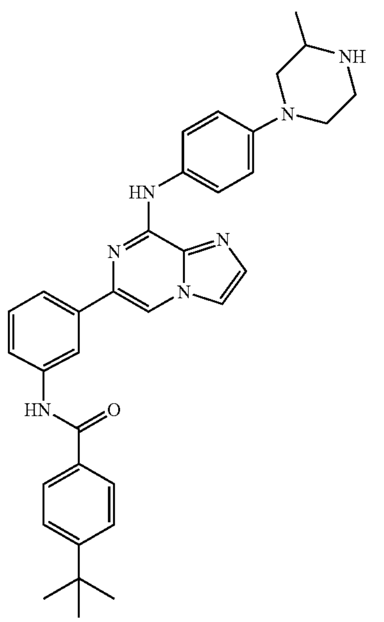 | 4-tert-Butyl-N-(3-{8-[4-(3-methyl-piperazin-1-yl)-phenylamino]-imidazo[1,2-a]pyrazin-6-yl}-phenyl)-benzamide<br>C34H37N7O | 559.31 | 560.35 |
| 56 | 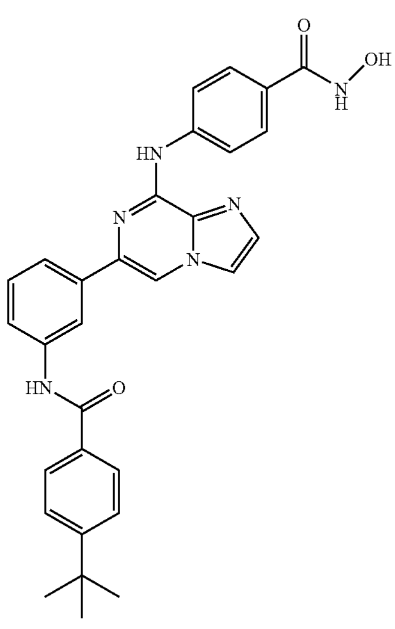 | 4-{6-[3-(4-tert-Butyl-benzoylamino)-phenyl]-imidazo[1,2-a]pyrazin-8-ylamino}-benzoic hydroxyl amide<br>C30H28N6O3 | 520.22 | 521.26 |

TABLE II-continued

| Cmp. # | STRUCTURE | NAME | MW | MS m/z (M+1) |
|---|---|---|---|---|
| 57 | 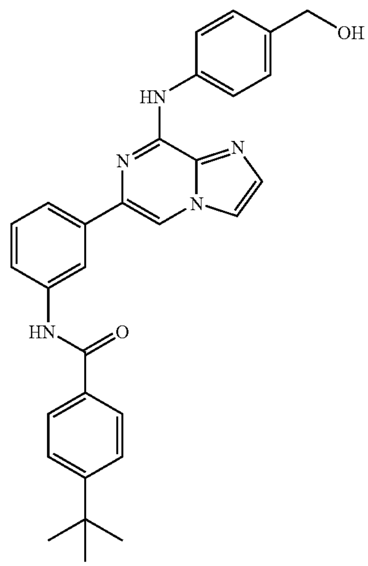 | 4-tert-Butyl-N-{3-[8-(4-hydroxymethyl-phenylamino)-imidazo[1,2-a]pyrazin-6-yl]-phenyl}-benzamide<br>C30H29N5O2 | 491.23 | 492.28 |
| 58 | 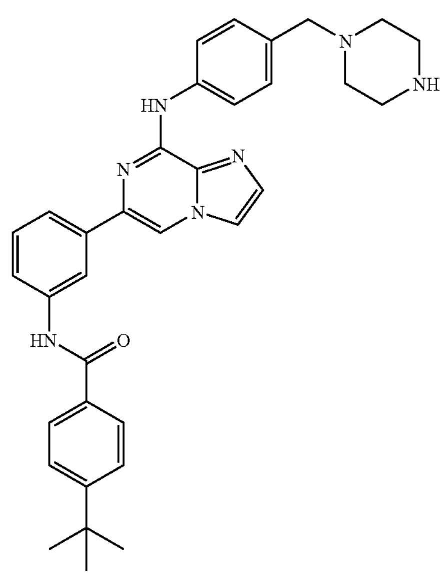 | 4-tert-Butyl-N-{3-[8-(4-piperazin-1-ylmethyl-phenylamino)-imidazo[1,2-a]pyrazin-6-yl]-phenyl}-benzamide<br>C34H37N7O | 559.31 | 560.37 |

TABLE II-continued
| Cmp. # | STRUCTURE | NAME | MW | MS m/z (M+1) |
|---|---|---|---|---|
| 59 | 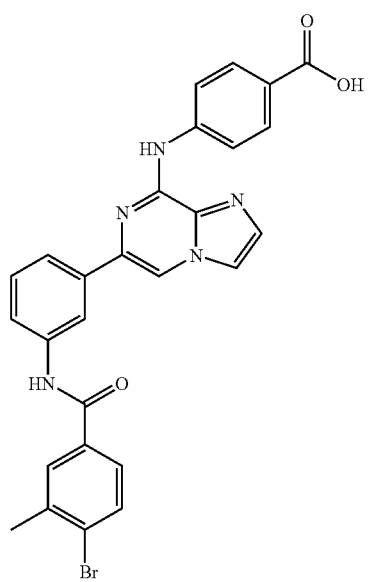 | 4-{6-[3-(4-Bromo-3-methyl-benzoylamino)-phenyl]-imidazo[1,2-a]pyrazin-8-ylamino}-benzoic acid C27H20BrN5O3 | 541.07 | 542.14 |
| 60 | 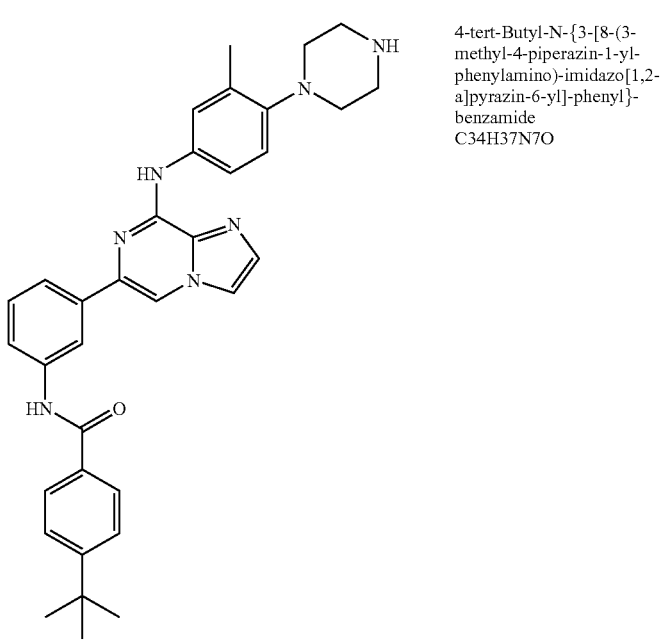 | 4-tert-Butyl-N-{3-[8-(3-methyl-4-piperazin-1-yl-phenylamino)-imidazo[1,2-a]pyrazin-6-yl]-phenyl}-benzamide C34H37N7O | 559.31 | 560.35 |

TABLE II-continued

| Cmp. # | STRUCTURE | NAME | MW | MS m/z (M+1) |
|---|---|---|---|---|
| 61 | 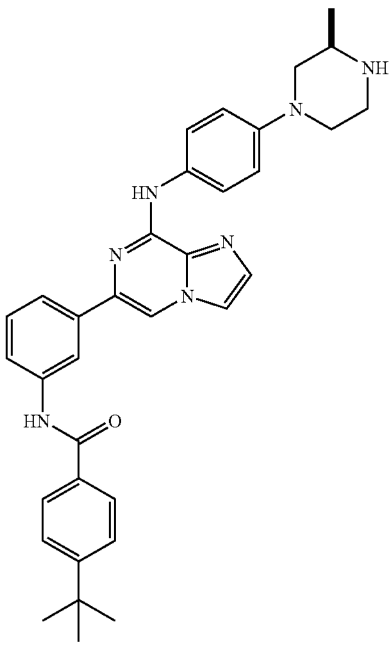 | 4-tert-Butyl-N-(3-{8-[4-(3-methyl-piperazin-1-yl)-phenylamino]-imidazo[1,2-a]pyrazin-6-yl}-phenyl)-benzamide<br>C34H37N7O | 559.31 | 560.26 |
| 62 | 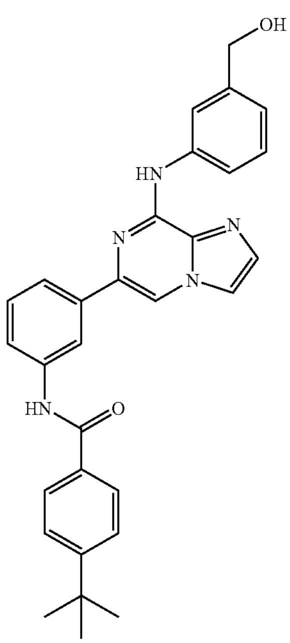 | 4-tert-Butyl-N-{3-[8-(3-hydroxymethyl-phenylamino)-imidazo[1,2-a]pyrazin-6-yl]-phenyl}-benzamide<br>C30H29N5O2 | 491.23 | 492.28 |

TABLE II-continued
| Cmp. # | STRUCTURE | NAME | MW | MS m/z (M+1) |
|---|---|---|---|---|
| 63 | 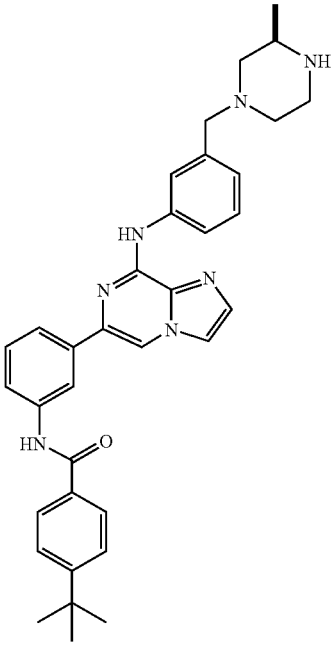 | 4-tert-Butyl-N-(3-{8-[3-(3-methyl-piperazin-1-ylmethyl)-phenylamino]-imidazo[1,2-a]pyrazin-6-yl}-phenyl)-benzamide C35H39N7O | 573.32 | 574.4 |
| 64 | 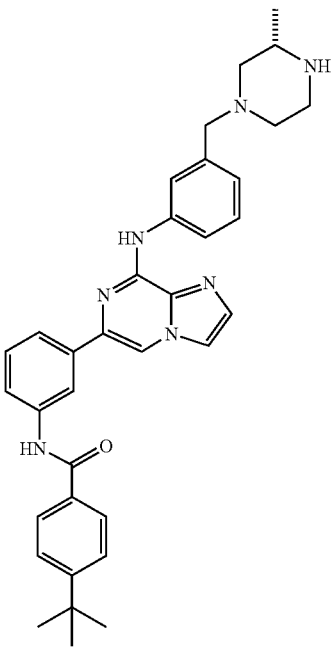 | 4-tert-Butyl-N-(3-{8-[3-(3-methyl-piperazin-1-ylmethyl)-phenylamino]-imidazo[1,2-a]pyrazin-6-yl}-phenyl)-benzamide C35H39N7O | 573.32 | 574.35 |

TABLE II-continued
| Cmp. # | STRUCTURE | NAME | MW | MS m/z (M$^{+1}$) |
|---|---|---|---|---|
| 65 | 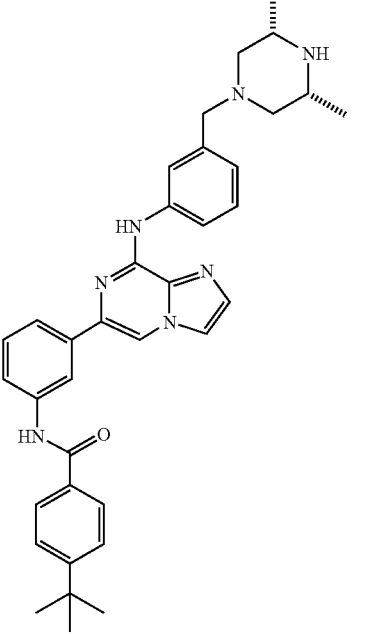 | 4-tert-Butyl-N-(3-{8-[3-(3,5-dimethyl-piperazin-1-ylmethyl)-phenylamino]-imidazo[1,2-a]pyrazin-6-yl}-phenyl)-benzamide C36H41N7O | 587.33 | 588.39 |
| 66 | 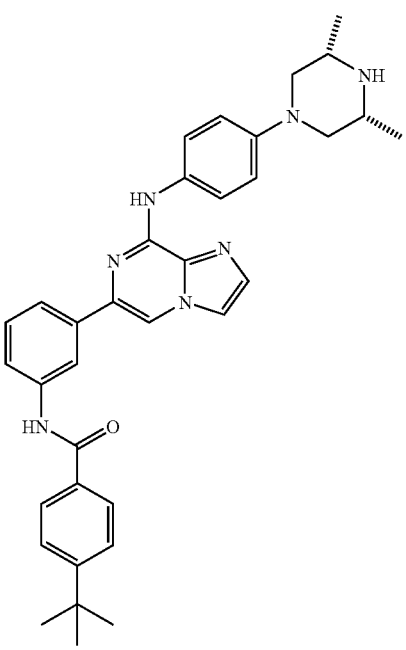 | 4-tert-Butyl-N-(3-{8-[4-(3,5-dimethyl-piperazin-1-yl)-phenylamino]-imidazo[1,2-a]pyrazin-6-yl}-phenyl)-benzamide C35H39N7O | 573.32 | 574.42 |

TABLE II-continued

| Cmp. # | STRUCTURE | NAME | MW | MS m/z (M$^{+1}$) |
|---|---|---|---|---|
| 67 | 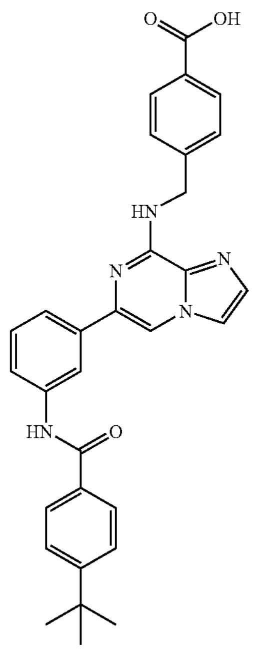 | 4-({6-[3-(4-tert-Butyl-benzoylamino)-phenyl]-imidazo[1,2-a]pyrazin-8-ylamino}-methyl)-benzoic acid<br>C31H29N5O3 | 519.22 | 520.4 |
| 68 | 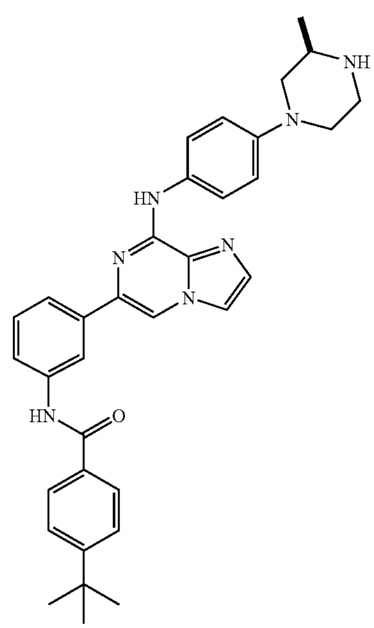 | 4-tert-Butyl-N-(3-{8-[4-(3-methyl-piperazin-1-yl)-phenylamino]-imidazo[1,2-a]pyrazin-6-yl}-phenyl)-benzamide<br>C34H37N7O | 559.3 | 560.47 |

TABLE II-continued
| Cmp. # | STRUCTURE | NAME | MW | MS m/z (M$^{+1}$) |
|---|---|---|---|---|
| 69 | 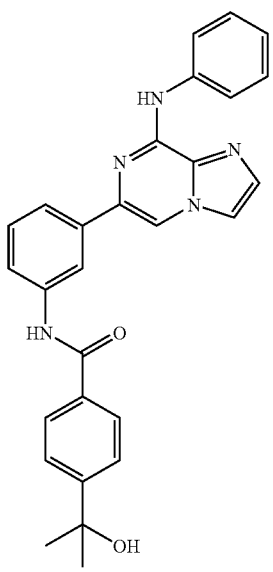 | 4-(1-Hydroxy-1-methyl-ethyl)-N-[3-(8-phenylamino-imidazo[1,2-a]pyrazin-6-yl)-phenyl]-benzamide C28H25N5O2 | 463.2 | 464.36 |
| 70 | 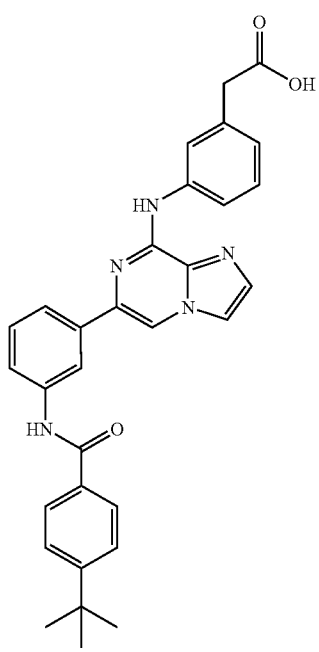 | (3-{6-[3-(4-tert-Butyl-benzoylamino)-phenyl]-imidazo[1,2-a]pyrazin-8-ylamino}-phenyl)-acetic acid C31H29N5O3 | 519.22 | 520.4 |

TABLE II-continued

| Cmp. # | STRUCTURE | NAME | MW | MS m/z (M$^{+1}$) |
|---|---|---|---|---|
| 71 | 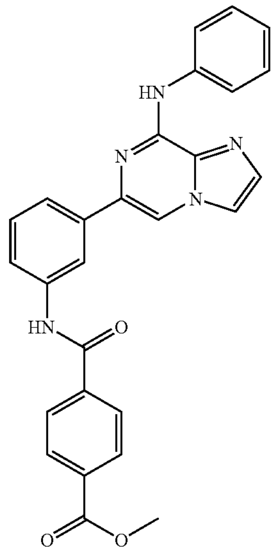 | N-[3-(8-Phenylamino-imidazo[1,2-a]pyrazin-6-yl)-phenyl]-terephthalamic acid methyl ester C27H21N5O3 | 463.16 | 464.32 |
| 72 | 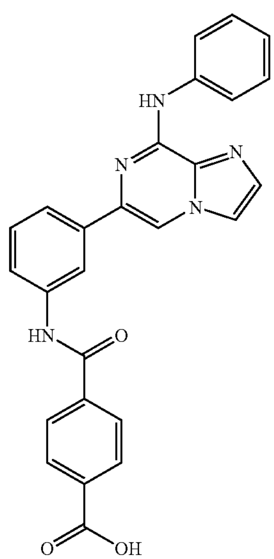 | N-[3-(8-Phenylamino-imidazo[1,2-a]pyrazin-6-yl)-phenyl]-terephthalamic acid C26H19N5O3 | 449.14 | 450.36 |

TABLE II-continued

| Cmp. # | STRUCTURE | NAME | MW | MS m/z (M$^{+1}$) |
|---|---|---|---|---|
| 73 | 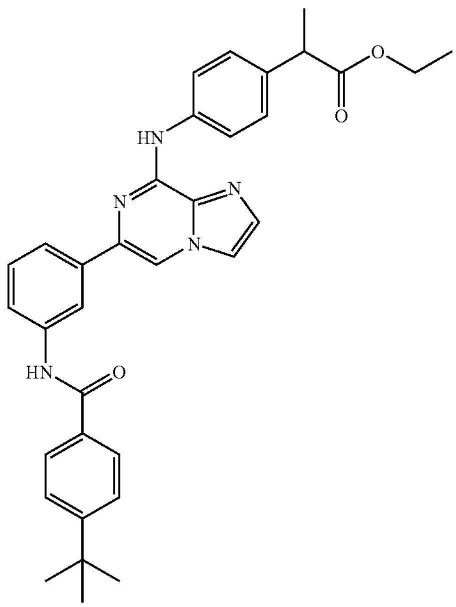 | 2-(4-{6-[3-(4-tert-Butyl-benzoylamino)-phenyl]-imidazo[1,2-a]pyrazin-8-ylamino}-phenyl)-propionic acid ethyl ester<br>C34H35N5O3 | 561.27 | 562.45 |
| 74 | 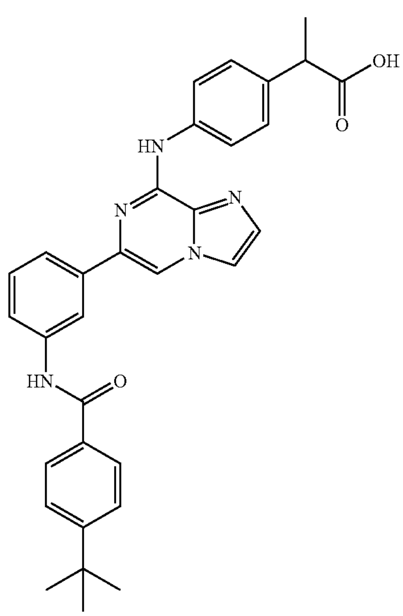 | 2-(4-{6-[3-(4-tert-Butyl-benzoylamino)-phenyl]-imidazo[1,2-a]pyrazin-8-ylamino}-phenyl)-propionic acid<br>C32H31N5O3 | 533.24 | 534.43 |

TABLE II-continued
| Cmp. # | STRUCTURE | NAME | MW | MS m/z (M+1) |
|---|---|---|---|---|
| 75 | 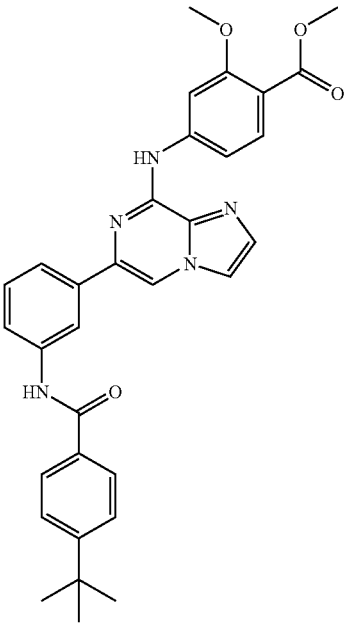 | 4-{6-[3-(4-tert-Butyl-benzoylamino)-phenyl]-imidazo[1,2-a]pyrazin-8-ylamino}-2-methoxy-benzoic acid methyl ester C32H31N5O4 | 549.23 | 550.42 |
| 76 | 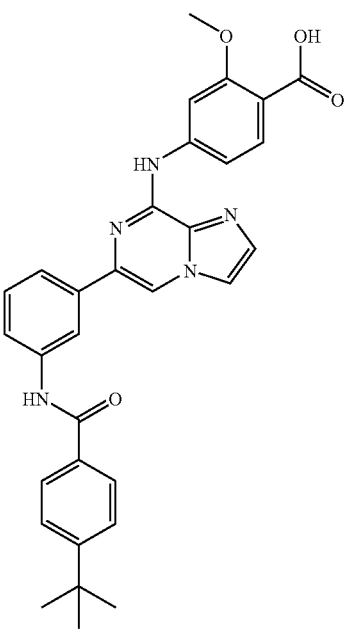 | 4-{6-[3-(4-tert-Butyl-benzoylamino)-phenyl]-imidazo[1,2-a]pyrazin-8-ylamino}-2-methoxy-benzoic acid C31H29N5O4 | 535.22 | 536.42 |

TABLE II-continued

| Cmp. # | STRUCTURE | NAME | MW | MS m/z (M+1) |
|---|---|---|---|---|
| 77 | 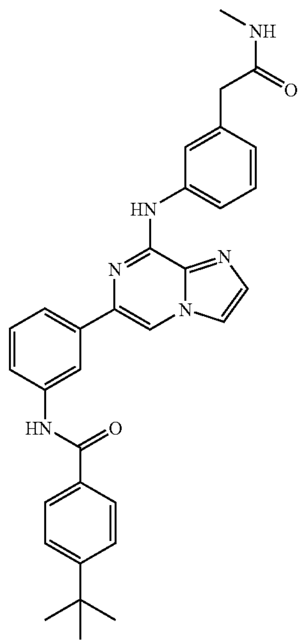 | 4-tert-Butyl-N-{3-[8-(3-methylcarbamoylmethyl-phenylamino)-imidazo[1,2-a]pyrazin-6-yl]-phenyl}-benzamide<br>C32H32N6O2 | 532.26 | 533.4 |
| 78 | 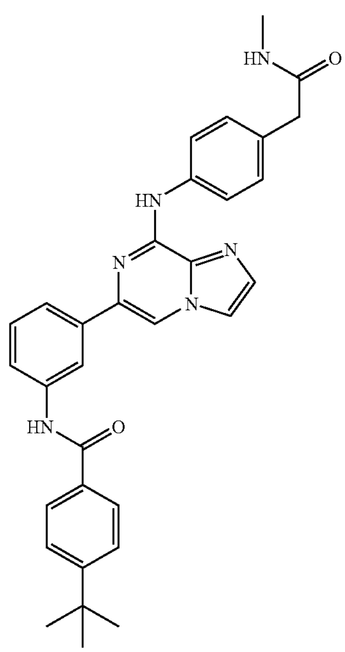 | 4-tert-Butyl-N-{3-[8-(4-methylcarbamoylmethyl-phenylamino)-imidazo[1,2-a]pyrazin-6-yl]-phenyl}-benzamide<br>C32H32N6O2 | 532.25 | 533.41 |

TABLE II-continued
| Cmp. # | STRUCTURE | NAME | MW | MS m/z (M$^{+1}$) |
|---|---|---|---|---|
| 79 | 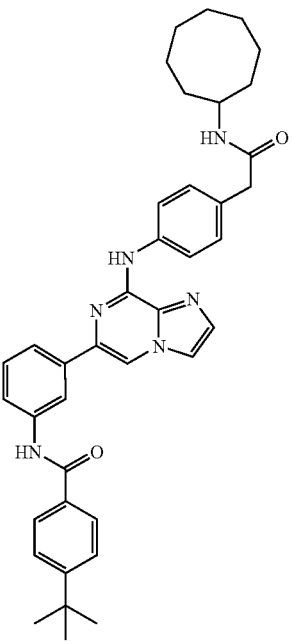 | 4-tert-Butyl-N-{3-[8-(4-cyclooctylcarbamoylmethyl-phenylamino)-imidazo[1,2-a]pyrazin-6-yl]-phenyl}-benzamide<br>C39H44N6O2 | 628.35 | 629.51 |
| 80 | 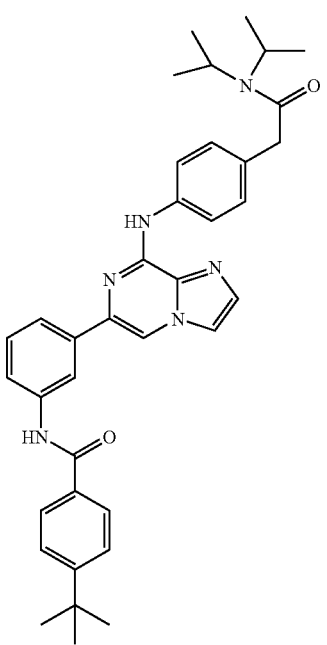 | 4-tert-Butyl-N-[3-(8-{4-[(diisopropylcarbamoyl)-methyl]-phenylamino}-imidazo[1,2-a]pyrazin-6-yl)-phenyl]-benzamide<br>C37H42N6O2 | 602.34 | 603.49 |

TABLE II-continued
| Cmp. # | STRUCTURE | NAME | MW | MS m/z (M+1) |
|---|---|---|---|---|
| 81 | 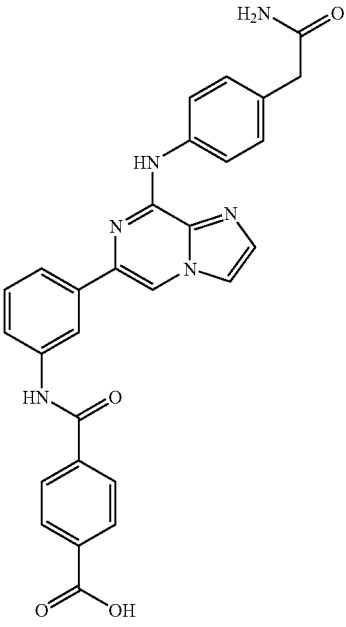 | 4-tert-Butyl-N-{3-[8-(4-carbamoylmethyl-phenylamino)-imidazo[1,2-a]pyrazin-6-yl]-phenyl}-benzamide<br>C31H30N6O2 | 518.24 | 519.48 |
| 82 | 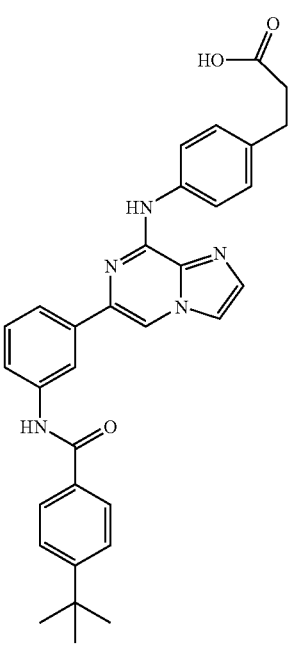 | 3-(4-{6-[3-(4-tert-Butyl-benzoylamino)-phenyl]-imidazo[1,2-a]pyrazin-8-ylamino}-phenyl)-propionic acid<br>C32H31N5O3 | 533.24 | 534.22 |

TABLE II-continued

| Cmp. # | STRUCTURE | NAME | MW | MS m/z (M$^{+1}$) |
|---|---|---|---|---|
| 83 | 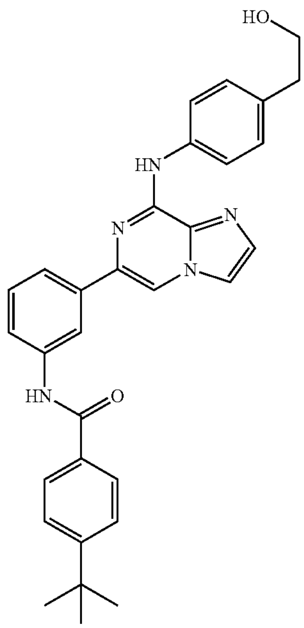 | 4-tert-Butyl-N-(3-{8-[4-(2-hydroxy-ethyl)-phenylamino]-imidazo[1,2-a]pyrazin-6-yl}-phenyl)-benzamide<br>C31H31N5O2 | 505.25 | 506.4 |
| 84 | 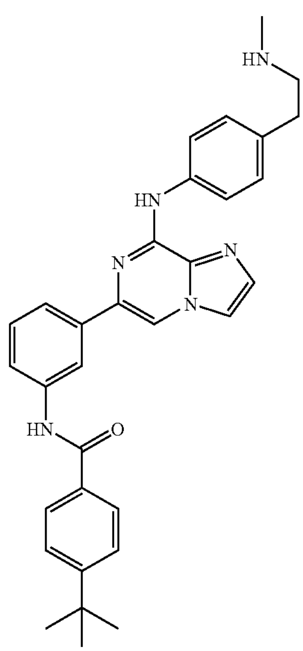 | 4-tert-Butyl-N-(3-{8-[4-(2-methylamino-ethyl)-phenylamino]-imidazo[1,2-a]pyrazin-6-yl}-phenyl)-benzamide<br>C32H34N6O | 518.3 | 519.45 |

| Cmp. # | STRUCTURE | NAME | MW | MS m/z (M$^{+1}$) |
|---|---|---|---|---|
| 85 | 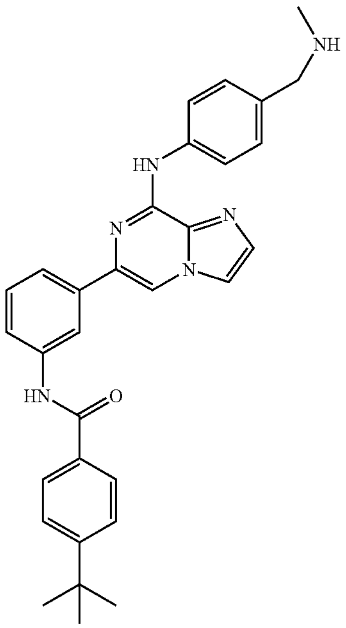 | 4-tert-Butyl-N-{3-[8-(4-methylaminomethyl-phenylamino)-imidazo[1,2-a]pyrazin-6-yl]-phenyl}-benzamide<br>C31H32N6O | 504.26 | 505.43 |
| 86 | 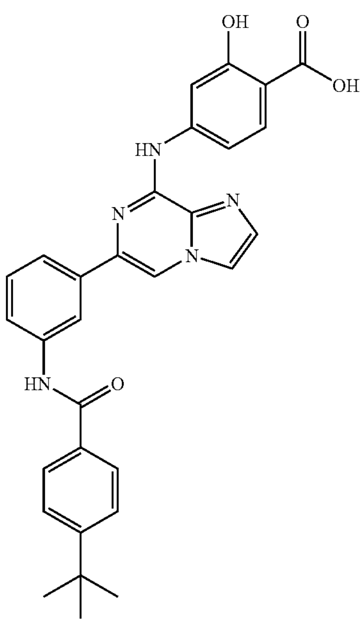 | 4-{6-[3-(4-tert-Butyl-benzoylamino)-phenyl]-imidazo[1,2-a]pyrazin-8-ylamino}-2-hydroxy-benzoic acid<br>C30H27N5O4 | 521.2 | 522.31 |

| Cmp. # | STRUCTURE | NAME | MW | MS m/z (M+1) |
|---|---|---|---|---|
| 87 | 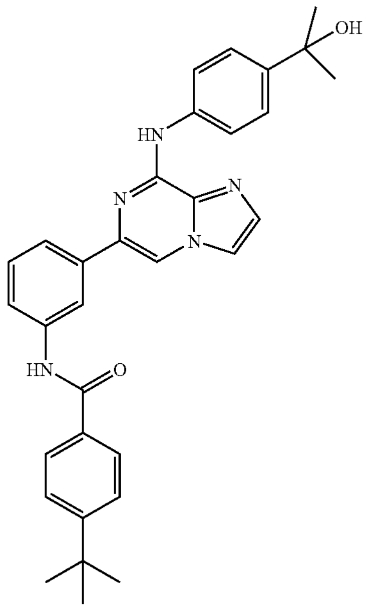 | 4-tert-Butyl-N-(3-{8-[4-(1-hydroxy-1-methyl-ethyl)-phenylamino]-imidazo[1,2-a]pyrazin-6-yl}-phenyl)-benzamide<br>C32H33N5O2 | 519.26 | 520.27 |
| 88 | 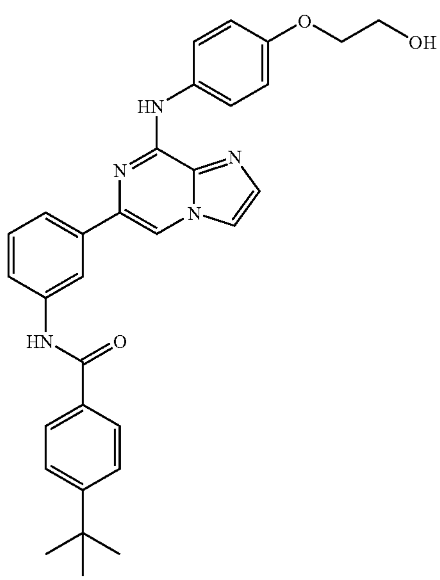 | 4-tert-Butyl-N-(3-{8-[4-(2-hydroxy-ethoxy)-phenylamino]-imidazo[1,2-a]pyrazin-6-yl}-phenyl)-benzamide<br>C31H31N5O3 | 521.24 | 522.25 |

| Cmp. # | STRUCTURE | NAME | MW | MS m/z (M+1) |
|---|---|---|---|---|
| 89 | 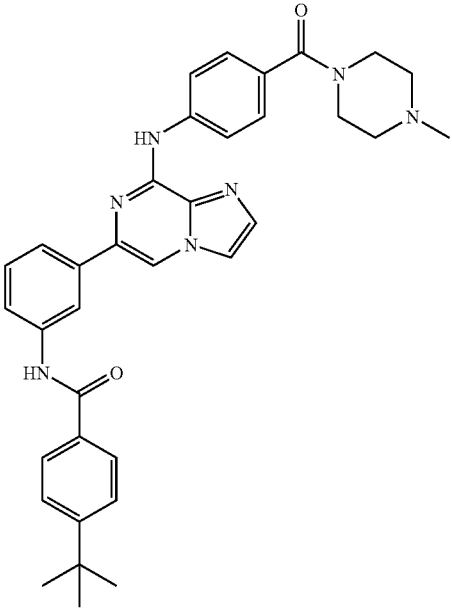 | 4-tert-Butyl-N-(3-{8-[4-(4-methyl-piperazine-1-carbonyl)-phenylamino]-imidazo[1,2-a]pyrazin-6-yl}-phenyl)-benzamide C35H37N7O2 | 587.3 | 588.28 |
| 90 | 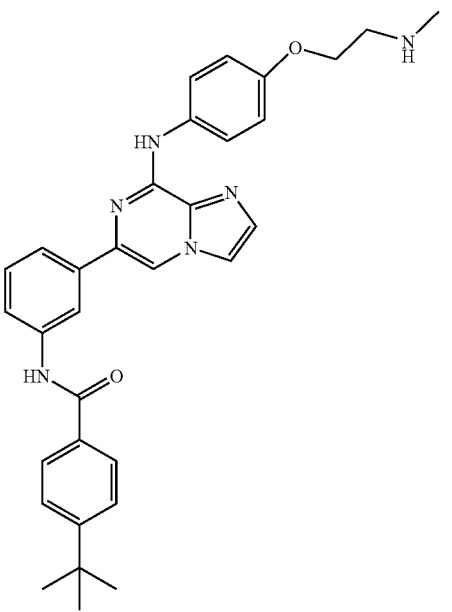 | 4-tert-Butyl-N-(3-{8-[4-(2-methylamino-ethoxy)-phenylamino]-imidazo[1,2-a]pyrazin-6-yl}-phenyl)-benzamide C32H34N6O2 | 534.27 | 535.27 |

-continued

| Cmp. # | STRUCTURE | NAME | MW | MS m/z (M+1) |
|---|---|---|---|---|
| 91 | 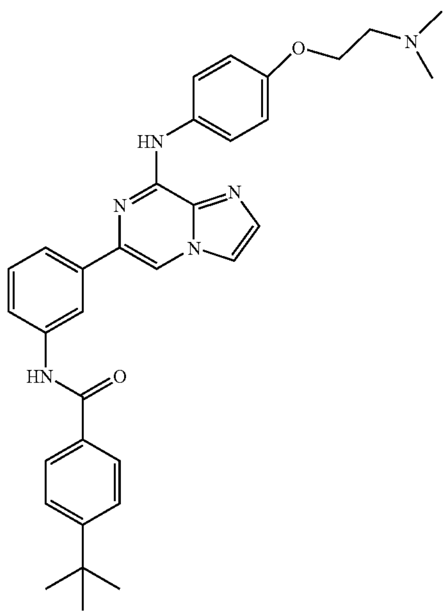 | 4-tert-Butyl-N-(3-{8-[4-(2-dimethylamino-ethoxy)-phenylamino]-imidazo[1,2-a]pyrazin-6-yl}-phenyl)-benzamide<br>C33H36N6O2 | 548.28 | 549.28 |
| 92 | 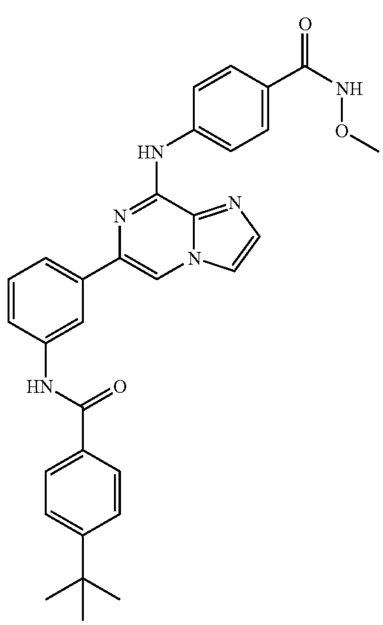 | 4-{6-[3-(4-tert-Butyl-benzoylamino)-phenyl]-imidazo[1,2-a]pyrazin-8-ylamino}-benzoic methoxy amide<br>C31H30N6O3 | 534.23 | 535.25 |

| Cmp. # | STRUCTURE | NAME | MW | MS m/z (M⁺¹) |
|---|---|---|---|---|
| 93 | 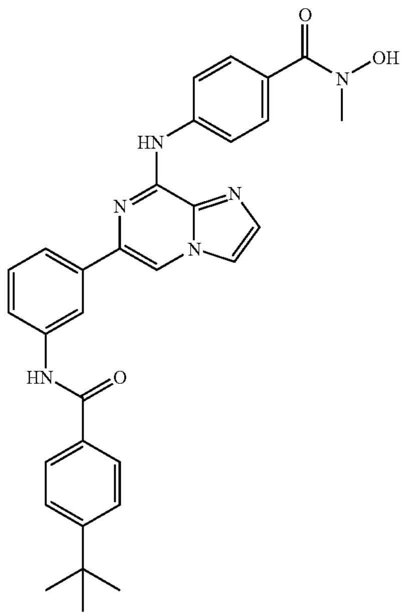 | 4-{6-[3-(4-tert-Butyl-benzoylamino)-phenyl]-imidazo[1,2-a]pyrazin-8-ylamino}-benzoic hyrdoxyl methyl amide<br>C31H30N6O3 | 534.23 | 535.25 |
| 94 | 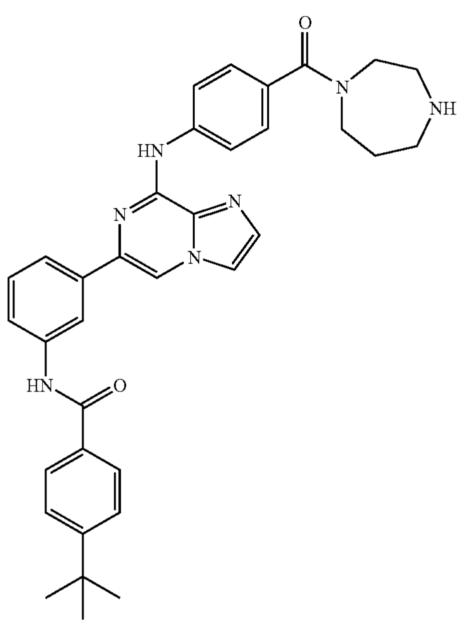 | 4-tert-Butyl-N-(3-{8-[4-([1,4]diazepane-1-carbonyl)-phenylamino]-imidazo[1,2-a]pyrazin-6-yl}-phenyl)-benzamide<br>C35H37N7O2 | 587.3 | 588.27 |

-continued

| Cmp. # | STRUCTURE | NAME | MW | MS m/z (M+1) |
|---|---|---|---|---|
| 95 | 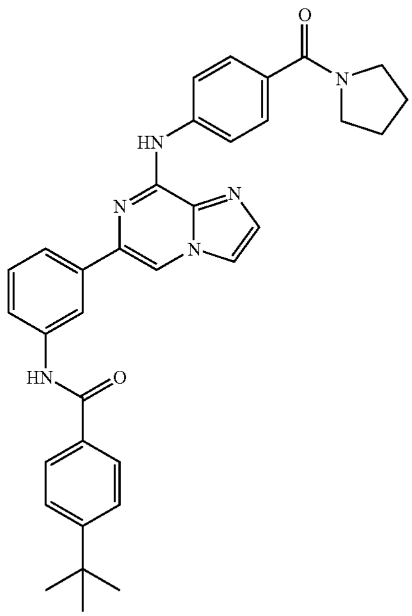 | 4-tert-Butyl-N-(3-{8-[4-(pyrrolidine-1-carbonyl)-phenylamino]-imidazo[1,2-a]pyrazin-6-yl}-phenyl)-benzamide<br>C34H34N6O2 | 558.27 | 559.25 |
| 96 | 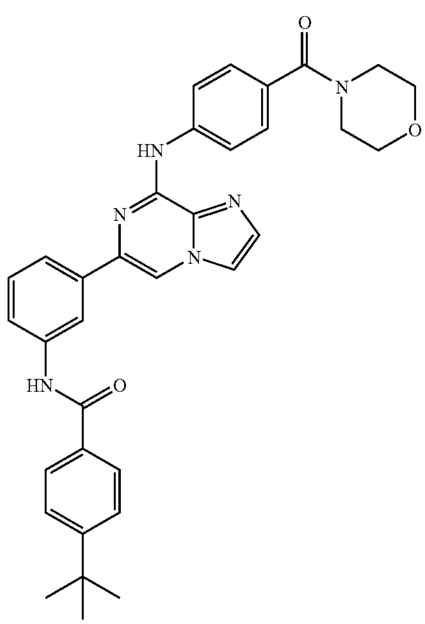 | 4-tert-Butyl-N-(3-{8-[4-(morpholine-4-carbonyl)-phenylamino]-imidazo[1,2-a]pyrazin-6-yl}-phenyl)-benzamide<br>C34H34N6O3 | 574.26 | 575.24 |

-continued

| Cmp. # | STRUCTURE | NAME | MW | MS m/z (M$^{+1}$) |
|---|---|---|---|---|
| 97 | 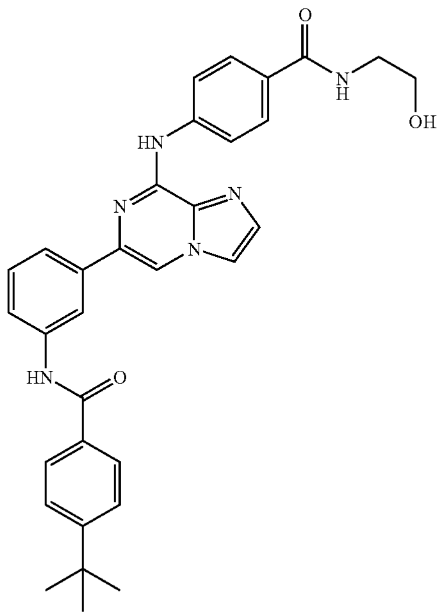 | 4-tert-Butyl-N-(3-{8-[4-(ethoxyamine-4-cabonyl)-phenylamino]-imidazo[1,2-a]pyrazin-6-yl}-phenyl)-benzamide<br>C33H34N6O3 | 548.25 | 549.22 |
| 98 | 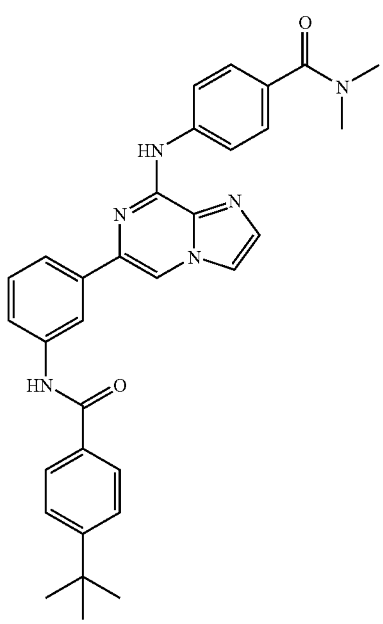 | 4-tert-Butyl-N-(3-{8-[4-(dimethylamine-4-carbonyl)-phenylamino]-imidazo[1,2-a]pyrazin-6-yl}-phenyl)-benzamide<br>C32H32N6O2 | 532.25 | 533.22 |

| Cmp. # | STRUCTURE | NAME | MW | MS m/z (M$^{+1}$) |
|---|---|---|---|---|
| 99 | 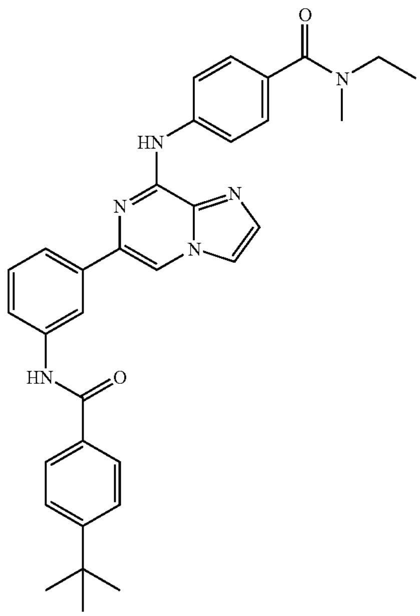 | 4-tert-Butyl-N-(3-{8-[4-(methylethylamine-4-carbonyl)-phenylamino]-imidazo[1,2-a]pyrazin-6-yl}-phenyl)-benzamide C33H34N6O2 | 546.27 | 547.24 |
| 100 | 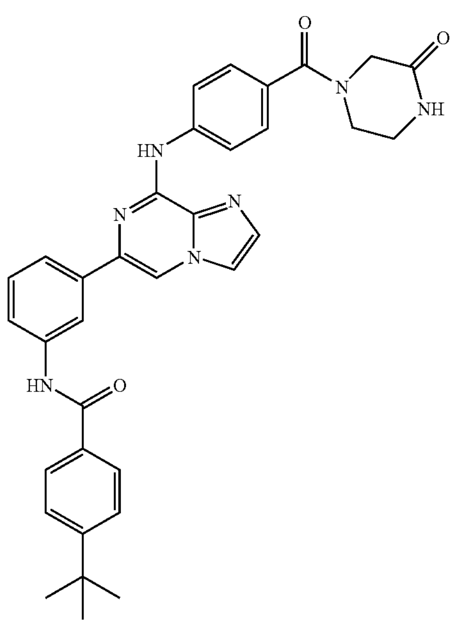 | 4-tert-Butyl-N-(3-{8-[4-(3-oxo-piperazine-1-carbonyl)-phenylamino]-imidazo[1,2-a]pyrazin-6-yl}-phenyl)-benzamide C34H33N7O3 | 587.26 | 588.28 |

-continued

| Cmp. # | STRUCTURE | NAME | MW | MS m/z (M⁺¹) |
|---|---|---|---|---|
| 101 | 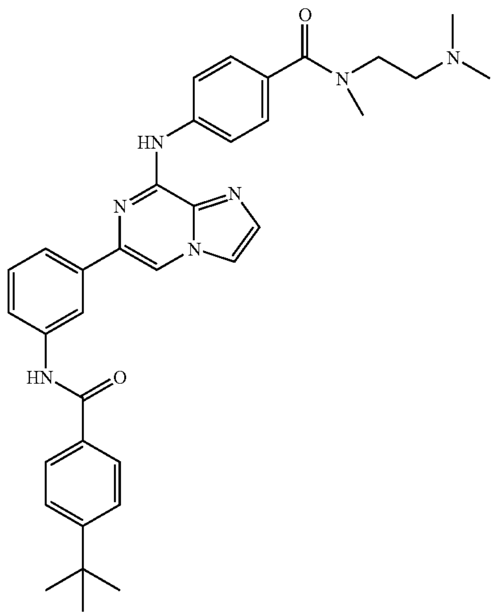 | 4-tert-Butyl-N-(3-{8-[N,N,N'-Trimethyl-ethane-1,2-diamine-4-carbonyl)-phenylamino]-imidazo[1,2-a]pyrazin-6-yl}-phenyl)-benzamide<br>C35H39N7O2 | 589.31 | 590.35 |
| 102 | 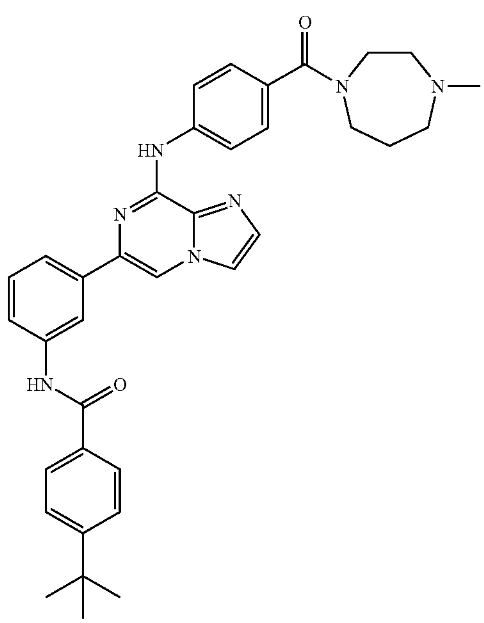 | 4-tert-Butyl-N-(3-{8-[4-(4-methyl-[1,4]diazepane-1-carbonyl)-phenylamino]-imidazo[1,2-a]pyrazin-6-yl}-phenyl)-benzamide<br>C36H39N7O2 | 601.31 | 602.32 |

-continued
| Cmp. # | STRUCTURE | NAME | MW | MS m/z (M+1) |
|---|---|---|---|---|
| 103 | 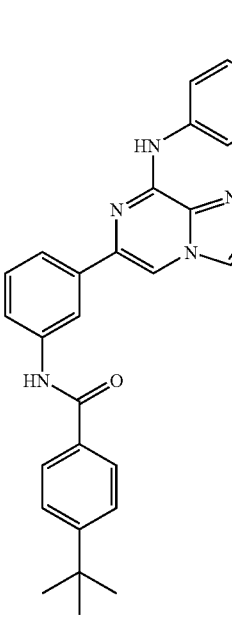 | 4-tert-Butyl-N-(3-{8-[4-(N-methyl ethoxyamine-4-carbonyl)-phenylamino]-imidazo[1,2-a]pyrazin-6-yl}-phenyl)-benzamide C33H34N6O3 | 562.26 | 563.29 |
| 104 | 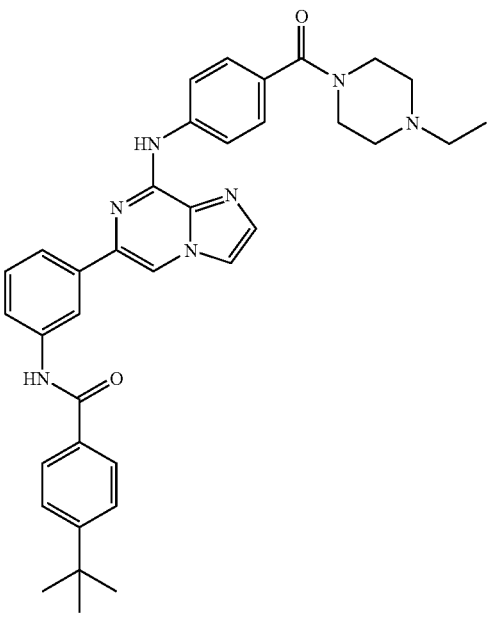 | 4-tert-Butyl-N-(3-{8-[4-(4-ethyl-piperazine-1-carbonyl)-phenylamino]-imidazo[1,2-a]pyrazin-6-yl}-phenyl)-benzamide C36H39N7O2 | 601.31 | 602.38 |

| Cmp. # | STRUCTURE | NAME | MW | MS m/z (M+1) |
|---|---|---|---|---|
| 105 | 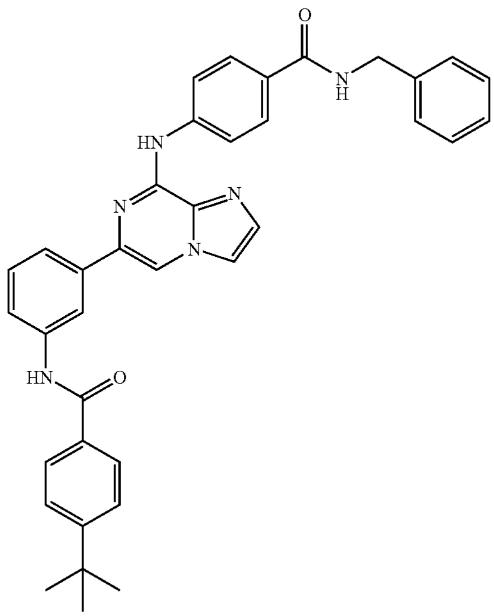 | 4-{6-[3-(4-tert-Butyl-benzoylamino)-phenyl]-imidazo[1,2-a]pyrazin-8-ylamino}-benzoic benzyl amide<br>C37H34N6O2 | 595.26 | 596.32 |
| 106 | 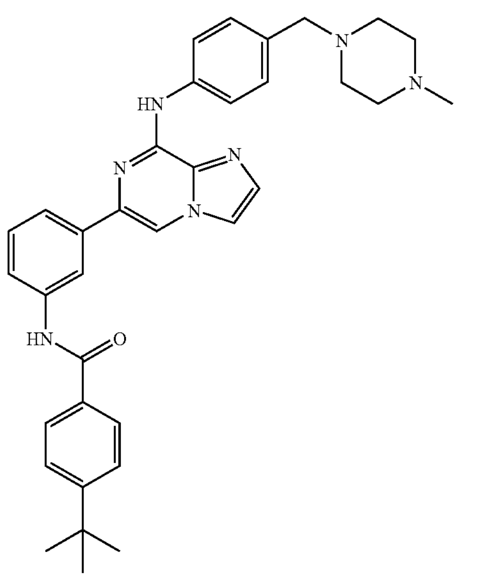 | 4-tert-Butyl-N-(3-{8-[4-(4-methyl-piperazin-1-ylmethyl)-phenylamino]-imidazo[1,2-a]pyrazin-6-yl}-phenyl)-benzamide<br>C35H39N7O | 573.32 | 574.39 |

-continued

| Cmp. # | STRUCTURE | NAME | MW | MS m/z (M+1) |
|---|---|---|---|---|
| 107 | 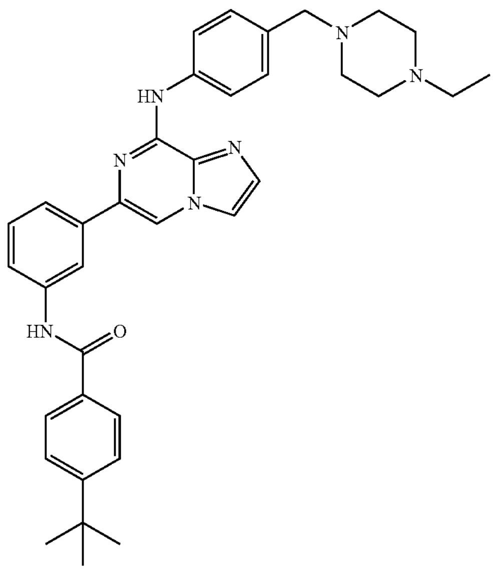 | 4-tert-Butyl-N-(3-{8-[4-(4-ethyl-piperazin-1-ylmethyl)-phenylamino]-imidazo[1,2-a]pyrazin-6-yl}-phenyl)-benzamide C34H41N7O | 587.33 | 588.42 |
| 108 | 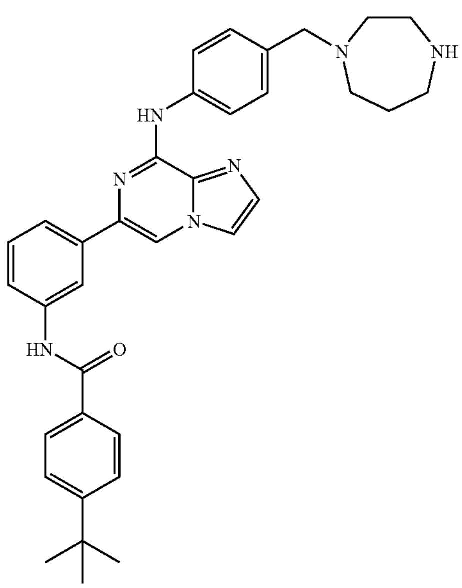 | 4-tert-Butyl-N-{3-[8-(4-[1,4]diazepan-1-ylmethyl-phenylamino)-imidazo[1,2-a]pyrazin-6-yl]-phenyl}-benzamide C35H39N7O | 573.32 | 574.39 |

| Cmp. # | STRUCTURE | NAME | MW | MS m/z (M+1) |
|---|---|---|---|---|
| 109 | 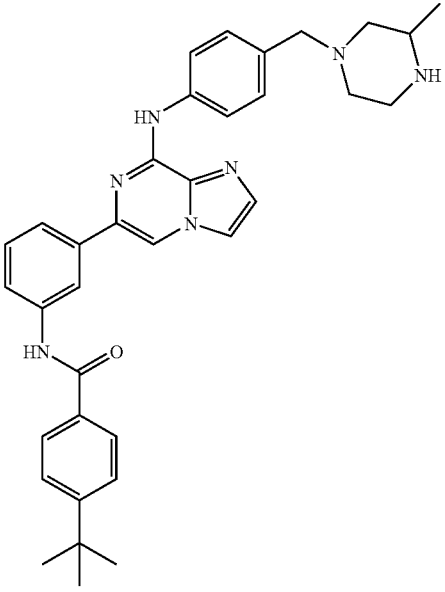 | 4-tert-Butyl-N-(3-{8-[4-(3-methyl-piperazin-1-ylmethyl)-phenylamino]-imidazo[1,2-a]pyrazin-6-yl}-phenyl)-benzamide<br>C35H39N7O | 573.32 | 574.38 |
| 110 | 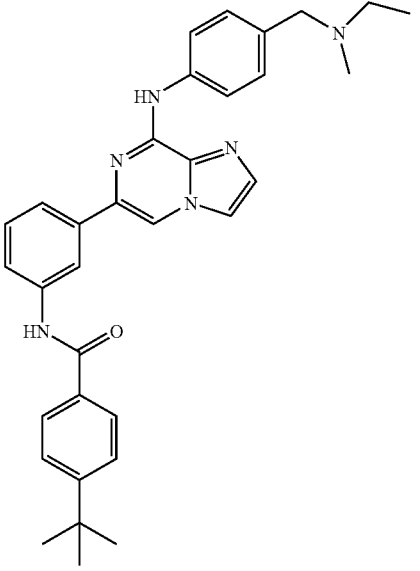 | 4-tert-Butyl-N-{3-[8-(4-dimethylaminomethyl-phenylamino)-imidazo[1,2-a]pyrazin-6-yl]-phenyl}-benzamide<br>C23H34N6O | 518.27 | 519.33 |

-continued
| Cmp. # | STRUCTURE | NAME | MW | MS m/z (M+1) |
|---|---|---|---|---|
| 111 | 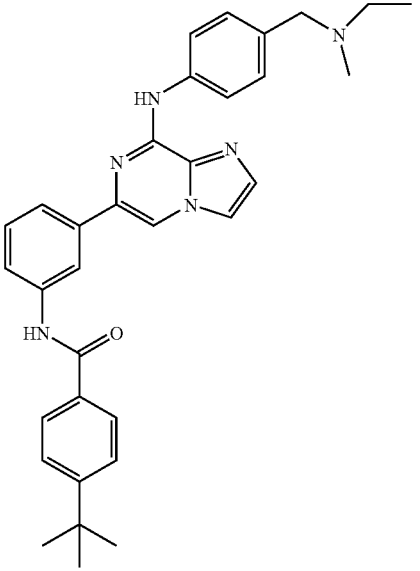 | 4-tert-Butyl-N-[3-(8-{4-[(ethyl-methyl-amino)-methyl]-phenylamino}-imidazo[1,2-a]pyrazin-6-yl)-phenyl]-benzamide C33H36N6O | 532.29 | 533.33 |
| 112 | 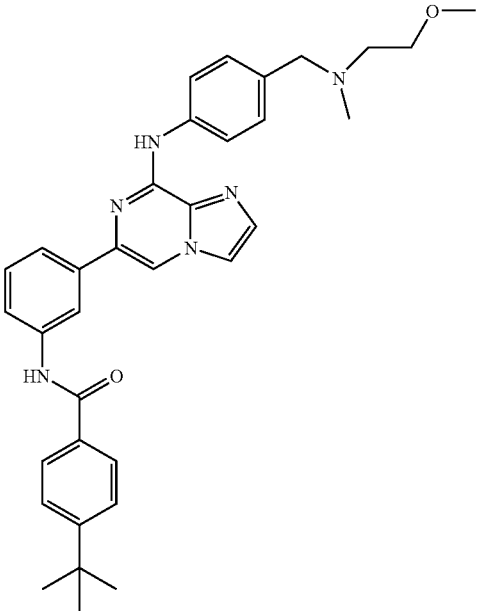 | 4-tert-Butyl-N-{3-[8-(4-{[(2-methoxy-ethyl)-methyl-amino]-methyl}-phenylamino)-imidazo[1,2-a]pyrazin-6-yl]-phenyl}-benzamide C34H38N6O2 | 562.31 | 563.33 |

-continued
| Cmp. # | STRUCTURE | NAME | MW | MS m/z (M+1) |
|---|---|---|---|---|
| 113 | 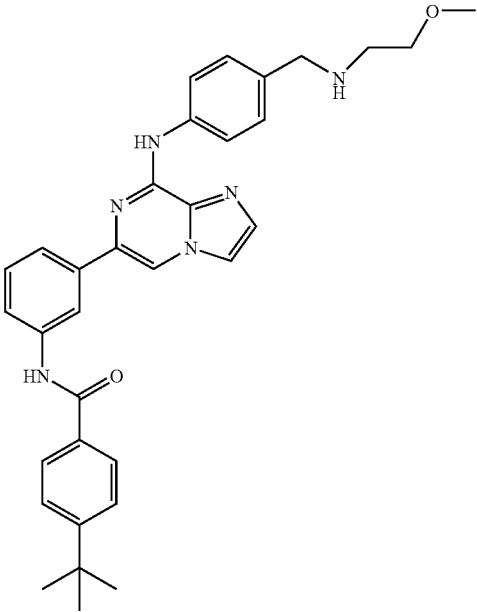 | 4-tert-Butyl-N-[3-(8-{4-[(2-methoxy-ethylamino)-methyl]-phenylamino}-imidazo[1,2-a]pyrazin-6-yl)-phenyl]-benzamide C33H36N6O2 | 548.28 | 549.32 |
| 114 | 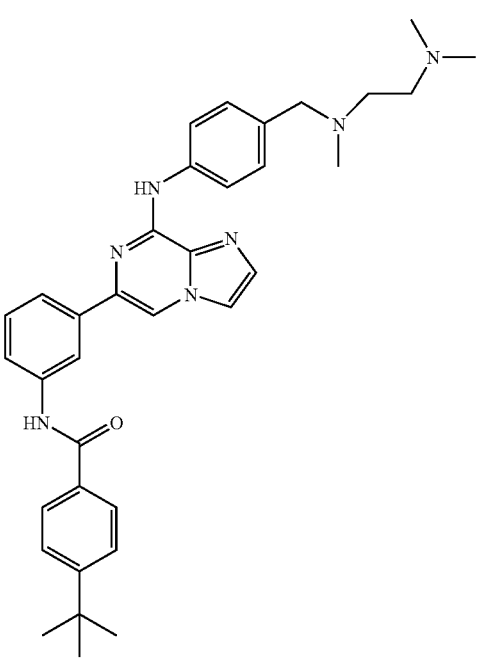 | 4-tert-Butyl-N-{3-[8-(4-{[(2-dimethylamino-ethyl)-methyl-amino]-methyl}-phenylamino)-imidazo[1,2-a]pyrazin-6-yl]-phenyl}-benzamide C35H41N7O | 575.33 | 576.39 |

-continued

| Cmp. # | STRUCTURE | NAME | MW | MS m/z (M$^{+1}$) |
|---|---|---|---|---|
| 115 | 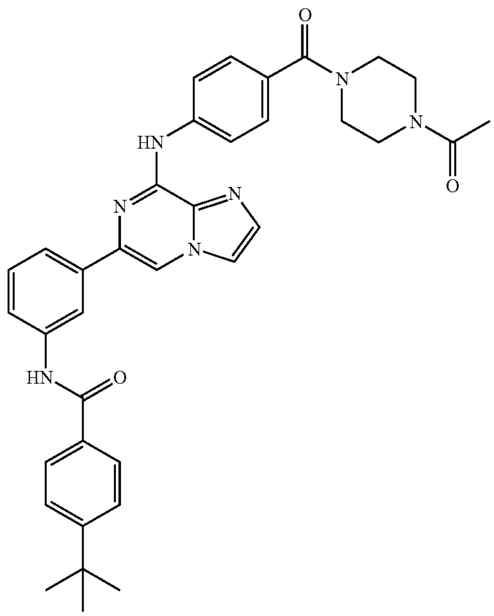 | N-(3-{8-[4-(4-Acetyl-piperazine-1-carbonyl)-phenylamino]-imidazo[1,2-a]pyrazin-6-yl}-phenyl)-4-tert-butyl-benzamide C36H37N7O3 | 615.29 | 616.31 |
| 116 | 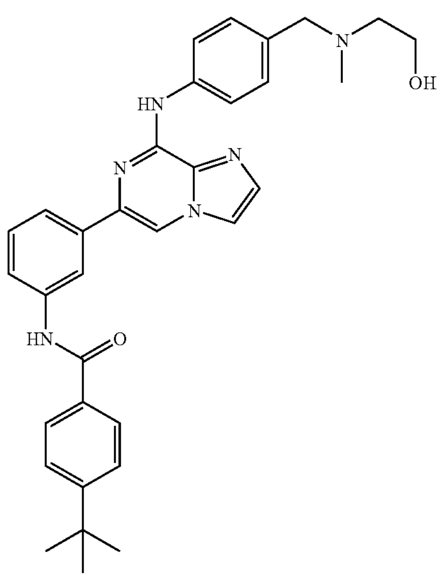 | 4-tert-Butyl-N-{3-[8-(4-{[(2-hydroxy-ethyl)-methyl-amino]-methyl}-phenylamino)-imidazo[1,2-a]pyrazin-6-yl]-phenyl}-benzamide C33H36N6O2 | 548.28 | 549.32 |

| Cmp. # | STRUCTURE | NAME | MW | MS m/z (M+1) |
|---|---|---|---|---|
| 117 | 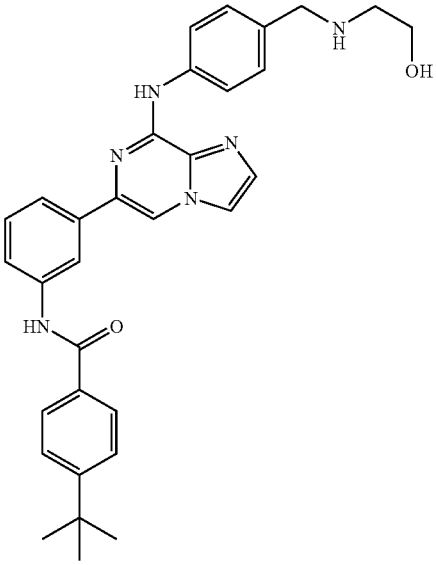 | 4-tert-Butyl-N-[3-(8-{4-[(2-hydroxy-ethylamino)-methyl]-phenylamino}-imidazo[1,2-a]pyrazin-6-yl)-phenyl]-benzamide C32H34N6O2 | 534.27 | 535.32 |
| 118 | 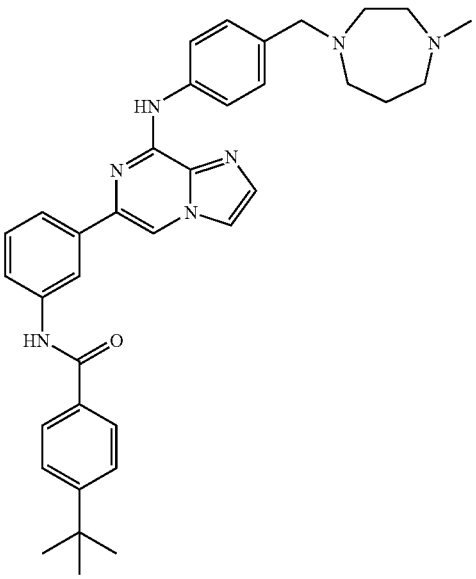 | 4-tert-Butyl-N-(3-{8-[4-(4-methyl-[1,4]diazepan-1-ylmethyl)-phenylamino]-imidazo[1,2-a]pyrazin-6-yl}-phenyl)-benzamide C36H41N7O | 587.33 | 588.37 |

-continued

| Cmp. # | STRUCTURE | NAME | MW | MS m/z (M+1) |
|---|---|---|---|---|
| 119 | 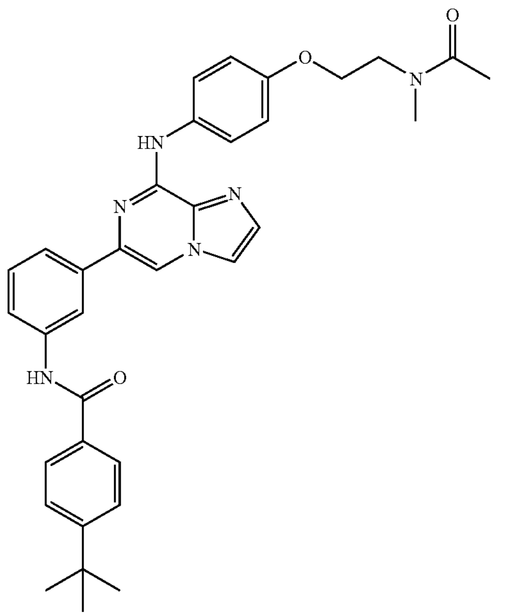 | N-[3-(8-{4-[2-(Acetyl-methyl-amino)-ethoxy]-phenylamino}-imidazo[1,2-a]pyrazin-6-yl)-phenyl]-4-tert-butyl-benzamide C34H36N6O3 | 576.28 | 577.32 |
| 120 | 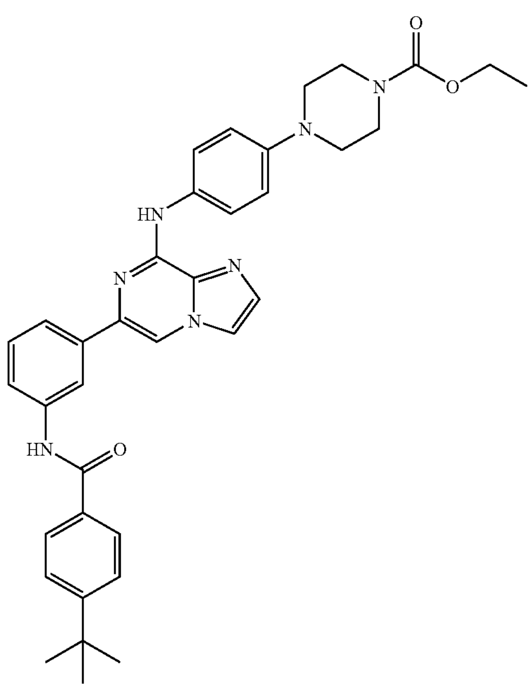 | 4-(4-{6-[3-(4-tert-Butyl-benzoylamino)-phenyl]-imidazo[1,2-a]pyrazin-8-ylamino}-phenyl)-piperazine-1-carboxylic acid ethyl ester C36H39N7O3 | 617.31 | 618.31 |

-continued

| Cmp. # | STRUCTURE | NAME | MW | MS m/z (M⁺¹) |
|---|---|---|---|---|
| 121 | 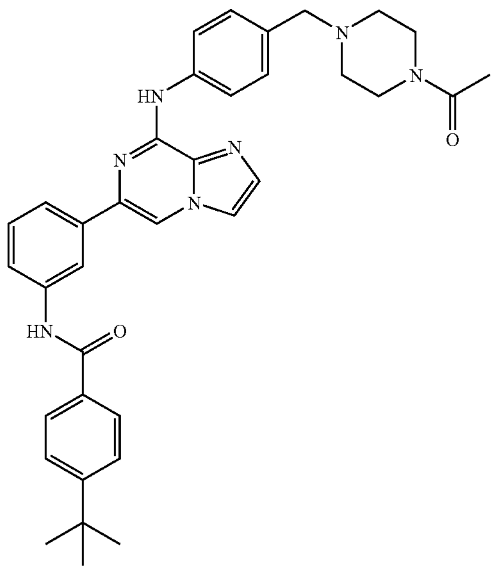 | N-(3-{8-[4-(4-Acetyl-piperazin-1-ylmethyl)-phenylamino]-imidazo[1,2-a]pyrazin-6-yl}-phenyl)-4-tert-butyl-benzamide C36H39N7O2 | 601.31 | 602.26 |
| 122 | 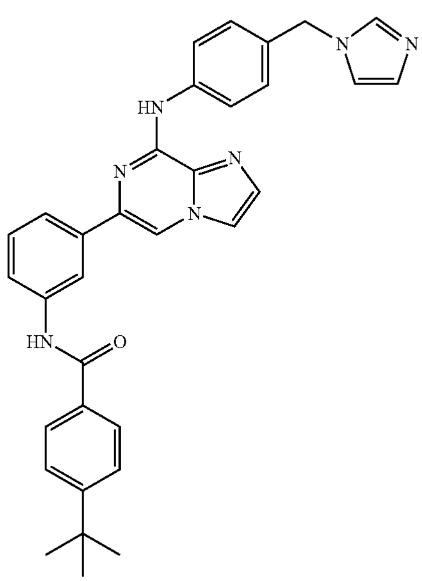 | 4-tert-Butyl-N-{3-[8-(4-imidazol-1-ylmethyl-phenylamino)-imidazo[1,2-a]pyrazin-6-yl]-phenyl}-benzamide C33H31N7O | 541.25 | 542.27 |

-continued

| Cmp. # | STRUCTURE | NAME | MW | MS m/z (M$^{+1}$) |
|---|---|---|---|---|
| 123 | 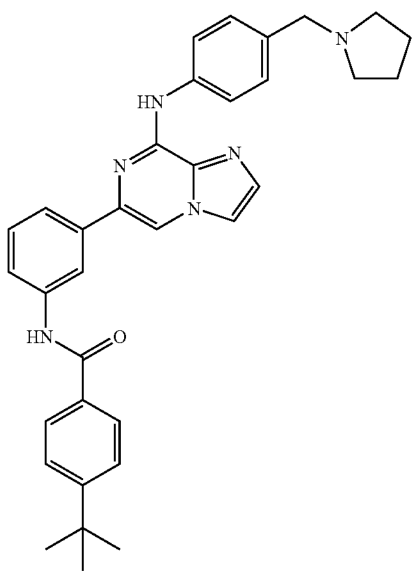 | 4-tert-Butyl-N-{3-[8-(4-pyrrolidin-1-ylmethyl-phenylamino)-imidazo[1,2-a]pyrazin-6-yl]-phenyl}-benzamide C34H36N6O | 544.29 | 545.3 |
| 124 | 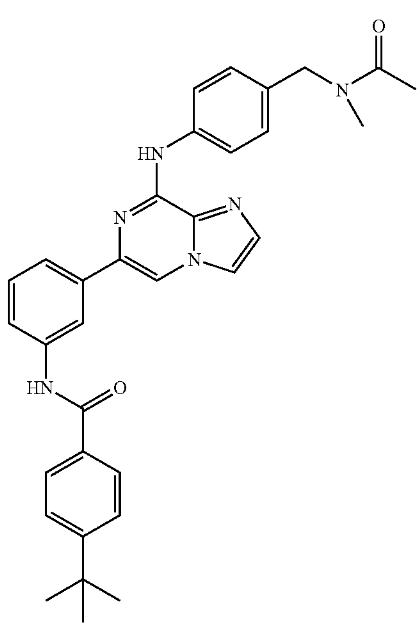 | N-[3-(8-{4-[(Acetyl-methyl-amino)-methyl]-phenylamino}-imidazo[1,2-a]pyrazin-6-yl)-phenyl]-4-tert-butyl-benzamide C33H34N6O2 | 546.27 | 547.33 |

| Cmp. # | STRUCTURE | NAME | MW | MS m/z (M⁺¹) |
|---|---|---|---|---|
| 125 | 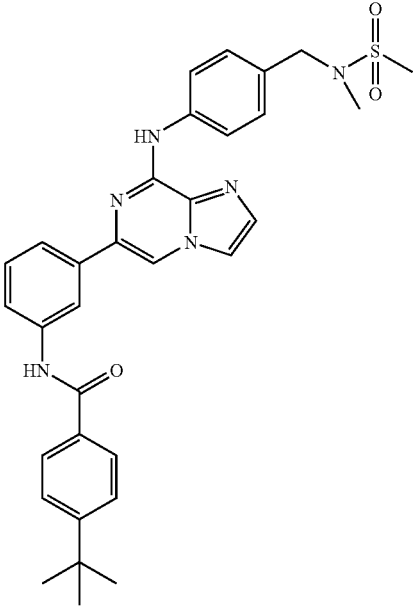 | 4-tert-Butyl-N-[3-(8-{4-[(methanesulfonyl-methyl-amino)-methyl]-phenylamino}-imidazo[1,2-a]pyrazin-6-yl)-phenyl]-benzamide C32H34N6O3S | 584.24 | 583.27 |
| 126 | 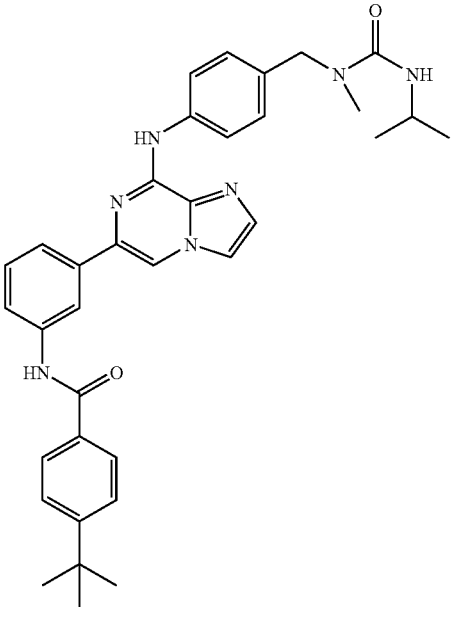 | 4-tert-Butyl-N-(3-{8-[4-(3-isopropyl-1-methyl-ureidomethyl)-phenylamino]-imidazo[1,2-a]pyrazin-6-yl}-phenyl)-benzamide C35H39N7O2 | 589.31 | 590.35 |

-continued

| Cmp. # | STRUCTURE | NAME | MW | MS m/z (M+1) |
|---|---|---|---|---|
| 127 | 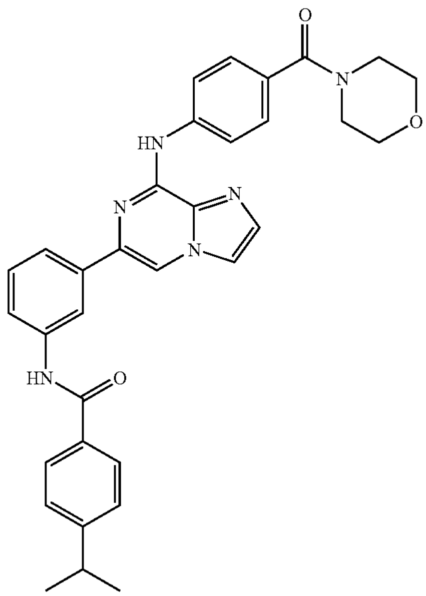 | 4-Isopropyl-N-(3-{8-[4-(morpholine-4-carbonyl)-phenylamino]-imidazo[1,2-a]pyrazin-6-yl}-phenyl)-benzamide C33H32N6O3 | 560.25 | 561.28 |
| 128 | 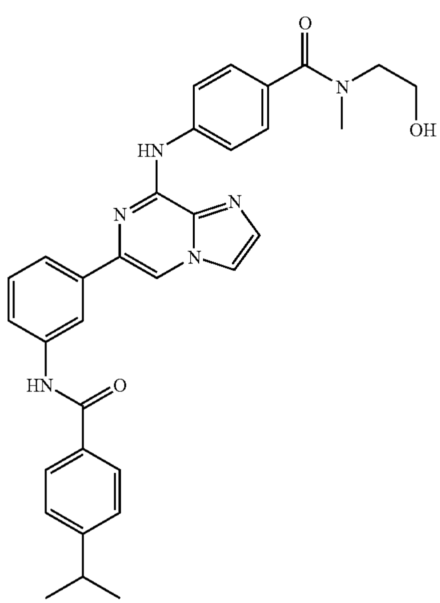 | N-{3-[8-(4-{[(2-Hydroxy-ethyl)-methyl-amino]-carbonyl}-phenylamino)-imidazo[1,2-a]pyrazin-6-yl]-phenyl}-4-isopropyl-benzamide C32H32N6O3 | 548.25 | 549.25 |

| Cmp. # | STRUCTURE | NAME | MW | MS m/z (M$^{+1}$) |
|---|---|---|---|---|
| 129 | 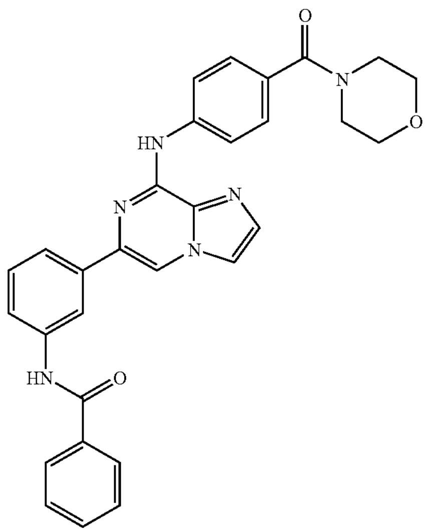 | N-(3-{8-[4-(Morpholine-4-carbonyl)-phenylamino]-imidazo[1,2-a]pyrazin-6-yl}-phenyl)-benzamide C30H26N6O3 | 518.2 | 519.22 |
| 130 | 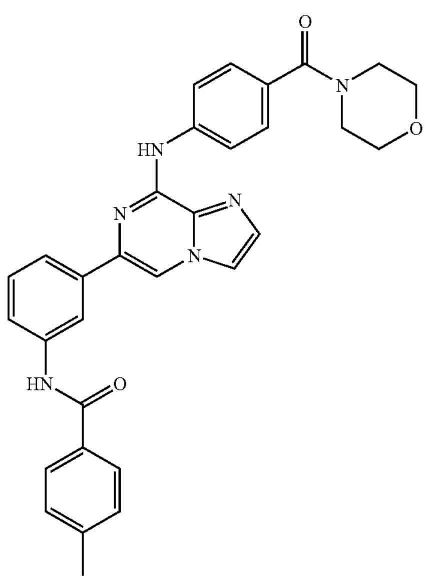 | 4-Methyl-N-(3-{8-[4-(morpholine-4-carbonyl)-phenylamino]-imidazo[1,2-a]pyrazin-6-yl}-phenyl)-benzamide C31H28N6O3 | 532.22 | 533.17 |

| Cmp. # | STRUCTURE | NAME | MW | MS m/z (M+1) |
|---|---|---|---|---|
| 131 | 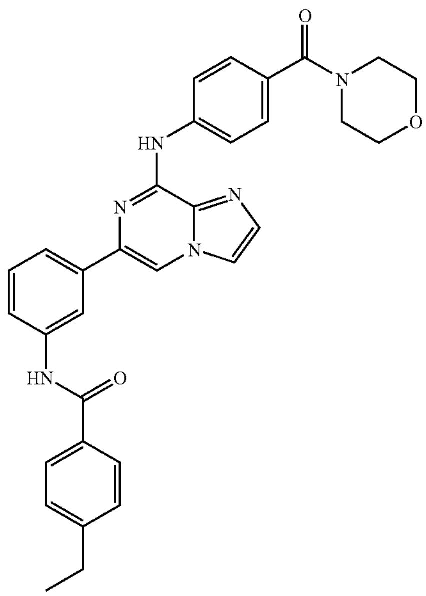 | 4-Ethyl-N-(3-{8-[4-(morpholine-4-carbonyl)-phenylamino]-imidazo[1,2-a]pyrazin-6-yl}-phenyl)-benzamide C32H30N6O3 | 546.23 | 547.17 |
| 132 | 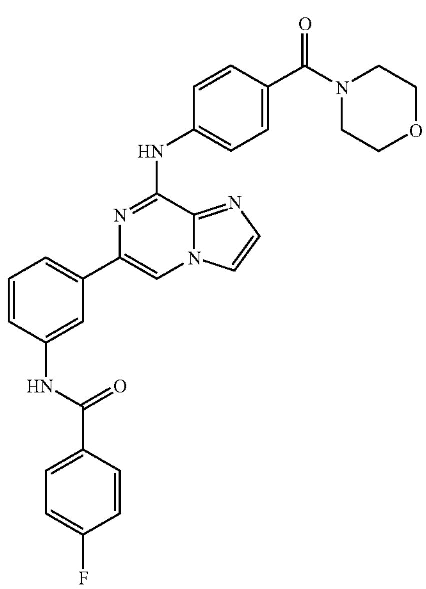 | 4-Fluoro-N-(3-{8-[4-(morpholine-4-carbonyl)-phenylamino]-imidazo[1,2-a]pyrazin-6-yl}-phenyl)-benzamide C30H25FN6O3 | 536.19 | 537.21 |

| Cmp. # | STRUCTURE | NAME | MW | MS m/z (M+1) |
|---|---|---|---|---|
| 133 | 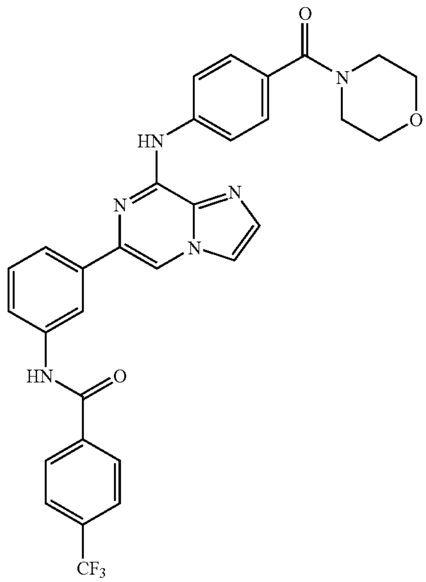 | N-(3-{8-[4-(Morpholine-4-carbonyl)-phenylamino]-imidazo[1,2-a]pyrazin-6-yl}-phenyl)-4-trifluoromethyl-benzamide<br>C31H25F3N6O3 | 586.19 | 587.2 |
| 134 | 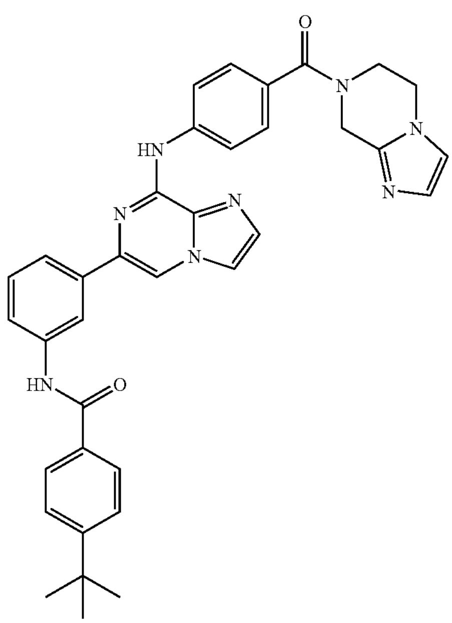 | 4-tert-Butyl-N-(3-{8-[4-(5,6-dihydro-8H-imidazo[1,2-a]pyrazine-7-carbonyl)-phenylamino]-imidazo[1,2-a]pyrazin-6-yl}-phenyl)-benzamide<br>C36H34N8O2 | 610.28 | 611.21 |

-continued

| Cmp. # | STRUCTURE | NAME | MW | MS m/z (M⁺¹) |
|---|---|---|---|---|
| 135 | 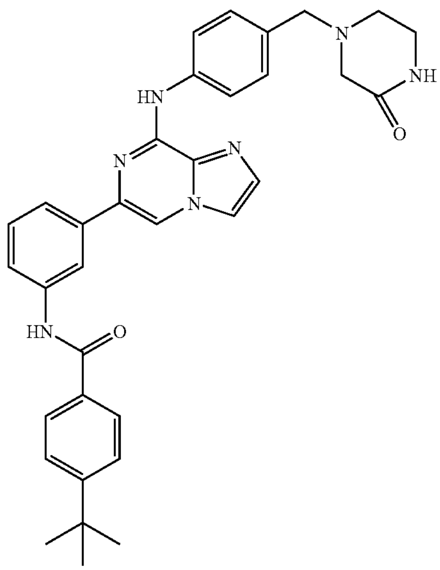 | 4-tert-Butyl-N-(3-{8-[4-(3-oxo-piperazin-1-ylmethyl)-phenylamino]-imidazo[1,2-a]pyrazin-6-yl}-phenyl)-benzamide<br>C34H35N7O2 | 573.28 | 574.18 |
| 136 | 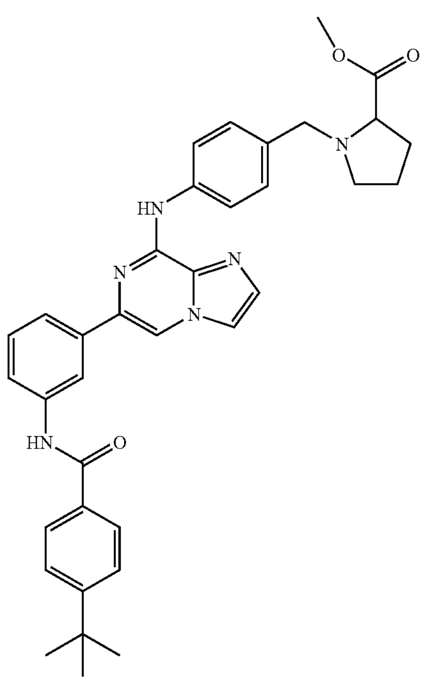 | 1-(4-{6-[3-(4-tert-Butyl-benzoylamino)-phenyl]-imidazo[1,2-a]pyrazin-8-ylamino}-benzyl)-pyrrolidine-2-carboxylic acid methyl ester<br>C36H38N6O3 | 602.3 | 603.39 |

-continued

| Cmp. # | STRUCTURE | NAME | MW | MS m/z (M+1) |
|---|---|---|---|---|
| 137 | 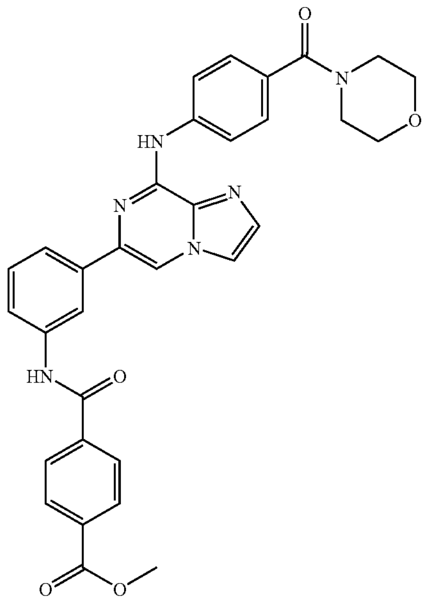 | N-(3-{8-[4-(Morpholine-4-carbonyl)-phenylamino]-imidazo[1,2-a]pyrazin-6-yl}-phenyl)-terephthalamic acid methyl ester C32H28N6O5 | 576.21 | 577.36 |
| 138 | 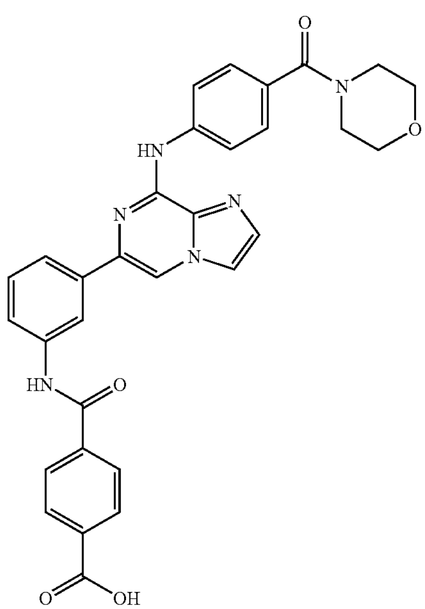 | N-(3-{8-[4-(Morpholine-4-carbonyl)-phenylamino]-imidazo[1,2-a]pyrazin-6-yl}-phenyl)-terephthalamic acid C31H26N6O5 | 562.19 | 563.33 |

| Cmp. # | STRUCTURE | NAME | MW | MS m/z (M⁺¹) |
|---|---|---|---|---|
| 139 | 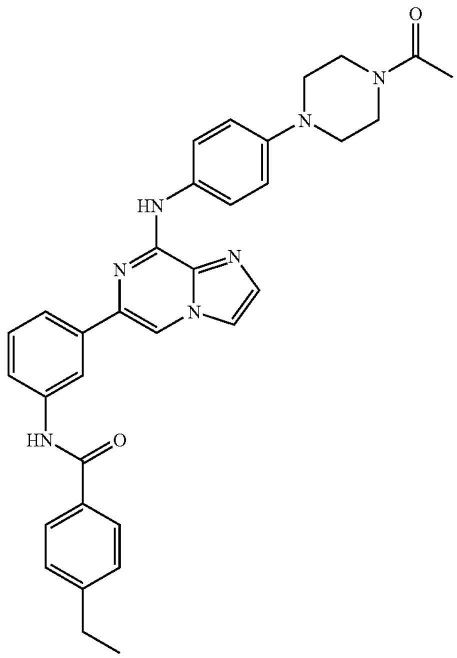 | N-(3-{8-[4-(4-Acetyl-piperazin-1-yl)-phenylamino]-imidazo[1,2-a]pyrazin-6-yl}-phenyl)-4-ethyl-benzamide C33H33N7O2 | 559.26 | 560.25 |
| 140 | 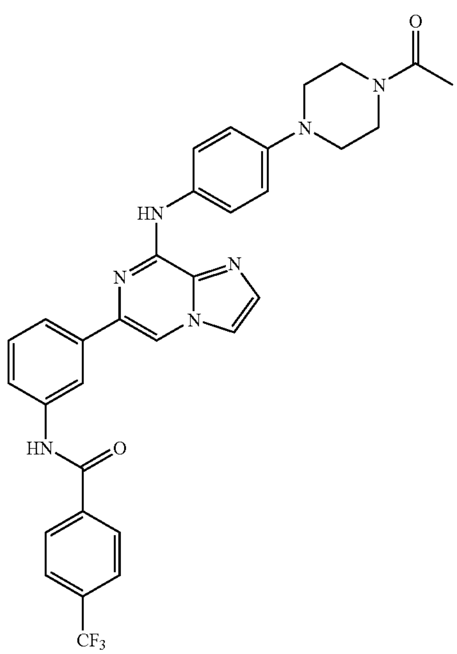 | N-(3-{8-[4-(4-Acetyl-piperazin-1-yl)-phenylamino]-imidazo[1,2-a]pyrazin-6-yl}-phenyl)-4-trifluoromethyl-benzamide C32H28F3N7O2 | 599.22 | 600.22 |

-continued

| Cmp. # | STRUCTURE | NAME | MW | MS m/z (M+1) |
|---|---|---|---|---|
| 141 | 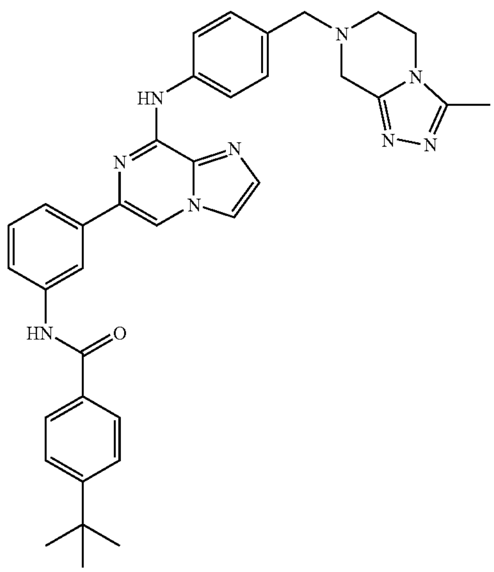 | 4-tert-Butyl-N-(3-{8-[4-(3-methyl-5,6-dihydro-8H-[1,2,4]triazolo[4,3-a]pyrazin-7-ylmethyl)-phenylamino]-imidazo[1,2-a]pyrazin-6-yl}-phenyl)-benzamide C36H37N9O | 611.31 | 612.41 |
| 142 | 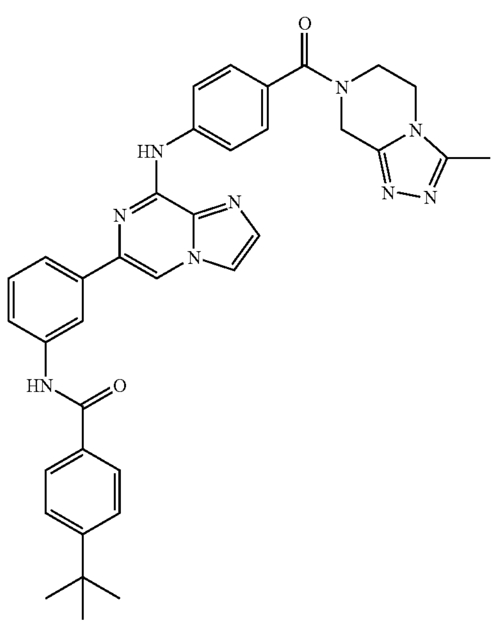 | 4-tert-Butyl-N-(3-{8-[4-(3-methyl-5,6-dihydro-8H-[1,2,4]triazolo[4,3-a]pyrazine-7-carbonyl)-phenylamino]-imidazo[1,2-a]pyrazin-6-yl}-phenyl)-benzamide C36H35N9O2 | 625.29 | 626.4 |

-continued

| Cmp. # | STRUCTURE | NAME | MW | MS m/z (M+1) |
|---|---|---|---|---|
| 143 | 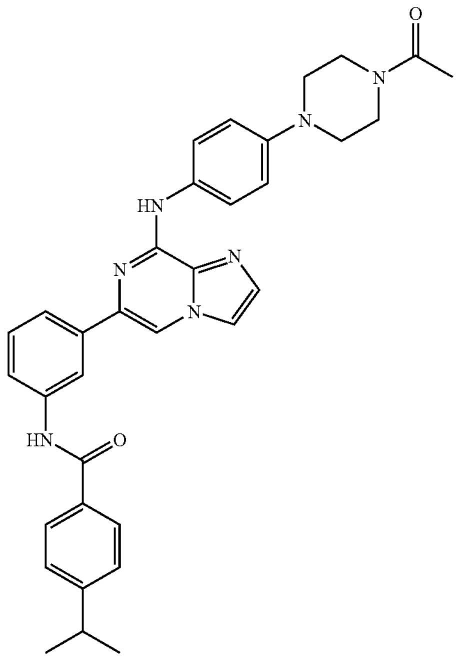 | N-(3-{8-[4-(4-Acetyl-piperazin-1-yl)-phenylamino]-imidazo[1,2-a]pyrazin-6-yl}-phenyl)-4-isopropyl-benzamide C34H35N7O2 | 573.28 | 574.38 |
| 144 | 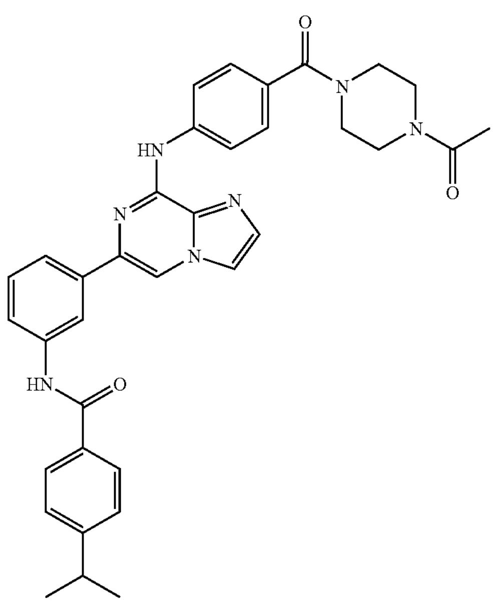 | N-(3-{8-[4-(4-Acetyl-piperazine-1-carbonyl)-phenylamino]-imidazo[1,2-a]pyrazin-6-yl}-phenyl)-4-isopropyl-benzamide C35H35N7O3 | 601.28 | 602.27 |

-continued
| Cmp. # | STRUCTURE | NAME | MW | MS m/z (M+1) |
|---|---|---|---|---|
| 145 | 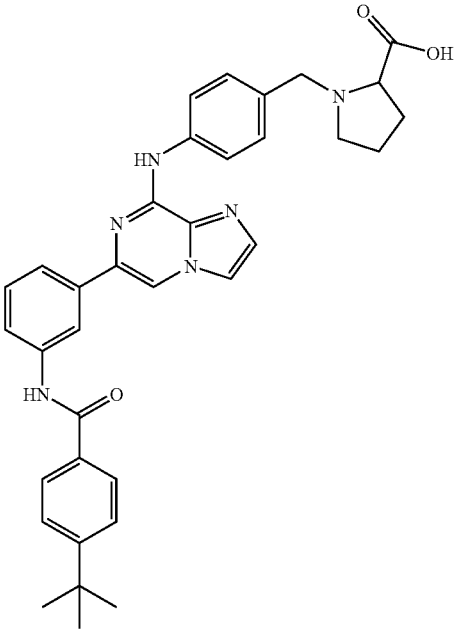 | 1-(4-{6-[3-(4-tert-Butyl-benzoylamino)-phenyl]-imidazo[1,2-a]pyrazin-8-ylamino}-benzyl)-pyrrolidine-2-carboxylic acid C35H36N6O3 | 588.28 | 589.25 |
| 146 | 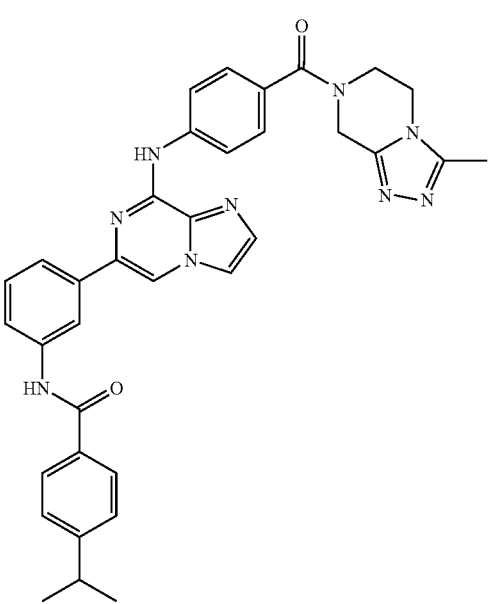 | 4-Isopropyl-N-(3-{8-[4-(3-methyl-5,6-dihydro-8H-[1,2,4]triazolo[4,3-a]pyrazine-7-carbonyl)-phenylamino]-imidazo[1,2-a]pyrazin-6-yl}-phenyl)-benzamide C35H33N9O2 | 611.27 | 612.26 |

| Cmp. # | STRUCTURE | NAME | MW | MS m/z (M+1) |
|---|---|---|---|---|
| 147 | 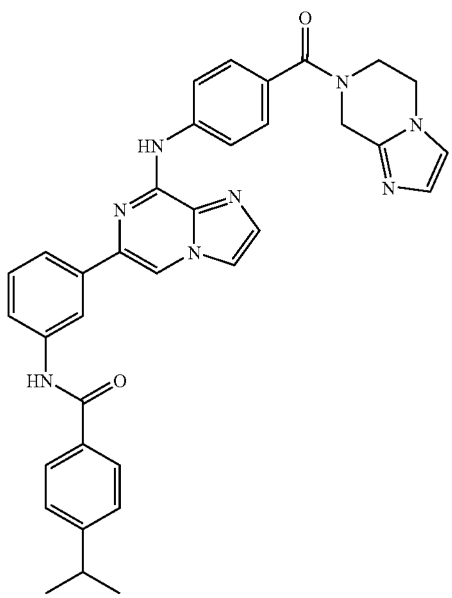 | N-(3-{8-[4-(5,6-Dihydro-8H-imidazo[1,2-a]pyrazine-7-carbonyl)-phenylamino]-imidazo[1,2-a]pyrazin-6-yl}-phenyl)-4-isopropyl-benzamide C35H32N8O2 | 596.26 | 597.26 |
| 148 | 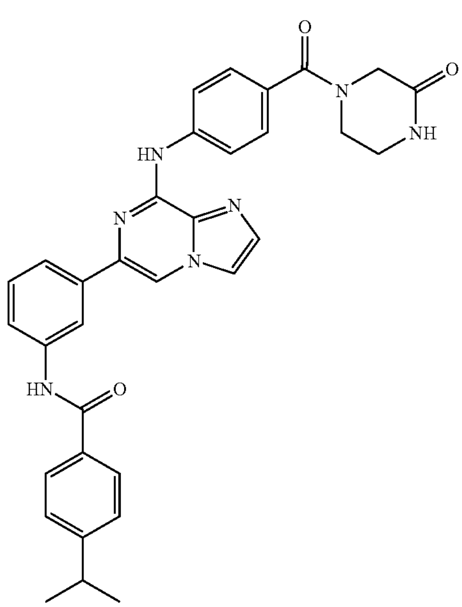 | 4-Isopropyl-N-(3-{8-[4-(3-oxo-piperazine-1-carbonyl)-phenylamino]-imidazo[1,2-a]pyrazin-6-yl}-phenyl)-benzamide C33H31N7O3 | 573.24 | 574.27 |

-continued

| Cmp. # | STRUCTURE | NAME | MW | MS m/z (M+1) |
|---|---|---|---|---|
| 149 | 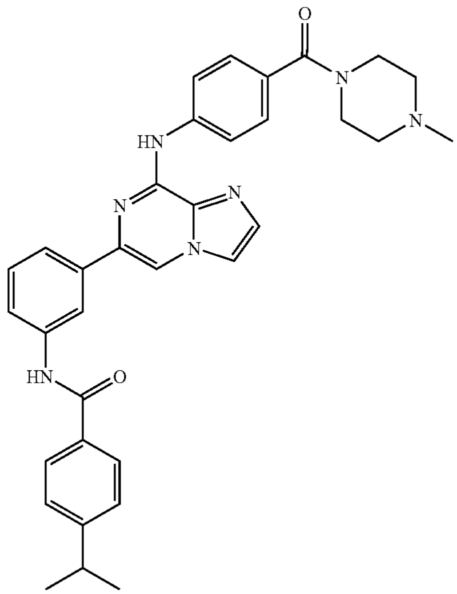 | 4-Isopropyl-N-(3-{8-[4-(4-methyl-piperazine-1-carbonyl)-phenylamino]-imidazol[1,2-a]pyrazin-6-yl}-phenyl)-benzamide C34H35N7O2 | 573.28 | 574.29 |
| 150 | 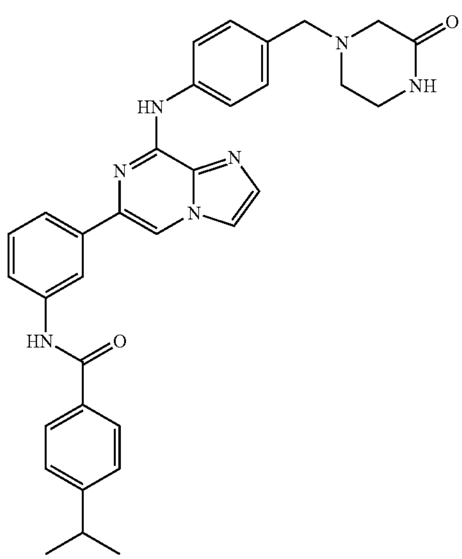 | 4-Isopropyl-N-(3-{8-[4-(3-oxo-piperazin-1-ylmethyl)-phenylamino]-imidazo[1,2-a]pyrazin-6-yl}-phenyl)-benzamide C33H33N7O2 | 559.26 | 560.29 |

-continued

| Cmp. # | STRUCTURE | NAME | MW | MS m/z (M+1) |
|---|---|---|---|---|
| 151 | 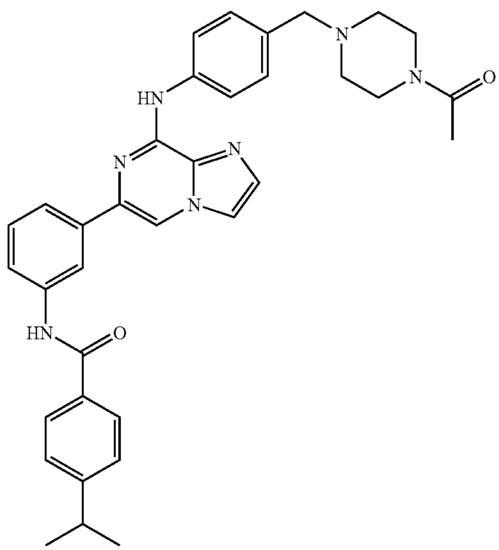 | N-(3-{8-[4-(4-Acetyl-piperazin-1-ylmethyl)-phenylamino]-imidazo[1,2-a]pyrazin-6-yl}-phenyl)-4-isopropyl-benzamide C35N37N7O2 | 587.3 | 588.31 |
| 152 | 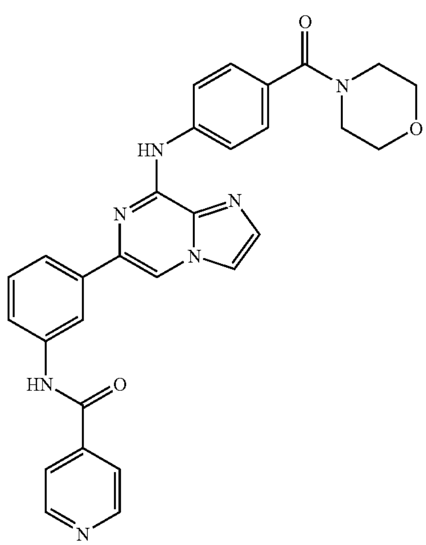 | N-(3-{8-[4-(Morpholine-4-carbonyl)-phenylamino]-imidazo[1,2-a]pyrazin-6-yl}-phenyl)-isonicotinamide C29H25N7O3 | 519.2 | 520.2 |

| Cmp. # | STRUCTURE | NAME | MW | MS m/z (M+1) |
|---|---|---|---|---|
| 153 | 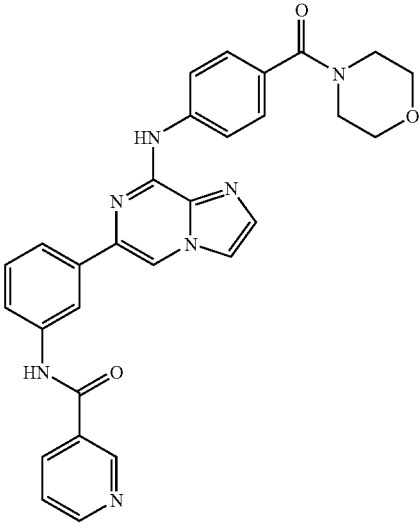 | N-(3-{8-[4-(Morpholine-4-carbonyl)-phenylamino]-imidazo[1,2-a]pyrazin-6-yl}-phenyl)-nicotinamide C29H25N7O3 | 519.2 | 520.19 |
| 154 | 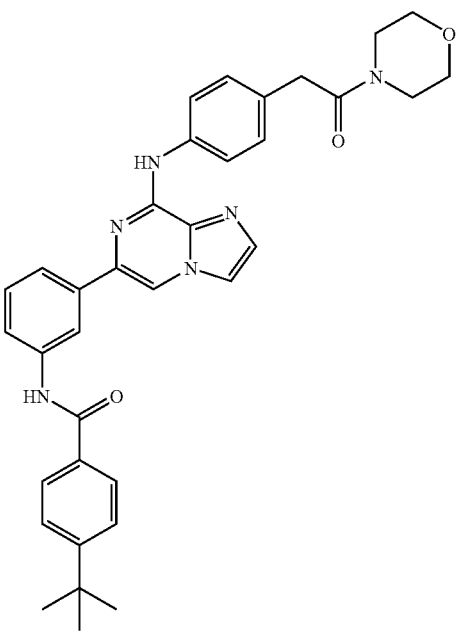 | 4-tert-Butyl-N-(3-{8-[4-(2-morpholin-4-yl-2-oxo-ethyl)-phenylamino]-imidazo[1,2-a]pyrazin-6-yl}-phenyl)-benzamide C35H36N6O3 | 588.28 | 589.28 |

-continued
| Cmp. # | STRUCTURE | NAME | MW | MS m/z (M+1) |
|---|---|---|---|---|
| 155 | 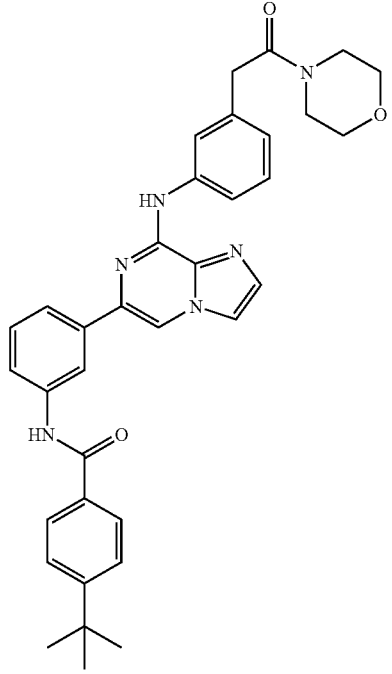 | 4-tert-Butyl-N-(3-{8-[3-(2-morpholin-4-yl-2-oxo-ethyl)-phenylamino]-imidazo[1,2-a]pyrazin-6-yl}-phenyl)-benzamide C35H36N6O3 | 588.28 | 589.29 |
| 156 | 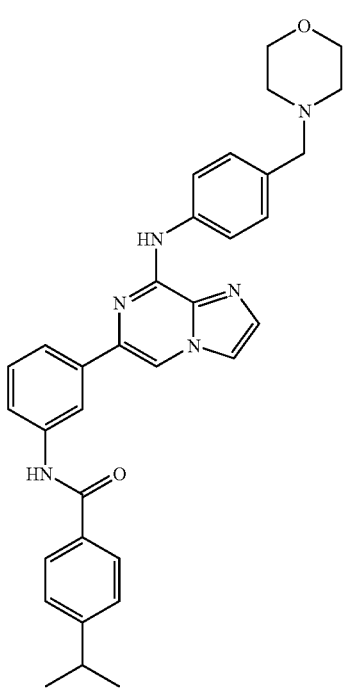 | 4-Isopropyl-N-{3-[8-(4-morpholin-4-ylmethyl-phenylamino)-imidazo[1,2-a]pyrazin-6-yl]-phenyl}-benzamide C33H34N6O2 | 546.27 | 547.28 |

-continued

| Cmp. # | STRUCTURE | NAME | MW | MS m/z (M+1) |
|---|---|---|---|---|
| 157 | 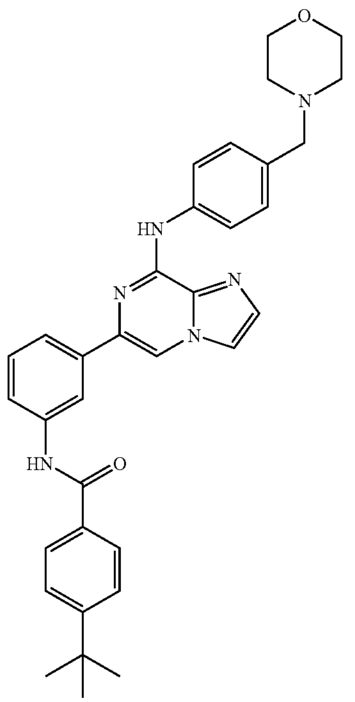 | 4-tert-Butyl-N-{3-[8-(4-morpholin-4-ylmethyl-phenylamino)-imidazo[1,2-a]pyrazin-6-yl]-phenyl}-benzamide C34H36N6O2 | 560.28 | 561.43 |
| 158 | 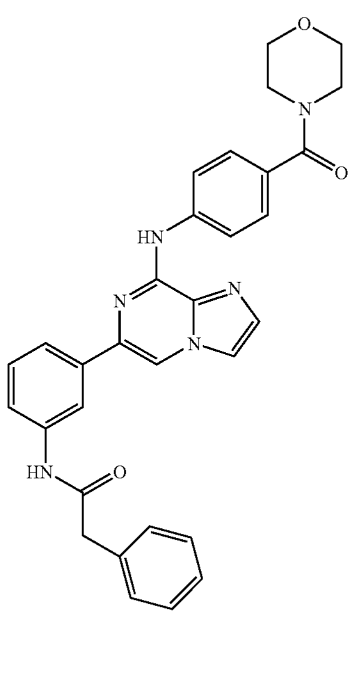 | N-(3-{8-[4-(Morpholine-4-carbonyl)-phenylamino]-imidazo[1,2-a]pyrazin-6-yl}-phenyl)-2-phenyl-acetamide C31H28N6O3 | 532.22 | 533.21 |

-continued
| Cmp. # | STRUCTURE | NAME | MW | MS m/z (M+1) |
|---|---|---|---|---|
| 159 | 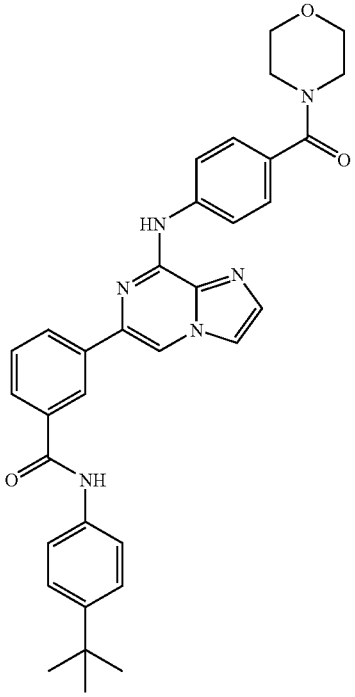 | N-(4-tert-Butyl-phenyl)-3-{8-[4-(morpholine-4-carbonyl)-phenylamino]-imidazo[1,2-a]pyrazin-6-yl}-benzamide C34H34N6O3 | 574.27 | 575.23 |
| 160 | 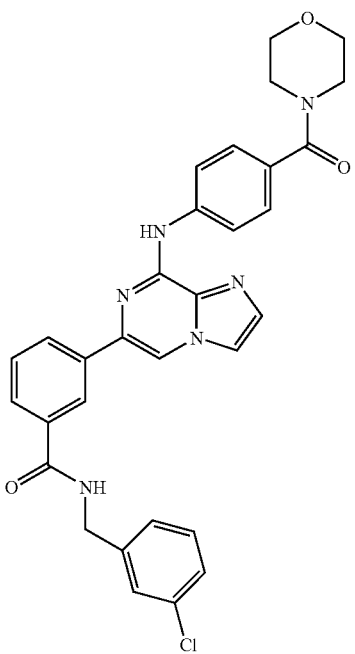 | N-(3-Chloro-benzyl)-3-{8-[4-(morpholine-4-carbonyl)-phenylamino]-imidazo[1,2-a]pyrazin-6-yl}-benzamide C31H27ClN6O3 | 566.18 | 567.17 |

-continued
| Cmp. # | STRUCTURE | NAME | MW | MS m/z (M+1) |
|---|---|---|---|---|
| 161 | 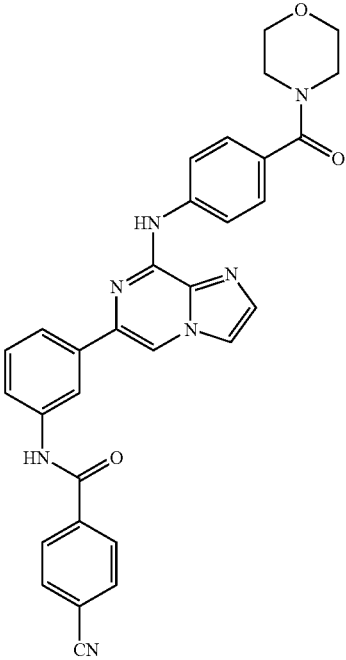 | 4-Cyano-N-(3-{8-[4-(morpholine-4-carbonyl)-phenylamino]-imidazo[1,2-a]pyrazin-6-yl}-phenyl)-benzamide<br>C31H25N7O3 | 543.2 | 544.32 |
| 162 | 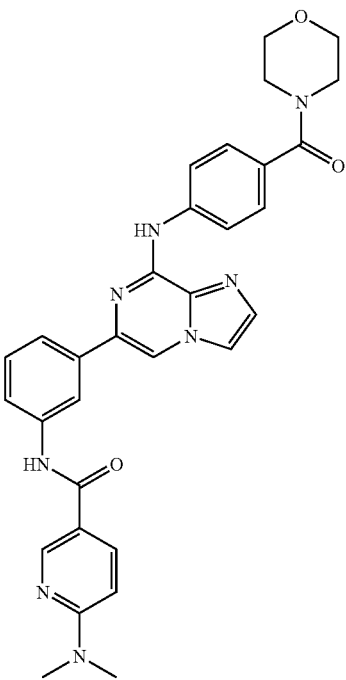 | 6-Dimethylamino-N-(3-{8-[4-(morpholine-4-carbonyl)-phenylamino]-imidazo[1,2-a]pyrazin-6-yl}-phenyl)-nicotinamide<br>C31N30N8O3 | 562.24 | 563.26 |

| Cmp. # | STRUCTURE | NAME | MW | MS m/z (M⁺¹) |
|---|---|---|---|---|
| 163 | 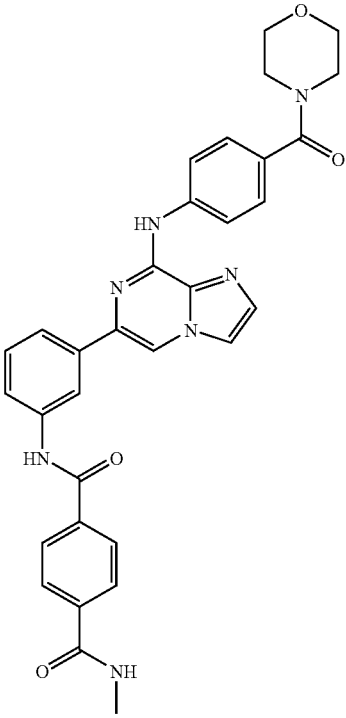 | N-Methyl-N'-(3-{8-[4-(morpholine-4-carbonyl)-phenylamino]-imidazo[1,2-a]pyrazin-6-yl}-phenyl)-terephthalamide C32H29N7O4 | 575.22 | 576.25 |
| 164 | 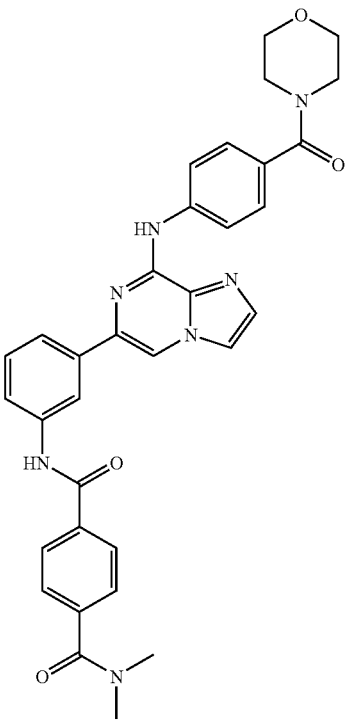 | N,N-Dimethyl-N'-(3-{8-[4-(morpholine-4-carbonyl)-phenylamino]-imidazo[1,2-a]pyrazin-6-yl}-phenyl)-terephthalamide C33H31N7O4 | 589.24 | 590.26 |

| Cmp. # | STRUCTURE | NAME | MW | MS m/z (M+1) |
|---|---|---|---|---|
| 165 | 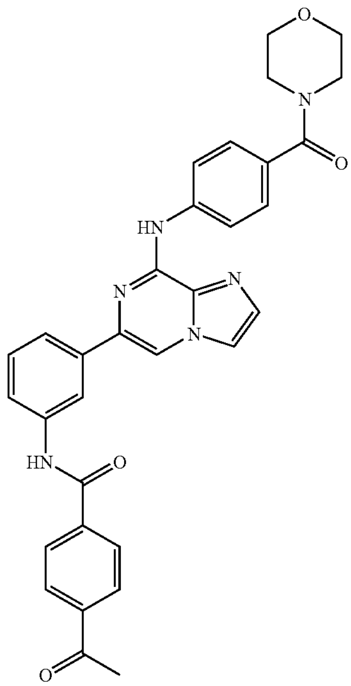 | 4-Acetyl-N-(3-{8-[4-(morpholine-4-carbonyl)-phenylamino]-imidazo[1,2-a]pyrazin-6-yl}-phenyl)-benzamide<br>C32H28N6O4 | 560.21 | 561.25 |
| 166 | 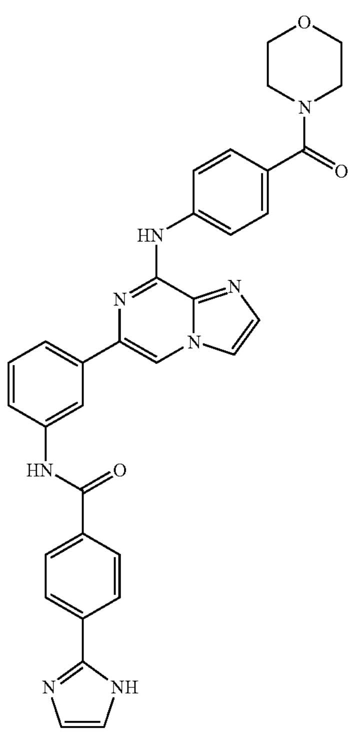 | 4-(1H-Imidazol-2-yl)-N-(3-{8-[4-(morpholine-4-carbonyl)-phenylamino]-imidazo[1,2-a]pyrazin-6-yl}-phenyl)-benzamide<br>C33H28N8O3 | 584.22 | 585.31 |

-continued

| Cmp. # | STRUCTURE | NAME | MW | MS m/z (M+1) |
|---|---|---|---|---|
| 167 | 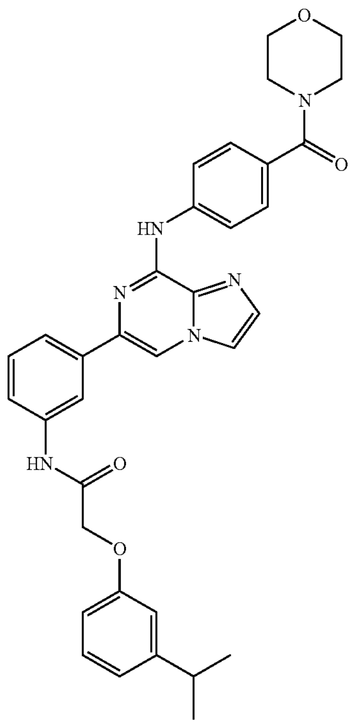 | 2-(3-Isopropyl-phenoxy)-N-(3-{8-[4-(morpholine-4-carbonyl)-phenylamino]-imidazo[1,2-a]pyrazin-6-yl}-phenyl)-acetamide<br>C34H34N6O4 | 590.26 | 591.32 |
| 168 | 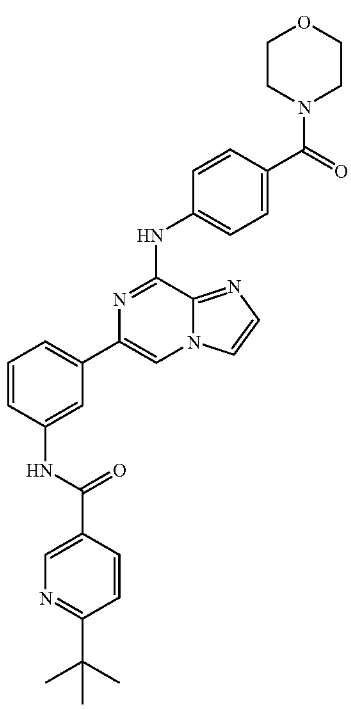 | 6-tert-Butyl-N-(3-{8-[4-(morpholine-4-carbonyl)-phenylamino]-imidazo[1,2-a]pyrazin-6-yl}-phenyl)-nicotinamide<br>C33H33N7O3 | 575.26 | 576.24 |

-continued

| Cmp. # | STRUCTURE | NAME | MW | MS m/z (M+1) |
|---|---|---|---|---|
| 169 | 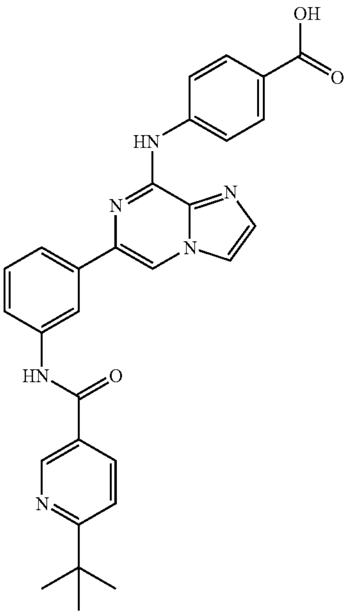 | 4-(6-{3-[(6-tert-Butyl-pyridine-3-carbonyl)-amino]-phenyl}-imidazo[1,2a]pyrazin-8-ylamino)-benzoic acid C29H26N6O3 | 506.2 | 507.21 |

The compounds disclosed in synthetic Examples 1 to 5 were tested in the Btk biochemical assay described in Example 6 and found to exhibit an $IC_{50}$ value less than or equal to 1 micromolar certain of these compounds were found to exhibit an $IC_{50}$ value less than or equal to 100 nM, and certain of these compounds exhibited an $IC_{50}$ value less than or equal to 10 nM. Some of the compounds disclosed in synthetic Examples 1 to 5 were tested in the B-cell proliferation assay of Example 8 and determined to exhibit an $IC_{50}$ value less than or equal to 10 micromolar, certain of these compounds exhibited an $IC_{50}$ value less than or equal to 1 micromolar, and certain of these compounds exhibited an $IC_{50}$ value less than or equal to 500 nM in this assay. Certain of these compounds do not inhibit T-cell proliferation and have $IC_{50}$ values greater than or equal to 5 micromolar when assayed under conditions described in Example 9. The compounds assayed in the Example 8 and Example 9 exhibited $IC_{50}$ values for inhibition of T-cell proliferation that were at least 3-fold, and in some instances 5-fold, or even 10-fold greater than the $IC_{50}$ values of these compounds for inhibition of B-cell proliferation.

Example 6

BIOCHEMICAL BTK ASSAY

A generalized procedure for one standard biochemical Btk Kinase Assay used to test compounds disclosed in this application is as follows.

A master mix minus Btk enzyme is prepared containing 1X Cell Signaling kinase buffer (25 mM Tris-HCl, pH 7.5, 5 mM β-glycerophosphate, 2 mM dithiothreitol, 0.1 mM $Na_3VO_4$, 10 mM $MgCl_2$), 0.5 μM Promega PTK Biotinylated peptide substrate 2, and 0.01% BSA. A master mix plus Btk enzyme is prepared containing 1X Cell Signaling kinase buffer, 0.5 μM PTK Biotinylated peptide substrate 2, 0.01% BSA, and 100 ng/well (0.06 mU/well) Btk enzyme. Btk enzyme is prepared as follows: full length human wildtype Btk (accession number NM-000061) with a $C_1$-terminal V5 and 6× His tag was subcloned into pFastBac vector for making baculovirus carrying this epitope-tagged Btk. Generation of baculovirus was done based on Invitrogen's instructions detailed in its published protocol "Bac-toBac Baculovirus Expression Systems" (Cat. Nos. 10359-016 and 10608-016). Passage 3 virus was used to infect Sf9 cells to overexpress the recombinant Btk protein. The Btk protein was then purified to homogeneity using Ni-NTA column. The purity of the final protein preparation was greater than 95% based on the sensitive Sypro-Ruby staining. A solution of 200 μM ATP is prepared in water and adjusted to pH7.4 with 1N NaOH. A quantity of 1.25 μL of compounds in 5%DMSO is transferred to a 96-well ½ area Costar polystyrene plate. Compounds are tested singly and with an 11-point dose-responsive curve (starting concentration is 10 μM; 1:2 dilution). A quantity of 18.75 μL of master mix minus enzyme (as a negative control) and master mix plus enzyme is transferred to appropriate wells in 96-well ½ area costar polystyrene plate. 5 μL of 200 μM ATP is added to that mixture in the 96-well ½ area Costar polystyrene plate for final ATP concentration of 40 μM. The reaction is allowed to incubate for 1 hour at room temperature. The reaction is stopped with Perkin Elmer 1X detection buffer containing 30 mM EDTA, 20 nM SA-APC, and 1 nM PT66 Ab. The plate is read using time-resolved fluorescence with a Perkin Elmer Envision using excitation filter 330 nm, emission filter 665 nm, and $2^{nd}$ emission filter 615 nm. $IC_{50}$ values are subsequently calculated.

Example 7

RAMOS CELL BTK ASSAY

Another generalized procedure for a standard cellular Btk Kinase Assay used to test compounds disclosed in this application is as follows.

Ramos cells are incubated at a density of 0.5×10⁷ cells/ml in the presence of test compound for 1 hr at 37° C. Cells are then stimulated by incubating with 10 μg/ml anti-human IgM F(ab)₂ for 5 minutes at 37° C. Cells are pelleted, lysed, and a protein assay is performed on the cleared lysate. Equal protein amounts of each sample are subject to SDS-PAGE and western blotting with either anti-phosphoBtk(Tyr223) antibody (Cell Signaling Technology #3531) to assess Btk autophosphorylation or an anti-Btk antibody (BD Transduction Labs #611116) to control for total amounts of Btk in each lysate.

Example 8

B-CELL PROLIFERATION ASSAY

B-cells are purified from spleens of 8-16 week old Balb/c mice using a B-cell isolation kit (Miltenyi Biotech, Cat # 130-090-862). Testing compounds are diluted in 0.25% DMSO and incubated with 2.5×10⁵ purified mouse splenic B-cells for 30 min prior to addition of 10 μg/ml of an anti-mouse IgM antibody (Southern Biotechnology Associates Cat # 1022-01) in a final volume of 100 μl. Following 24 hr incubation, 1 μCi ³h-thymidine is added and plates are incubated an additional 36 hr prior to harvest using the manufacturer's protocol for SPA[³h] thymidine uptake assay system (Amersham Biosciences # RPNQ 0130). SPA-bead based fluorescence is counted in a microbeta counter (Wallace Triplex 1450, Perkin Elmer).

Example 9

T CELL PROLIFERATION ASSAY

T cells are purified from spleens of 8-16 week old Balb/c mice using a Pan T cell isolation kit (Miltenyi Biotech, Cat # 130-090-861). Testing compounds are diluted in 0.25% DMSO and incubated with 2.5×10⁵ purified mouse splenic T cells in a final volume of 100 μl in flat clear bottom plates precoated for 90 min at 37° C. with 10 μg/ml each of anti-CD3 (BD # 553057) and anti-CD28 (BD # 553294) antibodies. Following 24 hr incubation, 1 μCi ³H-thymidine is added and plates incubated an additional 36 hr prior to harvest using the manufacturer's protocol for SPA[³h] thymidine uptake assay system (Amersham Biosciences # RPNQ 0130). SPA-bead based fluorescence was counted in a microbeta counter (Wallace Triplex 1450, Perkin Elmer).

What is claimed is:

1. A compound of Formula 1

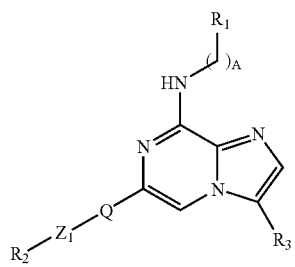

(Formula 1)

or a pharmaceutically acceptable salt, hydrate or diastereomer thereof, wherein
A is 0 and 1;
$R_1$ is
substituted phenyl wherein the substituent is
CHO,
—COOH,
—CONH₂,
—CONHOH,
$C_2$-$C_6$ alkenyl,
mono-, di-, or tri-substituted $C_2$-$C_6$ alkenyl, wherein the substituents are independently halogen, hydroxy, amino, oxo, —COOH, —CONH₂, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl,
$C_2$-$C_6$ alkynyl,
mono-, di- and tri-substituted $C_2$-$C_6$ alkynyl, wherein the substituents are independently halogen, hydroxy, amino, oxo, —COOH, —CONH₂, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl,
$C_1$-$C_6$hydroxyalkyl,
mono-, di- or tri-substituted $C_1$-$C_6$hydroxyalkyl, wherein the substituents are independently halogen, hydroxy, amino, oxo, —COOH, —CONH₂, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl,
$C_1$-$C_6$hydroxyalkoxy,
mono-, di- and tri-substituted $C_1$-$C_6$hydroxyalkoxy, wherein the substituents are independently halogen, hydroxy, amino, oxo, —COOH, —CONH₂, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl,
(mono-$C_1$-$C_6$alkylamino)$C_1$-$C_6$alkoxy,
mono-, di- and tri-substituted (mono-$C_1$-$C_6$alkylamino)$C_1$-$C_6$alkoxy, wherein the substituents are independently halogen, hydroxy, amino, oxo, —COOH, —CONH₂, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl,
(di-$C_1$-$C_6$alkylamino)$C_1$-$C_6$alkoxy,
mono-, di- or tri-substituted (di-$C_1$-$C_6$alkylamino)$C_1$-$C_6$alkoxy, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, (C$_1$-C$_6$alkoxy)(C$_1$-C$_6$alkylamino)C$_0$-C$_6$alkyl, mono-, di- and tri-substituted (C$_1$-C$_6$alkoxy)(C$_1$-C$_6$alkylamino)C$_0$-C$_6$alkyl, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, (C$_1$-C$_6$alkoxy)(C$_1$-C$_6$alkoxy)C$_1$-C$_6$alkoxy, mono-, di- and tri-substituted (C$_1$-C$_6$alkoxy)(C$_1$-C$_6$alkoxy)C$_1$-C$_6$alkoxy, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, heterocycloalkyl, mono-, di- and tri-substituted heterocycloalkyl, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, aryl, mono-, di- and tri-substituted aryl, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, heteroaryl, mono-, di- and tri-substituted heteroaryl, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, —C$_1$-C$_6$alkyl(C=O)OR$_{10}$, mono-, di- and tri-substituted —C$_1$-C$_6$alkyl(C=O)OR$_{10}$, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, —C$_0$-C$_6$alkyl(C=O)NR$_{10}$R$_{11}$, mono-, di- and tri-substituted —C$_0$-C$_6$alkyl(C=O)NR$_{10}$R$_{11}$, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, —C$_1$-C$_6$alkylNR$_{10}$(SO$_2$)R$_{11}$, mono-, di- and tri-substituted —C$_1$-C$_6$alkylNR$_{10}$(SO$_2$)R$_{11}$, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, —C$_0$-C$_6$alkylNR$_{10}$(C=O)R$_{11}$, mono-, di- and tri-substituted —C$_0$-C$_6$alkylNR$_{10}$(C=O)R$_{11}$, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, —C$_0$-C$_6$alkyl(SO$_2$)R$_{10}$, mono-, di- and tri-substituted —C$_0$-C$_6$alkyl(SO$_2$)R$_{10}$, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, —C$_0$-C$_6$alkylNR$_{10}$(C=O)NR$_{11}$R$_{12}$, mono-, di- and tri-substituted —C$_0$-C$_6$alkylNR$_{10}$(C=O)NR$_{11}$R$_{12}$, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, -L-G, where L is C$_1$-C$_2$alkylene, mono-, di- or tri-substituted C$_1$-C$_2$alkylene, wherein the substituents are independently halogen, hydroxy, amino, oxo, —COOH, —CONH$_2$, C$_1$-C$_4$alkyl, C$_2$-C$_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, $C_0$-$C_2$alkylene-O—, mono-, di- or tri-substituted $C_0$-$C_2$alkylene-O—, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl,

—(C=O)—,

—($C_1$-$C_2$alkylene)(C=O)—, mono-, di- or tri-substituted —($C_1$-$C_2$alkylene)(C=O)—, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, G is heterocycloalkyl, mono-, di- or tri-substituted heterocycloalkyl, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, $C_3$-$C_7$cycloalkyl, mono-, di- or tri-substituted $C_3$-$C_7$cycloalkyl, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, aryl, mono-, di- or tri-substituted aryl, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, heteroaryl, mono-, di- or tri-substituted heteroaryl, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, or substituted monocyclic heteroaryl wherein the substituent is oxo,

—CHO,

—COOH,

—CONH$_2$,

—CONHOH, $C_2$-$C_6$ alkenyl, mono-, di- or tri-substituted $C_2$-$C_6$ alkenyl, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, $C_2$-$C_6$ alkynyl, mono-, di- or tri-substituted $C_2$-$C_6$ alkynyl, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, $C_1$-$C_6$hydroxyalkyl, mono-, di- or tri-substituted $C_1$-$C_6$hydroxyalkyl, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, $C_1$-$C_6$hydroxyalkoxy, mono-, di- or tri-substituted $C_1$-$C_6$hydroxyalkoxy, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, (mono-$C_1$-$C_6$alkylamino)$C_1$-$C_6$alkoxy, mono-, di- or tri-substituted (mono-$C_1$-$C_6$alkylamino)$C_1$-$C_6$alkoxy, wherein the substituents are independently chosen from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, (di-$C_1$-$C_6$alkyiamino)$C_1$-$C_6$alkoxy, mono-, di- or tri-substituted ($C_1$-$C_6$alkylamino)($C_1$-$C_6$alkylamino)$C_1$-$C_6$alkoxy, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, (C$_1$-C$_6$alkoxy)(C$_1$-C$_6$alkylamino)C$_0$-C$_6$alkyl, mono-, di- or tri-substituted (C$_1$-C$_6$alkoxy)(C$_1$-C$_6$alkylamino)C$_0$-C$_6$alkyl, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, (C$_1$-C$_6$alkoxy)(C$_1$-C$_6$alkoxy)C$_1$-C$_6$alkoxy, mono-, di- or tri-substituted (C$_1$-C$_6$alkoxy)(C$_1$-C$_6$alkoxy)C$_1$-C$_6$alkoxy, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, heterocycloalkyl, mono-, di- or tri-substituted heterocycloalkyl, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, aryl, mono-, di- or tri-substituted aryl, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, heteroaryl, mono-, di- or tri-substituted heteroaryl, wherein the substituents are independently chosen from halogen, hydroxy, amino, oxo, —COOH, —CONH$_2$, C$_1$-C$_4$alkyl, C$_2$-C$_4$alkenyl, C$_2$-C$_4$alkynyl, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, —C$_1$-C$_6$alkyl(C=O)OR$_{10}$, mono-, di- or tri-substituted —C$_1$-C$_6$alkyl(C=O)OR$_{10}$, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, —C$_0$-C$_6$alkyl(C=O)NR$_{10}$R$_{11}$, mono-, di- or tri-substituted —C$_0$-C$_6$alkyl(C=O)NR$_{10}$R$_{11}$, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, —C$_1$-C$_6$alkylNR$_{10}$(SO$_2$)R$_{11}$, mono-, di- or tri-substituted —C$_1$-C$_6$alkylNR$_{10}$(SO$_2$)R$_{11}$, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, —C$_0$-C$_6$alkylNR$_{10}$(C=O)R$_{11}$, mono-, di- or tri-substituted —C$_0$-C$_6$alkylNR$_{10}$(C=O)R$_{11}$, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, —C$_0$-C$_6$alkyl(SO$_2$)R$_{10}$, mono-, di- or tri-substituted —C$_0$-C$_6$alkyl(SO$_2$)R$_{10}$, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, —C$_0$-C$_6$alkylNR$_{10}$(C=O)NR$_{11}$R$_{12}$, mono-, di- or tri-substituted —C$_0$-C$_6$alkylNR$_{10}$(C=O)NR$_{11}$R$_{12}$, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, or phenyl, -L-G, where L is C$_1$-C$_2$alkylene, mono-, di- or tri-substituted C$_1$-C$_2$alkylene, wherein the substituents are independently halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-$C_1$-$C_4$alkylamino, mono-$C_1$-$C_4$alkylcarboxamide, di-$C_1$-$C_4$alkylcarboxamide, or phenyl, $C_0$-$C_2$alkylene-O—, mono-, di- or tri-substituted $C_0$-$C_2$alkylene-O—, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl,

—(C=O)—,

—($C_1$-$C_2$alkylene)(C=O)—, mono-, di- or tri-substituted —($C_1$-$C_2$alkylene)(C=O)—, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, G is heterocycloalkyl, mono-, di- or tri-substituted heterocycloalkyl, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, $C_3$-$C_7$cycloalkyl, mono-, di- or tri-substituted $C_3$-$C_7$cycloalkyl, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, aryl, mono-, di- or tri-substituted aryl, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, heteroaryl, mono-, di- or tri-substituted heteroaryl, wherein the substituents are independently halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, or phenyl, $R_{10}$, $R_{11}$, and $R_{12}$ are independently hydrogen, hydroxy, $C_1$-$C_6$alkyl, $C_1$-$C_6$alkoxy, $C_3$-$C_{10}$cycloalkyl, or heterocycloalkyl, $R_1$ is optionally further substituted with 1 or more substituents which are independently hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono-$C_1$-$C_6$ alkylamino)$C_0$-$C_6$ alkyl, (di-$C_1$-$C_6$ alkylamino)$C_0$-$C_6$ alkyl, or $C_1$-$C_6$alkoxycarbonyl;

$R_2$ is $C_1$-$C_7$ alkyl, ($C_1$-$C_6$alkoxy)$C_0$-$C_6$alkoxy, (heterocycloalkyl) $C_0$-$C_2$alkyl, ($C_3$-$C_7$cycloalkyl)$C_0$-$C_2$alkyl, (phenyl)$C_0$-$C_2$alkyl, mono-, di-, and tri-substituted (phenyl)$C_0$-$C_2$alkyl, wherein the substituents are independently hydroxy, nitro, cyano, amino, halogen, —SO$_2$NH$_2$, oxo, —COOH, $C_1$-$C_6$ alkyl, $C_2$-$C_6$alkenyl, $C_2$-$C_6$alkynyl, $C_1$-$C_6$ alkoxy, $C_2$-$C_6$alkanoyl, $C_1$-$C_6$hydroxyalkyl, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$alkyl, mono-$C_1$-$C_6$alkylamino, di-$C_1$-$C_6$alkylamino, mono-$C_1$-$C_6$alkylcarboxamide, di-$C_1$-$C_6$alkylcarboxamide, $C_1$-$C_6$alkoxycarbonyl, phenyl, heteroaryl, or —(C=O)$R_{13}$ wherein $R_{13}$ is $C_1$-$C_6$alkyl, ($C_3$-$C_7$cycloalkyl)$C_0$-$C_2$alkyl, $C_1$-$C_3$haloalkyl, heterocycloalkyl, phenyl, and heteroaryl;

(phenoxy)$C_0$-$C_2$alkyl, mono-, di-, and tri-substituted (phenoxy)$C_0$-$C_2$alkyl, wherein the substituents are independently hydroxy, nitro, cyano, amino, halogen, —SO$_2$NH$_2$, oxo, —COOH, $C_1$-$C_6$ alkyl, $C_2$-$C_6$alkenyl, $C_2$-$C_6$alkynyl, $C_1$-$C_6$ alkoxy, $C_2$-$C_6$alkanoyl, $C_1$-$C_6$hydroxyalkyl, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$alkyl, mono-$C_1$-$C_6$alkylamino, di-$C_1$-$C_6$alkylamino, mono-$C_1$-$C_6$alkylcarboxamide, di-$C_1$-$C_6$alkylcarboxamide, $C_1$-$C_6$alkoxycarbonyl, phenyl, heteroaryl, or —(C=O)$R_{13}$ wherein $R_{13}$ is $C_1$-$C_6$alkyl, ($C_3$-$C_7$cycloalkyl)$C_0$-$C_2$alkyl, $C_1$-$C_3$haloalkyl, heterocycloalkyl, phenyl, or heteroaryl;

(heteroaryl)$C_0$-$C_2$alkyl, mono-, di-, and tri-substituted (heteroaryl)$C_0$-$C_2$alkyl, wherein the substituents are independently hydroxy, nitro, cyano, amino, halogen, —SO$_2$NH$_2$, oxo, —COOH, $C_1$-$C_6$ alkyl, $C_2$-$C_6$alkenyl, $C_2$-$C_6$alkynyl, $C_1$-$C_6$ alkoxy, $C_2$-$C_6$alkanoyl, $C_1$-$C_6$hydroxyalkyl, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$alkyl, mono-$C_1$-$C_6$alkylamino, di-$C_1$-$C_6$alkylamino, mono-$C_1$-$C_6$alkylcarboxamide, di-$C_1$-$C_6$alkylcarboxamide, $C_1$-$C_6$alkoxycarbonyl, phenyl, heteroaryl, or —(C=O)$R_{13}$ wherein $R_{13}$ is $C_1$-$C_6$alkyl, ($C_3$-$C_7$cycloalkyl)$C_0$-$C_2$alkyl, $C_1$-$C_3$haloalkyl, heterocycloalkyl, phenyl, or heteroaryl;

$Z_1$ is

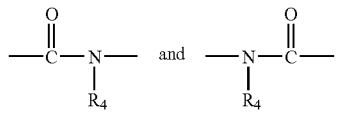

$R_4$ is
Hydrogen,
$C_1$-$C_6$alkyl,
substituted $C_1$-$C_6$alkyl wherein the substituent is hydroxy, nitro, cyano, amino, halogen, oxo, $C_1$-$C_6$ alkyl, $C_2$-$C_6$alkenyl, $C_2$-$C_6$alkynyl, $C_1$-$C_6$ alkoxy, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$ alkyl, mono-$C_1$-$C_6$ alkylamino, di-$C_1$-$C_6$ alkylamino, or —C(O)$R_{14}$ wherein $R_{14}$ is $C_1$-$C_6$ alkyl, $C_1$-$C_3$haloalkyl, or phenyl;
$C_3$-$C_7$cycloalkyl,
substituted $C_3$-$C_7$cycloalkyl, wherein the substituent is chosen from hydroxy, nitro, cyano, amino, halogen, oxo, $C_1$-$C_6$ alkyl, $C_2$-$C_6$alkenyl, $C_2$-$C_6$alkynyl, $C_1$-$C_6$ alkoxy, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$ alkyl, mono-$C_1$-$C_6$ alkylamino, di-$C_1$-$C_6$ alkylamino, or —C(O)$R_{14}$ wherein $R_{14}$ is $C_1$-$C_6$ alkyl, $C_1$-$C_3$haloalkyl, or phenyl;
heterocycloalkyl,
substituted heterocycloalkyl, wherein the substituent is hydroxy, nitro, cyano, amino, halogen, oxo, $C_1$-$C_6$ alkyl, $C_2$-$C_6$alkenyl, $C_2$-$C_6$alkynyl, $C_1$-$C_6$ alkoxy, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$ alkyl, mono-$C_1$-$C_6$ alkylamino, di-$C_1$-$C_6$ alkylamino, or —C(O)$R_{14}$ wherein $R_{14}$ is $C_1$-$C_6$ alkyl, $C_1$-$C_3$haloalkyl, or phenyl;
phenyl,
substituted phenyl, wherein the substituent is hydroxy, nitro, cyano, amino, halogen, oxo, $C_1$-$C_6$ alkyl, $C_2$-$C_6$alkenyl, $C_2$-$C_6$alkynyl, $C_1$-$C_6$ alkoxy, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$ alkyl, mono-$C_1$-$C_6$ alkylamino, di-$C_1$-$C_6$ alkylamino, or —C(O)$R_{14}$ wherein $R_{14}$ is $C_1$-$C_6$ alkyl, $C_1$-$C_3$haloalkyl, or phenyl;
heteroaryl,
substituted heteroaryl, wherein the substituent is hydroxy, nitro, cyano, amino, halogen, oxo, $C_1$-$C_6$ alkyl, $C_2$-$C_6$alkenyl, $C_2$-$C_6$alkynyl, $C_1$-$C_6$ alkoxy, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$ alkyl, mono-$C_1$-$C_6$ alkylamino, di-$C_1$-$C_6$ alkylamino, or —C(O)$R_{14}$ wherein $R_{14}$ is $C_1$-$C_6$ alkyl, $C_1$-$C_3$haloalkyl, or phenyl;
Q is phenyl and pyridyl;
$R_3$ is
hydrogen,
halogen,
$C_1$-$C_7$ alkyl,
heterocycloalkyl,
mono-, di-, and tri-substituted heterocycloalkyl, wherein the substituents are independently hydroxy, nitro, cyano, amino, halogen, —$SO_2NH_2$, oxo, $C_1$-$C_6$ alkyl, $C_2$-$C_6$alkenyl, $C_2$-$C_6$alkynyl, $C_1$-$C_6$ alkoxy, $C_1$-$C_3$haloalkyl, $C_1$-$C_3$haloalkoxy, $C_1$-$C_6$ alkylthio, ($C_1$-$C_6$-alkoxy)$C_1$-$C_6$ alkoxy, mono-$C_1$-$C_6$alkylamino, di-$C_1$-$C_6$alkylamino, amino$C_1$-$C_6$ alkyl, and —C(O)$R_{14}$,
$C_3$-$C_7$cycloalkyl,
mono-, di-, and tri-substituted $C_3$-$C_7$cycloalkyl, wherein the substituents are independently hydroxy, nitro, cyano, amino, halogen, —$SO_2NH_2$, oxo, $C_1$-$C_6$ alkyl, $C_2$-$C_6$alkenyl, $C_2$-$C_6$alkynyl, $C_1$-$C_6$ alkoxy, $C_1$-$C_3$haloalkyl, $C_1$-$C_3$haloalkoxy, $C_1$-$C_6$alkylthio, ($C_1$-$C_6$-alkoxy)$C_1$-$C_6$alkoxy, mono-$C_1$-$C_6$alkylamino, di-$C_1$-$C_6$alkylamino, amino$C_1$-$C_6$ alkyl, and —C(O)$R_{14}$,
heteroaryl,
mono-, di-, and tri-substituted heteroaryl, wherein the substituents are independently hydroxy, nitro, cyano, amino, halogen, —$SO_2NH_2$, oxo, $C_1$-$C_6$ alkyl, $C_2$-$C_6$alkenyl, $C_2$-$C_6$alkynyl, $C_1$-$C_6$ alkoxy, $C_1$-$C_3$haloalkyl, $C_1$-$C_3$haloalkoxy, $C_1$-$C_6$ alkylthio, ($C_1$-$C_6$-alkoxy)$C_1$-$C_6$ alkoxy, mono-$C_1$-$C_6$alkylamino, di-$C_1$-$C_6$alkylamino, amino$C_1$-$C_6$ alkyl, and —C(O)$R_{14}$.

2. The compound according to claim 1 wherein A is 0.
3. The compound according to claim 1 wherein A is 1.
4. The compound according to claim 1 wherein
$R_1$ is chosen from
phenyl substituted with
—CHO,
—COOH,
—$CONH_2$,
—CONHOH,
$C_2$-$C_6$ alkenyl,
substituted $C_2$-$C_6$ alkenyl chosen from mono-, di-, and tri-substituted $C_2$-$C_6$ alkenyl wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,
$C_2$-$C_6$ alkynyl,
substituted $C_2$-$C_6$ alkynyl chosen from mono-, di-, and tri-substituted $C_2$-$C_6$ alkynyl wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,
$C_1$-$C_6$hydroxyalkyl,
substituted $C_1$-$C_6$hydroxyalkyl chosen from mono-, di-, and tri-substituted $C_1$-$C_6$hydroxyalkyl wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,
$C_1$-$C_6$hydroxyalkoxy,
substituted $C_1$-$C_6$hydroxyalkoxy chosen from mono-, di-, and tri-substituted $C_1$-$C_6$hydroxyalkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_1$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, (mono-C$_1$-C$_6$alkylamino)C$_1$-C$_6$alkoxy, substituted (mono-C$_1$-C$_6$alkylamino)C$_1$-C$_6$alkoxy chosen from mono-, di-, and tri-substituted (mono-C$_1$-C$_6$alkylamino)C$_1$-C$_6$alkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, (di-C$_1$-C$_6$alkylamino)C$_1$-C$_6$alkoxy, substituted (di-C$_1$-C$_6$alkylamino)C$_1$-C$_6$alkoxy chosen from mono-, di-, and tri-substituted (di-C$_1$-C$_6$alkylamino)C$_1$-C$_6$alkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, (C$_1$-C$_6$alkoxy)(C$_1$-C$_6$alkylamino)C$_0$-C$_6$alkyl, substituted (C$_1$-C$_6$alkoxy)(C$_1$-C$_6$alkylamino)C$_0$-C$_6$alkyl chosen from mono-, di-, and tri-substituted (C$_1$-C$_6$alkoxy)(C$_1$-C$_6$alkylamino)C$_0$-C$_6$alkyl, wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, (C$_1$-C$_6$alkoxy)(C$_1$-C$_6$alkoxy)C$_1$-C$_6$alkoxy, substituted (C$_1$-C$_6$alkoxy)(C$_1$-C$_6$alkoxy)C$_1$-C$_6$alkoxy chosen from mono-, di-, and tri-substituted (C$_1$-C$_6$alkoxy)(C$_1$-C$_6$alkoxy)C$_1$-C$_6$alkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, heterocycloalkyl, substituted heterocycloalkyl chosen from mono-, di-, and tri-substituted heterocycloalkyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, heteroaryl, substituted heteroaryl chosen from mono-, di-, and tri-substituted heteroaryl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, —C$_1$-C$_6$alkyl(C=O)OR$_{10}$, substituted —C$_1$-C$_6$alkyl(C=O)OR$_{10}$ chosen from mono-, di-, and tri-substituted —C$_1$-C$_6$alkyl(C=O)OR$_{10}$ wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, —C$_0$-C$_6$alkyl(C=O)NR$_{10}$R$_{11}$, substituted —C$_0$-C$_6$alkyl(C=O)NR$_{10}$R$_{11}$ chosen from mono-, di-, and tri-substituted —C$_0$-C$_6$alkyl(C=O)NR$_{10}$R$_{11}$ wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, —C$_1$-C$_6$alkylNR$_{10}$(SO$_2$)R$_{11}$, substituted —C$_1$-C$_6$alkylNR$_{10}$(SO$_2$)R$_{11}$ chosen from mono-, di-, and tri-substituted —C$_1$-C$_6$alkylNR$_{10}$(SO$_2$)R$_{11}$ wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, —C$_0$-C$_6$alkylNR$_{10}$(C=O)R$_{11}$, substituted —C$_0$-C$_6$alkylNR$_{10}$(C=O)R$_{11}$ chosen from mono-, di-, and tri-substituted —C$_0$-C$_6$alkylNR$_{10}$(C=O)R$_{11}$, wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl($SO_2$)$R_{10}$, substituted —$C_0$-$C_6$alkyl($SO_2$)$R_{10}$ chosen from mono-, di-, and tri-substituted —$C_0$-$C_6$alkyl($SO_2$)$R_{10}$ wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl$NR_{10}$(C=O)$NR_{11}R_{12}$, substituted —$C_0$-$C_6$alkyl$NR_{10}$(C=O)$NR_{11}R_{12}$ chosen from mono-, di-, and tri-substituted —$C_0$-$C_6$alkyl$NR_{10}$(C=O)$NR_{11}R_{12}$, wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, -L-G, where L is chosen from $C_1$-$C_2$alkylene, substituted $C_1$-$C_2$alkylene chosen from mono-, di-, and tri-substituted $C_1$-$C_2$alkylene wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,

—(C=O)—,

—($C_1$-$C_2$alkylene)(C=O)—, and substituted —($C_1$-$C_2$alkylene)(C=O)— chosen from mono-, di-, and tri-substituted —($C_1$-$C_2$alkylene)(C=O)— wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and G is chosen from heterocycloalkyl, substituted heterocycloalkyl chosen from mono-, di-, and tri-substituted heterocycloalkyl, wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_3$-$C_7$cycloalkyl, substituted $C_3$-$C_7$cycloalkyl chosen from mono-, di-, and tri-substituted $C_3$-$C_7$cycloalkyl wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, substituted heteroaryl chosen from mono-, di-, and tri-substituted heteroaryl wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and pyridyl substituted with hydroxy,

—CHO,

—COOH,

—$CONH_2$,

—CONHOH, $C_2$-$C_6$alkenyl, substituted $C_2$-$C_6$ alkenyl chosen from mono-, di-, and tri-substituted $C_2$-$C_6$ alkenyl wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_2$-$C_6$ alkynyl, substituted $C_2$-$C_6$ alkynyl chosen from mono-, di-, and tri-substituted $C_2$-$C_6$ alkynyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_1$-$C_6$hydroxyalkyl, substituted $C_1$-$C_6$hydroxyalkyl chosen from mono-, di-, and tri-substituted $C_1$-$C_6$hydroxyalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_1$-$C_6$hydroxyalkoxy, substituted $C_1$-$C_6$hydroxyalkoxy chosen from mono-, di-, and tri-substituted $C_1$-$C_6$hydroxyalkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, (mono-$C_1$-$C_6$alkylamino)$C_1$-$C_6$alkoxy, substituted (mono-$C_1$-$C_6$alkylamino)$C_1$-$C_6$alkoxy chosen from mono-, di-, and tri-substituted (mono-$C_1$-$C_6$alkylamino)$C_1$-$C_4$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, (di-$C_1$-$C_6$alkylamino)$C_1$-$C_6$alkoxy, substituted (di-$C_1$-$C_6$alkylamino)$C_1$-$C_6$alkoxy chosen from mono-, di-, and tri-substituted (di-$C_1$-$C_6$alkylamino)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, ($C_1$-$C_6$alkoxy)($C_1$-$C_6$alkylamino)$C_0$-$C_6$alkyl, substituted ($C_1$-$C_6$alkoxy)($C_1$-$C_6$alkylamino)$C_0$-$C_6$alkyl chosen from mono-, di-, and tri-substituted ($C_1$-$C_6$alkoxy)($C_1$-$C_6$alkylamino)$C_0$-$C_6$alkyl, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, ($C_1$-$C_6$alkoxy)($C_1$-$C_6$alkoxy)$C_1$-$C_6$alkoxy substituted ($C_1$-$C_6$alkoxy)($C_1$-$C_6$alkoxy)$C_1$-$C_6$alkoxy chosen from mono-, di-, and tri-substituted ($C_1$-$C_6$alkoxy)($C_1$-$C_6$alkoxy)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heterocycloalkyl, substituted heterocycloalkyl chosen from mono-, di-, and tri-substituted heterocycloalkyl wherein the substituents are independently selected from halogen, hydroxy, amino, oxo, —COOH, —CONH$_2$, $C_1$-$C_4$alkyl, $C_1$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, substituted heteroaryl chosen from mono-, di-, and tri-substituted heteroaryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_1$-$C_6$alkyl(C=O)OR$_{10}$, substituted —$C_1$-$C_6$alkyl(C=O)OR$_{10}$ chosen from mono-, di-, and tri-substituted —$C_1$-$C_6$alkyl(C=O)OR$_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl(C=O)NR$_{10}$R$_{11}$, substituted —$C_0$-$C_6$alkyl(C=O)NR$_{10}$R$_{11}$ chosen from mono-, di-, and tri-substituted —$C_0$-$C_6$alkyl(C=O)NR$_{10}$R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_1$-$C_6$alkylNR$_{10}$(SO$_2$)R$_{11}$, substituted —$C_1$-$C_6$alkylNR$_{10}$(SO$_2$)R$_{11}$ chosen from mono-, di-, and tri-substituted —$C_1$-$C_6$alkylNR$_{10}$(SO$_2$)R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkylNR$_{10}$(C=O)R$_{11}$, substituted —$C_0$-$C_6$alkylNR$_{10}$(C=O)R$_{11}$ chosen from mono-, di-, and tri-substituted —$C_0$-$C_6$alkylNR$_{10}$(C=O)R$_{11}$, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl(SO$_2$)R$_{10}$, substituted —$C_0$-$C_6$alkyl(SO$_2$)R$_{10}$ chosen from mono-, di-, and tri-substituted —$C_0$-$C_6$alkyl(SO$_2$)R$_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkylNR$_{10}$(C=O)NR$_{11}$R$_{12}$, substituted —$C_0$-$C_6$alkylNR$_{10}$(C=O)NR$_{11}$R$_{12}$ chosen from mono-, di-, and tri-substituted —$C_0$-$C_6$alkylNR$_{10}$(C=O)NR$_{11}$R$_{12}$, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_4$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, -L-G, where L is chosen from $C_1$-$C_2$alkylene, substituted $C_1$-$C_2$alkylene chosen from mono-, di-, and tri-substituted $C_1$-$C_2$alkylene wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,

—(C=O)—,

—($C_1$-$C_2$alkylene)(C=O)—, and substituted —($C_1$-$C_2$alkylene)(C=O)— chosen from mono-, di-, and tri-substituted —($C_1$-$C_2$alkylene)(C=O)— wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and G is chosen from heterocycloalkyl, substituted heterocycloalkyl chosen from mono-, di-, and tri-substituted heterocycloalkyl, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_3$-$C_7$cycloalkyl, substituted $C_3$-$C_7$cycloalkyl chosen from mono-, di-, and tri-substituted $C_3$-$C_7$cycloalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, substituted heteroaryl chosen from mono-, di-, and tri-substituted heteroaryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and wherein $R_1$ is optionally further substituted with 1 or more substituents independently chosen from hydroxy, nitro, cyano, amino, —$SO_2NH_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono-$C_1$-$C_6$ alkylamino)$C_0$-$C_6$ alkyl, (di-$C_1$-$C_6$ alkylamino)$C_0$-$C_6$ alkyl, and $C_1$-$C_6$alkoxycarbonyl.

5. The compound according to claim 4, wherein
$R_1$ is chosen from
phenyl substituted with a group chosen from —CHO, —COOH, —$CONH_2$, and —CONHOH, and
pyridyl substituted with a group chosen from hydroxy, —CHO, —COOH, —$CONH_2$, and —CONHOH, and wherein $R_1$ is optionally further substituted with 1 or more substituents independently chosen from hydroxy, nitro, cyano, amino, —$SO_2NH_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono-$C_1$-$C_6$ alkylamino)$C_0$-$C_6$ alkyl, (di-$C_1$-$C_6$ alkylamino)$C_0$-$C_6$ alkyl, and $C_1$-$C_6$alkoxycarbonyl.

6. The compound according to claim 5, wherein
$R_1$ is chosen from
phenyl substituted with a group chosen from —CHO, —COOH, —$CONH_2$, and —CONHOH, and
pyridyl substituted with a group chosen from hydroxy, —CHO, —COOH, —$CONH_2$, and —CONHOH, wherein $R_1$ is optionally further mono-, di-, or tri-substituted with groups independently chosen from hydroxy, cyano, halogen, $C_1$-$C_4$alkyl, $C_2$-$C_4$alkanoyl, $C_1$-$C_2$haloalkyl, $C_1$-$C_2$haloalkoxy, $C_1$-$C_4$alkoxy, mono-$C_1$-$C_4$alkylamino, and $C_1$-$C_4$alkylamino.

7. The compound according to claim 6, wherein
$R_1$ is chosen from
phenyl substituted with a group chosen from —CHO, —COOH, —$CONH_2$, and —CONHOH, and
pyridyl substituted with a group chosen from hydroxy, —CHO, —COOH, —$CONH_2$, and —CONHOH, wherein $R_1$ is optionally further mono-, di-, or tri-substituted with groups independently chosen from hydroxy, cyano, halogen, $C_1$-$C_2$alkyl, and $C_1$-$C_2$alkoxy.

8. The compound according to claim 4 wherein
$R_1$ is chosen from
phenyl substituted with a group chosen from $C_2$-$C_6$ alkenyl, $C_2$-$C_6$ alkynyl, $C_1$-$C_6$hydroxyalkyl, $C_1$-$C_6$hydroxyalkoxy, (mono-$C_1$-$C_6$alkylamino)$C_1$-$C_6$alkoxy, (di-$C_1$-$C_6$alkylamino)$C_1$-$C_6$alkoxy, ($C_1$-$C_6$alkoxy)($C_1$-$C_6$alkylamino)$C_0$-$C_6$alkyl, ($C_1$-$C_6$alkoxy)($C_1$-$C_6$alkoxy)$C_1$-$C_6$alkoxy, heterocycloalkyl, aryl, and heteroaryl, each of which groups is optionally mono-, di-, or tri-substituted with substituents independently chosen from halogen, hydroxy, amino, oxo, —COOH, —$CONH_2$, $C_1$-$C_4$alkyl, $C_2$-$C_4$alkenyl, $C_1$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and pyridyl substituted with a group chosen from
$C_2$-$C_6$ alkenyl,
substituted $C_2$-$C_6$ alkenyl chosen from mono-, di-, and tri-substituted $C_2$-$C_6$ alkenyl wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_2$-$C_6$ alkynyl,
substituted $C_2$-$C_6$ alkynyl chosen from mono-, di-, and tri-substituted $C_2$-$C_6$ alkynyl wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_1$-$C_6$hydroxyalkyl,
substituted $C_1$-$C_6$hydroxyalkyl chosen from mono-, di-, and tri-substituted $C_1$-$C_6$hydroxyalkyl wherein the substituents are independently selected from halogen, hydroxy, amino, oxo, —COOH, —$CONH_2$, $C_1$-$C_4$alkyl, $C_2$-$C_4$alkenyl, $C_1$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_4$alkylcarboxamide, and phenyl, $C_1$-$C_6$hydroxyalkoxy,
substituted $C_1$-$C_6$hydroxyalkoxy chosen from mono-, di-, and tri-substituted $C_1$-$C_6$hydroxyalkoxy wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, (mono-$C_1$-$C_6$alkylamino)$C_1$-$C_6$alkoxy,
substituted (mono-$C_1$-$C_6$alkylamino)$C_1$-$C_6$alkoxy chosen from mono-, di-, and tri-substituted (mono-$C_1$-$C_6$alkylamino)$C_1$-$C_6$alkoxy wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, (di-$C_1$-$C_6$alkylamino)$C_1$-$C_6$alkoxy,
substituted (di-$C_1$-$C_6$alkylamino)$C_1$-$C_6$alkoxy chosen from mono-, di-, and tri-substituted (di-$C_1$-$C_6$alkylamino)$C_1$-$C_6$alkoxy wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, ($C_1$-$C_6$alkoxy)($C_1$-$C_6$alkylamino)$C_0$-$C_6$alkyl, substituted ($C_1$-$C_6$alkoxy)($C_1$-$C_6$alkylamino)$C_0$-$C_6$alkyl chosen from mono-, di-, and tri-substituted ($C_1$-$C_6$alkoxy)($C_1$-$C_6$alkylamino)$C_0$-$C_6$alkyl, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, ($C_1$-$C_6$alkoxy)($C_1$-$C_6$alkoxy)$C_1$-$C_6$alkoxy, substituted ($C_1$-$C_6$alkoxy)($C_1$-$C_6$alkoxy)$C_1$-$C_6$alkoxy chosen from mono-, di-, and tri-substituted ($C_1$-$C_6$alkoxy)($C_1$-$C_6$alkoxy)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino mono-$C_1$-$C_4$alkylcarboxamide, di-$C_1$-$C_4$alkylcarboxamide, and phenyl, heterocycloalkyl, substituted heterocycloalkyl chosen from mono-, di-, and tri-substituted heterocycloalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, substituted heteroaryl chosen from mono-, di-, and tri-substituted heteroaryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, wherein $R_1$ is optionally further substituted with 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono-$C_1$-$C_6$ alkylamino)$C_0$-$C_6$ alkyl, (di-$C_1$-$C_6$ alkylamino)$C_0$-$C_6$ alkyl, and $C_1$-$C_6$alkoxycarbonyl.

9. The compound according to claim 8 wherein $R_1$ is chosen from phenyl substituted with a group chosen from $C_1$-$C_6$hydroxyalkyl, substituted $C_1$-$C_6$hydroxyalkyl chosen from mono-, di-, and tri-substituted $C_1$-$C_6$hydroxyalkyl, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, $C_1$-$C_6$hydroxyalkoxy, substituted $C_1$-$C_6$hydroxyalkoxy chosen from mono-, di-, and tri-substituted $C_1$-$C_6$hydroxyalkoxy, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, (mono-$C_1$-$C_6$alkylamino)$C_1$-$C_6$alkoxy, substituted (mono-$C_1$-$C_6$alkylamino)$C_1$-$C_6$alkoxy chosen from mono-, di-, and tri-substituted (mono-$C_1$-$C_6$alkylamino)$C_1$-$C_6$alkoxy, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, (di-$C_1$-$C_6$alkylamino)$C_1$-$C_6$alkoxy, substituted (di-$C_1$-$C_6$alkylamino)$C_1$-$C_6$alkoxy chosen from mono-, di-, and tri-substituted (di-$C_1$-$C_6$alkylamino)$C_1$-$C_6$alkoxy, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, ($C_1$-$C_6$alkoxy)($C_1$-$C_6$alkylamino)$C_0$-$C_6$alkyl, substituted ($C_1$-$C_6$alkoxy)($C_1$-$C_6$alkylamino)$C_0$-$C_6$alkyl chosen from mono-, di-, and tri-substituted ($C_1$-$C_6$alkoxy)($C_1$-$C_6$alkylamino)$C_0$-$C_6$alkyl, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, ($C_1$-$C_6$alkoxy)($C_1$-$C_6$alkoxy) $C_1$-$C_6$alkoxy, substituted ($C_1$-$C_6$alkoxyl)($C_1$-$C_6$alkoxy)$C_1$-$C_6$alkoxy chosen from mono-, di-, and tri-substituted ($C_1$-$C_6$alkoxy)($C_1$-$C_6$alkoxy)$C_1$-$C_6$alkoxy, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, pyridyl substituted with a group chosen from
$C_1$-$C_6$hydroxyalkyl,
substituted $C_1$-$C_6$hydroxyalkyl chosen from mono-, di-, and tri-substituted $C_1$-$C_6$hydroxyalkyl, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,
$C_1$-$C_6$hydroxyalkoxy,
substituted $C_1$-$C_6$hydroxyalkoxy chosen from mono-, di-, and tri-substituted $C_1$-$C_6$hydroxyalkoxy, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,
(mono-$C_1$-$C_6$alkylamino)$C_1$-$C_6$alkoxy,
substituted (mono-$C_1$-$C_6$alkylamino)$C_1$-$C_6$alkoxy chosen from mono-, di-, and tri-substituted (mono-$C_1$-$C_6$alkylamino)$C_1$-$C_6$alkoxy, wherein the substituents are independently chosen from halogen, hydroxy, cyano, amino, oxo, —COOH, —CONH$_2$, $C_1$-$C_2$alkyl, $C_1$-$C_2$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,
(di-$C_1$-$C_6$alkylamino)$C_1$-$C_6$alkoxy,
substituted (di-$C_1$-$C_6$alkylamino)$C_1$-$C_6$alkoxy chosen from mono-, di-, and tri-substituted (di-$C_1$-$C_6$alkylamino)$C_1$-$C_6$alkoxy, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,
($C_1$-$C_6$alkoxy)($C_1$-$C_6$alkylamino)$C_0$-$C_6$alkyl,
substituted ($C_1$-$C_6$alkoxy)($C_1$-$C_6$alkylamino)$C_0$-$C_6$alkyl chosen from mono-, di-, and tri-substituted ($C_1$-$C_6$alkoxy)($C_1$-$C_6$alkylamino)$C_0$-$C_6$alkyl, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,
($C_1$-$C_6$alkoxy)($C_1$-$C_6$alkoxy)$C_1$-$C_6$alkoxy,
substituted ($C_1$-$C_6$alkoxy)($C_1$-$C_6$alkoxy)$C_1$-$C_6$alkoxy chosen from mono-, di-, and tri-substituted ($C_1$-$C_6$alkoxy)($C_1$-$C_6$alkoxy)$C_1$-$C_6$alkoxy, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, wherein $R_1$ is optionally further mono-, di- or tri-substituted with substituents independently chosen from hydroxy, cyano, halogen, $C_1$-$C_4$alkyl, $C_2$-$C_4$alkanoyl, $C_1$-$C_2$haloalkyl, $C_1$-$C_2$haloalkoxy, $C_1$-$C_4$alkoxy, mono-$C_1$-$C_4$alkylamino, and di-$C_1$-$C_4$alkylamino.

10. The compound according to claim 9 wherein
$R_1$ is chosen from
phenyl substituted with a group chosen from
$C_1$-$C_6$hydroxyalkyl, $C_1$-$C_6$hydroxyalkoxy, (mono-$C_1$-$C_6$alkylamino)$C_1$-$C_6$alkoxy, (di-$C_1$-$C_6$alkylamino)$C_1$-$C_6$alkoxy, ($C_1$-$C_6$alkoxy)($C_1$-$C_6$alkylamino)$C_0$-$C_6$alkyl, and ($C_1$-$C_6$alkoxy)($C_1$-$C_6$alkoxy)$C_1$-$C_6$alkoxy, and pyridyl substituted with a group chosen from
$C_1$-$C_6$hydroxyalkyl, $C_1$-$C_6$hydroxyalkoxy, (mono-$C_1$-$C_6$alkylamino)$C_1$-$C_6$alkoxy, (di-$C_1$-$C_6$alkylamino)$C_1$-$C_6$alkoxy, ($C_1$-$C_6$alkoxy)($C_1$-$C_6$alkylamino)$C_0$-$C_6$alkyl, and ($C_1$-$C_6$alkoxy)($C_1$-$C_6$alkoxy)$C_1$-$C_6$alkoxy, wherein $R_1$ is optionally further mono-, di-, or tri-substituted with substituents independently chosen from hydroxy, cyano, halogen, $C_1$-$C_2$alkyl, and $C_1$-$C_2$alkoxy.

11. The compound according to claim 4 wherein
$R_1$ is chosen from
phenyl substituted with a group chosen from
pyrrolidinyl
substituted pyrrolidinyl chosen from mono-, di- and tri-substituted pyrrolidinyl, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,
morpholinyl,
substituted morpholinyl chosen from mono-, di- and tri-substituted morpholinyl, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,
thiomorpholinyl,
substituted thiomorpholinyl chosen from mono-, di- and tri-substituted thiomorpholinyl, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,
piperazinyl,
substituted piperazinyl chosen from mono-, di- and tri-substituted piperazinyl, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-

C₄alkylcarboxamide, and di-C₁-C₄alkylcarboxamide, piperidinyl, substituted piperidinyl chosen from mono-, di- and tri-substituted piperidinyl, wherein the substituents are independently chosen from halogen, hydroxy, cyano, amino, oxo, —COOH, —CONH₂, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

[1,4]diazepanyl, substituted [1,4]diazepanyl chosen from mono-, di- and tri-substituted [1,4]diazepanyl, wherein the substituents are independently chosen from halogen, hydroxy, cyano, amino, oxo, —COOH, —CONH₂, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, phenyl, substituted phenyl chosen from mono-, di- and tri-substituted phenyl, wherein the substituents are independently chosen from halogen, hydroxy, cyano, amino, oxo, —COOH, —CONH₂, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, imidazolyl, substituted imidazolyl chosen from mono-, di- and tri-substituted imidazolyl, wherein the substituents are independently chosen from halogen, hydroxy, cyano, amino, oxo, —COOH, —CONH₂, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, 5,6-dihydro-8H-[1,2,4]triazolo[4,3-a]pyrazine, substituted 5,6-dihydro-8H-[1,2,4]triazolo[4,3-a]pyrazine chosen from mono-, di- and tri-substituted 5,6-dihydro-8H-[1,2,4]triazolo[4,3-a]pyrazine, wherein the substituents are independently chosen from halogen, hydroxy, cyano, amino, oxo, —COOH, —CONH₂, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, and pyridyl substituted with a group chosen from pyrrolidinyl, substituted pyrrolidinyl chosen from mono-, di- and tri-substituted pyrrolidinyl, wherein the substituents are independently chosen from halogen, hydroxy, cyano, amino, oxo, —COOH, —CONH₂, $C_1$-$C_4$alkyl, $C_1$-$C_4$alkoxy, $C_2$-$C_4$alkanoyl, $C_1$-$C_2$haloalkyl $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, morpholinyl, substituted morpholinyl chosen from mono-, di- and tri-substituted morpholinyl, wherein the substituents are independently chosen from halogen, hydroxy, cyano, amino, oxo, —COOH, —CONH₂, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, thiomorpholinyl, substituted thiomorpholinyl chosen from mono-, di- and tri-substituted thiomorpholinyl, wherein the substituents are independently chosen from halogen, hydroxy, cyano, amino, oxo, —COOH, —CONH₂, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperazinyl, substituted piperazinyl chosen from mono-, di- and tri-substituted piperazinyl, wherein the substituents are independently chosen from halogen, hydroxy, cyano, amino, oxo, —COOH, —CONH₂, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperidinyl, substituted piperidinyl chosen from mono-, di- and tri-substituted piperidinyl, wherein the substituents are independently chosen from halogen, hydroxy, cyano, amino, oxo, —COOH, —CONH₂, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

[1,4]diazepanyl, substituted [1,4]diazepanyl chosen from mono-, di- and tri-substituted [1,4]diazepanyl, wherein the substituents are independently chosen from halogen, hydroxy, cyano, amino, oxo, —COOH, —CONH₂, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, phenyl, substituted phenyl chosen from mono-, di- and tri-substituted phenyl, wherein the substituents are independently chosen from halogen, hydroxy, cyano, amino, oxo, —COOH, —CONH₂, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, imidazolyl, substituted imidazolyl chosen from mono-, di- and tri-substituted imidazolyl, wherein the substituents are independently chosen from halogen, hydroxy, cyano, amino, oxo, —COOH, —CONH₂, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-

$C_4$alkylamino, di-$C_1$-$C_4$alkylamino, mono-$C_1$-$C_4$alkylcarboxamide, and di-$C_1$-$C_4$alkylcarboxamide, and 5,6-dihydro-8H-[1,2,4]triazolo[4,3-a]pyrazine, and substituted 5,6-dihydro-8H-[1,2,4]triazolo[4,3-a]pyrazine chosen from mono-, di- and tri-substituted 5,6-dihydro-8H-[1,2,4]triazolo[4,3-a]pyrazine, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, wherein $R_1$ is optionally further mono-, di-, or tri-substituted with substituents independently chosen from hydroxy, cyano, halogen, $C_1$-$C_4$alkyl, $C_2$-$C_4$alkanoyl, $C_1$-$C_2$haloalkyl, $C_1$-$C_2$haloalkoxy, mono-$C_1$-$C_4$alkylamino, and di-$C_1$-$C_4$alkylamino.

12. The compound according to claim 11, wherein $R_1$ is chosen from phenyl substituted with a group chosen from pyrrolidinyl, substituted pyrrolidinyl chosen from mono- di- and tri-substituted pyrrolidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, morpholinyl, substituted morpholinyl chosen from mono-, di- and tri-substituted morpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, thiomorpholinyl, substituted thiomorpholinyl chosen from mono-, di- and tri-substituted thiomorpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperazinyl, substituted piperazinyl chosen from mono-, di- and tri-substituted piperazinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperidinyl, substituted piperidinyl chosen from mono-, di- and tri-substituted piperidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

[1,4]diazepanyl, substituted [1,4]diazepanyl chosen from mono-, di- and tri-substituted [1,4]diazepanyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, phenyl, substituted phenyl chosen from mono-, di- and tri-substituted phenyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, imidazolyl, substituted imidazolyl chosen from mono-, di- and tri-substituted imidazolyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, 5,6-dihydro-8H-[1,2,4]triazolo[4,3-a]pyrazine, and substituted 5,6-dihydro-8H-[1,2,4]triazolo[4,3-a]pyrazine chosen from mono-, di- and tri-substituted 5,6-dihydro-8H-[1,2,4]triazolo[4,3-a]pyrazine, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, pyridyl substituted with a group chosen from pyrrolidinyl, substituted pyrrolidinyl chosen from mono-, di- and tri-substituted pyrrolidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, morpholinyl, substituted morpholinyl chosen from mono-, di- and tri-substituted morpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl $C_1$-$C_4$alkoxycarbonyl mono-$C_1$-$C_4$alkylamino, di-$C_1$-$C_4$alkylamino mono-$C_1$-$C_4$alkylcarboxamide, and di-$C_1$-$C_4$alkylcarboxamide, thiomorpholinyl, substituted thiomorpholinyl chosen from mono-, di- and tri-substituted thiomorpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperazinyl, substituted piperazinyl chosen from mono-, di- and tri-substituted piperazinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperidinyl, substituted piperidinyl chosen from mono-, di- and tri-substituted piperidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino mono-$C_1$-$C_4$alkylcarboxamide, and di-$C_1$-$C_4$alkylcarboxamide,

[1,4]diazepanyl, substituted [1,4]diazepanyl chosen from mono-, di- and tri-substituted [1,4]diazepanyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, phenyl, substituted phenyl chosen from mono-, di- and tri-substituted phenyl, wherein the substituents are independently chosen from halogen, hydroxy, oxo, —COOH, —CONH$_2$ $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, imidazolyl, substituted imidazolyl chosen from mono-, di- and tri-substituted imidazolyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, 5,6-dihydro-8H-[1,2,4]triazolo[4,3-a]pyrazine, and substituted 5,6-dihydro-8H-[1,2,4]triazolo[4,3-a]pyrazine chosen from mono-, di- and tri-substituted 5,6-dihydro-8H-[1,2,4]triazolo[4,3-a]pyrazine, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, wherein $R_1$ is optionally further mono-, di-, or tri-substituted with from 0 to 3 substituents independently chosen from hydroxy, cyano, halogen, $C_1$-$C_2$alkyl, and $C_1$-$C_2$alkoxy.

13. The compound according to claim 4, wherein $R_1$ is chosen from phenyl substituted with a group chosen from —$C_1$-$C_6$alkyl(C=O)OR$_{10}$, substituted —$C_1$-$C_6$alkyl(C=O)OR$_{10}$ chosen from mono-, di-, and tri-substituted —$C_1$-$C_6$alkyl(C=O)OR$_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl(C=O)NR$_{10}$R$_{11}$, substituted —$C_0$-$C_6$alkyl(C=O)NR$_{10}$R$_{11}$ chosen from mono-, di-, and tri-substituted —$C_0$-$C_6$alkyl(C=O)NR$_{10}$R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_1$-$C_6$alkylNR$_{10}$(SO$_2$)R$_{11}$, substituted —$C_1$-$C_6$alkylNR$_{10}$(SO$_2$)R$_{11}$ chosen from mono-, di-, and tri-substituted —$C_1$-$C_6$alkylNR$_{10}$(SO$_2$)R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkylNR$_{10}$(C=O)R$_{11}$, substituted —$C_0$-$C_6$alkylNR$_{10}$(C=O)R$_{11}$ chosen from mono-, di-, and tri-substituted —$C_0$-$C_6$alkylNR$_{10}$(C=O)R$_{11}$, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl(SO$_2$)R$_{10}$, substituted —$C_0$-$C_6$alkyl(SO$_2$)R$_{10}$ chosen from mono-, di-, and tri-substituted —$C_1$-$C_0$-$C_6$alkyl(SO$_2$)R$_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkylNR$_{10}$(C=O)NR$_{11}$R$_{12}$, and substituted —$C_0$-$C_6$alkylNR$_{10}$(C=O)NR$_{11}$R$_{12}$ chosen from mono-, di-, and tri-substituted —$C_0$-$C_6$alkylNR$_{10}$(C=O)NR$_{11}$ R$_{12}$, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, pyridyl substituted with a group chosen from
- —$C_1$-$C_6$alkyl(C=O)O$R_{10}$,
- substituted —$C_1$-$C_6$alkyl(C=O)O$R_{10}$ chosen from mono-, di-, and tri-substituted —$C_1$-$C_6$alkyl(C=O)O$R_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,
- —$C_0$-$C_6$alkyl(C=O)N$R_{10}R_{11}$,
- substituted —$C_0$-$C_6$alkyl(C=O)N$R_{10}R_{11}$ chosen from mono-, di-, and tri-substituted —$C_0$-$C_6$alkyl(C=O)N$R_{10}R_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,
- —$C_1$-$C_6$alkylN$R_{10}$(SO$_2$)$R_{11}$,
- substituted —$C_1$-$C_6$alkylN$R_{10}$(SO$_2$)$R_{11}$ chosen from mono-, di-, and tri-substituted —$C_1$-$C_6$alkylN$R_{10}$(SO$_2$)$R_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,
- —$C_0$-$C_6$alkylN$R_{10}$(C=O)$R_{11}$,
- substituted —$C_0$-$C_6$alkylN$R_{10}$(C=O)$R_{11}$ chosen from mono-, di-, and tri-substituted —$C_0$-$C_6$alkylN$R_{10}$(C=O)$R_{11}$, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,
- —$C_0$-$C_6$alkyl(SO$_2$)$R_{10}$,
- substituted —$C_0$-$C_6$alkyl(SO$_2$)$R_{10}$ chosen from mono-, di-, and tri-substituted —$C_0$-$C_6$alkyl(SO$_2$)$R_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,
- —$C_0$-$C_6$alkylN$R_{10}$(C=O)N$R_{11}$ $R_{12}$
- substituted —$C_0$-$C_6$ alkylN$R_{10}$(C=O)N$R_{11}R_{12}$ chosen from mono-, di-, and tri-substituted —$C_0$-$C_6$alkylN$R_{10}$(C=O)N$R_{11}R_{12}$, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, wherein $R_1$ is optionally further substituted with 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono-$C_1$-$C_6$ alkylamino)$C_0$-$C_6$ alkyl, (di-$C_1$-$C_6$ alkylamino)$C_0$-$C_6$ alkyl, and $C_1$-$C_6$alkoxycarbonyl, and wherein $R_{10}$, $R_{11}$, and $R_{12}$ are independently chosen from hydrogen, hydroxy, $C_1$-$C_6$alkyl, $C_1$-$C_6$alkoxy, $C_3$-$C_7$cycloalkyl, and heterocycloalkyl.

14. The compound according to claim 13 wherein $R_1$ is chosen from phenyl substituted with a group chosen from
- —$C_1$-$C_4$alkyl(C=O)O$R_{10}$,
- substituted —$C_1$-$C_4$alkyl(C=O)O$R_{10}$ chosen from mono-, di-, and tri-substituted —$C_1$-$C_4$alkyl(C=O)O$R_{10}$ wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,
- —$C_0$-$C_4$alkyl(C=O)N$R_{10}R_{11}$,
- substituted —$C_0$-$C_4$alkyl(C=O)N$R_{10}R_{11}$ chosen from mono-, di-, and tri-substituted —$C_0$-$C_4$alkyl(C=O)N$R_{10}R_{11}$ wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,
- —$C_1$-$C_4$alkylN$R_{10}$(SO$_2$)$R_{11}$,
- substituted —$C_1$-$C_4$alkylN$R_{10}$(SO$_2$)$R_{11}$, chosen from mono-, di-, and tri-substituted —$C_1$-$C_4$alkylN$R_{10}$(SO$_2$)$R_{11}$ wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_4$alkylcarboxamide, and di-$C_1$-$C_4$alkylcarboxamide,
- —$C_0$-$C_4$alkylN$R_{10}$(C=O)$R_{11}$,
- substituted —$C_0$-$C_4$alkylN$R_{10}$(C=O)$R_{11}$ chosen from mono-, di-, and tri-substituted —$C_0$-$C_4$alkylN$R_{10}$(C=O)$R_{11}$, wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,
- —$C_0$-$C_4$alkyl(SO$_2$)$R_{10}$,
- substituted —$C_0$-$C_4$alkyl(SO$_2$)$R_{10}$ chosen from mono-, di-, and tri-substituted —$C_0$-$C_4$alkyl(SO$_2$)$R_{10}$ wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, —$C_0$-$C_4$alkylNR$_{10}$(C=O)NR$_{11}$R$_{12}$, and substituted —$C_0$-$C_4$alkylNR$_{10}$(C=O)NR$_{11}$R$_{12}$ chosen from mono-, di-, and tri-substituted —$C_0$-$C_4$alkylNR$_{10}$(C=O)NR$_{11}$R$_{12}$, wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, pyridyl substituted with a group chosen from —$C_1$-$C_4$alkyl(C=O)OR$_{10}$, substituted —$C_1$-$C_4$alkyl(C=O)OR$_{10}$ chosen from mono-, di-, and tri-substituted —$C_1$-$C_4$alkyl(C=O)OR$_{10}$ wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, —$C_0$-$C_4$alkyl(C=O)NR$_{10}$R$_{11}$, substituted —$C_0$-$C_4$alkyl(C=O)NR$_{10}$R$_{11}$ chosen from mono- di- and tri-substituted —$C_0$-$C_4$alkyl(C=O)NR$_{10}$R$_{11}$ wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, —$C_1$-$C_4$alkylNR$_{10}$(SO$_2$)R$_{11}$, substituted —$C_1$-$C_4$alkylNR$_{10}$(SO$_2$)R$_{11}$ chosen from mono-, di- and tri-substituted —$C_1$-$C_4$alkylNR$_{10}$(SO$_2$)R$_{11}$ wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino mono-$C_1$-$C_4$alkylcarboxamide, and di-$C_1$-$C_4$alkylcarboxamide, —$C_0$-$C_4$alkylNR$_{10}$(C=O)R$_{11}$, substituted —$C_0$-$C_4$alkylNR$_{10}$(C=O)R$_{11}$ chosen from mono-, di- and tri-substituted —$C_0$-$C_4$alkylNR$_{10}$(C=O)R$_{11}$, wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl mono-$C_1$-$C_4$alkylamino, di-$C_1$-$C_4$alkylamino, mono-$C_1$-$C_4$alkylcarboxamide, and di-$C_1$-$C_4$alkylcarboxamide, —$C_0$-$C_4$alkyl(SO$_2$)R$_{10}$, substituted —$C_0$-$C_4$alkyl(SO$_2$)R$_{10}$ chosen from mono-, di- and tri-substituted —$C_0$-$C_4$alkyl(SO$_2$)R$_{10}$ wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino mono-$C_1$-$C_4$alkylcarboxamide, and di-$C_1$-$C_4$alkylcarboxamide, —$C_0$-$C_4$alkylNR$_{10}$(C=O)NR$_{11}$R$_{12}$ and substituted —$C_0$-$C_4$alkylNR$_{10}$(C=O)NR$_{11}$R$_{12}$ chosen from mono-, di- and tri-substituted —$C_0$-$C_4$alkylNR$_{10}$(C=O)NR$_{11}$R$_{12}$, wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, wherein $R_1$ is optionally further mono-, di-, or tri-substituted with from substituents independently chosen from hydroxy, cyano, halogen, $C_1$-$C_2$alkyl, and $C_1$-$C_2$alkoxy, and wherein $R_{10}$, $R_{11}$ and $R_{12}$ are independently chosen from hydrogen, hydroxy, $C_1$-$C_6$alkyl $C_1$-$C_6$alkoxy, $C_3$-$C_{10}$cycloalkyl, pyrrolidinyl, morpholinyl, thiomorpholinyl, piperazinyl, piperidinyl, and [1,4]diazepanyl.

15. The compound according to claim 4 wherein $R_1$ is chosen from phenyl substituted with -L-G, where L is a group chosen from $C_1$-$C_2$alkylene, substituted $C_1$-$C_2$alkylene chosen from mono-, di-, and tri-substituted $C_1$-$C_2$alkylene wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, amino, oxo, —COOH, —CONH$_2$ $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio $C_1$-$C_2$haloalkyl, $C_1$-$C_2$haloalkoxy, $C_1$-$C_4$alkoxycarbonyl, mono-$C_1$-$C_4$alkylamino, di-$C_1$-$_1$-$C_4$alkylamino, mono-$C_1$-$C_4$alkylcarboxamide, di-$C_1$-$C_4$alkylcarboxamide, and phenyl,

—(C=O)—,

—($C_1$-$C_2$alkylene)(C=O)—, and substituted —($C_1$-$C_2$alkylene)(C=O)— chosen from mono-, di-, and tri-substituted —($C_1$-$C_2$alkylene)(C=O)— wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and G is a group chosen from heterocycloalkyl, substituted heterocycloalkyl chosen from mono-, di-, and tri-substituted heterocycloalkyl, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-

$C_4$alkylcarboxamide, di-$C_1$-$C_4$alkylcarboxamide, and phenyl, $C_3$-$C_7$cycloalkyl, substituted $C_3$-$C_7$cycloalkyl chosen from mono-, di-, and tri-substituted $C_3$-$C_7$cycloalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, and substituted heteroaryl chosen from mono-, di-, and tri-substituted heteroaryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and pyridyl substituted with -L-G, where L is a group chosen from $C_1$-$C_2$alkylene, substituted $C_1$-$C_2$alkylene chosen from mono-, di-, and tri-substituted $C_1$-$C_2$alkylene wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,

—(C=O)—,

—($C_1$-$C_2$alkylene)(C=O)—, and substituted -($C_1$-$C_2$alkylene)(C=O)— chosen from mono-, di-, and tri-substituted —($C_1$-$C_2$alkylene)(C=O)— wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and G is a group chosen from heterocycloalkyl, substituted heterocycloalkyl chosen from mono-, di-, and tri-substituted heterocycloalkyl, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_3$-$C_7$cycloalkyl, substituted $C_3$-$C_7$cycloalkyl chosen from mono-, di-, and tri-substituted $C_3$-$C_7$cycloalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, and substituted heteroaryl chosen from mono-, di-, and tri-substituted heteroaryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, wherein $R_1$ is optionally further substituted with 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono-$C_1$-$C_6$ alkylamino)$C_0$-$C_6$ alkyl, (di-$C_1$-$C_6$ alkylamino)$C_0$-$C_6$ alkyl, and $C_1$-$C_6$alkoxycarbonyl.

16. The compound according to claim 15, wherein $R_1$ is chosen from phenyl substituted with -L-G, where L is a group chosen from $C_1$-$C_2$alkylene, substituted $C_1$-$C_2$alkylene chosen from mono-, di-, and tri-substituted $C_1$-$C_2$alkylene wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

—(C=O)—,

—($C_1$-$C_2$alkylene)(C=O)—, substituted —($C_1$-$C_2$alkylene)(C=O)— chosen from mono-, di-, and tri-substituted —($C_1$-$C_2$alkylene)(C=O)— wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, and G is a group chosen from pyrrolidinyl, substituted pyrrolidinyl chosen from mono-, di-, and tri-substituted pyrrolidinyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, morpholinyl, substituted morpholinyl chosen from mono-, di-, and tri-substituted morpholinyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, thiomorpholinyl, substituted thiomorpholinyl chosen from mono-, di-, and tri-substituted thiomorpholinyl wherein the substituents are independently selected from halogen, hydroxy, cyano, amino, oxo, —COOH, —CONH$_2$, $C_1$-$C_4$alkyl $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperazinyl, substituted piperazinyl chosen from mono-, di-, and tri-substituted piperazinyl wherein the substituents are, independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperidinyl, substituted piperidinyl chosen from mono-, di-, and tri-substituted piperidinyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

[1,4]diazepanyl, substituted [1,4]diazepanyl chosen from mono-, di-, and tri-substituted [1,4]diazepanyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino mono-$C_1$-$C_4$alkylcarboxamide, and di-$C_1$-$C_4$alkylcarboxamide, phenyl, substituted phenyl chosen from mono-, di-, and tri-substituted phenyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, imidazolyl, substituted imidazolyl chosen from mono-, di-, and tri-substituted imidazolyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, 5,6-dihydro-8H-[1,2,4]triazolo[4,3-a]pyrazine, substituted 5,6-dihydro-8H-[1,2,4]triazolo[4,3-a]pyrazine chosen from mono-, di- and tri-substituted 5,6-dihydro-8H-[1,2,4]triazolo[4,3-a]pyrazine wherein the substituents are independently selected from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, and pyridyl substituted with -L-G, where L is a group chosen from C$_1$-C$_2$alkylene, substituted C$_1$-C$_2$alkylene chosen from mono-, di-, and tri-substituted C$_1$-C$_2$alkylene wherein the substituents are independently selected from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, C$_0$-C$_2$alkylene-O—, substituted C$_0$-C$_2$alkylene-O— chosen from mono-, di-, and tri-substituted C$_0$-C$_2$alkylene-O— wherein the substituents are independently selected from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide,

—(C=O)—,

—(C$_1$-C$_2$alkylene)(C=O)—, and substituted —(C$_1$-C$_2$alkylene)(C=O)— chosen from mono-, di-, and tri-substituted —(C$_1$-C$_2$alkylene)(C=O)— wherein the substituents are independently selected from halogen, hydroxy, cyano, amino, oxo, —COOH, —CONH$_2$, C$_1$-C$_4$alkyl C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, and G is a group chosen from pyrrolidinyl, substituted pyrrolidinyl chosen from mono-, di-, and tri-substituted pyrrolidinyl wherein the substituents are independently selected from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, morpholinyl, substituted morpholinyl chosen from mono-, di-, and tri-substituted morpholinyl wherein the substituents are independently selected from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, thiomorpholinyl, substituted thiomorpholinyl chosen from mono-, di-, and tri-substituted thiomorpholinyl wherein the substituents are independently selected from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, piperazinyl, substituted piperazinyl chosen from mono-, di-, and tri-substituted piperazinyl wherein the substituents are independently selected from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, piperidinyl, substituted piperidinyl chosen from mono-, di-, and tri-substituted piperidinyl wherein the substituents are independently selected from halogen, hydroxy, cyano, amino, oxo, —COOH, —CONH$_2$, C$_1$-C$_4$alkyl, C$_1$-C$_4$alkoxy C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide,

[1,4]diazepanyl, substituted [1,4]diazepanyl chosen from mono-, di-, and tri-substituted [1,4]diazepanyl wherein the substituents are independently selected from halogen, hydroxy, cyano, amino, oxo, —COOH, —CONH$_2$, C$_1$-C$_4$alkyl, C$_1$, C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, phenyl, substituted phenyl chosen from mono-, di-, and tri-substituted phenyl wherein the substituents are independently selected from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, imidazolyl, substituted imidazolyl chosen from mono-, di-, and tri-substituted imidazolyl wherein the substituents are independently selected from halogen, hydroxy, cyano, amino, oxo, —COOH, —CONH$_2$, C$_1$-C$_4$alkyl, C$_1$-C$_4$alkoxy C$_2$-C$_4$ alkanoyl, C$_1$-C$_2$haloalkyl, C$_1$-C$_2$haloalkoxy, C$_1$-C$_4$alkoxycarbonyl, mono-C$_1$-C$_4$alkylamino, di-$C_1$-$C_4$alkylamino, mono-$C_1$-$C_4$alkylcarboxamide, and di-$C_1$-$C_4$alkylcarboxamide, 5,6-dihydro-8H-[1,2,4]triazolo[4,3-a]pyrazine, and substituted 5,6-dihydro-8H-[1,2,4]triazolo[4,3-a]pyrazine chosen from mono-, di- and tri-substituted 5,6-dihydro-8H-[1,2,4]triazolo[4,3-a]pyrazine wherein the substituents are independently selected from halogen hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, wherein $R_1$ is optionally further mono-, di- or tri-substituted with substituents independently chosen from hydroxy, cyano, halogen, $C_1$-$C_4$alkyl, $C_2$-$C_4$alkanoyl, $C_1$-$C_2$haloalkyl, $C_1$-$C_2$haloalkoxy, $C_1$-$C_4$alkoxy, mono-$C_1$-$C_4$alkylamino, and di-$C_1$-$C_4$alkylamino.

17. The compound according to claim 16, wherein $R_1$ is chosen from phenyl substituted with -L-G, where L is a group chosen from $C_1$-$C_2$alkylene, substituted $C_1$-$C_2$alkylene chosen from mono-, di-, and tri-substituted $C_1$-$C_2$alkylene wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

—(C═O)—,

—($C_1$-$C_2$alkylene)(C═O)—, and substituted —($C_1$-$C_2$alkylene)(C═O)— chosen from mono-, di-, and tri-substituted —($C_1$-$C_2$alkylene)(C═O)— wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, and G is a group chosen from pyrrolidinyl substituted pyrrolidinyl chosen from mono-, di- and tri-substituted pyrrolidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, morpholinyl, substituted morpholinyl chosen from mono-, di- and tri-substituted morpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, thiomorpholinyl, substituted thiomorpholinyl chosen from mono-, di- and tri-substituted thiomorpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperazinyl, substituted piperazinyl chosen from mono-, di- and tri-substituted piperazinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperidinyl, substituted piperidinyl chosen from mono-, di- and tri-substituted piperidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino mono-$C_1$-$C_4$alkylcarboxamide, and di-$C_1$-$C_4$alkylcarboxamide,

[1,4]diazepanyl, substituted [1,4]diazepanyl chosen from mono-, di- and tri-substituted [1,4]diazepanyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, phenyl, substituted phenyl chosen from mono-, di- and tri-substituted phenyl wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, imidazolyl, substituted imidazolyl chosen from mono-, di- and tri-substituted imidazolyl, wherein the substituents are independently chosen from halogen, hydroxy, oxo, —COOH, —CONH$_2$, $C_1$-$C_4$ alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, 5,6-dihydro-8H-[1,2,4]triazolo[4,3-a]pyrazine, and substituted 5,6-dihydro-8H-[1,2,4]triazolo[4,3-a]pyrazine chosen from mono-, di- and tri-substituted 5,6-dihydro-8H-[1,2,4]triazolo[4,3-a]pyrazine, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, pyridyl substituted with -L-G, where L is a group chosen from $C_1$-$C_2$alkylene, substituted $C_1$-$C_2$alkylene chosen from mono-, di-, and tri-substituted $C_1$-$C_2$alkylene wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

—(C=O)—,

—($C_1$-$C_2$alkylene)(C=O)—, substituted —($C_1$-$C_2$alkylene)(C=O)— chosen from mono-, di-, and tri-substituted —($C_1$-$C_2$alkylene)(C=O)— wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, and G is a group chosen from pyrrolidinyl, substituted pyrrolidinyl chosen from mono-, di- and tri-substituted pyrrolidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, morpholinyl, substituted morpholinyl chosen from mono-, di- and tri-substituted morpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, thiomorpholinyl, substituted thiomorpholinyl chosen from mono-, di- and tri-substituted thiomorpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperazinyl, substituted piperazinyl chosen from mono-, di- and tri-substituted piperazinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperidinyl, substituted piperidinyl chosen from mono-, di- and tri-substituted piperidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

[1,4]diazepanyl, substituted [1,4]diazepanyl chosen from mono-, di- and tri-substituted [1,4]diazepanyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, phenyl, substituted phenyl chosen from mono-, di- and tri-substituted phenyl, wherein the substituents are independently chosen from halogen, hydroxy oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl mono-$C_1$-$C_4$alkylamino, di-$C_1$-$C_4$alkylamino, mono-$C_1$-$C_4$alkylcarboxamide, and di-$C_1$-$C_4$alkylcarboxamide, imidazolyl, substituted imidazolyl chosen from mono-, di- and tri-substituted imidazolyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, 5,6-dihydro-8H-[1,2,4]triazolo[4,3-a]pyrazine, and substituted 5,6-dihydro-8H-[1,2,4]triazolo[4,3-a]pyrazine chosen from mono-, di- and tri-substituted 5,6-dihydro-8H-[1,2,4]triazolo[4,3-a]pyrazine, wherein the substituents are independently chosen from halogen, hydroxy, oxo, —COOH, —CONH$_2$, C$_1$-C$_4$alkyl, C$_1$-C$_4$alkoxy, C$_2$-C$_4$alkanoyl, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, wherein R$_1$ is optionally further mono-, di-, or tri-substituted with from 0 to 3 substituents independently chosen from hydroxy, cyano, halogen, C$_1$-C$_2$alkyl, and C$_1$-C$_2$alkoxy.

18. The compound according to claim 17, wherein

L is chosen from phenyl substituted with a group chosen from —CH$_2$—, —(C=O)—, and —(CH$_2$)(C=O)—, and pyridyl substituted with a group chosen from —CH$_2$—, —(C=O)—, and —(CH$_2$)(C=O)—, and G is a group chosen from pyrrolidinyl, substituted pyrrolidinyl chosen from mono-, di- and tri-substituted pyrrolidinyl, wherein the substituents are independently chosen from halogen, hydroxy, oxo, —COOH, —CONH$_2$, C$_1$-C$_2$alkyl, C$_1$-C$_2$alkoxy, C$_2$alkanoyl, C$_1$-C$_2$alkoxycarbonyl, mono-C$_1$-C$_2$alkylamino, di-C$_1$-C$_2$alkylamino, mono-C$_1$-C$_2$alkylcarboxamide, and di-C$_1$-C$_2$alkylcarboxamide, morpholinyl, substituted morpholinyl chosen from mono-, di- and tri-substituted morpholinyl, wherein the substituents are independently chosen from halogen, hydroxy, oxo, —COOH, —CONH$_2$, C$_1$-C$_2$alkyl, C$_1$-C$_2$alkoxy, C$_2$alkanoyl, C$_1$-C$_2$alkoxycarbonyl, mono-C$_1$-C$_2$alkylamino, di-C$_1$-C$_2$alkylamino, mono-C$_1$-C$_2$alkylcarboxamide, and di-C$_1$-C$_2$alkylcarboxamide, thiomorpholinyl, substituted thiomorpholinyl chosen from mono-, di- and tri-substituted thiomorpholinyl, wherein the substituents are independently chosen from halogen, hydroxy, oxo, —COOH, —CONH$_2$, C$_1$-C$_2$alkyl, C$_1$-C$_2$alkoxy, C$_2$alkanoyl, C$_1$-C$_2$alkoxycarbonyl, mono-C$_1$-C$_2$alkylamino, di-C$_1$-C$_2$alkylamino, mono-C$_1$-C$_2$alkylcarboxamide, and di-C$_1$-C$_2$alkylcarboxamide, piperazinyl, substituted piperazinyl chosen from mono-, di- and tri-substituted piperazinyl, wherein the substituents are independently chosen from halogen, hydroxy, oxo, —COOH, —CONH$_2$, C$_1$-C$_2$alkyl, C$_1$-C$_2$alkoxy, C$_2$alkanoyl, C$_1$-C$_2$alkoxycarbonyl, mono-C$_1$-C$_2$alkylamino, di-C$_1$-C$_2$alkylamino, mono-C$_1$-C$_2$alkylcarboxamide, and di-C$_1$-C$_2$alkylcarboxamide, piperidinyl, substituted piperidinyl chosen from mono-, di- and tri-substituted piperidinyl, wherein the substituents are independently chosen from halogen, hydroxy, oxo, —COOH, —CONH$_2$, C$_1$-C$_2$alkyl, C$_1$-C$_2$alkoxy, C$_2$alkanoyl, C$_1$-C$_2$alkoxycarbonyl, mono-C$_1$-C$_2$alkylamino, di-C$_1$-C$_2$alkylamino, mono-C$_1$-C$_2$alkylcarboxamide, and di-C$_1$-C$_2$alkylcarboxamide,

[1,4]diazepanyl, and substituted [1,4]diazepanyl chosen from mono-, di- and tri-substituted [1,4]diazepanyl, wherein the substituents are independently chosen from halogen, hydroxy, oxo, —COOH, —CONH$_2$, C$_1$-C$_2$alkyl, C$_1$-C$_2$alkoxy, C$_2$alkanoyl, C$_1$-C$_2$alkoxycarbonyl, mono-C$_1$-C$_2$alkylamino, di-C$_1$-C$_2$alkylamino, mono-C$_1$-C$_2$alkylcarboxamide, and di-C$_1$-C$_2$alkylcarboxamide, wherein R$_1$ is optionally further mono-, di-, or tri-substituted with substituents independently chosen from hydroxy, halogen, C$_1$-C$_2$alkyl, and C$_1$-C$_2$alkoxy.

19. The compound according to claim 4, having a structure of Formula 2

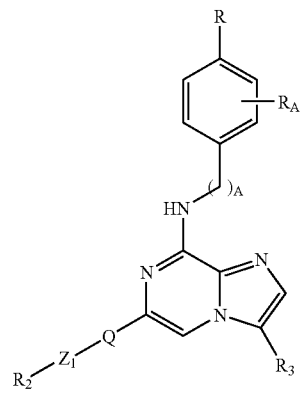

Formula 2 wherein R is chosen from

—CHO,

—COOH,

—CONH$_2$,

—CONHOH,

C$_2$-C$_6$ alkenyl, substituted C$_2$-C$_6$ alkenyl chosen from mono-, di-, and tri-substituted C$_2$-C$_6$ alkenyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, C$_2$-C$_6$ alkynyl, substituted C$_2$-C$_6$ alkynyl chosen from mono-, di-, and tri-substituted C$_2$-C$_6$ alkynyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$-haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, C$_1$-C$_6$hydroxyalkyl, substituted C$_1$-C$_6$hydroxyalkyl chosen from mono-, di-, and tri-substituted C$_1$-C$_6$hydroxyalkyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-

$C_4$alkylamino, di-$C_1$-$C_4$alkylamino, mono-$C_1$-$C_4$alkylcarboxamide, di-$C_1$-$C_4$alkylcarboxamide, and phenyl, $C_1$-$C_6$hydroxyalkoxy, substituted $C_1$-$C_6$hydroxyalkoxy chosen from mono-, di-, and tri-substituted $C_1$-$C_6$hydroxyalkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, (mono-$C_1$-$C_6$alkylamino)$C_1$-$C_6$alkoxy, substituted (mono-$C_1$-$C_6$alkylamino)$C_1$-$C_6$alkoxy chosen from mono-, di-, and tri-substituted (mono-$C_1$-$C_6$alkylamino)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, (di-$C_1$-$C_6$alkylamino)$C_1$-$C_6$alkoxy, substituted (di-$C_1$-$C_6$alkylamino)$C_1$-$C_6$alkoxy chosen from mono-, di-, and tri-substituted (di-$C_1$-$C_6$alkylamino)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, ($C_1$-$C_6$alkoxy)($C_1$-$C_6$alkylamino)$C_0$-$C_6$alkyl, substituted ($C_1$-$C_6$alkoxy)($C_1$-$C_6$alkylamino)$C_0$-$C_6$alkyl chosen from mono-, di-, and tri-substituted ($C_1$-$C_6$alkoxy)($C_1$-$C_6$alkylamino)$C_0$-$C_6$alkyl, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, ($C_1$-$C_6$alkoxy)($C_1$-$C_6$alkoxy)$C_1$-$C_6$alkoxy, substituted ($C_1$-$C_6$alkoxy)($C_1$-$C_6$alkoxy)$C_1$-$C_6$alkoxy chosen from mono-, di-, and tri-substituted ($C_1$-$C_6$alkoxy($C_1$-$C_6$alkoxy)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heterocycloalkyl, substituted heterocycloalkyl chosen from mono-, di-, and tri-substituted heterocycloalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, substituted heteroaryl chosen from mono-, di-, and tri-substituted heteroaryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_1$-$C_6$alkyl(C=O)OR$_{10}$, substituted —$C_1$-$C_6$alkyl(C=O)OR$_{10}$ chosen from mono-, di-, and tri-substituted —$C_1$-$C_6$alkyl(C=O)OR$_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl(C=O)NR$_{10}$R$_{11}$, substituted —$C_0$-$C_6$alkyl(C=O)NR$_{10}$R$_{11}$ chosen from mono-, di-, and tri-substituted —$C_0$-$C_6$alkyl(C=O)NR$_{10}$R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_1$-$C_6$alkylNR$_{10}$(SO$_2$)R$_{11}$, substituted —$C_1$-$C_6$alkylNR$_{10}$(SO$_2$)R$_{11}$ chosen from mono-, di-, and tri-substituted —$C_1$-$C_6$alkylNR$_{10}$(SO$_2$)R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkylNR$_{10}$(C=O)R$_{11}$, substituted —C₀-C₆alkylNR₁₀(C=O)R₁₁ chosen from mono-, di-, and tri-substituted —C₀-C₆alkylNR₁₀(C=O)R₁₁, wherein the substituents are independently selected from halogen, hydroxy, amino, oxo, —COOH, —CONH₂, C₁-C₄alkyl, C₂-C₄alkenyl, C₂-C₄alkynyl, C₁-C₄alkoxy, C₂-C₄alkanoyl, C₁-C₄alkylthio, C₁-C₂haloalkyl, C₁-C₂haloalkoxy, C₁-C₄alkoxycarbonyl, mono-C₁-C₄alkylamino, di-C₁-C₄alkylamino, mono-C₁-C₄alkylcarboxamide, di-C₁-C₄alkylcarboxamide, and phenyl, —C₀-C₆alkyl(SO₂)R₁₀, substituted —C₀-C₆alkyl(SO₂)R₁₀ chosen from mono-, di-, and tri-substituted —C₀-C₆alkyl(SO₂)R₁₀ wherein the substituents are independently selected from halogen, hydroxy, amino, oxo, —COOH, —CONH₂, C₁-C₄alkyl, C₂-C₄alkenyl, C₂-C₄alkynyl, C₁-C₄alkoxy, C₂-C₄alkanoyl, C₁-C₄alkylthio, C₁-C₂haloalkyl, C₁-C₂haloalkoxy, C₁-C₄alkoxycarbonyl, mono-C₁-C₄alkylamino, di-C₁-C₄alkylamino, mono-C₁-C₄alkylcarboxamide, di-C₁-C₄alkylcarboxamide, and phenyl, —C₀-C₆alkylNR₁₀(C=O)NR₁₁R₁₂, substituted —C₀-C₆alkylNR₁₀(C=O)NR₁₁R₁₂ chosen from mono-, di-, and tri-substituted —C₀-C₆alkylNR₁₀(C=O)NR₁₁R₁₂, wherein the substituents are independently selected from halogen, hydroxy, amino, oxo, —COOH, —CONH₂, C₁-C₄alkyl, C₂-C₄alkenyl, C₂-C₄alkynyl C₁-C₄alkoxy, C₂-C₄alkanoyl, C₁-C₄alkylthio, C₁-C₂haloalkyl, C₁-C₂haloalkoxy, C₁-C₄alkoxycarbonyl, mono-C₁-C₄alkylamino, di-C₁-C₄alkylamino, mono-C₁-C₄alkylcarboxamide, di-C₁-C₄alkylcarboxamide, and phenyl, and -L-G, where L is chosen from C₁-C₂alkylene, substituted C₁-C₂alkylene chosen from mono-, di-, and tri-substituted C₁-C₂alkylene wherein the substituents are independently selected from halogen, hydroxy, amino, oxo, —COOH, —CONH₂, C₁-C₄alkyl, C₂-C₄alkenyl, C₂-C₄alkynyl, C₁-C₄alkoxy, C₂-C₄alkanoyl, C₁-C₄alkylthio, C₁-C₂haloalkyl, C₁-C₂haloalkoxy, C₁-C₄alkoxycarbonyl, mono-C₁-C₄alkylamino, di-C₁-C₄alkylamino, mono-C₁-C₄alkylcarboxamide, di-C₁-C₄alkylcarboxamide, and phenyl, C₀-C₂alkylene-O—, substituted C₀-C₂alkylene-O— chosen from mono-, di-, and tri-substituted C₀-C₂alkylene-O— wherein the substituents are independently selected from halogen, hydroxy, amino, oxo, —COOH, —CONH₂, C₁-C₄alkyl, C₂-C₄alkenyl, C₂-C₄alkynyl, C₁-C₄alkoxy, C₂-C₄alkanoyl, C₁-C₄alkylthio, C₁-C₂haloalkyl, C₁-C₂haloalkoxy, C₁-C₄alkoxycarbonyl, mono-C₁-C₄alkylamino, di-C₁-C₄alkylamino, mono-C₁-C₄alkylcarboxamide, di-C₁-C₄alkylcarboxamide, and phenyl,

—(C=O)—,

—(C₁-C₂alkylene)(C=O)—, and substituted —(C₁-C₂alkylene)(C=O)— chosen from mono-, di-, and tri-substituted —(C₁-C₂alkylene)(C=O)— wherein the substituents are independently selected from halogen, hydroxy, amino, oxo, —COOH, —CONH₂, C₁-C₄alkyl, C₂-C₄alkenyl, C₂-C₄alkynyl, C₁-C₄alkoxy, C₂-C₄alkanoyl, C₁-C₄alkylthio, C₁-C₂haloalkyl, C₁-C₂haloalkoxy, C₁-C₄alkoxycarbonyl, mono-C₁-C₄alkylamino, di-C₁-C₄alkylamino, mono-C₁-C₄alkylcarboxamide, di-C₁-C₄alkylcarboxamide, and phenyl, and G is chosen from heterocycloalkyl, substituted heterocycloalkyl chosen from mono-, di-, and tri-substituted heterocycloalkyl, wherein the substituents are independently selected from halogen, hydroxy, amino, oxo, —COOH, —CONH₂, C₁-C₄alkyl, C₂-C₄alkenyl, C₂-C₄alkynyl, C₁-C₄alkoxy, C₂-C₄alkanoyl, C₁-C₄alkylthio, C₁-C₂haloalkyl, C₁-C₂haloalkoxy, C₁-C₄alkoxycarbonyl, mono-C₁-C₄alkylamino, di-C₁-C₄alkylamino, mono-C₁-C₄alkylcarboxamide, di-C₁-C₄alkylcarboxamide, and phenyl, C₃-C₇cycloalkyl, substituted C₃-C₇cycloalkyl chosen from mono-, di-, and tri-substituted C₃-C₇cycloalkyl wherein the substituents are independently selected from halogen, hydroxy, amino, oxo, —COOH, —CONH₂, C₁-C₄alkyl, C₂-C₄alkenyl, C₂-C₄alkynyl, C₁-C₄alkoxy, C₂-C₄alkanoyl, C₁-C₄alkylthio, C₁-C₂haloalkyl, C₁-C₂haloalkoxy, C₁-C₄alkoxycarbonyl, mono-C₁-C₄alkylamino, di-C₁-C₄alkylamino, mono-C₁-C₄alkylcarboxamide, di-C₁-C₄alkylcarboxamide, and phenyl, aryl, substituted aryl chosen from mono-, di-, and tri-substituted aryl wherein the substituents are independently selected from halogen, hydroxy, amino, oxo, —COOH, —CONH₂, C₁-C₄alkyl, C₂-C₄alkenyl, C₂-C₄alkynyl, C₁-C₄alkoxy, C₂-C₄alkanoyl, C₁-C₄alkylthio, C₁-C₂haloalkyl, C₁-C₂haloalkoxy, C₁-C₄alkoxycarbonyl, mono-C₁-C₄alkylamino, di-C₁-C₄alkylamino, mono-C₁-C₄alkylcarboxamide, di-C₁-C₄alkylcarboxamide, and phenyl, heteroaryl, and substituted heteroaryl chosen from mono-, di-, and tri-substituted heteroaryl wherein the substituents are independently selected from halogen, hydroxy, amino, oxo, —COOH, —CONH₂, C₁-C₄alkyl, C₂-C₄alkenyl, C₂-C₄alkynyl, C₁-C₄alkoxy, C₂-C₄alkanoyl, C₁-C₄alkylthio, C₁-C₂haloalkyl, C₁-C₂haloalkoxy, C₁-C₄alkoxycarbonyl, mono-C₁-C₄alkylamino, di-C₁-C₄alkylamino, mono-C₁-C₄alkylcarboxamide, di-C₁-C₄alkylcarboxamide and phenyl, wherein R₁₀, R₁₁ and R₁₂ are independently chosen from hydrogen, hydroxy C₁-C₆alkyl, C₁-C₆alkoxy, C₃-C₁₀cycloalkyl, and heterocycloalkyl and R_A is optional and when present, each occurrence is independently chosen from hydroxy, nitro, cyano, amino, —SO₂NH₂, halogen, C₁-C₆ alkyl, C₂-C₆alkanoyl, C₁-C₄haloalkyl, C₁-C₄haloalkoxy, C₁-C₆ alkylthio, C₃-C₇cycloalkyl, (C₁-C₆ alkoxy)C₀-C₆alkyl, (mono-C₁-C₆ alkylamino)C₀-C₆ alkyl, (di-C₁-C₆ alkylamino)C₀-C₆ alkyl, and C₁-C₆alkoxycarbonyl.

20. The compound according to claim 19 having a structure of Formula 3.

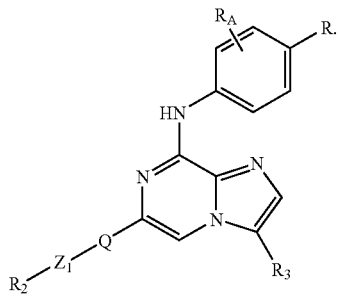

Formula 3

21. The compound according to claim 1, wherein
$R_2$ is chosen from
(phenyl)$C_0$-$C_2$alkyl,
substituted (phenyl)$C_0$-$C_2$alkyl chosen from mono-, di-, and tri-substituted (phenyl)$C_0$-$C_2$alkyl wherein the substituents are independently chosen from hydroxy, nitro, cyano, amino, halogen, —$SO_2NH_2$, oxo, —COOH, $C_1$-$C_6$ alkyl, $C_2$-$C_6$alkenyl, $C_2$-$C_6$alkynyl, $C_1$-$C_6$ alkoxy, $C_2$-$C_6$alkanoyl, $C_1$-$C_6$hydroxyalkyl, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$alkyl, mono-$C_1$-$C_6$ alkylamino, di-$C_1$-$C_6$ alkylamino, mono-$C_1$-$C_6$alkylcarboxamide, di-$C_1$-$C_6$alkylcarboxamide, $C_1$-$C_6$alkoxycarbonyl, phenyl, heteroaryl, and —(C=O)$R_{13}$ wherein $R_{13}$ is chosen from $C_1$-$C_6$alkyl, ($C_3$-$C_7$cycloalkyl)$C_0$-$C_2$alkyl, $C_1$-$C_3$haloalkyl, heterocycloalkyl, phenyl, and heteroaryl,
(phenoxy)$C_0$-$C_2$alkyl,
substituted (phenoxy)$C_0$-$C_2$alkyl chosen from mono-, di-, and tri-substituted (phenoxy)$C_0$-$C_2$alkyl wherein the substituents are independently chosen from hydroxy, nitro, cyano, amino, halogen, —$SO_2NH_2$, oxo, —COOH, $C_1$-$C_6$ alkyl, $C_2$-$C_6$alkenyl, $C_2$-$C_6$alkynyl, $C_1$-$C_6$alkoxy, $C_2$-$C_6$alkanoyl, $C_1$-$C_6$hydroxyalkyl, $C_1$-$C_3$haloalkyl, $C_1$-$C_3$haloalkoxy, $C_1$-$C_6$ alkylthio, ($C_1$-$C_6$ alkoxy) $C_1$-$C_6$ alkoxy, amino$C_1$-$C_6$alkyl, mono-$C_1$-$C_6$ alkylamino, di-$C_1$-$C_6$ alkylamino, mono-$C_1$-$C_6$alkylcarboxamide, di-$C_1$-$C_6$alkylcarboxamide, $C_1$-$C_6$alkoxycarbonyl, phenyl, heteroaryl, and —(C=O)$R_{13}$ wherein $R_{13}$ is chosen from $C_1$-$C_6$alkyl, ($C_3$-$C_7$cycloalkyl)$C_0$-$C_2$alkyl, $C_1$-$C_3$haloalkyl, heterocycloalkyl, phenyl and heteroaryl,
(pyridyl)$C_0$-$C_2$alkyl, and
substituted (pyridyl)$C_0$-$C_2$alkyl chosen from mono-, di-, and tri-substituted (pyridyl)$C_0$-$C_2$alkyl wherein the substituents are independently chosen from hydroxy, nitro, cyano, amino, halogen, —$SO_2NH_2$, oxo, —COOH, $C_1$-$C_6$ alkyl, $C_2$-$C_6$alkenyl, $C_2$-$C_6$alkynyl, $C_1$-$C_6$ alkoxy, $C_2$-$C_6$alkanoyl, $C_1$-$C_6$hydroxyalkyl, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$alkyl, mono-$C_1$-$C_6$ alkylamino, di-$C_1$-$C_6$ alkylamino, mono-$C_1$-$C_6$alkylcarboxamide, di-$C_1$-$C_6$alkylcarboxamide, $C_1$-$C_6$alkoxycarbonyl, phenyl, heteroaryl and —(C=O)$R_{13}$ wherein $R_{13}$ is chosen from $C_1$-$C_6$alkyl, ($C_3$-$C_7$cycloalkyl)$C_0$-$C_2$alkyl, $C_1$-$C_3$haloalkyl, heterocycloalkyl, phenyl, and heteroaryl.

22. The compound according to claim 21, wherein
$R_2$ is chosen from
(phenyl)$C_0$-$C_2$alkyl,
substituted (phenyl)$C_0$-$C_2$alkyl chosen from mono-, di-, and tri-substituted (phenyl)$C_0$-$C_2$alkyl wherein the substituents are independently chosen from hydroxy, cyano, amino, halogen, —$SO_2NH_2$, oxo, —COOH, $C_1$-$C_4$alkyl, $C_1$-$C_4$ alkoxy, $C_2$-$C_4$alkanoyl, $C_1$-$C_4$hydroxyalkyl, $C_1$-$C_2$haloalkyl, $C_1$-$C_2$haloalkoxy, mono-$C_1$-$C_6$alkylamino, di-$C_1$-$C_6$alkylamino, mono-$C_1$-$C_6$alkylcarboxamide, di-$C_1$-$C_6$alkylcarboxamide, $C_1$-$C_4$alkoxycarbonyl, phenyl, and imidazolyl,
(phenoxy)$C_0$-$C_2$alkyl,
substituted (phenoxy)$C_0$-$C_2$alkyl chosen from mono-, di-, and tri-substituted (phenoxy)$C_0$-$C_2$alkyl wherein the substituents are independently chosen from hydroxy, cyano, amino, halogen, —$SO_2NH_2$, oxo, —COOH, $C_1$-$C_4$ alkyl, $C_1$-$C_4$ alkoxy, $C_2$-$C_4$alkanoyl, $C_1$-$C_4$hydroxyalkyl, $C_1$-$C_2$haloalkyl, $C_1$-$C_2$haloalkoxy, mono-$C_1$-$C_6$alkylamino, di-$C_1$-$C_6$alkylamino, mono-$C_1$-$C_6$alkylcarboxamide, di-$C_1$-$C_6$alkylcarboxamide, $C_1$-$C_4$alkoxycarbonyl, phenyl, and imidazolyl,
(pyridyl)$C_0$-$C_2$alkyl, and
substituted (pyridyl)$C_0$-$C_2$alkyl chosen from mono-, di-, and tri-substituted (pyridyl)$C_0$-$C_2$alkyl wherein the substituents are independently chosen from hydroxy, cyano, amino, halogen, —$SO_2NH_2$, oxo, —COOH, $C_1$-$C_4$ alkyl, $C_1$-$C_4$ alkoxy, $C_2$-$C_4$alkanoyl, $C_1$-$C_4$hydroxyalkyl, $C_1$-$C_2$haloalkyl, $C_1$-$C_2$haloalkoxy, mono-$C_1$-$C_6$alkylamino, di-$C_1$-$C_6$alkylamino, mono-$C_1$-$C_6$alkylcarboxamide, di-$C_1$-$C_6$alkylcarboxamide, $C_1$-$C_4$alkoxycarbonyl, phenyl, and imidazolyl.

23. The compound according to claim 1 wherein
$Z_1$ is chosen from

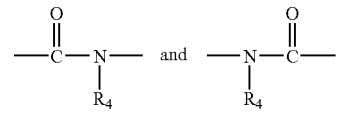

and
$R_4$ is chosen from hydrogen, $C_1$-$C_6$alkyl, and $C_3$-$C_7$cycloalkyl.

24. The compound according to claim 23, wherein $R_4$ is chosen from hydrogen and of methyl.

25. The compound according to claim 4, having a structure of Formula 4

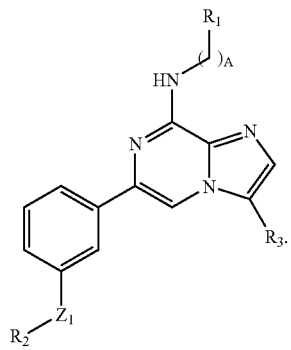

Formula 4

26. The compound according to claim 25, having a structure of Formula 5

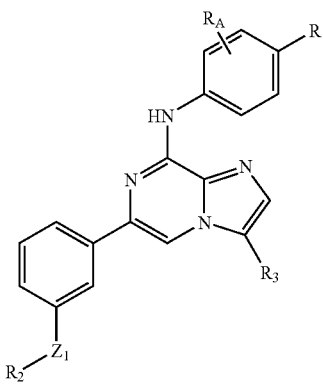

Formula 5 wherein
R is chosen from
—CHO,
—COOH,
—CONH$_2$,
—CONHOH,
C$_2$-C$_6$ alkenyl,
substituted C$_2$-C$_6$ alkenyl chosen from mono-, di-, and tri-substituted C$_2$-C$_6$alkenyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
C$_2$-C$_6$ alkynyl,
substituted C$_2$-C$_6$ alkynyl chosen from mono-, di-, and tri-substituted C$_2$-C$_6$ alkynyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
C$_1$-C$_6$hydroxyalkyl,
substituted C$_1$-C$_6$hydroxyalkyl chosen from mono-, di-, and tri-substituted C$_1$-C$_6$hydroxyalkyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
C$_1$-C$_6$hydroxyalkoxy,
substituted C$_1$-C$_6$hydroxyalkoxy chosen from mono-, di-, and tri-substituted C$_1$-C$_6$hydroxyalkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
(mono-C$_1$-C$_6$alkylamino)C$_1$-C$_6$alkoxy,
substituted (mono-C$_1$-C$_6$alkylamino)C$_1$-C$_6$alkoxy chosen from mono-, di-, and tri-substituted (mono-C$_1$-C$_6$alkylamino)C$_1$-C$_6$alkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
(di-C$_1$-C$_6$alkylamino)C$_1$-C$_6$alkoxy,
substituted (di-C$_1$-C$_6$alkylamino)C$_1$-C$_6$alkoxy chosen from mono-, di-, and tri-substituted (di-C$_1$-C$_6$alkylamino)C$_1$-C$_6$alkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
(C$_1$-C$_6$alkoxy)(C$_1$-C$_6$alkylamino)C$_0$-C$_6$alkyl,
substituted (C$_1$-C$_6$alkoxy)(C$_1$-C$_6$alkylamino)C$_0$-C$_6$alkyl chosen from mono-, di-, and tri-substituted (C$_1$-C$_6$alkoxy)(C$_1$-C$_6$alkylamino)C$_0$-C$_6$alkyl, wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
(C$_1$-C$_6$alkoxy)(C$_1$-C$_6$alkoxy)C$_1$-C$_6$alkoxy,
substituted (C$_1$-C$_6$alkoxy)(C$_1$-C$_6$alkoxy)C$_1$-C$_6$alkoxy chosen from mono-, di-, and tri-substituted (C$_1$-C$_6$alkoxy)(C$_1$-C$_6$alkoxy)C$_1$-C$_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heterocycloalkyl substituted heterocycloalkyl chosen from mono-, di-, and tri-substituted heterocycloalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanloyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, substituted heteroaryl chosen from mono-, di-, and tri-substituted heteroaryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_1$-$C_6$alkyl(C=O)OR$_{10}$, substituted —$C_1$-$C_6$alkyl(C=O)OR$_{10}$ chosen from mono-, di-, and tri-substituted —$C_1$-$C_6$alkyl(C=O)OR$_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl(C=O)NR$_{10}$R$_{11}$, substituted —$C_0$-$C_6$alkyl(C=O)NR$_{10}$R$_{11}$ chosen from mono-, di-, and tri-substituted —$C_0$-$C_6$alkyl(C=O)NR$_{10}$R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide di-$C_1$-$C_4$alkylcarboxamide, and phenyl, —$C_1$-$C_6$alkylNR$_{10}$(SO$_2$)R$_{11}$, substituted —$C_1$-$C_6$alkylNR$_{10}$(SO$_2$)R$_{11}$ chosen from mono-, di-, and tri-substituted —$C_1$-$C_6$alkylNR$_{10}$(SO$_2$)R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkylNR$_{10}$(C=O)R$_{11}$, substituted —$C_0$-$C_6$alkylNR$_{10}$(C=O)R$_{11}$ chosen from mono-, di-, and tri-substituted —$C_0$-$C_6$alkylNR$_{10}$(C=O)R$_{11}$, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl(SO$_2$)R$_{10}$, substituted —$C_0$-$C_6$alkyl(SO$_2$)R$_{10}$ chosen from mono-, di-, and tri-substituted —$C_0$-$C_6$alkyl(SO$_2$)R$_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkylNR$_{10}$(C=O)NR$_{11}$R$_{12}$, substituted —$C_0$-$C_6$alkylNR$_{10}$(C=O)NR$_{11}$R$_{12}$ chosen from mono-, di-, and tri-substituted —$C_0$-$C_6$alkylNR$_{10}$(C=O)NR$_{11}$R$_{12}$, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and -L-G, where L is chosen from $C_1$-$C_2$alkylene, substituted $C_1$-$C_2$alkylene chosen from mono-, di-, and tri-substituted $C_1$-$C_2$alkylene wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,

—(C=O)—,

—($C_1$-$C_2$alkylene)(C=O)—, and substituted —(C$_1$-C$_2$alkylene)(C=O)— chosen from mono-, di-, and tri-substituted —(C$_1$-C$_2$alkylene)(C=O)— wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, and G is chosen from heterocycloalkyl, substituted heterocycloalkyl chosen from mono-, di-, and tri-substituted heterocycloalkyl, wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, C$_3$-C$_7$cycloalkyl, substituted C$_3$-C$_7$cycloalkyl chosen from mono-, di-, and tri-substituted C$_3$-C$_7$cycloalkyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, heteroaryl, and substituted heteroaryl chosen from mono-, di- and tri-substituted heteroaryl wherein the substituents are independently selected from halogen, hydroxy, amino oxo —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino mono-C$_1$-C$_4$alkylcarboxamide, di-C$_1$-C$_4$alkylcarboxamide and phenyl, and R$_4$ is optional and when present, each occurrence is independently chosen from hydroxy, nitro, cyano, amino, —SO$_2$NH$_2$, halogen, C$_1$-C$_6$ alkyl, C$_2$-C$_6$alkanoyl, C$_1$-C$_4$haloalkoxy, C$_1$-C$_6$ alkylthio, C$_3$-C$_7$cycloalkyl, (C$_1$-C$_6$ alkoxy)C$_0$-C$_6$alkyl, (mono-C$_1$-C$_6$ alkylamino)C$_0$-C$_6$ alkyl, (di-C$_1$-C$_6$ alkylamino)C$_0$-C$_6$ alkyl, and C$_1$-C$_6$alkoxycarbonyl, and where R$_{10}$, R$_{11}$, and R$_{12}$ are independently chosen from hydrogen, hydroxy, C$_1$-C$_6$alkyl, C$_1$-C$_6$alkoxy, C$_3$-C$_{10}$cycloalkyl, and heterocycloalkyl.

27. The compound according to claim 1, wherein R$_3$ is chosen from hydrogen and methyl.

28. The compound having a structure of Formula 6

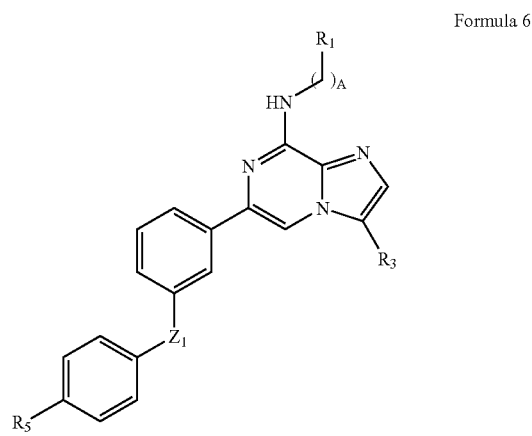

Formula 6 or a pharmaceutically acceptable salt, hydrate, or diastereomer thereof, wherein A is chosen from 0 and 1;

R$_1$ is chosen from phenyl, phenyl substituted with a group chosen from

—CHO,

—COOH,

—CONH$_2$,

—CONHOH,

C$_2$-C$_6$ alkenyl, substituted C$_2$-C$_6$ alkenyl chosen from mono-, di-, and tri-substituted C$_2$-C$_6$ alkenyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, C$_2$-C$_6$ alkynyl, substituted C$_2$-C$_6$ alkynyl chosen from mono-, di-, and tri-substituted C$_2$-C$_6$ alkynyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, C$_1$-C$_6$hydroxyalkyl, substituted C$_1$-C$_6$hydroxyalkyl chosen from mono-, di-, and tri-substituted C$_1$-C$_6$hydroxyalkyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_1$-$C_6$hydroxyalkoxy, substituted $C_1$-$C_6$hydroxyalkoxy chosen from mono-, di-, and tri-substituted $C_1$-$C_6$hydroxyalkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, (mono-$C_1$-$C_6$alkylamino)$C_1$-$C_6$alkoxy, substituted (mono-$C_1$-$C_6$alkylamino)$C_1$-$C_6$alkoxy chosen from mono-, di-, and tri-substituted (mono-$C_1$-$C_6$alkylamino)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, (di-$C_1$-$C_6$alkylamino)$C_1$-$C_6$alkoxy, substituted (di-$C_1$-$C_6$alkylamino)$C_1$-$C_6$alkoxy chosen from mono-, di-, and tri-substituted (di-$C_1$-$C_6$alkylamino)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_4$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, ($C_1$-$C_6$alkoxy)($C_1$-$C_6$alkylamino)$C_0$-$C_6$alkyl, substituted ($C_1$-$C_6$alkoxy)($C_1$-$C_6$alkylamino)$C_0$-$C_6$alkyl chosen from mono-, di- and tri-substituted ($C_1$-$C_6$alkoxy)($C_1$-$C_6$alkylamino)$C_0$-$C_6$alkyl, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, ($C_1$-$C_6$alkoxy)($C_1$-$C_6$alkoxy)$C_1$-$C_6$alkoxy, substituted ($C_1$-$C_6$alkoxy)($C_1$-$C_6$alkoxy)$C_1$-$C_6$alkoxy chosen from mono-, di-, and tri-substituted ($C_1$-$C_6$alkoxy)($C_1$-$C_6$alkoxy)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heterocycloalkyl, substituted heterocycloalkyl chosen from mono-, di-, and tri-substituted heterocycloalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, substituted heteroaryl chosen from mono-, di-, and tri-substituted heteroaryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_1$-$C_6$alkyl(C═O)OR$_{10}$, substituted —$C_1$-$C_6$alkyl(C═O)OR$_{10}$ chosen from mono-, di-, and tri-substituted —$C_1$-$C_6$alkyl (C═O)OR$_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl(C═O)NR$_{10}$R$_{11}$, substituted —$C_0$-$C_6$alkyl(C═O)NR$_{10}$R$_{11}$ chosen from mono-, di-, and tri-substituted $C_0$-$C_6$alkyl (C═O)NR$_{10}$R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_1$-$C_6$alkylNR$_{10}$(SO$_2$)R$_{11}$, substituted —$C_1$-$C_6$alkylNR$_{10}$(SO$_2$)R$_{11}$ chosen from mono-, di-, and tri-substituted —$C_1$-$C_6$alkylNR$_{10}$ (SO$_2$)R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl$NR_{10}$(C=O)$R_{11}$, substituted —$C_0$-$C_6$alkyl$NR_{10}$(C=O)$R_{11}$ chosen from mono-, di-, and tri-substituted —$C_0$-$C_6$alkyl$NR_{10}$(C=O)$R_{11}$, wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl$(SO_2)R_{10}$, substituted —$C_0$-$C_6$alkyl$(SO_2)R_{10}$ chosen from mono-, di-, and tri-substituted —$C_0$-$C_6$alkyl$(SO_2)R_{10}$ wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl$NR_{10}$(C=O)$NR_{11}R_{12}$ substituted —$C_0$-$C_6$alkyl$NR_{10}$(C=O)$NR_{11}R_{12}$ chosen from mono-, di-, and tri-substituted —$C_0$-$C_6$alkyl(C=O)$NR_{11}R_{12}$, wherein the substituents are independently selected from halogen, hydroxy, amino, oxo, —COOH, —CONH $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and -L-G, where L is chosen from $C_1$-$C_2$alkylene, substituted $C_1$-$C_2$alkylene chosen from mono-, di-, and tri-substituted $C_1$-$C_2$alkylene wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,

—(C=O)—,

—($C_1$-$C_2$alkylene)(C=O)—, and substituted —($C_1$-$C_2$alkylene)(C=O)— chosen from mono-, di-, and tri-substituted —($C_1$-$C_2$alkylene)(C=O)— wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_1$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and G is chosen from heterocycloalkyl, substituted heterocycloalkyl chosen from mono-, di-, and tri-substituted heterocycloalkyl, wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_3$-$C_7$cycloalkyl, substituted $C_3$-$C_7$cycloalkyl chosen from mono-, di-, and tri-substituted $C_3$-$C_7$cycloalkyl wherein the substituents are independently selected from halogen hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, and substituted heteroaryl chosen from mono-, di-, and tri-substituted heteroaryl wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-

C$_4$alkylcarboxamide, di-C$_1$-C$_4$alkylcarboxamide, and phenyl, and
monocyclic heteroaryl,
monocyclic heteroaryl substituted with a group chosen from
hydroxy,
—CHO,
—COOH,
—CONH$_2$,
—CONHOH,
C$_2$-C$_6$ alkenyl,
substituted C$_2$-C$_6$ alkenyl chosen from mono-, di-, and tri-substituted C$_2$-C$_6$ alkenyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
C$_2$-C$_6$ alkynyl,
substituted C$_2$-C$_6$alkynyl chosen from mono-, di-, and tri-substituted C$_2$-C$_6$ alkynyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
C$_1$-C$_6$hydroxyalkyl,
substituted C$_1$-C$_6$hydroxyalkyl chosen from mono-, di-, and tri-substituted C$_1$-C$_6$hydroxyalkyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
C$_1$-C$_6$hydroxyalkoxy,
substituted C$_1$-C$_6$hydroxyalkoxy chosen from mono-, di-, and tri-substituted C$_1$-C$_6$hydroxyalkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_4$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
(mono-C$_1$-C$_6$alkylamino)C$_1$-C$_6$alkoxy,
substituted (mono-C$_1$-C$_6$alkylamino)C$_1$-C$_6$alkoxy chosen from mono-, di-, and tri-substituted (mono-C$_1$-C$_6$alkylamino)C$_1$-C$_6$alkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
(di-C$_1$-C$_6$alkylamino)C$_1$-C$_6$alkoxy,
substituted (di-C$_1$-C$_6$alkylamino)C$_1$-C$_6$alkoxy chosen from mono-, di-, and tri-substituted (di-C$_1$-C$_6$alkylamino)C$_1$-C$_6$alkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
(C$_1$-C$_6$alkoxy)(C$_1$-C$_6$alkylamino)C$_0$-C$_6$alkyl
substituted (C$_1$-C$_6$alkoxy)(C$_1$-C$_6$alkylamino)C$_0$-C$_6$alkyl chosen from mono-, di-, and tri-substituted (C$_1$-C$_6$alkoxy)(C$_1$-C$_6$alkylamino)C$_0$-C$_6$alkyl, wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
(C$_1$-C$_6$alkoxy)(C$_1$-C$_6$alkoxy)C$_1$-C$_6$alkoxy,
substituted (C$_1$-C$_6$alkoxy)(C$_1$-C$_6$alkoxy)C$_1$-C$_6$alkoxy chosen from mono-, di-, and tri-substituted (C$_1$-C$_6$alkoxy)(C$_1$-C$_6$alkoxy)C$_1$-C$_6$alkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
heterocycloalkyl,
substituted heterocycloalkyl chosen from mono-, di-, and tri-substituted heterocycloalkyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
aryl,
substituted aryl chosen from mono-, di-, and tri-substituted aryl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
heteroaryl
substituted heteroaryl chosen from mono-, di-, and tri-substituted heteroaryl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-

C$_4$alkylcarboxamide, di-C$_1$-C$_4$alkylcarboxamide, and phenyl,

—C$_1$-C$_6$alkyl(C=O)OR$_{10}$, substituted —C$_1$-C$_6$alkyl(C=O)OR$_{10}$ chosen from mono-, di-, and tri-substituted —C$_1$-C$_6$alkyl(C=O)OR$_{10}$ wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, —C$_0$-C$_6$alkyl(C=O)NR$_{10}$R$_{11}$, substituted —C$_0$-C$_6$alkyl(C=O)NR$_{10}$R$_{11}$ chosen from mono-, di-, and tri-substituted —C$_0$-C$_6$alkyl(C=O)NR$_{10}$R$_{11}$ wherein the substituents are independently selected from halogen, hydroxy, amino, oxo, —COOH, —CONH$_2$, C$_1$-C$_4$alkyl, C$_2$-C$_4$alkenyl C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, —C$_1$-C$_6$alkylNR$_{10}$(SO$_2$)R$_{11}$, substituted —C$_1$-C$_6$alkylNR$_{10}$(SO$_2$)R$_{11}$ chosen from mono-, di-, and tri-substituted —C$_1$-C$_6$alkylNR$_{10}$(SO$_2$)R$_{11}$ wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, —C$_0$-C$_6$alkylNR$_{10}$(C=O)R$_{11}$, substituted —C$_0$-C$_6$alkylNR$_{10}$(C=O)R$_{11}$ chosen from mono-, di-, and tri-substituted —C$_0$-C$_6$alkylNR$_{10}$(C=O)R$_{11}$, wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, —C$_0$-C$_6$alkyl(SO$_2$)R$_{10}$, substituted —C$_0$-C$_6$-alkyl(SO$_2$)R$_{10}$ chosen from mono-, di-, and tri-substituted —C$_0$-C$_6$alkyl(SO$_2$)R$_{10}$ wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_6$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, —C$_0$-C$_6$alkylNR$_{10}$(C=O)NR$_{11}$R$_{12}$ and substituted —C$_0$-C$_6$alkylNR$_{10}$(C=O)NR$_{11}$R$_{12}$ chosen from mono-, di-, and tri-substituted —C$_0$-C$_6$alkylNR$_{10}$(C=O)NR$_{11}$R$_{12}$, wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, and -L-G, where L is chosen from C$_1$-C$_2$alkylene, substituted C$_1$-C$_2$alkylene chosen from mono-, di-, and tri-substituted C$_1$-C$_2$alkylene wherein the substituents are independently selected from halogen, hydroxy, amino, oxo, —COOH, —CONH$_2$, C$_1$-C$_4$alkyl C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, C$_0$-C$_2$alkylene-O—, substituted C$_0$-C$_2$alkylene-O— chosen from mono-, di-, and tri-substituted C$_0$-C$_2$alkylene-O— wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,

—(C=O)—,

—(C$_1$-C$_2$alkylene)(C=O)—, and substituted —(C$_1$-C$_2$alkylene)(C=O)— chosen from mono-, di-, and tri-substituted —(C$_1$-C$_2$alkylene)(C=O)— wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, and G is chosen from heterocycloalkyl, substituted heterocycloalkyl chosen from mono-, di-, and tri-substituted heterocycloalkyl, wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, C$_3$-C$_7$cycloalkyl, substituted C$_3$-C$_7$cycloalkyl chosen from mono-, di-, and tri-substituted C$_3$-C$_7$cycloalkyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, and substituted heteroaryl chosen from mono-, di-, and tri-substituted heteroaryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and wherein $R_{10}$, $R_{11}$, and $R_{12}$ are independently chosen from hydrogen, hydroxy, $C_1$-$C_6$alkyl, $C_1$-$C_6$alkoxy, $C_3$-$C_{10}$cycloalkyl and heterocycloalkyl, and wherein $R_1$ is further optionally substituted with 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono-$C_1$-$C_6$ alkylamino)$C_0$-$C_6$ alkyl, (di-$C_1$-$C_6$ alkylamino)$C_0$-$C_6$ alkyl, and $C_1$-$C_6$alkoxycarbonyl;

$R_3$ is chosen from hydrogen, halogen, $C_1$-$C_7$ alkyl, heterocycloalkyl, substituted heterocycloalkyl chosen from mono-, di-, and tri-substituted heterocycloalkyl, wherein the substituents are independently chosen from hydroxy, nitro, cyano, amino, halogen, —SO$_2$NH$_2$, oxo, $C_1$-$C_6$ alkyl, $C_2$-$C_6$alkenyl, $C_2$-$C_6$alkynyl, $C_1$-$C_6$ alkoxy, $C_1$-$C_3$haloalkyl, $C_1$-$C_3$haloalkoxy, $C_1$-$C_6$alkylthio, ($C_1$-$C_6$-alkoxy)$C_1$-$C_6$ alkoxy, mono-$C_1$-$C_6$alkylamino, di-$C_1$-$C_6$alkylamino, amino$C_1$-$C_6$ alkyl, and —C(O)R$_{14}$, $C_3$-$C_7$cycloalkyl, substituted $C_3$-$C_7$cycloalkyl chosen from mono-, di-, and tri-substituted $C_3$-$C_7$cycloalkyl, wherein the substituents are independently chosen from hydroxy, nitro, cyano, amino, halogen, —SO$_2$NH$_2$, oxo, $C_1$-$C_6$ alkyl, $C_2$-$C_6$alkenyl, $C_2$-$C_6$alkynyl, $C_1$-$C_6$alkoxy, $C_1$-$C_3$haloalkyl, $C_1$-$C_3$haloalkoxy, $C_1$-$C_6$ alkylthio, ($C_1$-$C_6$-alkoxy)$C_1$-$C_6$ alkoxy, mono-$C_1$-$C_6$alkylamino, di-$C_1$-$C_6$alkylamino, amino$C_1$-$C_6$ alkyl, and —C(O)R$_{14}$, heteroaryl, and substituted heteroaryl chosen from mono-, di-, and tri-substituted heteroaryl, wherein the substituents are independently chosen from hydroxy, nitro, cyano, amino, halogen, —SO$_2$NH$_2$, oxo, $C_1$-$C_6$ alkyl, $C_2$-$C_6$alkenyl, $C_2$-$C_6$alkynyl, $C_1$-$C_6$ alkoxy, $C_1$-$C_3$haloalkyl, $C_1$-$C_3$haloalkoxy, $C_1$-$C_6$ alkylthio, ($C_1$-$C_6$-alkoxy)$C_1$-$C_6$ alkoxy, mono-$C_1$-$C_6$alkylamino, di-$C_1$-$C_6$alkylamino, amino$C_1$-$C_6$ alkyl, and —C(O)R$_{14}$, $Z_1$ is chosen from

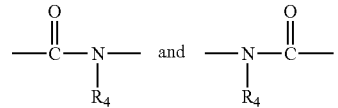

wherein $R_4$ is chosen from hydrogen, $C_1$-$C_6$alkyl, which is optionally substituted with 1 or more substituents independently chosen from hydroxy, nitro, cyano, amino, halogen, oxo, $C_1$-$C_6$ alkyl, $C_2$-$C_6$alkenyl, $C_2$-$C_6$alkynyl, $C_1$-$C_6$ alkoxy, $C_1$-$C_3$haloalkyl, $C_1$-$C_3$haloalkoxy, $C_1$-$C_6$ alkylthio, ($C_1$-$C_6$alkoxy)$C_1$-$C_6$ alkoxy, amino$C_1$-$C_6$ alkyl, mono-$C_1$-$C_6$ alkylamino, di-$C_1$-$C_6$ alkylamino, and —C(O)R$_{14}$ wherein $R_{14}$ is chosen from $C_1$-$C_6$ alkyl, $C_1$-$C_3$haloalkyl, and phenyl, $C_3$-$C_7$cycloalkyl, which is optionally substituted with 1 or more substituents independently chosen from hydroxy, nitro, cyano, amino, halogen, oxo, $C_1$-$C_6$ alkyl, $C_2$-$C_6$alkenyl, $C_2$-$C_6$alkynyl, $C_1$-$C_6$ alkoxy, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$ alkyl, mono-$C_1$-$C_6$ alkylamino, di-$C_1$-$C_6$ alkylamino, and —C(O)R$_{14}$ wherein $R_{14}$ is chosen from $C_1$-$C_6$ alkyl, $C_1$-$C_3$haloalkyl, and phenyl, heterocycloalkyl, which is optionally substituted with 1 or more substituents independently chosen from hydroxy, nitro, cyano, amino, halogen, oxo, $C_1$-$C_6$ alkyl, $C_2$-$C_6$alkenyl, $C_2$-$C_6$alkynyl, $C_1$-$C_6$alkoxy, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$ alkyl, mono-$C_1$-$C_6$ alkylamino, di-$C_1$-$C_6$ alkylamino, and —C(O)R$_{14}$ wherein $R_{14}$ is chosen from $C_1$-$C_6$ alkyl, $C_1$-$C_3$haloalkyl, and phenyl, phenyl, which is optionally substituted with 1 or more substituents independently chosen from hydroxy, nitro, cyano, amino, halogen, oxo, $C_1$-$C_6$ alkyl, $C_2$-$C_6$alkenyl, $C_2$-$C_6$alkynyl, $C_1$-$C_6$alkoxy, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$ alkyl, mono-$C_1$-$C_6$ alkylamino, di-$C_1$-$C_6$ alkylamino, and —C(O)R$_{14}$ wherein $R_{14}$ is chosen from $C_1$-$C_6$alkyl, $C_1$-$C_3$haloalkyl, and phenyl, and heteroaryl, which is optionally substituted with 1 or more substituents independently chosen from hydroxy, nitro, cyano, amino, halogen, oxo, $C_1$-$C_6$ alkyl, $C_2$-$C_6$alkenyl, $C_2$-$C_6$ alkynyl, $C_1$-$C_6$ alkoxy, $C_1$-$C_3$haloalkyl, $C_1$-$C_3$haloalkoxy, $C_1$-$C_6$ alkylthio, ($C_1$-$C_6$ alkoxy)$C_1$-$C_6$ alkoxy, amino$C_1$-$C_6$ alkyl, mono-$C_1$-$C_6$ alkylamino, di-$C_1$-$C_6$ alkylamino, and —C(O)R$_{14}$ wherein $R_{14}$ is chosen from $C_1$-$C_6$ alkyl, $C_1$-$C_3$haloalkyl, and phenyl, and $R_5$ is chosen from isopropyl and t-butyl.

29. The compound according to claim 28 wherein A is 0.

30. The compound according to claim 28 wherein A is 1.

31. The compound according to claim 28 wherein $R_1$ is chosen from phenyl phenyl substituted with
—CHO,
—COOH,
—CONH$_2$,
—CONHOH,
$C_2$-$C_4$alkenyl,
substituted $C_2$-$C_6$ alkenyl chosen from mono-, di-, and tri-substituted $C_2$-$C_6$ alkenyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_2$-$C_6$alkynyl,
substituted $C_2$-$C_6$ alkynyl chosen from mono-, di-, and tri-substituted $C_2$-$C_6$ alkynyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_1$-$C_6$hydroxyalkyl,
substituted $C_1$-$C_6$hydroxyalkyl chosen from mono-, di-, and tri-substituted $C_1$-$C_6$hydroxyalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_1$-$C_6$hydroxyalkoxy,
substituted $C_1$-$C_6$hydroxyalkoxy chosen from mono-, di-, and tri-substituted $C_1$-$C_6$hydroxyalkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, (mono-$C_1$-$C_6$alkylamino)$C_1$-$C_6$alkoxy,
substituted (mono-$C_1$-$C_6$alkylamino)$C_1$-$C_6$alkoxy chosen from mono-, di-, and tri-substituted (mono-$C_1$-$C_6$alkylamino)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, (di-$C_1$-$C_6$alkylamino)$C_1$-$C_6$alkoxy,
substituted (di-$C_1$-$C_6$alkylamino)$C_1$-$C_6$alkoxy chosen from mono-, di-, and tri-substituted (di-$C_1$-$C_6$alkylamino)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$$C_{-4}$alkylcarboxamide, di-$C_1$-$C_4$alkylcarboxamide, and phenyl, ($C_1$-$C_6$alkoxy)($C_1$-$C_6$alkylamino)$C_0$-$C_6$alkyl,
substituted ($C_1$-$C_6$alkoxy)($C_1$-$C_6$alkylamino)$C_0$-$C_6$alkyl chosen from mono-, di-, and tri-substituted ($C_1$-$C_6$alkoxy)($C_1$-$C_6$alkylamino)$C_0$-$C_6$alkyl, wherein the substituents are independently selected from halogen, hydroxy, amino, oxo, —COOH, —CONH$_2$, $C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, ($C_1$-$C_6$alkoxy)($C_1$-$C_6$alkoxy)$C_1$-$C_6$alkoxy,
substituted ($C_1$-$C_6$alkoxy)($C_1$-$C_6$alkoxy)$C_1$-$C_6$alkoxy chosen from mono-, di-, and tri-substituted ($C_1$-$C_6$alkoxy)($C_1$-$C_6$alkoxy)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heterocycloalkyl,
substituted heterocycloalkyl chosen from mono-, di-, and tri-substituted heterocycloalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl,
substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, substituted heteroaryl chosen from mono-, di-, and tri-substituted heteroaryl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, —C$_1$-C$_6$alkyl(C=O)OR$_{10}$, substituted —C$_1$-C$_6$alkyl(C=O)OR$_{10}$ chosen from mono-, di-, and tri-substituted —C$_1$-C$_6$alkyl(C=O)OR$_{10}$ wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, —C$_0$-C$_6$alkyl(C=O)NR$_{10}$R$_{11}$, substituted —C$_0$-C$_6$alkyl(C=O)NR$_{10}$R$_{11}$ chosen from mono-, di-, and tri-substituted —C$_0$-C$_6$alkyl(C=O)NR$_{10}$R$_{11}$ wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, —C$_1$-C$_6$alkylNR$_{10}$(SO$_2$)R$_{11}$, substituted —C$_1$-C$_6$alkylNR$_{10}$(SO$_2$)R$_{11}$ chosen from mono-, di-, and tri-substituted —C$_1$-C$_6$alkylNR$_{10}$(SO$_2$)R$_{11}$ wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, —C$_0$-C$_6$alkylNR$_{10}$(C=O)R$_{11}$, substituted —C$_0$-C$_6$alkylNR$_{10}$(C=O)R$_{11}$ chosen from mono-, di-, and tri-substituted —C$_0$-C$_6$alkylNR$_{10}$(C=O)R$_{11}$, wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, —C$_0$-C$_6$alkyl(SO$_2$)R$_{10}$, substituted —C$_0$-C$_6$alkyl(SO$_2$)R$_{10}$ chosen from mono-, di-, and tri-substituted —C$_0$-C$_6$alkyl(SO$_2$)R$_{10}$ wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide and phenyl, —C$_0$-C$_6$alkylNR$_{10}$(C=O)NR$_{11}$R$_{12}$, substituted —C$_0$-C$_6$alkylNR$_{10}$(C=O)NR$_{11}$R$_{12}$ chosen from mono-, di-, and tri-substituted —C$_0$-C$_6$alkylNR$_{10}$(C=O)NR$_{11}$R$_{12}$ wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, and -L-G, where L is chosen from C$_1$-C$_2$alkylene, substituted C$_1$-C$_2$alkylene chosen from mono-, di-, and tri-substituted C$_1$-C$_2$alkylene wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, C$_0$-C$_2$alkylene-O—, substituted C$_0$-C$_2$alkylene-O— chosen from mono-, di-, and tri-substituted C$_0$-C$_2$alkylene-O— wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,

—(C=O)—,

—(C$_1$-C$_2$alkylene)(C=O)—, and substituted —(C$_1$-C$_2$alkylene)(C=O)— chosen from mono-, di-, and tri-substituted —(C$_1$-C$_2$alkylene)(C=O)— wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, and G is chosen from heterocycloalkyl, substituted heterocycloalkyl chosen from mono-, di-, and tri-substituted heterocycloalkyl, wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, $C_1$-$C_4$alkoxycarbonyl mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_3$-$C_7$cycloalkyl, substituted $C_3$-$C_7$cycloalkyl chosen from mono-, di-, and tri-substituted $C_3$-$C_7$cycloalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, and substituted heteroaryl chosen from mono-, di-, and tri-substituted heteroaryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, pyridyl, pyridyl substituted with
hydroxy,
—CHO,
—COOH,
—CONH$_2$,
—CONHOH,
$C_2$-$C_6$ alkenyl, substituted $C_2$-$C_6$ alkenyl chosen from mono-, di-, and tri-substituted $C_2$-$C_6$ alkenyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_2$-$C_6$ alkynyl, substituted $C_2$-$C_6$ alkynyl chosen from mono-, di-, and tri-substituted $C_2$-$C_6$ alkynyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_1$-$C_6$hydroxyalkyl, substituted $C_1$-$C_6$hydroxyalkyl chosen from mono-, di-, and tri-substituted $C_1$-$C_6$hydroxyalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_1$-$C_6$hydroxyalkoxy, substituted $C_1$-$C_6$hydroxyalkoxy chosen from mono-, di-, and tri-substituted $C_1$-$C_6$hydroxyalkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, (mono-$C_1$-$C_6$alkylamino)$C_1$-$C_6$alkoxy, substituted (mono-$C_1$-$C_6$alkylamino)$C_1$-$C_6$alkoxy chosen from mono-, di-, and tri-substituted (mono-$C_1$-$C_6$alkylamino)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, (di-$C_1$-$C_6$alkylamino)$C_1$-$C_6$alkoxy, substituted (di-$C_1$-$C_6$alkylamino)$C_1$-$C_6$alkoxy chosen from mono-, di-, and tri-substituted (di-$C_1$-$C_6$alkylamino)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, ($C_1$-$C_6$alkoxy)($C_1$-$C_6$alkylamino)$C_0$-$C_6$alkyl, substituted ($C_1$-$C_6$alkoxy)($C_1$-$C_6$alkylamino)$C_0$-$C_6$alkyl chosen from mono-, di-, and tri-substituted ($C_1$-$C_6$alkoxy)($C_1$-$C_6$alkylamino)$C_0$-$C_6$alkyl, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, ($C_1$-$C_6$alkoxy)($C_1$-$C_6$alkoxy)$C_1$-$C_6$alkoxy, substituted ($C_1$-$C_6$alkoxy)($C_1$-$C_6$alkoxy)$C_1$-$C_6$alkoxy chosen from mono-, di-, and tri-substituted ($C_1$-$C_6$alkoxy)($C_1$-$C_6$alkoxy)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heterocycloalkyl, substituted heterocycloalkyl chosen from mono-, di-, and tri-substituted heterocycloalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, substituted heteroaryl chosen from mono-, di-, and tri-substituted heteroaryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_1$-$C_6$alkyl(C=O)OR$_{10}$, substituted —$C_1$-$C_6$alkyl(C=O)OR$_{10}$ chosen from mono-, di-, and tri-substituted —$C_1$-$C_6$alkyl(C=O)OR$_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl(C=O)NR$_{10}$R$_{11}$, substituted —$C_0$-$C_6$alkyl(C=O)NR$_{10}$R$_{11}$ chosen from mono-, di-, and tri-substituted —$C_0$-$C_6$alkyl(C=O)NR$_{10}$R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_1$-$C_6$alkylNR$_{10}$(SO$_2$)R$_{11}$, substituted —$C_1$-$C_6$alkylNR$_{10}$(SO$_2$)R$_{11}$ chosen from mono-, di-, and tri-substituted —$C_1$-$C_6$alkylNR$_{10}$(SO$_2$)R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkylNR$_{10}$(C=O)R$_{11}$, substituted —$C_0$-$C_6$alkylNR$_{10}$(C=O)R$_{11}$ chosen from mono-, di-, and tri-substituted —$C_0$-$C_6$alkylNR$_{10}$(C=O)R$_{11}$, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl(SO$_2$)R$_{10}$, substituted —$C_0$-$C_6$alkyl(SO$_2$)R$_{10}$ chosen from mono-, di-, and tri-substituted —$C_0$-$C_6$alkyl(SO$_2$)R$_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkylNR$_{10}$(C=O)NR$_{11}$R$_{12}$, and substituted —$C_0$-$C_6$alkylNR$_{10}$(C=O)NR$_{11}$R$_{12}$ chosen from mono-, di-, and tri-substituted —$C_0$-$C_6$alkylNR$_{10}$(C=O)NR$_{11}$R$_{12}$, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and -L-G, where L is chosen from $C_1$-$C_2$alkylene, substituted $C_1$-$C_2$alkylene chosen from mono-, di-, and tri-substituted $C_1$-$C_2$alkylene wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,

—(C=O)—,

—($C_1$-$C_2$alkylene)(C=O)—, and substituted —($C_1$-$C_2$alkylene)(C=O)— chosen from mono-, di-, and tri-substituted —($C_1$-$C_2$alkylene)(C=O)— wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and G is chosen from heterocycloalkyl, substituted heterocycloalkyl chosen from mono-, di-, and tri-substituted heterocycloalkyl, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_3$-$C_7$cycloalkyl, substituted $C_3$-$C_7$cycloalkyl chosen from mono-, di-, and tri-substituted $C_3$-$C_7$cycloalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, and substituted heteroaryl chosen from mono-, di-, and tri-substituted heteroaryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, wherein $R_1$ is optionally further substituted with 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono-$C_1$-$C_6$ alkylamino)$C_0$-$C_6$ alkyl, (di-$C_1$-$C_6$ alkylamino)$C_0$-$C_6$ alkyl, and $C_1$-$C_6$alkoxycarbonyl.

32. The compound according to claim 31, wherein $R_1$ is chosen from phenyl substituted with a group chosen from —CHO, —COOH, —CONH$_2$, —CONHOH, and pyridyl substituted with a group chosen from hydroxy, —CHO, —COOH, —CONH$_2$, and —CONHOH, and $R_1$ is optionally further substituted with 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono-$C_1$-$C_6$ alkylamino)$C_0$-$C_6$ alkyl, (di-$C_1$-$C_6$ alkylamino)$C_0$-$C_6$ alkyl, and $C_1$-$C_6$alkoxycarbonyl.

33. The compound according to claim 32, wherein $R_1$ is chosen from phenyl substituted with a group chosen from —CHO, —COOH, —CONH$_2$, and —CONHOH, and pyridyl substituted with a group chosen from hydroxy, —CHO, —COOH, —CONH$_2$, and —CONHOH, and $R_1$ is optionally further mono-, di-, or tri-substituted with substituents independently chosen from hydroxy, cyano, halogen, $C_1$-$C_4$alkyl, $C_2$-$C_4$alkanoyl, $C_1$-$C_2$haloalkyl, $C_1$-$C_2$haloalkoxy, $C_1$-$C_4$alkoxy, mono-$C_1$-$C_4$alkylamino, and di-$C_1$-$C_4$alkylamino.

34. The compound according to claim 33, wherein $R_1$ is chosen from phenyl substituted with a group chosen from —CHO, —COOH, —CONH$_2$, and —CONHOH, and pyridyl substituted with a group chosen from hydroxy, —CHO, —COOH, —CONH$_2$, and —CONHOH, and $R_1$ is optionally further mono-, di-, or tri-substituted with substituents independently chosen from hydroxy, cyano, halogen, $C_1$-$C_2$alkyl, and $C_1$-$C_2$alkoxy.

35. The compound according to claim 31 wherein $R_1$ is chosen from phenyl substituted with a group chosen from $C_2$-$C_6$ alkenyl, substituted $C_2$-$C_6$ alkenyl chosen from mono-, di-, and tri-substituted $C_2$-$C_6$ alkenyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_2$-$C_6$ alkynyl, substituted $C_2$-$C_6$ alkynyl chosen from mono-, di-, and tri-substituted $C_2$-$C_6$ alkynyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_1$-$C_6$hydroxyalkyl, substituted $C_1$-$C_6$hydroxyalkyl chosen from mono-, di-, and tri-substituted $C_1$-$C_6$hydroxyalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_1$-$C_6$hydroxyalkoxy, substituted $C_1$-$C_6$hydroxyalkoxy chosen from mono-, di-, and tri-substituted $C_1$-$C_6$hydroxyalkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, (mono-$C_1$-$C_6$alkylamino)$C_1$-$C_6$alkoxy, substituted (mono-$C_1$-$C_6$alkylamino)$C_1$-$C_6$alkoxy chosen from mono-, di-, and tri-substituted (mono-$C_1$-$C_6$alkylamino)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, (di-$C_1$-$C_6$alkylamino)$C_1$-$C_6$alkoxy substituted (di-$C_1$-$C_6$alkylamino)$C_1$-$C_6$alkoxy chosen from mono-, di-, and tri-substituted (di-$C_1$-$C_6$alkylamino)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, (di-$C_1$-$C_6$alkylamino) $C_1$-$C_6$alkoxy, substituted (di-$C_1$-$C_6$alkylamino)$C_1$-$C_6$alkoxy chosen from mono-, di-, and tri-substituted (di-$C_1$-$C_6$alkylamino)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, ($C_1$-$C_6$alkoxy)($C_1$-$C_6$alkylamino)$C_0$-$C_6$alkyl, substituted ($C_1$-$C_6$alkoxy)($C_1$-$C_6$alkylamino)$C_0$-$C_6$alkyl chosen from mono-, di-, and tri-substituted ($C_1$-$C_6$alkoxy)($C_1$-$C_6$alkylamino)$C_0$-$C_6$alkyl, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, ($C_1$-$C_6$alkoxy)($C_1$-$C_6$alkoxy)$C_1$-$C_6$alkoxy, substituted ($C_1$-$C_6$alkoxy)($C_1$-$C_6$alkoxy)$C_1$-$C_6$alkoxy chosen from mono-, di-, and tri-substituted ($C_1$-$C_6$alkoxy)($C_1$-$C_6$alkoxy)$C_1$-$C_6$alkoxy wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heterocycloalkyl, substituted heterocycloalkyl chosen from mono-, di-, and tri-substituted heterocycloalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, and substituted heteroaryl chosen from mono-, di-, and tri-substituted heteroaryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and pyridyl substituted with a group chosen from, $C_2$-$C_6$ alkenyl, substituted $C_2$-$C_6$ alkenyl chosen from mono-, di-, and tri-substituted $C_2$-$C_6$ alkenyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_2$-$C_6$ alkynyl, substituted $C_2$-$C_6$ alkynyl chosen from mono-, di-, and tri-substituted $C_2$-$C_6$alkynyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_1$-$C_6$hydroxyalkyl, substituted $C_1$-$C_6$hydroxyalkyl chosen from mono-, di-, and tri-substituted $C_1$-$C_6$hydroxyalkyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, C$_1$-C$_6$hydroxyalkoxy, substituted C$_1$-C$_6$hydroxyalkoxy chosen from mono-, di-, and tri-substituted C$_1$-C$_6$hydroxyalkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, (mono-C$_1$-C$_6$alkylamino)C$_1$-C$_6$alkoxy, substituted (mono-C$_1$-C$_6$alkylamino)C$_1$-C$_6$alkoxy chosen from mono-, di-, and tri-substituted (mono-C$_1$-C$_6$alkylamino)C$_1$-C$_6$alkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, (di-C$_1$-C$_6$alkylamino)C$_1$-C$_6$alkoxy, substituted (di-C$_1$-C$_6$alkylamino)C$_1$-C$_6$alkoxy chosen from mono-, di-, and tri-substituted (di-C$_1$-C$_6$alkylamino)C$_1$-C$_6$alkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, (C$_1$-C$_6$alkoxy)(C$_1$-C$_6$alkylamino)C$_0$-C$_6$alkyl, substituted (C$_1$-C$_6$alkoxy)(C$_1$-C$_6$alkylamino, C$_0$-C$_6$alkyl chosen from mono-, di-, and tri-substituted (C$_1$-C$_6$alkoxy)(C$_1$-C$_6$alkylamino)C$_0$-C$_6$alkyl, wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, (C$_1$-C$_6$alkoxy)(C$_1$-C$_6$alkoxy)C$_1$-C$_6$alkoxy, substituted (C$_1$-C$_6$alkoxy)(C$_1$-C$_6$alkoxy)C$_1$-C$_6$alkoxy chosen from mono-, di-, and tri-substituted (C$_1$-C$_6$alkoxy)(C$_1$-C$_6$alkoxy)C$_1$-C$_6$alkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$ alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, heterocycloalkyl, substituted heterocycloalkyl chosen from mono-, di-, and tri-substituted heterocycloalkyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, heteroaryl, and substituted heteroaryl chosen from mono-, di-, and tri-substituted heteroaryl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, wherein R$_1$ is optionally further substituted with 1 or more substituents independently chosen from hydroxy, nitro, cyano, amino, —SO$_2$NH$_2$, halogen, C$_1$-C$_6$ alkyl, C$_2$-C$_6$alkanoyl, C$_1$-C$_4$haloalkyl, C$_1$-C$_4$haloalkoxy, C$_1$-C$_6$ alkylthio, C$_3$-C$_7$cycloalkyl, (C$_1$-C$_6$ alkoxy)C$_0$-C$_6$alkyl, (mono-C$_1$-C$_6$ alkylamino)C$_0$-C$_6$ alkyl, (di-C$_1$-C$_6$ alkylamino)C$_0$-C$_6$ alkyl, and C$_1$-C$_6$alkoxycarbonyl.

36. The compound according to claim 35 wherein

R$_1$ is chosen from phenyl substituted with a group chosen from C$_1$-C$_6$hydroxyalkyl, substituted C$_1$-C$_6$hydroxyalkyl chosen from mono-, di-, and tri-substituted C$_1$-C$_6$hydroxyalkyl, wherein the substituents are independently chosen from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, C$_1$-C$_6$hydroxyalkoxy, substituted C$_1$-C$_6$hydroxyalkoxy chosen from mono-, di-, and tri-substituted C$_1$-C$_6$hydroxyalkoxy, wherein the substituents are independently chosen from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, (mono-C$_1$-C$_6$alkylamino)C$_1$-C$_6$alkoxy, substituted (mono-$C_1$-$C_6$alkylamino)$C_1$-$C_6$alkoxy chosen from mono-, di-, and tri-substituted (mono-$C_1$-$C_6$alkylamino)$C_1$-$C_6$alkoxy, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, (di-$C_1$-$C_6$alkylamino)$C_1$-$C_6$alkoxy, substituted (di-$C_1$-$C_6$alkylamino)$C_1$-$C_6$alkoxy chosen from mono-, di-, and tri-substituted (di-$C_1$-$C_6$alkylamino)$C_1$-$C_6$alkoxy, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, ($C_1$-$C_6$alkoxy)($C_1$-$C_6$alkylamino)$C_0$-$C_6$alkyl, substituted ($C_1$-$C_6$alkoxy)($C_1$-$C_6$alkylamino)$C_0$-$C_6$alkyl chosen from mono-, di-, and tri-substituted ($C_1$-$C_6$alkoxy)($C_1$-$C_6$alkylamino)$C_0$-$C_6$alkyl, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, ($C_1$-$C_6$alkoxy)($C_1$-$C_6$alkoxy)$C_1$-$C_6$alkoxy, substituted ($C_1$-$C_6$alkoxy)($C_1$-$C_6$alkoxy)$C_1$-$C_6$alkoxy chosen from mono-, di-, and tri-substituted ($C_1$-$C_6$alkoxy)($C_1$-$C_6$alkoxy)$C_1$-$C_6$alkoxy, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, and pyridyl substituted with a group chosen from $C_1$-$C_6$hydroxyalkyl, substituted $C_1$-$C_6$hydroxyalkyl chosen from mono-, di-, and tri-substituted $C_1$-$C_6$hydroxyalkyl, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, $C_1$-$C_6$hydroxyalkoxy, substituted $C_1$-$C_6$hydroxyalkoxy chosen from mono-, di-, and tri-substituted $C_1$-$C_6$hydroxyalkoxy, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, (mono-$C_1$-$C_6$alkylamino)$C_1$-$C_6$alkoxy, substituted (mono-$C_1$-$C_6$alkylamino)$C_1$-$C_6$alkoxy chosen from mono-, di-, and tri-substituted (mono-$C_1$-$C_6$alkylamino)$C_1$-$C_6$alkoxy, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, (di-$C_1$-$C_6$alkylamino)$C_1$-$C_6$alkoxy, substituted (di-$C_1$-$C_6$alkylamino)$C_1$-$C_6$alkoxy chosen from mono-, di-, and tri-substituted (di-$C_1$-$C_6$alkylamino)$C_1$-$C_6$alkoxy, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, ($C_1$-$C_6$alkoxy)($C_1$-$C_6$alkylamino)$C_0$-$C_6$alkyl, substituted ($C_1$-$C_6$alkoxy)($C_1$-$C_6$alkylamino)$C_0$-$C_6$alkyl chosen from mono-, di-, and tri-substituted ($C_1$-$C_6$alkoxy)($C_1$-$C_6$alkylamino)$C_0$-$C_6$alkyl, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, ($C_1$-$C_6$alkoxy) ($C_1$-$C_6$alkoxy)$C_1$-$C_6$alkoxy, substituted ($C_1$-$C_6$alkoxy)($C_1$-$C_6$alkoxy)$C_1$-$C_6$alkoxy chosen from mono-, di-, and tri-substituted ($C_1$-$C_6$alkoxy)($C_1$-$C_6$alkoxy)$C_1$-$C_6$alkoxy, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, wherein $R_1$ is optionally further mono-, di-, or tri-substituted with substituents independently chosen from hydroxy, cyano, halogen, $C_1$-$C_4$alkyl, $C_2$-$C_4$alkanoyl, $C_1$-$C_2$haloalkyl, $C_1$-$C_2$haloalkoxy, $C_1$-$C_4$alkoxy, mono-$C_1$-$C_4$alkylamino, and di-$C_1$-$C_4$alkylamino.

37. The compound according to claim 36 wherein $R_1$ is chosen from phenyl substituted with $C_1$-$C_6$hydroxyalkyl, $C_1$-$C_6$hydroxyalkoxy, (mono-$C_1$-$C_6$alkylamino)$C_1$-$C_6$alkoxy, (di-$C_1$-$C_6$alkylamino)$C_1$-$C_6$alkoxy, ($C_1$-$C_6$alkoxy)($C_1$-$C_6$alkylamino)$C_0$-$C_6$alkyl, and ($C_1$-$C_6$alkoxy)($C_1$-$C_6$alkoxy)$C_1$-$C_6$alkoxy, and pyridyl, substituted with $C_1$-$C_6$hydroxyalkyl, $C_1$-$C_6$hydroxyalkoxy, (mono-$C_1$-$C_6$alkylamino)$C_1$-$C_6$alkoxy, (di-$C_1$-$C_6$alkylamino)$C_1$-$C_6$alkoxy, ($C_1$-$C_6$alkoxy)($C_1$-$C_6$alkylamino)$C_0$-$C_6$alkyl, and ($C_1$-$C_6$alkoxy)($C_1$-$C_6$alkoxy)$C_1$-$C_6$alkoxy, wherein $R_1$ is optionally further mono-, di- or tri-substituted with substituents independently chosen from hydroxy, cyano, halogen, $C_1$-$C_2$alkyl, and $C_1$-$C_2$alkoxy.

38. The compound according to claim 31 wherein R$_1$ is chosen from phenyl substituted with a group chosen form
- pyrrolidinyl,
  - substituted pyrrolidinyl chosen from mono-, di- and tri-substituted pyrrolidinyl, wherein the substituents are independently chosen from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide,
- morpholinyl,
  - substituted morpholinyl chosen from mono-, di- and tri-substituted morpholinyl, wherein the substituents are independently chosen from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide,
- thiomorpholinyl,
  - substituted thiomorpholinyl chosen from mono-, di- and tri-substituted thiomorpholinyl, wherein the substituents are independently chosen from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide,
- piperazinyl,
  - substituted piperazinyl chosen from mono-, di- and tri-substituted piperazinyl, wherein the substituents are independently chosen from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide,
- piperidinyl,
  - substituted piperidinyl chosen from mono-, di- and tri-substituted piperidinyl, wherein the substituents are independently chosen from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide,
- [1,4]diazepanyl,
  - substituted [1,4]diazepanyl chosen from mono-, di- and tri-substituted [1.4]diazepanyl, wherein the substituents are independently chosen from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide,
- phenyl,
  - substituted phenyl chosen from mono-, di- and tri-substituted phenyl, wherein the substituents are independently chosen from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide,
- imidazolyl,
  - substituted imidazolyl chosen from mono-, di- and tri-substituted imidazolyl, wherein the substituents are independently chosen from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide,
- 5,6-dihydro-8H-[1,2,4]triazolo[4,3-a]pyrazine, and
  - substituted 5,6-dihydro-8H-[1,2,4]triazolo[4,3-a]pyrazine chosen from mono-, di- and tri-substituted 5,6-dihydro-8H-[1,2,4]triazolo[4,3-a]pyrazine, wherein the substituents are independently chosen from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, and pyridyl substituted with a group chosen form
- pyrrolidinyl,
  - substituted pyrrolidinyl chosen from mono-, di- and tri-substituted pyrrolidinyl, wherein the substituents are independently chosen from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide,
- morpholinyl,
  - substituted morpholinyl chosen from mono-, di- and tri-substituted morpholinyl, wherein the substituents are independently chosen from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide,
- thiomorpholinyl,
  - substituted thiomorpholinyl chosen from mono-, di- and tri-substituted thiomorpholinyl, wherein the substituents are independently chosen from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide,
- piperazinyl,
  - substituted piperazinyl chosen from mono-, di- and tri-substituted piperazinyl, wherein the substituents are independently chosen from halogen, hydroxy, cyano, amino, oxo, —COOH, —CONH$_2$, C$_1$-C$_4$alkyl, C$_1$-C$_4$alkoxy, C$_2$-C$_4$alkanoyl, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-

$C_4$alkylcarboxamide, and di-$C_1$-$C_4$alkylcarboxamide, piperidinyl, substituted piperidinyl chosen from mono-, di- and tri-substituted piperidinyl, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

[1,4]diazepanyl, substituted [1,4]diazepanyl chosen from mono-, di- and tri-substituted [1,4]diazepanyl, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, phenyl, substituted phenyl chosen from mono-, di- and tri-substituted phenyl, wherein the substituents are independently chosen from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, imidazolyl, substituted imidazolyl chosen from mono-, di- and tri-substituted imidazolyl, wherein the substituents are independently chosen from halogen, hydroxy, cyano amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, 5,6-dihydro-8H-[1,2,4]triazolo[4,3-a]pyrazine, and substituted 5,6-dihydro-8H-[2,4]triazolo[4,3-a]pyrazine chosen from mono-, di- and tri-substituted 5,6-dihydro-8H-[1,2,4]triazolo[4,3-a]pyrazine, wherein the substituents are independently chosen from halogen hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, wherein $R_1$ is optionally further mono-, di-, or tri-substituted with substituents independently chosen from hydroxy, cyano, halogen, $C_1$-$C_4$alkyl, $C_2$-$C_4$alkanoyl, $C_1$-$C_2$haloalkyl, $C_1$-$C_2$haloalkoxy, $C_1$-$C_4$alkoxy, mono-$C_1$-$C_4$alkylamino, and di-$C_1$-$C_4$alkylamino.

39. The compound according to claim 38, wherein $R_1$ is chosen from phenyl substituted with a group chosen from pyrrolidinyl, substituted pyrrolidinyl chosen from mono-, di- and tri-substituted pyrrolidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, morpholinyl, substituted morpholinyl chosen from mono-, di- and tri-substituted morpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, thiomorpholinyl, substituted thiomorpholinyl chosen from mono-, di- and tri-substituted thiomorpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperazinyl, substituted piperazinyl chosen from mono-, di- and tri-substituted piperazinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperidinyl, substituted piperidinyl chosen from mono-, di- and tri-substituted piperidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

[1,4]diazepanyl, substituted [1,4]diazepanyl chosen from mono-, di- and tri-substituted [1,4]diazepanyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino mono-$C_1$-$C_4$alkylcarboxamide, and di-$C_1$-$C_4$alkylcarboxamide, phenyl, substituted phenyl chosen from mono-, di- and tri-substituted phenyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, imidazolyl, substituted imidazolyl chosen from mono-, di- and tri-substituted imidazolyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-

$C_4$alkylcarboxamide, and di-$C_1$-$C_4$alkylcarboxamide, 5,6-dihydro-8H-[1,2,4]triazolo[4,3-a]pyrazine, and substituted 5,6-dihydro-8H-[1,2,4]triazolo[4,3-a]pyrazine chosen from mono-, di- and tri-substituted 5,6-dihydro-8H-[1,2,4]triazolo[4,3-a]pyrazine, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, and pyridyl substituted with a group chosen from pyrrolidinyl substituted pyrrolidinyl chosen from mono-, di- and tri-substituted pyrrolidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, morpholinyl, substituted morpholinyl chosen from mono-, di- and tri-substituted morpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, thiomorpholinyl, substituted thiomorpholinyl chosen from mono-, di- and tri-substituted thiomorpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperazinyl, substituted piperazinyl chosen from mono-, di- and tri-substituted piperazinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperidinyl, substituted piperidinyl chosen from mono-, di- and tri-substituted piperidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

[1,4]diazepanyl, substituted [1,4]diazepanyl chosen from mono-, di- and tri-substituted [1,4]diazepanyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, phenyl, substituted phenyl chosen from mono-, di- and tri-substituted phenyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, imidazolyl, substituted imidazolyl chosen from mono-, di- and tri-substituted imidazolyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, 5,6-dihydro-8H-[1,2,4]triazolo[4,3-a]pyrazine, and substituted 5,6-dihydro-8H-[1,2,4]triazolo[4,3-a]pyrazine chosen from mono-, di- and tri-substituted 5,6-dihydro-8H-[1,2,4]triazolo[4,3-a]pyrazine, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, wherein $R_1$ is optionally further mono-, di-, or tri-substituted with from substituents independently chosen from hydroxy, cyano, halogen, $C_1$-$C_2$alkyl, and $C_1$-$C_2$alkoxy.

40. The compound according to claim 31, wherein $R_1$ is chosen from phenyl substituted with a group chosen from —$C_1$-$C_6$alkyl(C=O)OR$_{10}$, substituted —$C_1$-$C_6$alkyl(C=O)OR$_{10}$ chosen from mono-, di- and tri-substituted —$C_1$-$C_6$alkyl(C=O)OR$_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl(C=O)NR$_{10}$R$_{11}$, substituted —$C_0$-$C_6$alkyl(C=O)NR$_{10}$R$_{11}$ chosen from mono-, di-, and tri-substituted —$C_0$-$C_6$alkyl(C=O)NR$_{10}$R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_1$-$C_6$alkylNR$_{10}$(SO$_2$)R$_{11}$, substituted —$C_1$-$C_6$alkylNR$_{10}$(SO$_2$)R$_{11}$ chosen from mono-, di-, and tri-substituted —$C_1$-$C_6$alkylNR$_{10}$(SO$_2$)R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkylNR$_{10}$(C=O)R$_{11}$, substituted —$C_0$-$C_6$alkylNR$_{10}$(C=O)R$_{11}$ chosen from mono-, di-, and tri-substituted —$C_0$-$C_6$alkylNR$_{10}$(C=O)R$_{11}$, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl(SO$_2$)R$_{10}$, substituted —$C_0$-$C_6$alkyl(SO$_2$)R$_{10}$ chosen from mono-, di-, and tri-substituted —$C_0$-$C_6$alkyl(SO$_2$)R$_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkylNR$_{10}$(C=O)NR$_{11}$R$_{12}$ and substituted —$C_0$-$C_6$alkylNR$_{10}$(C=O)NR$_{11}$R$_{12}$ chosen from mono-, di-, and tri-substituted —$C_0$-$C_6$alkylNR$_{10}$(C=O)NR$_{11}$R$_{12}$, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, where $R_{10}$, $R_{11}$, and $R_{12}$ are independently hydrogen, hydroxy, $C_1$-$C_6$alkyl, $C_1$-$C_6$alkoxy $C_3$-$C_7$cycloalkyl, and heterocycloalkyl, and pyridyl substituted with a group chosen from —$C_1$-$C_6$alkyl(C=O)OR$_{10}$, substituted —$C_1$-$C_6$alkyl(C=O)OR$_{10}$ chosen from mono-, di-, and tri-substituted —$C_1$-$C_6$alkyl(C=O)OR$_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl(C=O)NR$_{10}$R$_{11}$, substituted —$C_0$-$C_6$alkyl(C=O)NR$_{10}$R$_{11}$ chosen from mono-, di-, and tri-substituted —$C_0$-$C_6$alkyl(C=O)NR$_{10}$R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_1$-$C_6$alkylNR$_{10}$(SO$_2$)R$_{11}$, substituted —$C_1$-$C_6$alkylNR$_{10}$(SO$_2$)R$_{11}$ chosen from mono-, di-, and tri-substituted —$C_1$-$C_6$alkylNR$_{10}$(SO$_2$)R$_{11}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkylNR$_{10}$(C=O)R$_{11}$, substituted —$C_0$-$C_6$alkylNR$_{10}$(C=O)R$_{11}$ chosen from mono-, di-, and tri-substituted —$C_0$-$C_6$alkylNR$_{10}$(C=O)R$_{11}$, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl(SO$_2$)R$_{10}$, substituted —$C_0$-$C_6$alkyl(SO$_2$)R$_{10}$ chosen from mono-, di-, and tri-substituted —$C_0$-$C_6$alkyl(SO$_2$)R$_{10}$ wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkylNR$_{10}$(C=O)R$_{11}$R$_{12}$ and substituted —$C_0$-$C_6$alkylNR$_{10}$(C=O)NR$_{11}$R$_{12}$ chosen from mono-, di-, and tri-substituted —$C_0$-$C_6$alkylNR$_{10}$(C=O)NR$_{11}$R$_{12}$, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, where $R_{10}$, $R_{11}$ and $R_{12}$ are independently hydrogen, hydroxy, $C_1$-$C_6$alkyl, $C_1$-$C_6$alkoxy, $C_3$-$C_7$cycloalkyl, and heterocycloalkyl, wherein $R_1$ is optionally further substituted with 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono-alkylamino)$C_0$-$C_6$ alkyl, (di-$C_1$-$C_6$ alkylamino)$C_0$-$C_6$ alkyl, and $C_1$-$C_6$alkoxycarbonyl.

41. The compound according to claim 40 wherein $R_1$ is chosen from phenyl substituted with a group chosen from —$C_1$-$C_4$alkyl(C=O)OR$_{10}$, substituted —$C_1$-$C_4$alkyl(C=O)OR$_{10}$ chosen from mono-, di-, and tri-substituted —$C_1$-$C_4$alkyl(C=O)OR$_{10}$ wherein the substituents are independently selected from halogen, hydroxy, amino, oxo, —COOH, —CONH$_2$, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, —$C_0$-$C_4$alkyl(C=O)NR$_{10}$R$_{11}$, substituted —$C_0$-$C_4$alkyl(C=O)NR$_{10}$R$_{11}$ chosen from mono-, di-, and tri-substituted —$C_0$-$C_4$alkyl(C=O)NR$_{10}$R$_{11}$ wherein the substituents are independently selected from halogen, hydroxy, amino, oxo, —COOH, —CONH$_2$, C$_1$-C$_4$alkoxy, C$_2$-C$_4$alkanoyl, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, —C$_1$-C$_4$alkylNR$_{10}$(SO$_2$)R$_{11}$, substituted —C$_1$-C$_4$alkylNR$_{10}$(SO$_2$)R$_{11}$ chosen from mono-, di-, and tri-substituted —C$_1$-C$_4$alkylNR$_{10}$(SO$_2$)R$_{11}$ wherein the substituents are independently selected from halogen, hydroxy, amino, oxo, —COOH, —CONH$_2$, C$_1$-C$_4$alkoxy, C$_2$-C$_4$alkanoyl, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, —C$_0$-C$_4$alkylNR$_{10}$(C=O)R$_{11}$, substituted —C$_0$-C$_4$alkylNR$_{10}$(C=O)R$_{11}$ chosen from mono-, di-, and tri-substituted —C$_0$-C$_4$alkylNR$_{10}$(C=O)R$_{11}$, wherein the substituents are independently selected from halogen, hydroxy, amino, oxo, —COOH, —CONH$_2$, C$_1$-C$_4$alkoxy, C$_2$-C$_4$alkanoyl, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, —C$_0$-C$_4$alkyl(SO$_2$)R$_{10}$, substituted —C$_1$-C$_4$alkyl(SO$_2$)R$_{10}$ chosen from mono-, di-, and tri-substituted —C$_0$-C$_4$alkyl(SO$_2$)R$_{10}$ wherein the substituents are independently selected from halogen, hydroxy, amino, oxo, —COOH, —CONH$_2$, C$_1$-C$_4$alkoxy, C$_2$-C$_4$alkanoyl, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, —C$_0$-C$_4$alkylNR$_{10}$(C=O)NR$_{11}$R$_{12}$ and substituted —C$_0$-C$_4$alkylNR$_{10}$(C=O)NR$_{11}$R$_{12}$ chosen from mono-, di-, and tri-substituted —C$_0$-C$_4$alkylNR$_{10}$(C=O)NR$_{11}$R$_{12}$ wherein the substituents are independently selected from halogen, hydroxy, amino, oxo, —COOH, —CONH$_2$, C$_1$-C$_4$alkoxy, C$_2$-C$_4$alkanoyl, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, where R$_{10}$, R$_{11}$, and R$_{12}$ are independently chosen from hydrogen, hydroxy, C$_1$-C$_6$alkyl, C$_1$-C$_6$alkoxy, C$_3$-C$_{10}$cycloalkyl, pyrrolidinyl, morpholinyl, thiomorpholinyl, piperazinyl, piperidinyl, and [1,4]diazepanyl, and pyridyl substituted with a group chosen from —C$_1$-C$_4$alkyl(C=O)OR$_{10}$, substituted —C$_1$-C$_4$alkyl(C=O)OR$_{10}$ chosen from mono-, di-, and tri-substituted —C$_1$-C$_6$alkyl(C=O)OR$_{10}$ wherein the substituents are independently selected from halogen, hydroxy, amino, oxo, —COOH, —CONH$_2$, C$_1$-C$_4$alkoxy, C$_2$-C$_4$alkanoyl, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, —C$_0$-C$_4$alkyl(C=O)NR$_{10}$R$_{11}$, substituted —C$_0$-C$_4$alkyl(C=O)NR$_{10}$R$_{11}$ chosen from mono-, di-, and tri-substituted —C$_0$-C$_6$alkyl(C=O)NR$_{10}$R$_{11}$ wherein the substituents are independently selected from halogen, hydroxy, amino, oxo, —COOH, —CONH$_2$, C$_1$-C$_4$alkoxy, C$_2$-C$_4$alkanoyl, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, —C$_1$-C$_4$alkylNR$_{10}$(SO$_2$)R$_{11}$, substituted —C$_1$-C$_4$alkylNR$_{10}$(SO$_2$)R$_{11}$ chosen from mono-, di-, and tri-substituted —C$_1$-C$_4$alkylNR$_{10}$(SO$_2$)R$_{11}$ wherein the substituents are independently selected from halogen, hydroxy, amino, oxo, —COOH, —CONH$_2$, C$_1$-C$_4$alkoxy, C$_2$-C$_4$alkanoyl, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, —C$_0$-C$_4$alkylNR$_{10}$(C=O)R$_{11}$, substituted —C$_0$-C$_4$alkylNR$_{10}$(C=O)R$_{11}$ chosen from mono-, di-, and tri-substituted —C$_0$-C$_4$alkylNR$_{10}$(C=O)R$_{11}$, wherein the substituents are independently selected from halogen, hydroxy, amino, oxo, —COOH, —CONH$_2$, C$_1$-C$_4$alkoxy, C$_2$-C$_4$alkanoyl, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, —C$_0$-C$_4$alkyl(SO$_2$)R$_{10}$, substituted —C$_0$-C$_4$alkyl(SO$_2$)R$_{10}$ chosen from mono-, di-, and tri-substituted —C$_0$-C$_4$alkyl(SO$_2$)R$_{10}$ wherein the substituents are independently selected from halogen, hydroxy, amino, oxo, —COOH, —CONH$_2$, C$_1$-C$_4$alkoxy, C$_2$-C$_4$alkanoyl, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, —C$_0$-C$_4$alkylNR$_{10}$(C=O)NR$_{11}$R$_{12}$ and substituted —C$_0$-C$_4$alkylNR$_{10}$(C=O)NR$_{11}$R$_{12}$ chosen from mono-, di-, and tri-substituted —C$_0$-C$_4$alkylNR$_{10}$(C=O)NR$_{11}$R$_{12}$, wherein the substituents are independently selected from halogen, hydroxy, amino, oxo, —COOH, —CONH$_2$, C$_1$-C$_4$alkoxy, C$_2$-C$_4$alkanoyl, C$_1$-C$_4$alkoxycarbonyl, mono-C$_1$-C$_4$alkylamino, di-C$_1$-C$_4$alkylamino, mono-C$_1$-C$_4$alkylcarboxamide, and di-C$_1$-C$_4$alkylcarboxamide, where R$_{10}$, R$_{11}$, and R$_{12}$ are independently chosen from hydrogen, hydroxy, C$_1$-C$_6$alkyl, C$_1$-C$_6$alkoxy, C$_3$-C$_{10}$cycloalkyl, pyrrolidinyl, morpholinyl, thiomorpholinyl, piperazinyl, piperidinyl, and [1,4]diazepanyl, wherein R$_1$ is optionally further mono-, di-, or tri-substituted with from substituents independently chosen from hydroxy, cyano, halogen, C$_1$-C$_2$alkyl, and C$_1$-C$_2$alkoxy.

42. The compound according to claim 31 wherein

R$_1$ is chosen from phenyl substituted with a group chosen from

-L-G, where

L is a group chosen from

C$_1$-C$_2$alkylene, substituted C$_1$-C$_2$alkylene chosen from mono-, di-, and tri-substituted C$_1$-C$_2$alkylene wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl, C$_0$-C$_2$alkylene-O—, substituted C$_0$-C$_2$alkylene-O— chosen from mono-, di-, and tri-substituted C$_0$-C$_2$alkylene-O— wherein the substituents are independently selected from halogen, hydroxy, amino, oxo, —COOH, —CONH$_2$, C$_1$-C$_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,

—(C=O)—,

—($C_1$-$C_2$alkylene)(C=O)—, and substituted —($C_1$-$C_2$alkylene)(C=O)— chosen from mono-, di-, and tri-substituted —($C_1$-$C_2$alkylene)(C=O)— wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and G is chosen from heterocycloalkyl substituted heterocycloalkyl chosen from mono-, di-, and tri-substituted heterocycloalkyl, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino mono-$C_1$-$C_4$alkylcarboxamide di-$C_1$-$C_4$alkylcarboxamide, and phenyl, $C_3$-$C_7$cycloalkyl, substituted $C_3$-$C_7$cycloalkyl chosen from mono-, di-, and tri-substituted $C_3$-$C_7$cycloalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, and substituted heteroaryl chosen from mono-, di-, and tri-substituted heteroaryl wherein the substituents are independently selected from halogen, hydroxy, amino, oxo, —COOH, —CONH$_2$, $C_1$-$C_4$alkyl $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and pyridyl substituted with a group chosen from -L-G, where L is a group chosen from $C_1$-$C_2$alkylene, substituted $C_1$-$C_2$alkylene chosen from mono-, di-, and tri-substituted $C_1$-$C_2$alkylene wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,

—(C=O)—,

—($C_1$-$C_2$alkylene)(C=O)—, and substituted —($C_1$-$C_2$alkylene)(C=O)— chosen from mono-, di-, and tri-substituted —($C_1$-$C_2$alkylene)(C=O)— wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and G is chosen from heterocycloalkyl, substituted heterocycloalkyl chosen from mono-, di-, and tri-substituted heterocycloalkyl, wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_3$-$C_7$cycloalkyl, substituted $C_3$-$C_7$cycloalkyl chosen from mono-, di-, and tri-substituted $C_3$-$C_7$cycloalkyl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, and substituted heteroaryl chosen from mono-, di-, and tri-substituted heteroaryl wherein the substituents are independently selected from halogen, hydroxy, amino, oxo, —COOH, —CONH$_2$, $C_1$-$C_4$alkyl $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, wherein $R_1$ is optionally further substituted with 1 or more substituents independently chosen from hydroxy, nitro, cyano, amino, —SO$_2$NH$_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono-$C_1$-$C_6$ alkylamino)$C_0$-$C_6$ alkyl, (di-$C_1$-$C_6$ alkylamino)$C_0$-$C_6$ alkyl, and $C_1$-$C_6$alkoxycarbonyl.

43. The compound according to claim 42, wherein
$R_1$ is chosen from
phenyl substituted with -L-G, where
L is a group chosen from
$C_1$-$C_2$alkylene, substituted $C_1$-$C_2$alkylene chosen from mono-, di-, and tri-substituted $C_1$-$C_2$alkylene wherein the substituents are independently selected from halogen, hydroxy, cyano, amino, oxo, —COOH, —CONH$_2$, $C_1$-$C_4$ alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, cyano, amino, oxo, —COOH, —CONH$_2$, $C_1$-$C_4$ alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

—(C═O)—,

—($C_1$-$C_2$alkylene)(C═O)—, substituted —($C_1$-$C_2$alkylene)(C═O)— chosen from mono-, di-, and tri-substituted —($C_1$-$C_2$alkylene)(C═O)— wherein the substituents are independently selected from halogen, hydroxy, cyano, amino, oxo, —COOH, —CONH$_2$, $C_1$-$C_4$ alkyl $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, and G is a chosen from pyrrolidinyl, substituted pyrrolidinyl chosen from mono-, di-, and tri-substituted pyrrolidinyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, morpholinyl, substituted morpholinyl chosen from mono-, di-, and tri-substituted morpholinyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, thiomorpholinyl, substituted thiomorpholinyl chosen from mono-, di-, and tri-substituted thiomorpholinyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperazinyl substituted piperazinyl chosen from mono-, di-, and tri-substituted piperazinyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperidinyl, substituted piperidinyl chosen from mono-, di-, and tri-substituted piperidinyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

[1,4]diazepanyl, substituted [1,4]diazepanyl chosen from mono-, di-, and tri-substituted [1,4]diazepanyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, phenyl, substituted phenyl chosen from mono-, di-, and tri-substituted phenyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, imidazolyl, substituted imidazolyl chosen from mono-, di-, and tri-substituted imidazolyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, 5,6-dihydro-8H-[1,2,4]triazolo[4,3-a]pyrazine, substituted 5,6-dihydro-8H-[1,2,4]triazolo[4,3-a]pyrazine chosen from mono-, di- and tri-substituted 5,6-dihydro-8H-[1,2,4]triazolo[4,3-a]pyrazine wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, and of pyridyl substituted with -L-G, where L is a group chosen from $C_1$-$C_2$alkylene, substituted $C_1$-$C_2$alkylene chosen from mono-, di-, and tri-substituted $C_1$-$C_2$alkylene wherein the substituents are independently selected from halogen, hydroxy, cyano, amino, oxo, —COOH, —CONH$_2$, $C_1$-$C_4$alkyl $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

—(C=O)—,

—($C_1$-$C_2$alkylene)(C=O)—, and substituted —($C_1$-$C_2$alkylene)(C=O)— chosen from mono-, di-, and tri-substituted —($C_1$-$C_2$alkylene)(C=O)— wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, and G is a group chosen from pyrrolidinyl, substituted pyrrolidinyl chosen from mono-, di-, and tri-substituted pyrrolidinyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, morpholinyl, substituted morpholinyl chosen from mono-, di-, and tri-substituted morpholinyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, thiomorpholinyl, substituted thiomorpholinyl chosen from mono-, di-, and tri-substituted thiomorpholinyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperazinyl, substituted piperazinyl chosen from mono-, di-, and tri-substituted piperazinyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperidinyl, substituted piperidinyl chosen from mono-, di-, and tri-substituted piperidinyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

[1,4]diazepanyl, substituted [1,4]diazepanyl chosen from mono-, di-, and tri-substituted [1,4]diazepanyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, phenyl, substituted phenyl chosen from mono-, di-, and tri-substituted phenyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, imidazolyl, substituted imidazolyl chosen from mono-, di-, and tri-substituted imidazolyl wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, 5,6-dihydro-8H-[1,2,4]triazolo[4,3-a]pyrazine, and substituted 5,6-dihydro-8H-[1,2,4]triazolo[4,3-a]pyrazine chosen from mono-, di- and tri-substituted 5,6-dihydro-8H-[1,2,4]triazolo[4,3-a]pyrazine wherein the substituents are independently selected from halogen, hydroxy, cyano, amino, oxo, —COOH, —CONH$_2$, $C_1$-$C_4$alkyl, $C_1$-$C_4$alkoxy, $C_2$-$C_4$alkanoyl, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, wherein wherein $R_1$ is optionally further mono-, di-, or tri-substituted with substituents independently chosen from hydroxy, cyano, halogen, $C_1$-$C_4$alkyl, $C_2$-$C_4$alkanoyl, $C_1$-$C_2$haloalkyl, $C_1$-$C_2$haloalkoxy, $C_1$-$C_4$alkoxy, mono-$C_1$-$C_4$alkylamino, and di-$C_1$-$C_4$alkylamino.

44. The compoun according to claim 43, wherein $R_1$ is chosen from phenyl substituted with -L-G, where L is a group chosen from $C_1$-$C_2$alkylene, substituted $C_1$-$C_2$alkylene chosen from mono-, di-, and tri-substituted $C_1$-$C_2$alkylene wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, oxo, —COOH, —CONH$_2$, $C_1$-$C_4$alkyl, $C_1$-$C_4$alkoxy, $C_1$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide.

—(C=O)—,

—($C_1$-$C_2$alkylene)(C=O)—, and substituted —($C_1$-$C_2$alkylene)(C=O)— chosen from mono-, di-, and tri-substituted —($C_1$-$C_2$alkylene)(C=O)— wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, and G is a group chosen from pyrrolidinyl, substituted pyrrolidinyl chosen from mono-, di- and tri-substituted pyrrolidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, morpholinyl, substituted morpholinyl chosen from mono-, di- and tri-substituted morpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, thiomorpholinyl, substituted thiomorpholinyl chosen from mono-, di- and tri-substituted thiomorpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperazinyl, substituted piperazinyl chosen from mono-, di- and tri-substituted piperazinyl, wherein the substituents are independently chosen from halogen, hydroxy oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-

$C_4$alkylcarboxamide, and di-$C_1$-$C_4$alkylcarboxamide, piperidinyl, substituted piperidinyl chosen from mono-, di- and tri-substituted piperidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

[1,4]diazepanyl substituted [1,4]diazepanyl chosen from mono-, di- and tri-substituted [1,4]diazepanyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, phenyl, substituted phenyl chosen from mono-, di- and tri-substituted phenyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, imidazolyl, substituted imidazolyl chosen from mono-, di- and tri-substituted imidazolyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, 5,6-dihydro-8H-[1,2,4]triazolo[4,3-a]pyrazine, and substituted 5,6-dihydro-8H-[1,2,4]triazolo[4,3-a]pyrazine chosen from mono-, di- and tri-substituted 5,6-dihydro-8H-[1,2,4]triazolo[4,3-a]pyrazine, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, pyridyl substituted with -L-G, where L is a group chosen from $C_1$-$C_2$alkylene, substituted $C_1$-$C_2$alkylene chosen from mono-, di-, and tri-substituted $C_1$-$C_2$alkylene wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

—(C=O)—,

—($C_1$-$C_2$alkylene)(C=O)—, substituted —($C_1$-$C_2$alkylene)(C=O)— chosen from mono-, di-, and tri-substituted —($C_1$-$C_2$alkylene)(C=O)— wherein the substituents are independently selected from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, and G is a group chosen from pyrrolidinyl substituted pyrrolidinyl chosen from mono-, di- and tri-substituted pyrrolidinyl wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, morpholinyl, substituted morpholinyl chosen from mono-, di- and tri-substituted morpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, thiomorpholinyl, substituted thiomorpholinyl chosen from mono-, di- and tri-substituted thiomorpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperazinyl, substituted piperazinyl chosen from mono-, di- and tri-substituted piperazinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperidinyl, substituted piperidinyl chosen from mono-, di- and tri-substituted piperidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide,

[1,4]diazepanyl, substituted [1,4]diazepanyl chosen from mono-, di- and tri-substituted [1,4]diazepanyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, phenyl, substituted phenyl chosen from mono-, di- and tri-substituted phenyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, imidazolyl, substituted imidazolyl chosen from mono-, di- and tri-substituted imidazolyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, 5,6-dihydro-8H-[1,2,4]triazolo[4,3-a]pyrazine, and substituted 5,6-dihydro-8H-[1,2,4]triazolo[4,3-a]pyrazine chosen from mono-, di- and tri-substituted 5,6-dihydro-8H-[1,2,4]triazolo[4,3-a]pyrazine, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, wherein $R_1$ is optionally further mono-, di-, or tri-substituted with substituents independently chosen from hydroxy, cyano, halogen, $C_1$-$C_2$alkyl, and $C_1$-$C_2$alkoxy.

45. The compound according to claim 44, wherein

L is chosen from phenyl substituted with a group chosen from —CH$_2$—, —(C=O)—, and —(CH$_2$)(C=O)— and pyridyl substituted with a group chosen from —CH$_2$—, —(C=O)—, and —(CH$_2$)(C=O)— and G is chosen from pyrrolidinyl, substituted pyrrolidinyl chosen from mono-, di- and tri-substituted pyrrolidinyl, wherein the substituents are independently chosen from halogen hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, morpholinyl, substituted morpholinyl chosen from mono-, di- and tri-substituted morpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, thiomorpholinyl, substituted thiomorpholinyl chosen from mono-, di- and tri-substituted thiomorpholinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperazinyl, substituted piperazinyl chosen from mono-, di- and tri-substituted piperazinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, piperidinyl, substituted piperidinyl chosen from mono-, di- and tri-substituted piperidinyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_4$alkylamino, mono-$C_1$-$C_4$alkylcarboxamide, and di-$C_1$-$C_4$alkylcarboxamide, or [1,4]diazepanyl, and substituted [1,4]diazepanyl chosen from mono-, di- and tri-substituted [1,4]diazepanyl, wherein the substituents are independently chosen from halogen, hydroxy, oxo, —COOH, —CONH$_2$, $C_1$-$C_4$alkyl, $C_1$-$C_4$alkoxy, $C_2$-$C_4$alkanoyl, $C_1$-$C_4$alkoxycarbonyl, mono-$C_1$-$C_4$alkylamino, di-$C_1$-$C_{alkylamino}$, mono-$C_1$-$C_4$alkylcarboxamide, and di-$C_1$-$C_4$alkylcarboxamide.

46. The compound according to claim 31, having a structure of Formula 7

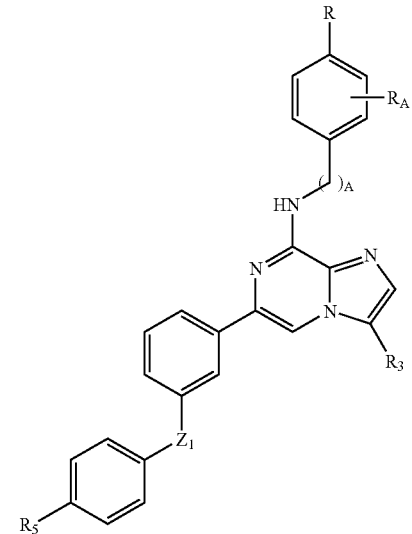

Formula 7 wherein R is chosen from

—CHO,
—COOH,
—CONH$_2$,
—CONHOH,
C$_2$-C$_6$ alkenyl,
substituted C$_2$-C$_6$ alkenyl chosen from mono-, di-, tri-substituted C$_2$-C$_6$ alkenyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
C$_2$-C$_6$ alkynyl,
substituted C$_2$-C$_6$ alkynyl chosen from mono-, di-, and tri-substituted C$_2$-C$_6$ alkynyl, wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_{-C4}$alkoxycarbonyl, mono-C$_1$-C$_4$alkylamino, di-C$_1$-C$_4$alkylamino mono-C$_1$-C$_4$alkylcarboxamide, di-C$_1$-C$_4$alkylcarboxamide, and phenyl,
C$_1$-C$_6$hydroxyalkyl,
substituted C$_1$-C$_6$hydroxyalkyl chosen from mono-, di-, and tri-substituted C$_1$-C$_6$hydroxyalkyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
C$_1$-C$_6$hydroxyalkoxy,
substituted C$_1$-C$_6$hydroxyalkoxy chosen from mono-, di-, and tri-substituted C$_1$-C$_6$hydroxyalkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
(mono-C$_1$-C$_6$alkylamino)C$_1$-C$_6$alkoxy,
substituted (mono-C$_1$-C$_6$alkylamino)C$_1$-C$_6$alkoxy chosen from mono-, di-, and tri-substituted (mono-C$_1$-C$_6$alkylamino)C$_1$-C$_6$alkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
(di-C$_1$-C$_6$alkylamino)C$_1$-C$_6$alkoxy,
substituted (di-C$_1$-C$_6$alkylamino)C$_1$-C$_6$alkoxy chosen from mono-, di-, and tri-substituted (di-C$_1$-C$_6$alkylamino)C$_1$-C$_6$alkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
(C$_1$-C$_6$alkoxy)(C$_1$-C$_6$alkylamino)C$_0$-C$_6$alkyl,
substituted (C$_1$-C$_6$alkoxy)(C$_1$-C$_6$alkylamino)C$_0$-C$_6$alkyl chosen from mono-, di-, and tri-substituted (C$_1$-C$_6$alkoxy)(C$_1$-C$_6$alkylamino)C$_0$-C$_6$alkyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
(C$_1$-C$_6$alkoxy)(C$_1$-C$_6$alkoxy)C$_1$-C$_6$alkoxy,
substituted (C$_1$-C$_6$alkoxy)(C$_1$-C$_6$alkoxy)C$_1$-C$_6$alkoxy chosen from mono-, di-, and tri-substituted (C$_1$-C$_6$alkoxy)(C$_1$-C$_6$alkoxy)C$_1$-C$_6$alkoxy wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
heterocycloalkyl,
substituted heterocycloalkyl chosen from mono-, di-, and tri-substituted heterocycloalkyl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
aryl,
substituted aryl chosen from mono-, di-, and tri-substituted aryl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
heteroaryl,
substituted heteroaryl chosen from mono-, di-, and tri-substituted heteroaryl wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, C$_1$-C$_4$alkoxycarbonyl, mono-C$_1$-C$_4$alkylamino, di-C$_1$-C$_4$alkylamino, mono-C$_1$-C$_4$alkylcarboxamide, di-C$_1$-C$_4$alkylcarboxamide, and phenyl,
—C$_1$-C$_6$alkyl(C═O)OR$_{10}$,
substituted —C$_1$-C$_6$alkyl(C═O)OR$_{10}$ chosen from mono-, di-, and tri-substituted —C$_1$-C$_6$alkyl(C═O)OR$_{10}$ wherein the substituents are independently selected from halogen, hydroxy, amino, oxo, —COOH, —CONH$_2$, C$_1$-C$_4$alkyl, C$_2$-C$_4$alkenyl, C$_2$-C$_4$alkynyl, C$_1$-C$_4$alkoxy, C$_2$-C$_4$alkanoyl, C$_1$-C$_4$alkylthio, C$_1$-C$_2$haloalkyl, C$_1$-C$_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl(C=O)$NR_{10}R_{11}$, substituted —$C_0$-$C_6$alkyl(C=O)$NR_{10}R_{11}$ chosen from mono-, di-, and tri-substituted —$C_0$-$C_6$alkyl(C=O)$NR_{10}R_{11}$ wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_1$-$C_6$alkyl$NR_{10}(SO_2)R_{11}$, substituted —$C_1$-$C_6$alkyl$NR_{10}(SO_2)R_{11}$ chosen from mono-, di-, and tri-substituted —$C_1$-$C_6$alkyl$NR_{10}(SO_2)R_{11}$ wherein the substituents are independently selected from halogen, hydroxy, amino, oxo, —COOH, —$CONH_2$, $C_1$-$C_4$-alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl$NR_{10}$(C=O)$R_{11}$, substituted —$C_0$-$C_6$alkyl$NR_{10}$(C=O)$R_{11}$ chosen from mono-, di-, and tri-substituted —$C_0$-$C_6$alkyl$NR_{10}$(C=O)$R_{11}$, wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkylcarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl$(SO_2)R_{10}$, substituted —$C_0$-$C_6$alkyl$(SO_2)R_{10}$ chosen from mono-, di-, and tri-substituted —$C_0$-$C_6$alkyl$(SO_2)R_{10}$ wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, —$C_0$-$C_6$alkyl$NR_{10}$(C=O)$NR_{11}R_{12}$ substituted —$C_0$-$C_6$alkyl$NR_{10}$(C=O)$NR_{11}R_{12}$ chosen from mono-, di-, and tri-substituted —$C_0$-$C_6$alkyl$NR_{10}$(C=O)$NR_{11}R_{12}$ wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$ alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkyl carboxamide, and phenyl, where $R_{10}$, $R_{11}$, and $R_{12}$ are independently chosen from hydrogen, hydroxy, $C_1$-$C_6$alkyl, $C_1$-$C_6$alkoxy, $C_3$-$C_{10}$cycloalkyl, and of heterocycloalkyl, -L-G, where L is chosen from $C_1$-$C_2$alkylene, substituted $C_1$-$C_2$alkylene chosen from mono-, di-, and tri-substituted $C_1$-$C_2$alkylene wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_0$-$C_2$alkylene-O—, substituted $C_0$-$C_2$alkylene-O— chosen from mono-, di-, and tri-substituted $C_0$-$C_2$alkylene-O— wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl,

—(C=O)—,

—($C_1$-$C_2$alkylene)(C=O)—, and substituted —($C_1$-$C_2$alkylene)(C=O)— chosen from mono-, di-, and tri-substituted —($C_1$-$C_2$alkylene)(C=O)— wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, and and G is chosen from heterocycloalkyl, substituted heterocycloalkyl chosen from mono-, di-, and tri-substituted heterocycloalkyl, wherein the substituents are independently selected from halogen, hydroxy, amino, oxo, —COOH, —$CONH_2$, $C_1$-$C_4$ alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, $C_3$-$C_7$cycloalkyl, substituted $C_3$-$C_7$cycloalkyl chosen from mono-, di-, and tri-substituted $C_3$-$C_7$cycloalkyl wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, aryl, substituted aryl chosen from mono-, di-, and tri-substituted aryl wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl, heteroaryl, and substituted heteroaryl chosen from mono-, di-, and tri-substituted heteroaryl wherein the substituents are independently selected from halogen, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono-$C_1$-$C_4$alkylamino, di-$C_1$-$C_4$alkylamino, mono-$C_1$-$C_4$alkylcarboxamide, di-$C_1$-$C_4$alkylcarboxamide, and phenyl and $R_4$ is optional and when present each occurrence is independently chosen from hydroxy, nitro, cyano, amino, —$SO_2NH_2$, halogen, $C_1$-$C_6$ alkyl, $C_2$-$C_6$alkanoyl, $C_1$-$C_4$haloalkyl, $C_1$-$C_4$haloalkoxy, $C_1$-$C_6$ alkylthio, $C_3$-$C_7$cycloalkyl, ($C_1$-$C_6$ alkoxy)$C_0$-$C_6$alkyl, (mono-$C_1$-$C_6$alkylamino)$C_0$-$C_6$ alkyl, (di-$C_1$-$C_6$ alkylamino)$C_0$-$C_6$ alkyl, and $C_1$-$C_6$alkoxycarbonyl.

47. The compound according to claim 46, having a structure of Formula 8

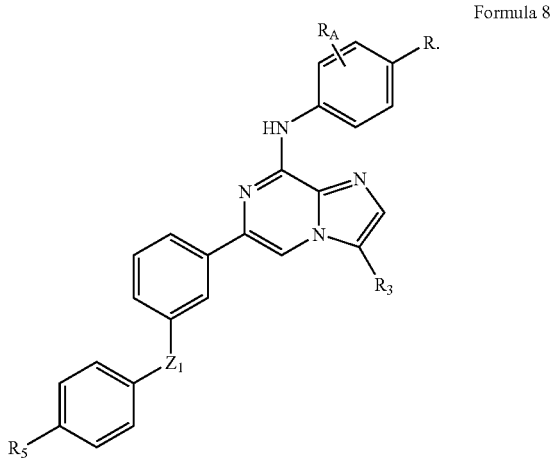

Formula 8

48. The compound according to claim 47, having a structure of Formula 9

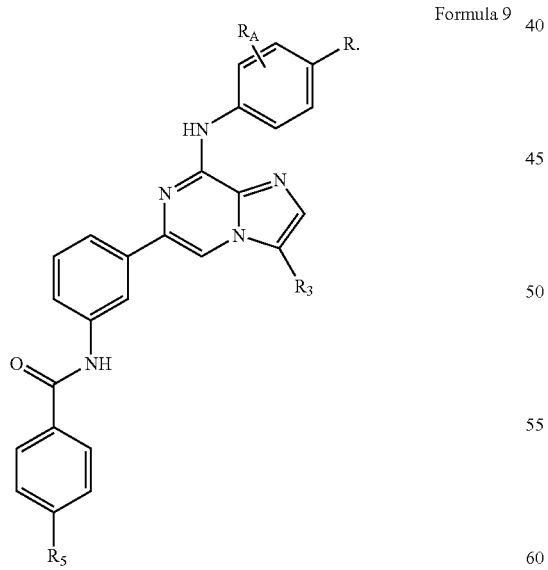

Formula 9

49. The compound according to claim 29, wherein $R_3$ is chosen from hydrogen and methyl.

50. The compound according to of claim 1, which exhibits an $IC_{50}$ of 1 micromolar or less in an in vitro biochemical assay of Btk activity.

51. The compound according to claim 1, which exhibits an $IC_{50}$ of 100 nanomolar or less in an in vitro biochemical assay of Btk activity.

52. The compound according to claim 1, which exhibits an $IC_{50}$ of 10 nanomolar or less in an in vitro biochemical assay of Btk activity.

53. The compound according to claim 1, which exhibits an $IC_{50}$ of 10 micromolar or less in an assay for inhibition of B-cell proliferation.

54. The compound according to claim 1, which exhibits an $IC_{50}$ of 1 micromolar or less in an assay for inhibition of B-cell proliferation.

55. The compound according to claim 1, which exhibits an $IC_{50}$ of 500 nanomolar or less in an assay for inhibition of B-cell proliferation.

56. The compound according to claim 1, which exhibits an $IC_{50}$ value in an assay for inhibition of T-cell proliferation that is at least 3-fold greater than an $IC_{50}$ value thereof in an assay for inhibition of B-cell proliferation.

57. The compound according to claim 1, which exhibits an $IC_{50}$ value in an assay for inhibition of T-cell proliferation that is at least 5-fold greater than an $IC_{50}$ value exhibited in an assay for inhibition of B-cell proliferation.

58. The compound according to claim 1, which exhibits an $IC_{50}$ value in an assay for inhibition of T-cell proliferation that is at least 10-fold greater than an $IC_{50}$ exhibited in an assay for inhibition of B-cell proliferation.

59. The compound, which is
4-tert-Butyl-N-[3-(8-phenylamino-imidazo[1,2-a]pyrazin-6-yl)-phenyl]-benzamide;
4-Isopropyl-N-[3-(8-phenylamino-imidazo[1,2-a]pyrazin-6-yl)-phenyl]-benzamide;
4-tert-Butyl-N-{3-[8-(pyridin-3-ylamino)-imidazo[1,2-a]pyrazin-6-yl]-phenyl}-benzamide;
4-tert-Butyl-N-{3-[8-(4-methoxy-phenylamino)-imidazo[1,2-a]pyrazin-6-yl]-phenyl}-benzamide;
4-tert-Butyl-N-{3-[8-(pyridin-4-ylamino)-imidazo[1,2-a]pyrazin-6-yl]-phenyl}-benzamide;
4-tert-Butyl-N-{3-[8-(4-fluoro-phenylamino)-imidazo[1,2-a]pyrazin-6-yl]-phenyl}-benzamide;
4-tert-Butyl-N-{3-[8-(3-fluoro-phenylamino)-imidazo[1,2-a]pyrazin-6-yl]-phenyl}-benzamide;
4-{6-[3-(4-tert-Butyl-benzoylamino)-phenyl]-imidazo[1,2-a]pyrazin-8-ylamino}-benzoic acid;
4-tert-Butyl-N-{3-[8-(3-methoxy-phenylamino)-imidazo[1,2-a]pyrazin-6-yl]-phenyl}-benzamide
4-tert-Butyl-N-{3-[8-(6-methoxy-pyridin-3-ylamino)-imidazo[1,2-a]pyrazin-6-yl]-phenyl}-benzamide;
3-{6-[3-(4-tert-Butyl-benzoylamino)-phenyl]-imidazo[1,2-a]pyrazin-8-ylamino}-benzoic acid
4-{6-[3-(4-Isopropyl-benzoylamino)-phenyl]-imidazo[1,2-a]pyrazin-8-ylamino}-benzoic acid;
4-tert-Butyl-N-{3-[8-(4-cyano-phenylamino)-imidazo[1,2-a]pyrazin-6-yl]-phenyl}-benzamide;
4-{6-[3-(4-tert-Butyl-benzoylamino)-phenyl]-imidazo[1,2-a]pyrazin-8-ylamino}-benzamide;
4-tert-Butyl-N-{3-[8-(4-morpholin-4-yl-phenylamino)-imidazo[1,2-a]pyrazin-6-yl]-phenyl}-benzamide;
3-{6-[3-(4-tert-Butyl-benzoylamino)-phenyl]-imidazo[1,2-a]pyrazin-8-ylamino}-benzoic acid;
4-tert-Butyl-N-{3-[8-(3-fluoro-4-methoxy-phenylamino)-imidazo[1,2-a]pyrazin-6-yl]-phenyl}-benzamide;
4-{6-[3-(4-tert-Butyl-benzoylamino)-phenyl]-imidazo[1,2-a]pyrazin-8-ylamino}-benzoic N-Methyl amide;
4-tert-Butyl-N-{3-[8-(4-piperazin-1-yl-phenylamino)-imidazo[1,2-a]pyrazin-6-yl]-phenyl}-benzamide;

4-tert-Butyl-N-[3-(8-m-tolylamino-imidazo[1,2-a]pyrazin-6-yl)-phenyl]-benzamide;
(4-{6-[3-(4-tert-Butyl-benzoylamino)-phenyl]-imidazo[1,2-a]pyrazin-8-ylamino}-phenyl)-acetic acid methyl ester;
(4-{6-[3-(4-tert-Butyl-benzoylamino)-phenyl]-imidazo[1,2-a]pyrazin-8-ylamino}-phenyl)-acetic acid;
4-tert-Butyl-N-(3-{8-[4-(piperazine-1-carbonyl)-phenylamino]-imidazo[1,2-a]pyrazin-6-yl}-phenyl)-benzamide;
4-tert-Butyl-N-(3-{8-[4-(2-methoxy-ethoxymethoxy)-phenylamino]-imidazo[1,2-a]pyrazin-6-yl}-phenyl)-benzamide;
4-tert-Butyl-N-{3-[8-(6-piperazin-1-yl-pyridin-3-ylamino)-imidazo[1,2-a]pyrazin-6-yl]-phenyl}-benzamide;
4-tert-Butyl-N-(3-{8-[4-(4-methyl-piperazin-1-yl)-phenylamino]-imidazo[1,2-a]pyrazin-6-yl}-phenyl)-benzamide;
4-tert-Butyl-N-{3-[8-(4-[1,4]diazepan-1-yl-phenylamino)-imidazo[1,2-a]pyrazin-6-yl]-phenyl}-benzamide;
4-tert-Butyl-N-(3-{8-[4-(4-oxo-piperidin-1-yl)-phenylamino]-imidazo[1,2-a]pyrazin-6yl}-phenyl)-benzamide;
(4-{6-[3-(4-tert-Butyl-benzoylamino)-phenyl]-imidazo[1,2-a]pyrazin-8-ylamino}-benzoylamino)-acetic acid methyl ester;
(4-{6-[3-(4-tert-Butyl-benzoylamino)-phenyl]-imidazo[1,2-a]pyrazin-8-ylamino}-benzoylamino)-acetic acid;
N-(3-{8-[4-(4-Acetyl-piperazin-1-yl)-phenylamino]-imidazo[1,2-a]pyrazin-6-yl}-phenyl)-4-tert-butyl-benzamide;
4-tert-Butyl-N-(3-{8-[4-(3-methyl-piperazin-1-yl)-phenylamino]-imidazo[1,2-a]pyrazin-6-yl}phenyl)-benzamide;
4-{6-[3-(4-tert-Butyl-benzoylamino)-phenyl]-imidazo[1,2-a]pyrazin-8-ylamino}-benzoic hydroxyl amide;
4-tert-Butyl-N-{3-[8-(4-hydroxymethyl-phenylamino)-imidazo[1,2-a]pyrazin-6-yl]-phenyl}-benzamide;
4-tert-Butyl-N-{3-[8-(4-piperazin-1-ylmethyl-phenylamino)-imidazo[1,2-a]pyrazin-6-yl]-phenyl}-benzamide;
4-{6-[3-(4-Bromo-3-methyl-benzoylamino)-phenyl]-imidazo[1,2-a]pyrazin-8-ylamino}-benzoic acid;
4-tert-Butyl-N-{3-[8-(3-methyl-4-piperazin-1-yl-phenylamino)-imidazo[1,2-a]pyrazin-6-yl]-phenyl}-benzamide;
4-tert-Butyl-N-(3-{8-[4-(3-methyl-piperazin-1-yl)-phenylamino]-imidazo[1,2-a]pyrazin-6-yl}-phenyl)-benzamide;
4-tert-Butyl-N-{3-[8-(3-hydroxymethyl-phenylamino)-imidazo[1,2-a]pyrazin-6-yl]-phenyl}-benzamide;
4-tert-Butyl-N-(3-{8-[3-(3-methyl-piperazin-1-ylmethyl)-phenylamino]-imidazo[1,2-a]pyrazin-6-yl}-phenyl)-benzamide;
4-tert-Butyl-N-(3-{8-[3-(3,5-dimethyl-piperazin-1-ylmethyl)-phenylamino]-imidazo[1,2-a]pyrazin-6-yl}-phenyl)-benzamide;
4-tert-Butyl-N-(3-{8-[3-(3,5-dimethyl-piperazin-1-ylmethyl)-phenylamino]-imidazo[1,2-a]pyrazin-6-yl}-phenyl)-benzamide;
4-tert-Butyl-N-(3-{8-[4-(3,5-dimethyl-piperazin-1-yl)-phenylamino]-imidazo[1,2-a]pyrazin-6-yl}-phenyl)-benzamide;
4-({6-[3-(4-tert-Butyl-benzoylamino)-phenyl]-imidazo[1,2-a]pyrazin-8-ylamino}-methyl)-benzoic acid;
4-tert-Butyl-N-(3-{8-[4-(3-methyl-piperazin-1-yl)-phenylamino]-imidazo[1,2-a]pyrazin-6-yl}-phenyl)-benzamide;
4-(1-Hydroxy-1-methyl-ethyl)-N-[3-(8-phenylamino-imidazo[1,2-a]pyrazin-6-yl)-phenyl]-benzamide;
(3-{6-[3-(4-tert-Butyl-benzoylamino)-phenyl]-imidazo[1,2-a]pyrazin-8-ylamino}-phenyl)-acetic acid;
N-[3-(8-Phenylamino-imidazo[1,2-a]pyrazin-6-yl)-phenyl]-terephthalamic acid methyl ester;
N-[3-(8-Phenylamino-imidazo[1,2-a]pyrazin-6-yl)-phenyl]-terephthalamic acid;
2-(4-{6-[3-(4-tert-Butyl-benzoylamino)-phenyl]-imidazo[1,2-a]pyrazin-8-ylamino}-phenyl)-propionic acid ethyl ester;
2-(4-{6-[3-(4-tert-Butyl-benzoylamino)-phenyl]-imidazo[1,2-a]pyrazin-8-ylamino}-phenyl)-propionic acid;
4-{6-[3-(4-tert-Butyl-benzoylamino)-phenyl]-imidazo[1,2-a]pyrazin-8-ylamino}-2-methoxy-benzoic acid methyl ester;
4-{6-[3-(4-tert-Butyl-benzoylamino)-phenyl]-imidazo[1,2-a]pyrazin-8-ylamino}-2-methoxy-benzoic acid;
4-tert-Butyl-N-{3-[8-(3-methylcarbamoylmethyl-phenylamino)-imidazo[1,2-a]pyrazin-6-yl]-phenyl}-benzamide;
4-tert-Butyl-N-{3-[8-(4-methylcarbamoylmethyl-phenylamino)-imidazo[1,2-a]pyrazin-6-yl]-phenyl}-benzamide;
4-tert-Butyl-N-{3-[8-(4-cyclooctylcarbamoylmethyl-phenylamino)-imidazo[1,2-a]pyrazin-6-yl]-phenyl}-benzamide;
4-tert-Butyl-N-[3-(8-{4[(diisopropylcarbamoyl)-methyl]-phenylamino}-imidazo[1,2-a]pyrazin-6-yl)-phenyl]-benzamide;
4-tert-Butyl-N-{3-[8-(4-carbamoylmethyl-phenylamino)-imidazo[1,2-a]pyrazin-6-yl]-phenyl}-benzamide;
3-(4-{6-[3-(4-tert-Butyl-benzoylamino)-phenyl]-imidazo[1,2-a]pyrazin-8-ylamino}-phenyl)-propionic acid;
4-tert-Butyl-N-(3-{8-[4-(2-hydroxy-ethyl)-phenylamino]-imidazo[1,2-a]pyrazin-6-yl}-phenyl)-benzamide;
4-tert-Butyl-N-(3-{8-[4-(2-methylamino-ethyl)-phenylamino]-imidazo[1,2-a]pyrazin-6-yl}-phenyl)-benzamide;
4-tert-Butyl-N-{3-[8-(4-methylaminomethyl-phenylamino)-imidazo[1,2-a]pyrazin-6-yl]-phenyl}-benzamide;
4-{6-[3-(4-tert-Butyl-benzoylamino)-phenyl]-imidazo[1,2-a]pyrazin-8-ylamino}-2-hydroxy-benzoic acid;
4-tert-Butyl-N-(3-{8-[4-(1-hydroxy-1-methyl-ethyl)-phenylamino]-imidazo[1,2-a]pyrazin-6-yl}-phenyl)-benzamide;
4-tert-Butyl-N-(3-{8-[4-(2-hydroxy-ethoxy)-phenylamino]-imidazo[1,2-a]pyrazin-6-yl}phenyl)-benzamide;
4-tert-Butyl-N-(3-{8-[4-(4-methyl-piperazine-1-carbonyl)-phenylamino]-imidazo[1,2-a]pyrazin-6-yl}-phenyl)-benzamide;
4-tert-Butyl-N-(3-{8-[4-(2-methylamino-ethoxy)-phenylamino]-imidazo[1,2-a]pyrazin-6-yl}-phenyl)-benzamide;
4-tert-Butyl-N-(3-{8-[4-(2-dimethylamino-ethoxy)-phenylamino]-imidazo[1,2-a]pyrazin-6-yl}-phenyl)-benzamide;
4-{6-[3-(4-tert-Butyl-benzoylamino)-phenyl]-imidazo[1,2-a]pyrazin-8-ylamino}-benzoic methoxy amide;

4-{6-[3-(4-tert-Butyl-benzoylamino)-phenyl]-imidazo[1,2-a]pyrazin-8-ylamino}-benzoic hyrdoxyl methyl amide;

4-tert-Butyl-N-(3-{8-[4-([1,4]diazepane-1-carbonyl)-phenylamino]-imidazo[1,2-a]pyrazin-6-yl}-phenyl)-benzamide;

4-tert-Butyl-N-(3-{8-[4-(pyrrolidine-1-carbonyl)-phenylamino]-imidazo[1,2-a]pyrazin-6-yl}-phenyl)-benzamide;

4-tert-Butyl-N-(3-{8-[4-(morpholine-4-carbonyl)-phenylamino]-imidazo[1,2-a]pyrazin-6-yl}-phenyl)-benzamide;

4-tert-Butyl-N-(3-{8-[4-(ethoxyamine-4-carbonyl)-phenylamino]-imidazo[1,2-a]pyrazin-6-yl}-phenyl)-benzamide;

4-tert-Butyl-N-(3-{8-[4-(dimethylamine-4-carbonyl)-phenylamino]-imidazo[1,2-a]pyrazin-6}-phenyl)-benzamide;

4-tert-Butyl-N-(3-{8-[4-(methylethylamine-4-carbonyl)-phenylamino]-imidazo[1,2-a]pyrazin-6-yl}-phenyl)-benzamide;

4-tert-Butyl-N-(3-{8-[4-(3-oxo-piperazine-1-carbonyl)-phenylamino]-imidazo[1,2-a]pyrazin-6-yl}-phenyl)-benzamide;

4-tert-Butyl-N-(3-{8[N,N,N'-Trimethyl-ethane-1,2-diamine-4-carbonyl)-phenylamino]-imidazo[1,2-a]pyrazin-6-yl}-phenyl)-benzamide;

4-tert-Butyl-N-(3-{8-[4-(4-methyl-[1,4]diazepane-1-carbonyl)-phenylamino]-imidazo[1,2-a]pyrazin-6-yl}-phenyl)-benzamide;

4-tert-Butyl-N-(3-{8-[4-(N-methyl ethoxyamine-4-carbonyl)-phenylamino]-imidazo[1,2-a]pyrazin-6-yl}-phenyl)-benzamide;

4-tert-Butyl-N-(3-{8-[4-(4-ethyl-piperazine-1-carbonyl)-phenylamino]-imidazo[1,2-a]pyrazin-6-yl}-phenyl)-benzamide;

4-{6-[3-(4-tert-Butyl-benzoylamino)-phenyl]-imidazo[1,2-a]pyrazin-8-ylamino}-benzoic benzyl amide;

4-tert-Butyl-N-(3-{8-[4-(4-methyl-piperazin-1-ylmethyl)-phenylamino]-imidazo[1,2-a]pyrazin-6-yl}-phenyl)-benzamide;

4-tert-Butyl-N-(3-{8-[4-(4-ethyl-piperazin-1-ylmethyl)-phenylamino]-imidazo[1,2-a]pyrazin-6-yl}-phenyl)-benzamide;

4-tert-Butyl-N-{3-[8-(4-[1,4]diazepan-1-ylmethyl-phenylamino)-imidazo[1,2-a]pyrazin-6-yl]-phenyl}-benzamide;

4-tert-Butyl-N-(3-{8-[4-(3-methyl-piperazin-1-ylmethyl)-phenylamino]-imidazo[1,2-a]pyrazin-6-yl}-phenyl)-benzamide;

4-tert-Butyl-N-{3-[8-(4-dimethylaminomethyl-phenylamino)-imidazo[1,2-a]pyrazin-6-yl]-phenyl}-benzamide;

4-tert-Butyl-N-[3-(8-{4-[(ethyl-methyl-amino)-methyl]-phenylamino}-imidazo[1,2-a]pyrazin-6-yl)-phenyl]-benzamide;

4-tert-Butyl-N-{3-[8-(4-{[(2-methoxy-ethyl)-methyl-amino]-methyl}-phenylamino)-imidazo[1,2-a]pyrazin-6-yl]-phenyl}-benzamide;

4-tert-Butyl-N-[3-(8-{4-[(2-methoxy-ethylamino)-methyl]-phenylamino}-imidazo[1,2-a]pyrazin-6-yl)-phenyl]-benzamide;

4-tert-Butyl-N-{3-[8-(4-{[(2-dimethylamino-ethyl)-methyl-amino]-methyl}-phenylamino)-imidazo[1,2-a]pyrazin-6-yl]-phenyl}-benzamide;

N-(3-{8-[4-(4-Acetyl-piperazine-1-carbonyl)-phenylamino]-imidazo[1,2-a]pyrazin-6-yl}-phenyl)-4-tert-butyl-benzamide;

4-tert-Butyl-N-{3-[8-(4-{[(2-hydroxy-ethyl)-methyl-amino]-methyl}-phenylamino)-imidazo[1,2-a]pyrazin-6-yl]-phenyl}-benzamide;

4-tert-Butyl-N-[3-(8-{4-[(2-hydroxy-ethylamino)-methyl]-phenylamino}-imidazo[1,2-a]pyrazin-6-yl)-phenyl]-benzamide;

4-tert-Butyl-N-(3-{8-[4-(4-methyl-[1,4]diazepan-1-ylmethyl)-phenylamino]-imidazo[1,2-a]pyrazin-6-yl}-phenyl)-benzamide;

N-[3-(8-{4-[2-(Acetyl-methyl-amino)-ethoxy]-phenylamino}-imidazo[1,2-a]pyrazin-6-yl) -phenyl]-4-tert-butyl-benzamide;

4-(4-{6-[3-(4-tert-Butyl-benzoylamino)-phenyl]-imidazo[1,2-a]pyrazin-8-ylamino}-phenyl)-piperazine-1-carboxylic acid ethyl ester;

N-(3-{8-[4-(4-Acetyl-piperazin-1-ylmethyl)-phenylamino]-imidazo[1,2-a]pyrazin-6-yl}-phenyl-4-tert-butyl-benzamide;

4-tert-Butyl-N-{3-[8-(4-imidazol-1-ylmethyl-phenylamino)-imidazo[1,2-a]pyrazin-6-yl]-phenyl}-benzamide;

4-tert-Butyl-N-{3-[8-(4-pyrrolidin-1-ylmethyl-phenylamino)-imidazo[1,2-a]pyrazin-6-yl]-phenyl}-benzamide;

N-[3-(8-{4-[(Acetyl-methyl-amino)-methyl]-phenylamino}-imidazo[1,2-a]pyrazin-6-yl)-phenyl]-4-tert-butyl-benzamide;

4-tert-Butyl-N-[3-(8-{4-[(methanesulfonyl-methyl-amino)-methyl]-phenylamino}-imidazo[1,2-a]pyrazin-6-yl)-phenyl]-benzamide;

4-tert-Butyl-N-(3-{8-[4-(3-isopropyl-1-methyl-ureidomethyl)-phenylamino]-imidazo[1,2-a]pyrazin-6-yl}-phenyl)-benzamide;

4-Isopropyl-N-(3-{8-[4-(morpholine-4-carbonyl)-phenylamino]-imidazo[1,2-a]pyrazin-6-yl}-phenyl)-benzamide;

N-}3-[8-(4-}[(2-Hydroxy-ethyl)-methyl-amino]-carbonyl}-phenylamino)-imidazo[1,2-a]pyrazin-6yl]-phenyl}-4-isopropyl-benzamide;

N-(3-{8-[4-(Morpholine-4-carbonyl)-phenylamino]-imidazo[1,2-a]pyrazin-6-yl}-phenyl)-benzamide;

4-Methyl-N-(3-{8-[4-(morpholine-4-carbonyl)-phenylamino]-imidazo[1,2-a]pyrazin-6-yl}-phenyl)-benzamide;

4-Ethyl-N-(3-{8-[4-(morpholine-4-carbonyl)-phenylamino]-imidazo[1,2-a]pyrazin-6-yl}-phenyl)-benzamide;

4-Fluoro-N-(3-{8-[4-(morpholine-4-carbonyl)-phenylamino]-imidazo[1,2-a]pyrazin-6-yl}-phenyl)-benzamide;

N-(3-{8-[4-(Morpholine-4-carbonyl)-phenylamino]-imidazo[1,2-a]pyrazin-6-yl}-phenyl)-4-trifluoromethyl-benzamide;

4-tert-Butyl-N-(3-{8-[4-(5,6-dihydro-8H-imidazo[1,2-a]pyrazine-7-carbonyl)-phenylamino]imidazo[1,2-a]pyrazin-6-yl}-phenyl)-benzamide;

4-tert-Butyl-N-(3-{8-[4-(3-oxo-piperazin-1-ylmethyl)-phenylamino]-imidazo[1,2-a]pyrazin-6-yl}-phenyl)-benzamide;

1-(4-{6-[3-(4-tert-Butyl-benzoylamino)-phenyl]-imidazo[1,2-a]pyrazin-8-ylamino}-benzyl)-pyrrolidine-2-carboxylic acid methyl ester;

N-(3-{8-[4-(Morpholine-4-carbonyl)-phenylamino]-imidazo[1,2-a]pyrazin-6-yl}-phenyl)-terephthalamic acid methyl ester;

N-(3-{8-[4-(Morpholine-4-carbonyl)-phenylamino]-imidazo[1,2-a]pyrazin-6-yl}-phenyl)-terephthalamic acid;

N-(3-{8-[4-(4-Acetyl-piperazin-1-yl)-phenylamino]-imidazo[1,2-a]pyrazin-6-yl}-phenyl)-4-ethyl-benzamide;

N-(3-{8-[4-(4-Acetyl-piperazin-1-yl)-phenylamino]-imidazo[1,2-a]pyrazin-6-yl}-phenyl)-4-trifluoromethyl-benzamide;

4-tert-Butyl-N-(3-{8-[4-(3-methyl-5,6-dihydro-8H-[1,2,4]triazolo[4,3-a]pyrazin-7-ylmethyl-phenylamino]-imidazo[1,2-a]pyrazin-6-yl}-phenyl)-benzamide;

4-tert-Butyl-N-(3-{8-[4-(3-methyl-5,6-dihydro-8H-[1,2,4]triazolo[4,3-a]pyrazine-7-carbonyl)-phenylamino]-imidazo[1,2-a]pyrazin-6-yl}-phenyl)-benzamide;

N-(3-{8-[4-(4-Acetyl-piperazin-1-yl)-phenylamino]-imidazo[1,2-a]pyrazin-6-yl}-phenyl)-4-isopropyl-benzamide;

N-(3-{8-[4-(4-Acetyl-piperazine-1-carbonyl)-phenylamino]-imidazo[1,2-a]pyrazin-6-yl}phenyl)-4-isopropyl-benzamide;

1-(4-{6-[3-(4-tert-Butyl-benzoylamino)-phenyl]-imidazo[1,2-a]pyrazin-8-ylamino}-benzyl)-pyrrolidine-2-carboxylic acid;

4-Isopropyl-N-(3-{8-[4-(3-methyl-5,6-dihydro-8H-[1,2,4]triazolo[4,3-a]pyrazine-7-carbonyl)-phenylamino]-imidazo[1,2-a]pyrazin-6-yl}-phenyl)-benzamide;

N-(3-{8-[4-(5,6-Dihydro-8H-imidazo[1,2-a]pyrazine-7-carbonyl)-phenylamino]-imidazo[1,2-a]pyrazin-6-yl}-phenyl)-4-isopropyl-benzamide;

4-Isopropyl-N-(3-{8-[4-(3-oxo-piperazine-1-carbonyl)-phenylamino]-imidazo[1,2-a]pyrazin-6-yl}-phenyl)-benzamide;

4-Isopropyl-N-(3-{8-[4-(4-methyl-piperazine-1-carbonyl)-phenylamino]-imidazo[1,2-a]pyrazin-6-yl}-phenyl)-benzamide;

4-Isopropyl-N-(3-{8-[4-(3-oxo-piperazin-1-ylmethyl)-phenylamino]-imidazo[1,2-a]pyrazin-6-yl}-phenyl)-benzamide;

N-(3-{8-[4-(4-Acetyl-piperazin-1-ylmethyl)-phenylamino]-imidazo[1,2-a]pyrazin-6-yl}-phenyl)-4-isopropyl-benzamide;

N-(3-{8-[4-(Morpholine-4-carbonyl)-phenylamino]-imidazo[1,2-a]pyrazin-6-yl}-phenyl)-isonicotinamide;

N-(3-{8-[4-(Morpholine-4-carbonyl)-phenylamino]-imidazo[1,2-a]pyrazin-6-yl}-phenyl)-nicotinamide;

4-tert-Butyl-N-(3-{8-[4-(2-morpholin-4-yl-2-oxo-ethyl)-phenylamino]-imidazo[1,2-a]pyrazin-6-yl}-phenyl)-benzamide;

4-tert-Butyl-N-(3-{8-[3-(2-morpholin-4-yl-2-oxo-ethyl)-phenylamino]-imidazo[1,2-a]pyrazin-6-yl}-phenyl)-benzamide;

4-Isopropyl-N-{3-[8-(4-morpholin-4-ylmethyl-phenylamino)-imidazo[1,2-a]pyrazin-6-yl]-phenyl}-benzamide;

4-tert-Butyl-N-{3-[8-(4-morpholin-4-ylmethyl-phenylamino)-imidazo[1,2-a]pyrazin-6-yl]-phenyl}-benzamide;

N-(3-{8-[4-(Morpholine-4-carbonyl)-phenylamino]-imidazo[1,2-a]pyrazin-6-yl}-phenyl)-2-phenyl-acetamide;

N-(4-tert-Butyl-phenyl)-3-}8-[4-(morpholine-4-carbonyl)-phenylamino]-imidazo[1,2-a]pyrazin-6-yl}-benzamide;

N-(3-Chloro-benzyl)-3-{8-[4-(morpholine-4-carbonyl)-phenylamino]-imidazo[1,2-a]pyrazin-6-yl}-benzamide;

4-Cyano-N-(3-{8-[4-(morpholine-4-carbonyl)-phenylamino]-imidazo[1,2-a]pyrazin-6-yl}-phenyl)-benzamide;

6-Dimethylamino-N-(3-{8-[4-(morpholine-4-carbonyl)-phenylamino]-imidazo[1,2-a]pyrazin-6-yl}-phenyl)-nicotinamide;

N-Methyl-N'-(3-{8-[4-(morpholine-4-carbonyl)-phenylamino]-imidazo[1,2-a]pyrazin-6-yl}-phenyl)-terephthalamide;

N,N-Dimethyl-N'-(3-{8-[4-(morpholine-4-carbonyl)-phenylamino]-imidazo[1,2-a]pyrazin-6-yl}-phenyl)-terephthalamide;

4-Acetyl-N-(3-{8-[4-(morpholine-4-carbonyl)-phenylamino]-imidazo[1,2-a]pyrazin-6-yl}-phenyl)-benzamide;

4-(1H-Imidazol-2-yl)-N-(3-{8-[4-(morpholine-4-carbonyl)-phenylamino]-imidazo[1,2-a]pyrazin-6-yl}-phenyl)-benzamide;

2-(3-Isopropyl-phenoxy)-N-(3-{8-[4-(morpholine-4-carbonyl)-phenylamino]-imidazo[1,2-a]pyrazin-6-yl}-phenyl)-acetamide;

6-tert-Butyl-N-(3-{8-[4-(morpholine-4-carbonyl)-phenylamino]-imidazo[1,2-a]pyrazin-6-yl}-phenyl)-nicotinamide; or 4-(6-{3[(6-tert-Butyl-pyridine-3-carbonyl)-amino]-phenyl}-imidazo[1,2a]pyrazin-8-ylamino)-benzoic acid or a pharmaceutically acceptable salt, hydrate or diastereomer thereof.

* * * * *

UNITED STATES PATENT AND TRADEMARK OFFICE
CERTIFICATE OF CORRECTION

| | |
|---|---|
| PATENT NO. | : 7,405,295 B2 |
| APPLICATION NO. | : 10/861791 |
| DATED | : July 29, 2008 |
| INVENTOR(S) | : Kevin S. Currie et al. |

It is certified that error appears in the above-identified patent and that said Letters Patent is hereby corrected as shown below:

Column 216, line 47 reads "$-C_1-C_o$" should read -- $-C_0$ --

Column 239, line 42 reads "is chose from" should read --is chosen from hydroxy,--

Column 244, line 31 reads "chosen from" should read --chosen from – hydroxyl--

Column 255, line 5 reads "substituted with" should read --substituted with hyroxy,--

Column 272, line 28 reads "form" should read --from--

Column 279, line 45 reads "{14}" should read --{1,4}--

Column 280, line 43 reads "from substituents" should read --substituents--

Column 292, line 32 reads "or {1,4}" should read --{1,4}--

Column 293, line 1 should read --hydroxy,-- on first line

Signed and Sealed this

Eighth Day of June, 2010

David J. Kappos
*Director of the United States Patent and Trademark Office*